(12) United States Patent
Crain et al.

(10) Patent No.: US 8,617,577 B2
(45) Date of Patent: Dec. 31, 2013

(54) METHODS AND COMPOSITIONS FOR TREATING DISTRESS DYSFUNCTION AND ENHANCING SAFETY AND EFFICACY OF SPECIFIC MEDICATIONS

(71) Applicant: Pondera Biotechnologies, LLC, Pownal, ME (US)

(72) Inventors: Steven Crain, State College, PA (US); William E. Crain, Pownal, ME (US); Stanley M. Crain, State College, PA (US); Michael Crain, Essex, CT (US)

(73) Assignee: Pondera Biotechnologies Inc., Pownal, ME (US)

( * ) Notice: Subject to any disclaimer, the term of this patent is extended or adjusted under 35 U.S.C. 154(b) by 0 days.

(21) Appl. No.: 13/764,543

(22) Filed: Feb. 11, 2013

(65) Prior Publication Data

US 2013/0156874 A1 Jun. 20, 2013

Related U.S. Application Data

(63) Continuation of application No. 13/460,467, filed on Apr. 30, 2012, now Pat. No. 8,372,414, which is a continuation of application No. 12/973,839, filed on Dec. 20, 2010, now Pat. No. 8,202,525.

(60) Provisional application No. 61/289,293, filed on Dec. 22, 2009, provisional application No. 61/309,766, filed on Mar. 2, 2010, provisional application No. 61/322,665, filed on Apr. 9, 2010, provisional application No. 61/323,465, filed on Apr. 13, 2010, provisional application No. 61/330,631, filed on May 3, 2010, provisional application No. 61/351,653, filed on Jun. 4, 2010, provisional application No. 61/375,463, filed on Aug. 20, 2010, provisional application No. 61/385,873, filed on Sep. 23, 2010, provisional application No. 61/386,952, filed on Sep. 27, 2010.

(51) Int. Cl.
*A61K 9/00* (2006.01)

(52) U.S. Cl.
USPC .......................................................... 424/400

(58) Field of Classification Search
USPC .......................................................... 424/400
See application file for complete search history.

(56) References Cited

U.S. PATENT DOCUMENTS

| | | | |
|---|---|---|---|
| 5,585,348 A | 12/1996 | Crain et al. | |
| 6,096,756 A | 8/2000 | Crain | |
| 6,284,765 B1 * | 9/2001 | Caffrey | 514/263.32 |
| 6,375,957 B1 | 4/2002 | Kaiko | |
| 6,395,705 B2 | 5/2002 | Crain et al. | |
| 6,458,795 B1 | 10/2002 | Bergeron, Jr. | |
| 6,664,270 B2 | 12/2003 | Bergeron, Jr. | |
| 6,818,656 B2 | 11/2004 | Bergeron, Jr. | |
| 6,972,291 B2 | 12/2005 | Bernstein | |
| 7,026,329 B2 | 4/2006 | Crain et al. | |
| 7,655,231 B2 | 2/2010 | Shelton et al. | |
| 2002/0198227 A1 | 12/2002 | Bernstein | |
| 2003/0191147 A1 | 10/2003 | Sherman et al. | |
| 2003/0211157 A1 | 11/2003 | Simon | |
| 2004/0072864 A1 | 4/2004 | Bergeron, Jr. | |
| 2005/0090513 A1 | 4/2005 | Geiss et al. | |
| 2006/0009478 A1 | 1/2006 | Friedmann et al. | |
| 2006/0069086 A1 | 3/2006 | Michalow | |
| 2007/0099947 A1 | 5/2007 | Dean, III et al. | |
| 2007/0178216 A1 | 8/2007 | Kandaswami et al. | |
| 2008/0045610 A1 | 2/2008 | Michalow | |
| 2008/0207601 A1 | 8/2008 | Sabnani | |
| 2008/0255097 A1 | 10/2008 | Sabnani et al. | |
| 2010/0144645 A1 | 6/2010 | Kirk et al. | |
| 2010/0168119 A1 | 7/2010 | Bear et al. | |

FOREIGN PATENT DOCUMENTS

| | | |
|---|---|---|
| CA | 2677691 | 8/2008 |
| WO | WO 00/67739 | 11/2000 |
| WO | WO2005/120507 | * 12/2005 |
| WO | WO 2006/034343 A2 | 3/2006 |
| WO | WO 2006/110557 A2 | 10/2006 |
| WO | WO 2007/056300 A2 | 5/2007 |
| WO | WO 2007/100775 A2 | 9/2007 |
| WO | WO 2007/120864 A2 | 10/2007 |
| WO | WO 2008/094571 A1 | 8/2008 |
| WO | WO 2009/017625 A1 | 2/2009 |
| WO | WO 2010/053835 A1 | 5/2010 |
| WO | WO 2010/015147 A1 | 11/2010 |

OTHER PUBLICATIONS

Reents (Chest, vol. 92, Jan. 1988, pp. 217-219).*
International Search Report and Written Opinion related International Patent Application No. PCT/US2010/061275, mailed Sep. 30, 2011.
Shapira et al., "Open-Label Pilot Study of Tramadol Hydrochloride in Treatment-Refractory Obsessive-Compulsive Disorder," *Depression and Anxiety*, No. 6, pp. 170-173 (1997).
Subbiah, "Guarana Consumption," *Alternative and Complementary Therapies*, vol. 11, No. 4, pp. 212-213 (2005).
Chakraborty et al., Behavioural Brain Research, No. 179, pp. 321-325 (2007).
Malonne et al., "Pharmacokinetic evaluation of a new oral sustained release dosage form of tramadol," *Br. J. Clin. Pharmacol.*, vol. 57, No. 3, pp. 270-278 (2004).
Klodzinska et al., "Anxiolytic-like effects of MTEP, a potent and selective mGlu5 receptor agonist does not involve $GABA_A$ signaling," *Neuropharmacology* vol. 47, pp. 342-350 (2004).
Kupferberg, "Antiepileptic Drug Development Program: A Cooperative Effort of Government and Industry," *Epilepsia*, vol. 30 (Suppl. 1), S51-S56 (1989).
Todd (http://www.thereeltodd.com/2008/06/red-energy-intense-nrg-concent.html, Jun. 8, 2008).
NRG (http://www.evitamins.com/nrg-conentrate-red-ener-epic-nutrition-13171; accessed Aug. 8, 2013).
Coffeefaq (http://coffeefaq.com/site/how-much-caffeine; accessed Aug. 8, 2013).
Office Action in related U.S. Appl. No. 13/830,895, dated Aug. 15, 2013.

* cited by examiner

*Primary Examiner* — David J Blanchard
*Assistant Examiner* — Devang Thakor
(74) *Attorney, Agent, or Firm* — Foley & Lardner LLP

(57) ABSTRACT

The present invention relates to methods and compositions for reducing distress dysfunction, including emotional and physical distress. The invention entails co-administration of at least one Receptor Switcher and at least one Endorphin Enhancer. Additionally, at least one Synergistic Enhance and/or at least one Exogenous Opioid are also administered to enhance or prolong the therapeutic effects.

6 Claims, 5 Drawing Sheets

METHODS AND COMPOSITIONS FOR TREATING DISTRESS DYSFUNCTION AND ENHANCING SAFETY AND EFFICACY OF SPECIFIC MEDICATIONS

CROSS-REFERENCE TO RELATED APPLICATIONS

This application is a continuation of U.S. patent application Ser. No. 13/460,467, filed Apr. 30, 2012, now U.S. Pat. No. 8,372,414, which is a continuation of U.S. patent application Ser. No. 12/973,839, filed Dec. 20, 2010, now U.S. Pat. No. 8,202,525, which claims priority of U.S. Patent Application No. 61/289,293, filed on Dec. 22, 2009, U.S. Patent Application No. 61/309,766, filed on Mar. 2, 2010, U.S. Patent Application No. 61/322,665, filed on Apr. 9, 2010, U.S. Patent Application No. 61/323,465, filed on Apr. 13, 2010, U.S. Patent Application No. 61/330,631, filed on May 3, 2010, U.S. Patent Application No. 61/351,653, filed on Jun. 4, 2010, U.S. Patent Application No. 61/375,463, filed on Aug. 20, 2010, U.S. Patent Application No. 61/385,873, filed on Sep. 23, 2010, and U.S. Patent Application No. 61/386,952, filed on Sep. 27, 2010. The contents of these applications are incorporated herein by reference in their entirety.

FIELD OF INVENTION

The present invention relates to methods and compositions for reducing Distress Dysfunction by restoring and maintaining homeostatic balance in the neurotransmitter systems underlying the Stress Response and the experience of emotional and physical distress and hedonic tone. The invention also relates to methods and compositions for treating respiratory disorders, neuropathy, neonatal apnea, and nociceptive pain by restoring and maintaining homeostatic balance in the neurotransmitter systems during the administration of treatment medications.

BACKGROUND OF THE PRIOR ART

Without the understanding taught by this invention, prior teachings and practice have focused on limited and, at times, iatrogenic treatments for Distress Dysfunctions. Treatments for emotional and physical distress, such as anxiety, depression, anger, insomnia, mood disorders, substance and behavioral addictions, eating disorders, sexual disorders, gastrointestinal disorders, attention-deficit disorders, and distressing pain, have generally involved the administration of anti-anxiety and anti-depressant medications, opioid and non-opioid analgesics, and stimulants. These treatments have been limited and often ineffective as well as the cause of serious, but avoidable, side effects. Conventional treatment lacks the knowledge and teaching described and developed through this invention, especially regarding the critical role of the protracted excitatory receptor mode and diminished neurotransmitter levels in endogenous opioid and related systems, characteristic of most Distress Dysfunction disorders, conditions, and symptoms.

Prior teachings and practices frequently resorted to supplementing endogenous neurotransmitters with exogenous substitutes, such as the extensive use of narcotic opioid drugs. Unfortunately, this approach has revealed very serious and dangerous consequences including the development of hyperalgesia, tolerance, dependence, and addiction, which, according to our discoveries, result directly from the homeostatic compensatory response of the endogenous opioid system that includes protracted suppression of endogenous neurotransmitters, such as endorphins, as well as protracted fixation of the receptors in the excitatory mode. In other words, use of exogenous opioids literally produces a protracted imbalance in the endogenous opioid system, exacerbating protracted distress symptoms, increasing the reliance on these drugs, and setting the stage for drug dependence and addiction. A similar problem exists in current opioid addiction treatment, in which "treatment" is simply administering more exogenous opioid drugs, such as buprenorphine, which continues the drug dependency and impairment of the homeostatic functioning of the stress-related neurotransmitter systems.

There is also growing evidence that many other pain and distress relieving agents, including NSAIDs, such as celecoxib and acetaminophen, function through the endogenous opioid system, as shown in cross-tolerance studies. In fact, there is evidence that celecoxib reduces pain, at least in part, by triggering the release of endogenous opioids. Given our discoveries regarding the impact of increasing endorphins when opioid receptors are in a distress, or protracted excitatory state, it is likely that many of the noxious side effects of NSAIDs, such as celecoxib, including tolerance and gastrointestinal symptoms, occur due to the triggering of protracted opioid excitatory signaling, similar to the impact of exogenous opioid drugs. Furthermore, the pain relieving effects, as shown in induced pain and clinical trials, are rather weak with non-opioid analgesics, and not sufficient for moderate-to-severe pain. Therefore, conventional treatment for emotional and physical distress is limited, with the more potent pharmaceuticals causing very dangerous and, at times, fatal consequences.

Clearly, neurotransmitter replacements, such as exogenous opioid and non-opioid analgesics, have had an important role in the management of physical and emotional distress, especially pain, despite their serious problems. However, using the discoveries underlying this invention, fortunately they can now be used as a last resort, in relatively small doses, in our novel formulations that have been developed to minimize the need for, and the iatrogenic impact of agents that compete with, and interfere with, healthy functioning of the stress response neurotransmitter systems.

An alternative approach to the treatment of emotional and physical distress has been the administration of agents that may increase the production, release, and functioning of neurotransmitters in the stress response system, rather than attempt to replace them with exogenous substitutes. For instance, the popular use of Selective Serotonin Reuptake Inhibitor (SSRI) and Selective Norepinephrine Reuptake Inhibitor (SNRI) medications, which increase the level of serotonin and norepinephrine, has shown partial effectiveness, with estimates that they generally may reduce distress symptoms of depression by about 10%. The variability of effectiveness is also striking, with many individuals having no benefit, or even an exacerbation of symptoms, using SSRI and SNRI medications. The problem, discovered by this invention, is that this popular treatment does not consider the important homeostatic interrelationship among the serontonergic and opioidergic and related neurotransmitter systems and the critical role of protracted excitatory opioid receptor signaling in reducing the therapeutic benefits from SSRIs, SNRIs, and other neurotransmitter enhancing agents. Cross-tolerance studies of exogenous serotonin and opioid agents demonstrate this underlying problem. There is evidence to suggest that tolerance and withdrawal effects often develop with the use of various anti-anxiety and anti-depressant medications, producing imbalances in these systems, ironically leading to increased protracted distress over time. Until this invention, there was no understanding of nor solution for, this problem with these medications.

A similar problem exists in the growing field of supplements used to reduce emotional and physical distress. This approach attempts to stimulate the production and release of stress-related neurotransmitters to enhance healthy neurotransmitter functioning. Most of this field focuses on administering forms of amino acids, vitamins and minerals, which target the production and release of specific neurotransmitters. For instance, tryptophan and 5HTP are often used to trigger the release of serotonin in an attempt to reduce distress and increase a sense of well-being. Similarly, dl-phenylalanine (DLPA) has been used to increase the release and maintenance of endorphins. This may have modest effectiveness when the receptors are in healthy homeostatic balance. Unfortunately, these agents provide either minimal effectiveness, or paradoxically, an increase in distress when individuals who suffer from Distress Dysfunction symptoms, caused by protracted opioid receptor excitatory signaling, use them. This understanding explains the limited and highly variable effectiveness of simply administering these supplements without the use of a Receptor Switcher, as discovered and defined by this invention. In fact, ironically, clinical experience has revealed that the more distress an individual experienced chronically, the more the administration of amino acid supplements, such as DLPA, produced increased, rather than reduced, distress. Until this invention, however, there was no explanation or solution to this variable and, at times, iatrogenic effects of neurotransmitter enhancing agents.

Another approach to the reduction of distress, especially used in the field of drug and alcohol dependence, has been to administer a large dose of neurotransmitter antagonists, such as naltrexone, in an attempt to reduce cravings and prevent the effects of these abused substances on the neurotransmitter system. While these high dose opioid antagonists effectively block protracted excitatory signaling, they also block inhibitory signaling as well, leading to reduced pleasure and pain control. This treatment has very poor compliance because individuals typically become anhedonic, leading to limited motivation to continue taking the antagonist. Recently approved medications remove the daily choice from this method of treatment by administering long-term dosing of these drugs. Unfortunately, this approach to treating distress dysfunction is counterproductive because it blocks the release of endogenous opioids and related neurotransmitters, thereby dramatically impairing homeostatic balance in these systems and causing a continuous state of anhedonia and hyperalgesia, which, in turn, mitigates against long-term success and compliance. In certain ways, it could be considered a more finely tuned chemical lobotomy.

Similarly, investigators at Orexigen Therapeutics have taught the combination of certain opioid antagonists, such as naltrexone, with certain Synergistic Enhancers, specifically SSRIs. Unfortunately, without an understanding of Receptor Switchers, they use conventional doses of naltrexone, which, according to the discoveries of this invention, will have reduced, if any, initial benefits as well as long-term iatrogenic effects since higher doses of opioid antagonists block all opioid receptor signaling.

A similar problem exists with prior teachings that suggested high dose naltrexone in combination with Nerve Growth Factor (NGF) for the treatment of HIV-induced and diabetic neuropathy. NGF can be an effective treatment for various conditions, including HIV-induced and diabetic neuropathy, but it is well known that NGF produces hyperalgesia and pain, reflecting protracted excitatory opioid receptor signaling. Although Crain et al. (U.S. Pat. No. 5,585,348) recognized the potential of a co-treatment approach for diabetic neuropathy to reduce the painful side-effects of NGF, they taught the use of oral naltrexone in the dose range of 25-50 milligrams. The present invention indicates that this is not only ineffective, but will produce serious noxious side effects since naltrexone at this dose literally blocks all opioid receptor activity, including inhibitory signaling. Therefore, as recommended by this prior teaching, the net effect of combining NGF with high dose naltrexone is an increase in Distress Dysfunction, including pain and hyperalgesia, over time.

A group of investigators at Pfizer has taken an even more problematic route. Noting that exogenous nerve growth factor (NGF) produces a serious side effect of pain, they postulated that treatment that reduces endogenous NGF levels in the body could be an effective treatment for chronic pain (U.S. Pat. No. 7,655,231 for "Methods for treating pain by administering a nerve growth factor antagonist and an NSAID"). While early results weakly support this theory, this approach is likely to lead to very serious long-term consequences since endogenous NGF is known to have extremely important roles in a wide variety of physiological processes. Therefore, a fundamentally different methodology is needed to reduce the noxious hyperalgesic effects of exogenous as well as endogenous NGF. The use of Receptor Switchers, as discovered and defined by this patent, provides a safe and effective solution to this problem.

Dr. Stanley Crain discovered the existence and function of agents that block excitatory opioid receptor signaling during his pioneering electrophysiological nervous tissue culture studies. His research led to the discovery that endogenous opioid receptors are bimodal and have two signaling modes—inhibitory and excitatory. When the receptor is in the inhibitory mode, endogenous opioids, such as endorphins, trigger inhibitory signaling, leading to immediate reduction of distressful pain signals. However, when the receptor is in the excitatory mode, endorphins trigger excitatory signaling, sending out distressing alert signals, often experienced as pain. If the neurotransmitter system is in homeostatic balance, the system is very efficient and effective, switching back and forth between excitatory (pain) and inhibitory (relief) signaling. However, Dr. Crain discovered that when exogenous opioid agents are administered, the system adapts rather quickly, leading to protracted excitatory signaling. In subsequent studies, Dr. Crain discovered that ultra-low-dose opioid antagonists, such as ultra-low-dose naltrexone (ULDN), reduced and/or eliminated protracted excitatory signaling. Dr. Crain later discovered that GM1 ganglioside attenuators, such as oseltamivir, also selectively block excitatory opioid receptor signaling.

Dr. Crain used these discoveries to develop improved approaches for the treatment of nociceptive pain and opioid drug addiction. He developed a method to reduce many of the noxious side effects of exogenous opioid drugs, such as tolerance and dependence, using co-treatment formulations that added specific agents, such as ULDN or oseltamivir, when administering opioid drugs (U.S. Pat. No. 7,026,329 for "Method of simultaneously enhancing analgesic potency and attenuating dependence liability caused by morphine and other bimodally-acting opioid agonists"; and WO 2010/0015147 for "Methods for increasing analgesic potency and attenuating adverse excitatory effects of bimodally-acting opioid agonists by inhibiting GM1-ganglioside").

Dr. Crain also discovered that by combining agents, such as rolipram and monosodium glutamate (MSG), that normally increase hyperalgesia and pain, presumably by triggering excitatory opioid receptor signaling, with agents such as ULDN or oseltamivir, the hyperalgesic effects could be blocked and reversed, producing analgesia. These preclinical studies led Dr. Crain to propose novel non-opioid formulations for the treatment of nociceptive pain and opioid addiction (WO 2010/0203084 for "Method for treating pain or opioid dependence using a specific type of non-opioid agent in combination with a selective excitatory-opioid-receptor inactivator").

While Dr. Stanley Crain's preclinical studies revealed the importance of agents that selectively block excitatory opioid receptor signaling, his research was exclusively focused on nociceptive pain and the endogenous opioid system and not on the emotional and physical distress syndromes, which are the focus of this invention, and the critical interconnected role of other stress-related neurotransmitter systems, such as the serotonin, dopamine, glutamate, epinephrine, and norepinephrine systems. Dr. Crain's combination of Receptor Switchers, such as ultra-low-dose-naltrexone, with either Exogenous Opioids or Endorphin Enhancers, such as rolipram, was limited to nociceptive pain and opioid withdrawal. Dr. Crain neither addressed nor articulated any principles that predicted or contemplated the role of these formulations in the treatment of the comprehensive set of disorders, conditions, and symptoms that are manifested by Distress Dysfunction, as defined in this application, such as dysfunctional worries and anxieties, anger and irritability, despair and depression, sexual and sleep impairments, cravings for alcohol and food, or hypersensitivity or exaggerated responsivity to perceived pain and stress.

Regarding one Distress Dysfunction disorder that Dr. Crain's team did address, Irritable Bowel Syndrome (U.S. Pat. No. 6,395,705), they taught the use of low-dose naltrexone alone, which, without agents that simultaneously enhance endorphin levels (Endorphin Enhancers), has been shown to be ineffective for symptom reduction over time. Similarly, teachings from Dr. Stanley Crain and Dr. Paolo Mannelli have suggested the use of ultra-low-dose and very-low-dose naltrexone alone to facilitate withdrawal from chronic opioid dependence. However, they neglected the critical principle, discovered by this invention, that co-treatment with at least an Endorphin Enhancer, such as roflumilast or ginkgo biloba, is critical to enhance depleted endorphins and other stress-related neurotransmitters underlying substance dependence. Furthermore, this invention uniquely teaches the synergistic treatment benefits that are seen when adding Synergistic Enhancers, such as specific amino acids, to these co-treatment formulations.

One group at Pharmorx has recently taught the use of ultra-low-dose opioid antagonists for "preventing or reversing loss of therapeutic effect, where loss is associated with the repeated administration" of dopamine-related agents (WO 2010/0168119). However, their discovery only relates to the loss of effects of dopamine-related agents, with no teaching regarding the extensive therapeutic benefits, well beyond tolerance, for a wide variety of Distress Dysfunction disorders, of using ultra-low-dose and very-low-dose opioid antagonists, and a variety of other Receptor Switchers, in combination with the Endorphin Enhancers, such as the cAMP PDE inhibitors and excitatory amino acids, and the Synergistic Enhancers, such as the serotonin reuptake inhibitors, norepinephrine reuptake inhibitors, and the analgesics, discovered by this invention. Furthermore, these investigators only used ultra-low-dose opioid antagonists (up to a maximum of "1.5 µg/kg"), which ignores the limited oral bioavailabilty of these agents, such as naltrexone. Our findings show that relatively higher doses of agents, such as naltrexone in the 125-150 microgram range, are more likely to have reliable and consistent benefits across people and conditions. Furthermore, their teaching ignores the remarkable therapeutic benefits of the other Receptor Switchers, such as neuraminidase inhibitors, discovered by this invention.

With regard to the treatment of nociceptive pain and opioid dependence, although Dr. Crain conducted nervous tissue culture and animal models, he neither studied nor identified the formulations and agents that would, in fact, be appropriate, safe and effective agents for human consumption and clinical application. (Indeed rolipram, the only agent that Dr. Crain twice referred to in his patent as part of a "preferred embodiment" has been shown to exhibit noxious gastrointestinal effects, thereby making it unsuitable for human clinical application in humans.) Furthermore, Dr. Crain's teachings are silent regarding the critical importance of using Exogenous Opioids only in combination with both Receptor Switchers and Endorphin Enhancers, which serves to minimize the need and dose of Exogenous Opioids. Moreover there has been no teaching regarding the therapeutic benefits of adding specific Synergistic Enhancers, such as SSRI, NSAID, and amino acids, to these endorphinergic formulations of Receptor Switchers and Endorphin Enhancers, for nociceptive pain. Therefore, what is clearly needed is a way to block the noxious, hyperalgesic protracted excitatory signaling of opioid and related neurotransmitter receptors, without inhibiting the de-stressing pain-reducing inhibitory signaling.

A group of investigators at Avigen found evidence that ibudilast, a cAMP PDE inhibitor drug similar to rolipram, but more tolerable for human consumption, can be used for the treatment of pain and various addictions, though they attribute the benefits to glial cell mechanism and not to its cAMP PDE inhibition functions (WO 2006/0160843 and WO 2008/0181876). However, these investigators assert that the effectiveness of ibudilast for these disorders is based on its administration as a stand-alone medication, or in combination with Exogenous Opioids. As a result, they suggest no teachings regarding the critical need for the co-administration of any agent to reduce protracted excitatory opioid receptor signaling, such as a ULDN, with ibudilast for the most effective treatment of pain and addiction. Not only is this approach less effective, but also potentially iatrogenic since the administration of ibudilast and other PDE-inhibitors, as well as Exogenous Opioids without a Receptor Switcher, such as ULDN or VLDN, is likely to leave the receptors in the endogenous opioid system in a protracted excitatory state, making it much less effective for treating Distress Dysfunction and might even exacerbate emotional and physical distress, thereby exacerbating Distress Dysfunctions.

Additional examples of prior art directed to administering opioid antagonists and the treatment of pain, IBS, and other Distress Dysfunctions include US Patent Publication No. 20020198227 for "Method for curbing dietary craving" (describing administration of low dose naltrexone); US Patent Publication No. 20030191147 for "Opioid antagonist compositions and dosage forms"; US Patent Publication No. 20030211157 for "Semi-sol delivery blend for water soluble molecules"; US Patent Publication No. 20040072864 for "Method and composition for treatment of irritable bowel disease"; US Patent Publication No. 20060009478 for "Methods for the treatment of back pain" (does not describe the use of ultra low does naltrexone in combination with a non-opioid analgesic); US Patent Publication No. 20060069086 for "Methods for regulating neurotransmitter systems by inducing counteradaptations" (does not describe ultra low does naltrexone or co-treatment); US Patent Publication No. 20070099947 for "Methods and compositions for the treatment of brain reward system disorders by combination therapy" (does not describe ultra low does naltrexone); US Patent Publication No. 20080045610 for "Methods for regulating neurotransmitter systems by inducing counteradaptations"; US Patent Publication No. 20080207601 for "Methods of and Compositions For the Prevention of Anxiety, Substance Abuse, and Dependence" (cotreatment agents are steroids); US Patent Publication No. 20080255097 for "Methods for the Treatment of Substance Abuse and Dependence"; US Patent Publication No. 20100144645 for "Compositions and Methods for Enhancing Analgesic Potency of Covalently Bound-Compounds . . . "; US Patent Publication No. 20100168119 for "Compositions and Methods for Minimizing or Reducing Agonist-Induced Desensitization"; U.S. Pat. Nos. 6,458,795, 6,664,270 and 6,818,656, all for "Method and composition for treatment of irritable bowel disease"; U.S. Pat. No. 6,972,291 for "Method for reducing food intake" (describing administration of low does (not ultra low does) naltrexone); WO 2007/056300 for "Methods and Compositions for the Treatment of Brain Reward System Disorders by Combination Therapy"; WO 2000/067739 for "Opioid Antagonists Containing Compositions for Enhancing Analgesic Potency of Tramadol and Attenuating its Adverse Side Effects"; WO 2006/034343 for "Methods for regulating neurotransmitter systems by inducing counteradaptations"; WO 2006/110557 for "Methods for the Treatment of Substance Abuse and Dependence"; WO 2007/100775 for "Methods for Regulating Neurotransmitter Systems by Inducing Counteradaptations"; WO 2007/120864 for "Compositions and Methods for Enhancing Analgesic Potency of Covalently Bound Compounds . . . "; WO 2008/094571 for "Methods for Treating Acute and Subchronic Pain"; WO 2009/017625 for "Treatment of Depression, Psychosis, and Anxiety"; and WO 2010/053835 for "Compositions and Methods for Minimizing or Reversing Agonist-Induced Desensitization." However, there is no prior art that teaches the critical importance of understanding the role of protracted excitatory opioid (and related) receptor signaling, together with diminished opioid (and related) neurotransmitters, in Distress Dysfunctions, and its clinical implication for the use of Receptor Balancers combined with Endorphin Enhancers and/or Synergistic Enhancers and/or Exogenous Opioids for safe and effective treatment.

There is a need in the art for improved methods and compositions for treating Distress Dysfunctions. The present invention satisfies these needs.

SUMMARY OF THE INVENTION

Distress Dysfunction refers to the experience of dysfunctional emotional and physical distress that interferes with the individual's quality of life and functioning. While there are a wide variety of emotional and physical manifestations of this negative hedonic tone, it is often experienced as unwarranted and/or exaggerated fear, anger, anxiety, depression, insomnia, sexual and eating problems, cravings, substance and behavioral addictions, hyperactivity, hyperalgesia, and distressing physical discomfort and pain. This invention is directed to compositions and methods which reduce dysfunctional emotional and physical distress. The methods comprise co-administration of agents from four classes that, together, improve, restore, and maintain homeostatic balance in the Stress Response, particularly the endogenous opioid, serotonin, dopamine, glutamate, norepinephrine, glutamate, and epinephrine neurotransmitter systems. This invention teaches the surprising and dramatic synergistic reduction of emotional and physical distress that results from the combination of at least one agent from Class I with at least one agent from Classes II and/or III and/or IV, such that the combination is more effective for the reduction of emotional and/or physical symptoms of distress than the agents administered alone. This invention also teaches that these novel formulations can be used to synergistically potentiate the therapeutic benefit of various medications, in surprising and dramatic ways, including analgesics, stimulants, and anti-depressant drugs and medications for respiratory disorders and HIV-induced and diabetic neuropathy as well as for the reduction of distress symptoms ("side effects") produced by these medications. In this way, novel pharmaceutical formulations have been discovered for the treatment of a wide variety of Distress Dysfunctions as well as respiratory disorders, such as COPD, asthma, and neonatal apnea, neuropathy, such as diabetic and HIV-induced, and nociceptive pain.

In one embodiment of the invention, encompassed is a method to safely and effectively treat Distress Dysfunction conditions, symptoms and/or disorders in a subject in need comprising: (a) administering at least one Receptor Switcher to the subject; and (b) administering at least one compound to the subject selected from the group consisting of an Endorphin Enhancer, an Exogenous Opioid, a Synergistic Enhancer, and any combination thereof.

In another embodiment of the invention, the RECEPTOR SWITCHER, when co-administered with CLASS II, III, and/or IV AGENTS, reduces and/or resolves one or more Distress Dysfunction symptoms. The RECEPTOR SWITCHER can be selected from the group consisting of agents that selectively block and/or inhibit opioid receptor excitatory signaling, ultra-low-dose and very-low-dose opioid antagonists, ultra-low-dose and very-low-dose naltrexone, naloxone, diprenorphine, nalmefene, and norbinaltorphimine, agents that inhibit synthesis or activity of GM1 ganglioside, neuraminidase inhibitors, agents that increase sulfates in the body, methylsulfonylmethane (MSM), magnesium sulfate, sodium sulfate, chondroitin sulfate, n-acetyl-cysteine (NAC), zanamivir, laninamivir, peramivir, oseltamivir, scutellaria, and 5,7,4'-trihydroxy-8-methoxyflavone.

In another embodiment of the invention, the ENDORPHIN ENHANCER, when co-administered with at least one RECEPTOR SWITCHER, reduces and/or resolves one or more Distress Dysfunction symptoms. The ENDORPHIN ENHANCER can be selected from the group consisting of agents that enhance the release, production, and/or functioning of endogenous opioids (i.e., endorphins), cyclic adenosine monophosphate (cAMP) phosphodiesterase (PDE) inhibitors or agents that directly enhance cAMP, a cAMP phosphodiesterase (PDE) inhibitor, an agent that directly enhances cAMP, a specific or non-specific cAMP PDE inhibitor, a specific cAMP PDE-4 inhibitor, theophylline, roflumilast, ibudilast, cilomilast, ardenafil, tadalafil, sildenafil, zaprinast, rolipram, methylxanthine, milrinone, inaminone, cilostazol, caffeine, guarana, ginkgo biloba, forskolin, excitatory amino acids, a salt of an excitatory amino acid, all forms of excitatory amino acids, glutamic acid, aspartic acid, glutamine, mono-sodium glutamate (MSG), and N-methyl-D-asparate (NMDA), phenylalanine, dl-phenylalanine (DLPA), celecoxib, and nerve growth factor (NGF).

In another embodiment of the invention, the EXOGENOUS OPIOID, when co-administered with at least one RECEPTOR SWITCHER, reduces and/or resolves one or more DISTRESS DYSFUNCTION symptoms. The EXOGENOUS OPIOID can be selected from the group consisting of exogenous opioid agonist (full, partial, mixed) agents, tramadol, morphine, oxycodone, hydrocodone, papaverine, codeine, dihydrocodeine, fentanyl, hydromorphone, buprenorphine, butorphanol, methadone, alfentanil, loperamide, levorphanol, menthol, meperidine, nalbuphine, oxymorphone, pentazocine, pentazocine, propoxyphene, remifentanil, and sufenta.

In another embodiment of the invention, the SYNERGISTIC ENHANCER, when co-administered with at least one RECEPTOR SWITCHER, reduces and/or resolves one or more DISTRESS DYSFUNCTION symptoms. The SYNERGISTIC ENHANCER cam be selected from the group consisting of agents that enhance the release, production and/or functioning of serotonin, dopamine, epinephrine, norepinephrine, and glutamate neurotransmitters, non-opioid analgesics, non-steroidal anti-inflammatory drugs (NSAIDs), acetaminophen, celecoxib, white willow bark, acetylsalicylic acid, salicin, ibuprofen, naproxen, ketoprofen, indomethacin, fenoprofen, tolmetin, sulindac, meclofenamate, piroxicam, flurbiprofen, diclofenac, stimulants, selective serotonin reuptake inhibitors (SSRI), serotonin agonists, antagonists and modulators, selective norepinephrine reuptake inhibitors (SNRIs), citalopram, dapoxetine, escitalopram, fluoxetine fluvoxamine, paroxetine, sertraline, fluvoxamine, zimelidine, dapoxetine, venlaflafaxine, duloxetine, desvenlafaxine, alosetron, ondansetron, granisetron, bemesetron, eplivanserine, deramciclane, agomelatine, elazasonan, pruvanserin, asenapine, zomari, valazodone, bifeprunox, buspirone, ritanseron, geperone, paliperidone, clomipram, doxepin, haloperidol, risperidone, methylphenidate, amino acids, a salt of an inhibitory amino acid, all forms of amino acids, gamma-aminobutrynic acid (GABA), pharmaGABA, glycine, taurine, tryptophan, SHIP, phenylalanine, dl-phenylalanine (DLPA), s-adenosylmethionine (SAMe), acetyl-L-carinitine (ALC), valine, threonine, methionine, lysine, leucine, isoleucine, tyrosine, alanine, arginine, histidine, serine, selenocfysteine, proline, glycine, cysteine, aspargine, alanine, cannabis, all formas and derivatives of cannabis, L-DOPA, vitamins and minerals, luteolin, quercetin, qercetin-3-O-methylether (3-MQ, 2), quercetin-3,7,4'-O-trimethylether, ayanin, quercetin-3,7,3',4'-O-tetramethylether, quercetin-3,5,7,3',4'-O-petamethylether, quercetin-3,5,7,3',4'-O-pentaacetate, quercetin-3-O-methyl-5,7,3',4'-O-tetraacetate, methylcobalamin, vitamin C, vitamin D, vitamin D-3, vitamins B1, B2, B3, B6, and B12, folic acid, niacin, or niacinamide, folinic acid, calcium folinate, methylcobalamin, pyridoxal-5'-phosphate (P5P), alkaloids, flavonoids, and saponins, hesperetin, hesperidin, naringin, naringenin, epigallocatechin-3-gallate (EGCG), dioclein, genistein, daidzein, eriodictyol, prunetin, biochanin A, apigenin, myricetin, liquiritigenin, liquiritin, kaempferol, isoliquiritigenin, chrysin, rutin, cyanidin, delphinidin, pelargonidin, isorhamnetin, vitamin C, St. John's Wort, passion flower, hyperforin, hypericin, biotin, vitamin B5 (pantothenic acid), magnesium, alpha-ketoglutarate, copper, zinc, L-theanine, iron, california poppy, ginseng (Panax spp.), licorice, night-blooming cereus (Selenicereus grandiflorus; Cactus grandiflorus), hordenine, nutmeg, myristicin, tyramine, scotch broom, green tea, ephedra, yohimbe, DMSO, arginine, myhhr, boswellia, frankinsence, peppermint oil, and menthol.

In yet another embodiment of the invention, the subject has previously been prescribed an ENDORPHIN ENHANCER, an EXOGENOUS OPIOID, a SYNERGISTIC ENHANCER, or any combination thereof.

In one embodiment of the invention, encompassed is a method to enhance the therapeutic benefit and/or reduce the side effects of an ENDORPHIN ENHANCER, EXOGENOUS OPIOID, and/or a SYNERGISTIC ENHANCER in a subject comprising co-administering to a subject at least one RECEPTOR SWITCHER.

In another embodiment of the invention, encompassed is a method to enhance the therapeutic benefit and/or reduce the side effects of an ENDORPHIN ENHANCER and/or an EXOGENOUS OPIOID and/or a SYNERGISTIC ENHANCER by co-administering to a subject at least one RECEPTOR SWITCHER combined with at least one ENDORPHIN ENHANCER and/or a SYNERGISTIC ENHANCER.

In yet another embodiment of the invention, the RECEPTOR SWITCHER is a low dose opioid antagonist. For example, the RECEPTOR SWITCHER can be low dose naltrexone or naloxone. In another embodiment, naltrexone as a RECEPTOR SWITCHER can be administered: (a) in the ultra low dose amount of about 125 micrograms or less; (b) in the very-low-dose range of about 125-about 500 micrograms; or (c) in the low-dose range of about 500-about 1000 micrograms. In another embodiment, naloxone as a RECEPTOR SWITCHER can be administered: (a) at an ultra low dosing of about 0.25 $\mu g \cdot kg^{-1} \cdot h^{-1}$; (b) at about 400 micrograms naloxone in 1000 ml crystalloid given in 24 h to a patient weighing 70 kg; (c) at a-low-dosing of about 1.0 $\mu g \cdot kg^{-1} \cdot h^{-1}$; or (d) at about 0.01 $\mu g \cdot kg^{-1}$ $h^{-1}$ to about 5 $\mu g \cdot kg^{-1} \cdot h^{-1}$.

In yet another embodiment of the invention, encompassed is a method wherein the RECEPTOR SWITCHER is selected from the group consisting of a neuramindase inhibitor, n-acetyl-cysteine, magnesium sulfate, and methylsulfonylmethane (MSM).

In one embodiment of the invention, encompassed is a method wherein the ENDORPHIN ENHANCER is selected from the group consisting of a cAMP enhancing agent, a cAMP PDE inhibitor, roflumilast, theophylline, ginkgo biloba, caffeine, guarana, ibudilast, an excitatory amino acid, glutamic acid, mono-sodium-glutamate, DL-Phenylalanine (DLPA), celecoxib, or nerve growth factor (NGF).

In one embodiment of the invention, encompassed is a method wherein the EXOGENOUS OPIOID is selected from the group consisting of tramadol, oxycodone, hydrocodone, loperamide, buprenorphine, menthol, codeine, and morphine.

In another embodiment of the invention, encompassed is a method wherein the SYNERGISTIC ENHANCER: (a) is a selective serotonin reuptake inhibitor (SSRI) or a selective norepinephrine reuptake inhibitor (SNRI); (b) is a non-opioid analgesic; (c) is a non-steroidal anti-inflammatory agent (NSAID); or (d) is cannabis, in any form or derivative. For example, the SSRI or SNRI can be selected from the group consisting of citalopram, escitalopram oxalate, fluoxetine, venlaflafaxine, or duloxetine.

In another embodiment of the invention, encompassed is a method wherein the SYNERGISTIC ENHANCER is selected from the group consisting of acetaminophen, celecoxib, aspirin, white willow bark, ibuprofen, methylphenidate, an amino acid in any form or derivative, including a salt, 5HTP, tryptophan, S-adenosylmethionine (SAMe), GABA in any form, tyrosine, taurine, acetyl-L-carinitine (ALC), DMSO, myhhr, boswellia, and arginine.

In one embodiment of the invention, encompassed is a method wherein: (a) the RECEPTOR SWITCHER is naloxone, the SYNERGISTIC ENHANCER is ibuprofen, and the co-administration further includes administering arginine; or (b) the RECEPTOR SWITCHER is naloxone, the SYNERGISTIC ENHANCER is ibuprofen, the EXOGENOUS OPIOID is morphine, and the co-administration further includes administering arginine.

Any pharmaceutically acceptable administration method can be used for the invention. For example, the mode of administration can be selected from the group consisting of oral, pulmonary, nasal, sublingual, parenteral, transdermal, topical, and suppository. Moreover, the composition of the invention can be in any pharmaceutically acceptable dosage form. For example, the pharmaceutical formulation used in the methods of the invention can be delivered in a pharmaceutically-acceptable carrier that is rapid release, immediate-release, slow-release, controlled-release, delayed-released, and combination controlled and immediate release, including nano-encapsulation formulations, as well as any and all technologies that maximize therapeutic effectiveness, such as extended and slow release of the pharmaceutical formulation. In addition, the pharmaceutical formulation used in the methods of the invention can be delivered in an abuse-resistant delivery system.

In yet another embodiment of the invention, encompassed is a method wherein: (a) the ENDORPHIN ENHANCER is a glutamate or glutamine, such as monosodium glutamate (MSG); and (b) the RECEPTOR SWITCHER is magnesium sulfate, NAC, or a combination thereof, wherein the combination of the ENDORPHIN ENHANCER with a RECEPTOR SWITCHER provides an effective treatment for the allergic and other noxious side effects of MSG, and wherein by preserving the flavor enhancing characteristics of MSG and attenuating and eliminating the noxious side effects of MSG, the formulation is appropriate and useful as a food additive, condiment, and flavor enhancer.

In yet another embodiment of the invention, encompassed is a method wherein: (a) the ENDORPHIN ENHANCER is a PDE inhibitor selected from the group consisting of roflumilast, ibudilast, rolipram, ginkgo biloba, caffeine, guarana, aminophylline, and theophylline, and (b) by combining the PDE inhibitors with a RECEPTOR SWITCHER, including, but not limited to, ultra-low-dose and very-low-dose opioid antagonists, n-acetyl cysteine (NAC), methylsulfonylmethane (MSM), magnesium sulfate, and neuromimidase inhibitors, wherein the formulation (i) reduces side effects that would occur when the PDE inhibitor is administered alone; (ii) reduces hyperalgesia that would occur when the PDE inhibitor is administered alone; (iii) improves the therapeutic efficacy of the PDE inhibitor when administered alone; and/or (iv) improves the therapeutic benefit of the PDE inhibitor in the treatment of respiratory conditions including, but not limited to, COPD, asthma, and neonatal apnea, as compared to the administration of the PDE inhibitor alone. In such an embodiment, (a) the ENDORPHIN ENHANCER can be a specific cAMP PDE-4 inhibitor, and the RECEPTOR SWITCHER is ultra-low-dose or very-low-dose naltrexone; (b) the ENDORPHIN ENHANCER can be roflumilast, ibudilast, theophylline, aminophylline, caffeine, guarana, or ginkgo biloba, and the RECEPTOR SWITCHER can be ultra-low-dose or very-low-dose naltrexone; (c) the ENDORPHIN ENHANCER can be a specific cAMP PDE-4 inhibitor, and the RECEPTOR SWITCHER can be n-acetyl-cysteine; (d) the ENDORPHIN ENHANCER can be roflumilast, ibudilast, caffeine, guarana, aminophylline, or theophylline, and the RECEPTOR SWITCHER can be n-acetyl-cysteine; (e) the ENDORPHIN ENHANCER can be ginkgo biloba, and the RECEPTOR SWITCHER can be n-acetyl-cysteine; (f) the ENDORPHIN ENHANCER can be a specific cAMP PDE-4 inhibitor, and the RECEPTOR SWITCHER can be magnesium sulfate; (g) the ENDORPHIN ENHANCER can be roflumilast, ibudilast, caffeine, guarana, aminophylline, or theophylline, and the RECEPTOR SWITCHER can be magnesium sulfate; or (h) the ENDORPHIN ENHANCER can be ginkgo biloba, and the RECEPTOR SWITCHER can be magnesium sulfate.

In yet another embodiment of the invention, encompassed is a method wherein the ENDORPHIN ENHANCER is nerve growth factor (NGF), and by combining NGF with one or more RECEPTOR SWITCHERS, including, but not limited to, ultra-low-dose and very-low-dose opioid antagonists and neuromimidase inhibitors, the resultant formulation: (a) reduces side effects, that would occur when NGF is administered alone; (b) reduces hyperalgesia and pain that would occur when NGF is administered alone; (c) improves the therapeutic efficacy of NGF when administered alone; (d) improves the therapeutic benefit of NGF in the treatment of neuropathy, including diabetic and HIV-induced, and/or Distress Dysfunction, including pain, stress, anxiety, and depression, as compared to the administration of NGF alone; or (e) any combination thereof. In such a method, nerve growth factor is combined with, for example: (a) ultra-low-dose or very-low-dose naltrexone; (b) n-acetyl-cysteine; (c) methylsulfonylmethane; or (d) magnesium sulfate.

In one embodiment of the invention, encompassed is a method wherein a safe and effective treatment for nociceptive pain comprises: (a) administering at least one Receptor Switcher to the subject; and (b) administering at least one compound to the subject selected from the group consisting of an Endorphin Enhancer, an Exogenous Opioid, a Synergistic Enhancer, and any combination thereof.

In yet another embodiment of the invention, encompassed is a method wherein a safe and effective method to produce pain relief and/or analgesia in a subject experiencing nociceptive pain comprises: (a) administering (i) at least one Receptor Switcher to the subject with (ii) at least one Endorphin Enhancer in combination with (iii) one or more Exogenous Opioids and/or Synergistic Enhancers; or (b) administering at least one Receptor Switcher to the subject in combination with at least one Synergistic Enhancer.

In one embodiment of the invention, encompassed is a method wherein a safe and effective method to produce pain relief and/or analgesia in a subject experiencing nociceptive pain comprises: (a) administering one or more of the following agents to the subject: methylsulfonylmethane (MSM), n-acetyl-cysteine (NAC), scutellaria, and 5,7,4'-trihydroxy-8-methoxyflavone, in combination with (b) at least one compound selected from the group consisting of at least one Endorphin Enhancer, at least one Exogenous Opioid, at least one Synergistic Enhancer, and any combination, thereof.

In yet another embodiment of the invention, encompassed is a method wherein a safe and effective method to produce pain relief and/or analgesia in a subject experiencing nociceptive pain comprises: (a) administering one or more Receptor Switchers, in combination with (b) one or more of the following agents: caffeine, guarana, ginkgo biloba, phenylalanine, dl-phenylalanine (DLPA), celecoxib, theophylline, roflumilast, and nerve growth factor (NGF).

In another embodiment, the Distress Dysfunction conditions, symptoms and/or disorders treated by the methods of the invention can be selected from the group consisting of: (1) Anxiety Disorders; (2) Mood Disorders; (3) Somatoform Disorders; (4) Factitious Disorders; (5) Dissociative Disorders; (6) Sexual Dysfunction; (7) Eating Disorders; (8) Gastrointestinal Disorders; (9) Pre-Menstrual Syndrome (PMS) and other hormonally-related distress signs and symptoms; (10) Movement Disorders; (11) Fibromyalgia; (12) Sleep Disorders; (13) Impulse-Control Disorders; (14) Psychological Factors Affecting Medical Conditions; (15) Medication-Induced Movement Disorders; (16) Alcohol-Related Disorders; (17) Opioid-Related Disorders; (18) Caffeine-Related Disorders; (19) Cannabis-Related Disorders; (20) Amphetamine (or Amphetamine-Like)-Related Disorders; (21) Cocaine-Related Disorders; (22) Nicotine-Related Disorders; (23) Inhalant-Related Disorders; (24) Phencyclidine- Related Disorders; (25) Sedative-, Hypnotic-, or Anxiolytic-Related Disorders; (26) Polysubstance-Related Disorders; (27) Pervasive Developmental Disorders; (28) Attention-Deficit and Disruptive Behavior Disorders; (29) Chronic Fatigue Disorder; (30) Psychotic Disorders; (31) Behavioral addictions, compulsions, and dysfunctions; (32) Pain disorders; (33) Psychotic disorders; (34) Unpleasant or deleterious side effects of CLASS II, III, or IV agents when such agents are administered alone (i.e., without co-administration with an CLASS I agent) which may, or may not, interfere with the potential therapeutic benefits of CLASS II, III, or IV agents, including, but not limited to PDE inhibitors, opioid and non-opioid analgesics, stimulants, SSRIs, SNRIs, nerve growth factor (NGF), and amino acids; (35) Respiratory disorders; (36) Inflammatory disorders; (37) Nerve damage and neuropathy; (38) Allergic and non-allergic glutamate and monosodium glutamate related disorders; and (39) Emotional and physical malaise, distress, discomfort, pain, restlessness, irritability, worries, cravings, compulsions, obsessions, agitation, addictions, and other related complaints and signs of protracted negative hedonic tone that may, or may not, be part of a traditional medical or psychiatric disorder.

Examples of Anxiety Disorders include, but are not limited to, Panic Disorders, Agoraphobia, Specific Phobias, Social Phobias, Obsessive-Compulsive Disorder, Post-Traumatic Stress Disorder, Acute Stress Disorder, Generalized Anxiety Disorder, Substance-Induced Anxiety, Anxiety Related to Medical Disorders, Anxiety Disorder Not Otherwise Specified (NOS), as well as signs and symptoms of anxiety, stress, agitation, and worry that are not classified as an Anxiety Disorder. Examples of Mood Disorders include, but are not limited to, Depressive Disorders, Dysthymic Disorder, Bipolar I Disorder, Bipolar II Disorder, Bipolar Disorder NOS, Cyclothymic Disorder, Mood Disorders Related to Medical Conditions, Seasonal Affective Disorder. Mood Disorders NOS, as well as signs and symptoms of depressed mood, anhedonia, despair, anhedonia, hypomania, mania, and negative hedonic tone that are not classified as a Mood Disorder. Examples of Somatoform Disorders include, but are not limited to, Somatization Disorder, Somatoform Disorder, Conversion Disorder, Pain Disorder Associated with Psychological Factors, Pain Disorder Associated with Medical Conditions, Hypochondriasis, Body Dysmorphic Disorder, and Somatoform Disorder NOS. Examples of Factitious Disorders include, but are not limited to, Factitious Disorders with Psychological Signs and Symptoms, Factitious Disorders with Physical Signs and Symptoms Factitious Disorders with Combined Psychological and Physical Signs and Symptoms, and Factitious Disorder NOS. Examples of Sexual Dysfunction include, but are not limited to, Sexual Desire Disorders, Sexual Arousal Disorders, Orgasmic Disorders, Premature Ejaculation, Erectile Dysfunction, Sexual Pain Disorder, Sexual Dysfunction to a General Medical Condition, Substance-Induced Sexual Dysfunction, Sexual Dysfunction NOS, as well as signs and symptoms of sexual dissatisfaction and dysfunction that are not classified as a Sexual Dysfunction disorder. Examples of Eating Disorders include, but are not limited to, Bulimia Nervosa, Anorexia Nervosa, Binge Eating, Eating Disorder NOS, as well as signs and symptoms of eating and appetite problems that are not classified as an Eating Disorder. Examples of Gastrointestinal Disorders include, but are not limited to, Irritable Bowel Syndrome (IBS) with Predominately Diarrhea, IBS with Predominately Constipation, and IBS Mixed Type, Crohn's Disease, as well as GI distress including, but not limited to, nausea, vomiting, diarrhea, constipation, and bloating. Examples of Movement Disorders include, but are not limited to, Restless Leg Syndrome and Medication-Induced Movement Disorders. Examples of Sleep Disorder include, but are not limited to, Insomnia, Dyssomnias, Parasomnias as well as signs and symptoms of sleep problems that are not classified as a Sleep Disorder. Examples of Impulse-Control Disorder include, but are not limited to, Intermittent Explosive Disorder, Kleptomania, Pyromania, Pathological Gambling, Trichotillomania, Impulse Control Disorder NOS as well as signs and symptoms of impulsivity that are not classified as an Impulse-Control Disorder. Examples of Alcohol-Related Disorders include, but are not limited to, Alcohol Dependence, Alcohol Abuse, Alcohol Addiction, Alcohol-Induced Disorders, Alcohol-Related Disorder NOS as well as alcohol-related problems that are not classified as an Alcohol-Related Disorder. Examples of Opioid-Related Disorders include, but are not limited to, Opioid Dependence, Opioid Addiction, Opioid Abuse, Opioid-Induced Disorders, Opioid-Related Disorder NOS, as well as opioid-related problems that are not classified as an Opioid-Related Disorder. Examples of a Caffeine-Related Disorder include, but are not limited to, Caffeine Dependence, Caffeine Addiction, Caffeine Abuse, Caffeine-Induced Disorders, Caffeine-Related Disorders NOS as well as caffeine-related problems that are not classified as a Caffeine-Related Disorder. Examples of a Cannabis-Related Disorder include, but are not limited to, Cannabis Dependence, Cannabis Addiction, Cannabis Abuse, Cannabis-Induced Disorders, and Cannabis-Related Disorder NOS. Examples of an Amphetamine (or Amphetamine-Like)-Related Disorder include, but are not limited to, Amphetamine Dependence, Amphetamine Addiction, Amphetamine Abuse, Amphetamine-Induced Disorders, and Amphetamine-Related Disorder NOS. Examples of a Cocaine-Related Disorder include, but are not limited to, Cocaine Dependence, Cocaine Addiction, Cocaine Abuse, Cocaine-Induced Disorders, and Cocaine-Related Disorder NOS. Examples of a Nicotine-Related Disorder include, but are not limited to, Nicotine Dependence, Nicotine Addiction, Nicotine Abuse, Nicotine-Induced Disorders, and Nicotine-Related Disorder NOS. Examples of an Inhalant-Related Disorder include, but are not limited to, Inhalant Dependence, Inhalant Addiction, Inhalant Abuse, Inhalant-Induced Disorders, and Inhalant-Related Disorder NOS. Examples of a Phencyclidine-Related Disorder include, but are not limited to, Phencyclidine Dependence, Phencyclidine Addiction, Phencyclidine Abuse, Phencyclidine-Induced Disorders, and Phencyclidine-Related Disorder NOS. Examples of a Sedative-, Hypnotic-, or Anxiolytic-Related Disorder include, but are not limited to, Sedative-, Hypnotic-, or Anxiolytic Dependence, Addiction, and/or Abuse, Sedative-, Hypnotic-, or Anxiolytic-Induced Disorders, and Sedative-, Hypnotic-, or Anxiolytic-Related Disorder NOS. Examples of a Pervasive Developmental Disorder include, but are not limited to, Autism Disorder, Rhett's Disorder, Asperger's Disorder, or Pervasive Developmental Disorder NOS. Examples of an Attention-Deficit and Disruptive Behavior Disorder include, but are not limited to, Attention-Deficit/Hyperactivity Disorder, Conduct Disorder, Oppositional Disorder, Disruptive Behavior Disorder NOS as well as attentional and concentration problems that are not classified as an Attention-Deficit Disorder. Examples of a Behavioral addiction, compulsion, and/or dysfunction include, but are not limited to, sex, pornography, gambling, shopping, eating, drinking, smoking, computer use, and cleaning. Examples of a Pain disorder include, but are not limited to, distressing, nociceptive, neuropathic, migraine and psychogenic pain. An example of a Psychotic disorder is schizophrenia. Examples of a Respiratory disorder include, but are not limited to, asthma, COPD and neonatal apnea. An example of Nerve damage is HIV-induced and diabetic neuropathy.

In another embodiment of the invention, encompassed are compositions useful in the methods of the invention. An exemplary composition useful in safely and effectively treating DISTRESS DYSFUNCTION comprises: (a) at least one RECEPTOR SWITCHER; and (b) at least one compound selected from the group consisting of an ENDORPHIN ENHANCER, an EXOGENOUS OPIOID, a SYNERGISTIC ENHANCER, and any combination thereof.

In one embodiment of the invention, encompassed is a composition wherein the RECEPTOR SWITCHER: (a) when co-administered with CLASS II, III, and/or IV AGENTS, reduces and/or resolves one or more Distress Dysfunction symptoms; and (b) can be selected from the group consisting of agents that selectively block and/or inhibit opioid receptor excitatory signaling, ultra-low-dose, very-low-dose, and low-dose opioid antagonists, ultra-low-dose, very-low-dose, and low-dose naltrexone, naloxone, diprenorphine, nalmefene, and norbinaltorphimine, agents that inhibit synthesis or activity of GM1 ganglioside, neuraminidase inhibitors, agents that increase sulfates in the body, methylsulfonylmethane (MSM), magnesium sulfate, sodium sulfate, chondroitin sulfate, n-acetyl-cysteine (NAC), zanamivir, oseltamivir, laninamivir, peramivir, scutellaria, and 5,7,4'-trihydroxy-8-methoxyflavone.

In another embodiment of the invention, encompassed is a composition wherein the ENDORPHIN ENHANCER: (a) when co-administered with at least one RECEPTOR SWITCHER, reduces and/or resolves one or more Distress Dysfunction symptoms; and (b) can be selected from the group consisting of agents that enhance the release, production, and/or functioning of endogenous opioids (i.e., endorphins), cyclic adenosine monophosphate (cAMP) phosphodiesterase (PDE) inhibitors or agents that directly enhance cAMP, a cAMP phosphodiesterase (PDE) inhibitor, an agent that directly enhances cAMP, a specific or non-specific cAMP PDE inhibitor, a specific cAMP PDE-4 inhibitor, theophylline, aminophylline, roflumilast, ibudilast, cilomilast, ardenafil, tadalafil, sildenafil, zaprinast, rolipram, methylxanthine, milrinone, inaminone, cilostazol, caffeine, guarana, ginkgo biloba, forskolin, celecoxib, excitatory amino acids, a salt of an excitatory amino acid, all forms of excitatory amino acids, glutamic acid, aspartic acid, glutamine, monosodium glutamate (MSG), and N-methyl-D-asparate (NMDA), phenylalanine, dl-phenylalanine (DLPA), and nerve growth factor (NGF).

In yet another embodiment of the invention, encompassed is a composition wherein the EXOGENOUS OPIOID: (a) when co-administered with at least one RECEPTOR SWITCHER, reduces and/or resolves one or more DISTRESS DYSFUNCTION symptoms; and (b) can be selected from the group consisting of exogenous opioid agonist (full, partial, mixed) agents, tramadol, morphine, oxycodone, hydrocodone, papaverine, codeine, dihydrocodeine, fentanyl, hydromorphone, buprenorphine, butorphanol, methadone, alfentanil, loperamide, buprenorphine, menthol, codeine, levorphanol, meperidine, nalbuphine, oxymorphone, pentazocine, pentazocine, propoxyphene, remifentanil, and sufenta.

In yet another embodiment of the invention, encompassed is a composition wherein the SYNERGISTIC ENHANCER: (a) when co-administered with at least one RECEPTOR SWITCHER, reduces and/or resolves one or more DISTRESS DYSFUNCTION symptoms; and (b) is selected from the group consisting of agents that enhance the release, production and/or functioning of serotonin, dopamine, epinephrine, norepinephrine, and glutamate neurotransmitters, non-opioid analgesics, non-steroidal anti-inflammatory drugs (NSAIDs), acetaminophen, celecoxib, white willow bark, acetylsalicylic acid, salicin, ibuprofen, naproxen, ketoprofen, indomethacin, fenoprofen, tolmetin, sulindac, meclofenamate, piroxicam, flurbiprofen, diclofenac, stimulants, selective serotonin reuptake inhibitors (SSRI), serotonin agonists, antagonists and modulators, selective norepinephrine reuptake inhibitors (SNRIs), citalopram, dapoxetine, escitalopram, fluoxetine fluvoxamine, paroxetine, sertraline, fluvoxamine, venlaflafaxine, duloxetine, desvenlafaxine, zimelidine, dapoxetine, alosetron, ondansetron, granisetron, bemesetron, eplivanserine, deramciclane, agomelatine, elazasonan, pruvanserin, asenapine, zomari, valazodone, bifeprunox, buspirone, ritanseron, geperone, paliperidone, clomipram, doxepin, haloperidol, risperidone, methylphenidate, amino acids, a salt of an inhibitory amino acid, all forms of amino acids, gamma-aminobutrynic acid (GABA), all forms of GABA, PharmaGABA, glycine, taurine, tryptophan, 5HTP, phenylalanine, dl-phenylalanine (DLPA), s-adenosyl-methionine (SAMe), valine, threonine, methionine, lysine, leucine, isoleucine, tyrosine, alanine, arginine, histidine, serine, selenocfysteine, proline, glycine, cysteine, aspargine, alanine, acetyl-L-carinitine, DMSO, cannabis, all forms and dervatives of cannabis, L-DOPA, vitamins and minerals, luteolin, quercetin, qercetin-3-O-methylether (3-MQ, 2), quercetin-3,7,4'-O-trimethylether, ayanin, quercetin-3,7,3', 4'-O-tetramethylether, quercetin-3,5,7,3',4'-O-petamethylether, quercetin-3,5,7,3',4'-O-pentaacetate, quercetin-3-O-methyl-5,7,3',4'-O-tetraacetate, methylcobalamin, vitamin C, vitamin D, vitamin D-3, vitamins B1, B2, B3, B6, and B12, folic acid, niacin, or niacinamide, folinic acid, calcium folinate, methylcobalamin, pyridoxal-5'-phosphate (P5P), alkaloids, flavonoids, and saponins, hesperetin, hesperidin, naringin, naringenin, epigallocatechin-3-gallate (EGCG), dioclein, genistein, daidzein, eriodictyol, prunetin, biochanin A, apigenin, myricetin, liquiritigenin, liquiriti, kaempferol, isoliquiritigenin, chrysin, rutin, cyanidin, delphinidin, pelargonidin, isorhamnetin, vitamin C, St. John's Wort, passion flower, hyperforin, hypericin, biotin, vitamin B5 (pantothenic acid), magnesium, alpha-ketoglutarate, copper, zinc, L-theanine, iron, california poppy, ginseng (*Panax* spp.), licorice, night-blooming cereus (*Selenicereus grandiflorus; Cactus grandiflorus*), hordenine, nutmeg, myristicin, tyramine, scotch broom, green tea, ephedra, yohimbe, myhhr, boswellia, frankinsence, peppermint oil, and menthol.

In one embodiment of the invention, encompassed is a composition wherein the RECEPTOR SWITCHER: (a) is an ultra-low-dose, very-low-dose, or low-dose opioid antagonist; and/or (b) is ultra-low-dose, very-low-dose, or low-dose naltrexone; and/or (c) is ultra-low-dose, very-low-dose, or low-dose naloxone. In such a composition, (a) the naltrexone can be administered in an ultra low dose range of about 125 micrograms or less; (b) the naltrexone can be administered in a very low dose range of about 125 to about 500 micrograms; (c) the naltrexone can be administered in the low dose range of about 500 to about 1000 micrograms; (d) the dosing of naloxone can be an ultra low dosing of about $0.25 \text{ mg} \cdot \text{kg}^{-1} \cdot \text{h}^{-1}$; (e) the dosing of naloxone can be about 400 micrograms naloxone in 1000 ml crystalloid given in 24 h to a patient weighing 70 kg; (f) the dosing of naloxone can be a very-low-dosing of about $1.0 \text{ mg} \cdot \text{kg}^{-1} \cdot \text{h}^{-1}$; and/or (g) the dosing range of naloxone can be $0.01 \text{ μg} \cdot \text{kg}^{-1} \cdot \text{h}^{-1}$ to $5 \text{ mg} \cdot \text{kg}^{-1} \cdot \text{h}^{-1}$.

In another embodiment of the invention, encompassed is a composition wherein the RECEPTOR SWITCHER is selected from the group consisting of a neuramindase inhibitor, n-acetyl-cysteine (NAC), *scutellaria,* 5,7,4'-trihydroxy- 8-methoxyflavone, magnesium sulfate, sodium sulfate, and methylsulfonylmethane (MSM).

In another embodiment of the invention, encompassed is a composition wherein the ENDORPHIN ENHANCER is selected from the group consisting of a cAMP PDE inhibitor, roflumilast, theophylline, aminophylline, ginkgo biloba, guarana, caffeine, ibudilast, an excitatory amino acid, glutamic acid, mono-sodium-glutamate, DL-Phenylalanine (DLPA), celecoxib, and nerve growth factor (NGF).

In another embodiment of the invention, encompassed is a composition wherein the EXOGENOUS OPIOID is selected from the group consisting of tramadol, oxycodone, oxycodone, hydrocodone, morphine loperamide, buprenorphine, menthol, and codeine.

In another embodiment of the invention, encompassed is a composition wherein the SYNERGISTIC ENHANCER can be: (a) a selective serotonin reuptake inhibitor (SSRI) or a selective norepinephrine reuptake inhibitor (SNRI); (b) a non-opioid analgesic; (c) a non-steroidal anti-inflammatory agent (NSAID); (d) acetaminophen; (e) aspirin; (f) white willow bark; (1) ibuprofen; (g) celecoxib; (h) methylphenidate; (i) an amino acid in any form or derivative, including a salt; (j) 5HTP; (k) tryptophan; (1) 5-adenosylmethionine (SAMe); (m) GABA; (n) tyrosine; (o) taurine; (p) acetyl-L-carnitine (ALC); (q) arginine; (r) menthol; (s) cannabis; (t) myhrr; or (u) boswellia, all in any form or derivative. For example, the SSRI or SNRI can be selected from the group consisting of citalopram, escitalopram oxalate, fluoxetine, venlaflafaxine, or duloxetine.

In one embodiment of the invention, encompassed is a composition wherein: (a) the RECEPTOR SWITCHER is naloxone, the SYNERGISTIC ENHANCER is ibuprofen, and the co-administration further includes administering arginine; (b) the RECEPTOR SWITCHER is naloxone, the SYNERGISTIC ENHANCER is ibuprofen, the EXOGENOUS OPIOID is morphine, and the co-administration further includes administering arginine.

In another embodiment of the invention, encompassed is a composition wherein the ENDORPHIN ENHANCER is a PDE inhibitor selected from the group consisting of roflumilast, ibudilast, rolipram, ginkgo biloba, guarana, caffeine, aminophylline, and theophylline. For example, (a) the ENDORPHIN ENHANCER can be a specific cAMP PDE-4 inhibitor, and the RECEPTOR SWITCHER can be ultra-low-dose or very-low-dose naltrexone or naloxone; (b) the ENDORPHIN ENHANCER can be rofllumilast, ibudilast, theophylline, aminophylline, caffeine, or ginkgo biloba, and the RECEPTOR SWITCHER can be ultra-low-dose or very-low-dose naltrexone or naloxone; (c) the ENDORPHIN ENHANCER can be a specific cAMP PDE-4 inhibitor, and the RECEPTOR SWITCHER is n-acetyl-cysteine; (d) the ENDORPHIN ENHANCER can be rofllumilast, ibudilast, aminophylline, caffeine, guarana, or theophylline, and the RECEPTOR SWITCHER can be n-acetyl-cysteine; and/or (e) the ENDORPHIN ENHANCER can be ginkgo biloba, and the RECEPTOR SWITCHER can be n-acetyl-cysteine. (f) the ENDORPHIN ENHANCER can be a specific cAMP PDE-4 inhibitor, and the RECEPTOR SWITCHER is magnesium sulfate; (g) the ENDORPHIN ENHANCER can be rofilumilast, ibudilast, aminophylline, caffeine, guarana, or theophylline, and the RECEPTOR SWITCHER can be magnesium sulfate; and/or (h) the ENDORPHIN ENHANCER can be ginkgo biloba, and the RECEPTOR SWITCHER can be magnesium sulfate.

In one embodiment of the invention, encompassed is a composition wherein the ENDORPHIN ENHANCER is nerve growth factor (NGF), and the RECEPTOR SWITCHER is selected from the group consisting of ultra-low-dose, very-low-dose, and low-dose opioid antagonists, neuromimidase inhibitors, n-acetyl-cysteine, methylsulfonylmethane, magnesium sulfate, and any combination thereof.

In another embodiment of the invention, encompassed is a composition useful in a safe and effective treatment for nociceptive pain, wherein the composition comprises: (a) at least one Receptor Switcher; and (b) at least one compound selected from the group consisting of an Endorphin Enhancer, an Exogenous Opioid, a Synergistic Enhancer, and any combination thereof.

In another embodiment of the invention, encompassed is a composition useful in a safe and effective method to produce pain relief and/or analgesia in a subject experiencing nociceptive pain, wherein the composition comprises: (a) (i) at least one Receptor Switcher, (ii) at least one Endorphin Enhancer, and (iii) at least one Exogenous Opioid, at least one Synergistic Enhancer, or any combination thereof; or (b) at least one Receptor Switcher in combination with at least one Synergistic Enhancer.

In another embodiment of the invention, encompassed is a composition useful in a safe and effective method to produce pain relief and/or analgesia in a subject experiencing nociceptive pain, wherein the composition comprises: (a) a compound selected from the group consisting of methylsulfonylmethane (MSM), n-acetyl-cysteine (NAC), scutellaria, and 5,7,4'-trihydroxy-8-methoxyflavone, and any combination thereof; and (b) at least one Endorphin Enhancer and/or Exogenous Opioid and/or Synergistic Enhancer, or any combination, thereof.

In another embodiment of the invention, encompassed is a composition useful in a safe and effective method to produce pain relief and/or analgesia in a subject experiencing nociceptive pain comprises: (a) at least one Receptor Switchers, in combination with (b) at least one agent selected from the group consisting of guarana, ginkgo biloba, phenylalanine, dl-phenylalanine (DLPA), celecoxib, and nerve growth factor (NGF).

The compositions of the invention can be formulated into any pharmaceutically acceptable dosage forms. For example, the compositions of the invention can be formulated into a dosage form selected from the group consisting of rapid release, immediate-release, slow-release, sublingual, intravenous, controlled release, delayed-release, a combination of immediate and controlled release, nano-encapsulation formulations, and a tamper-resistant or abuse-resistant delivery system.

The foregoing general description and following brief description of the drawings and the detailed description are exemplary and explanatory and are intended to provide further explanation of the invention as claimed. Other objects, advantages, and novel features will be readily apparent to those skilled in the art from the following detailed description of the invention.

DETAILED DESCRIPTION OF INVENTION

Figure 1:
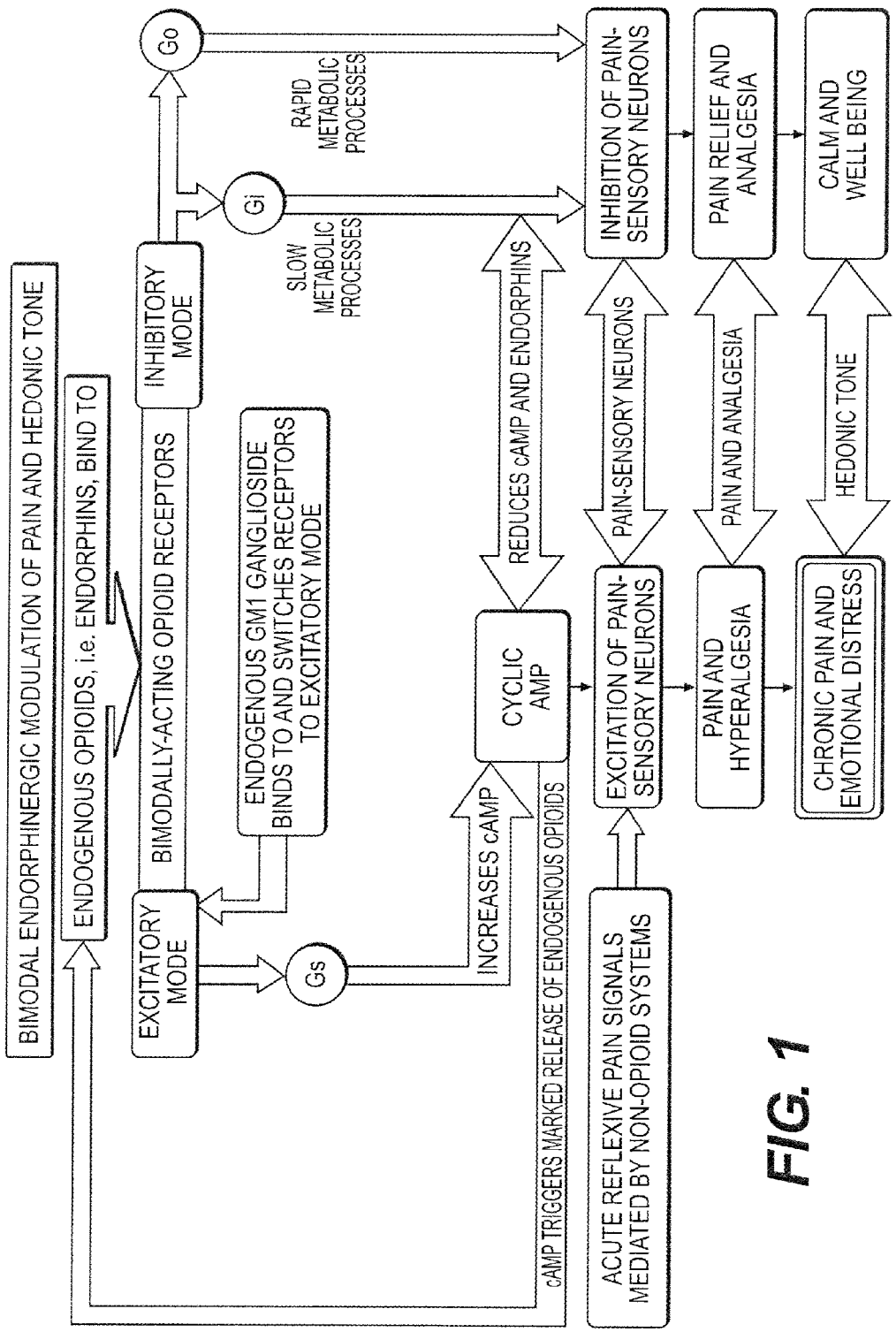
FIG. 1: Shows the basic biochemical processes of Bimodal Endorphinergic Modulation of Pain and Hedonic Tone.
Figure 2:
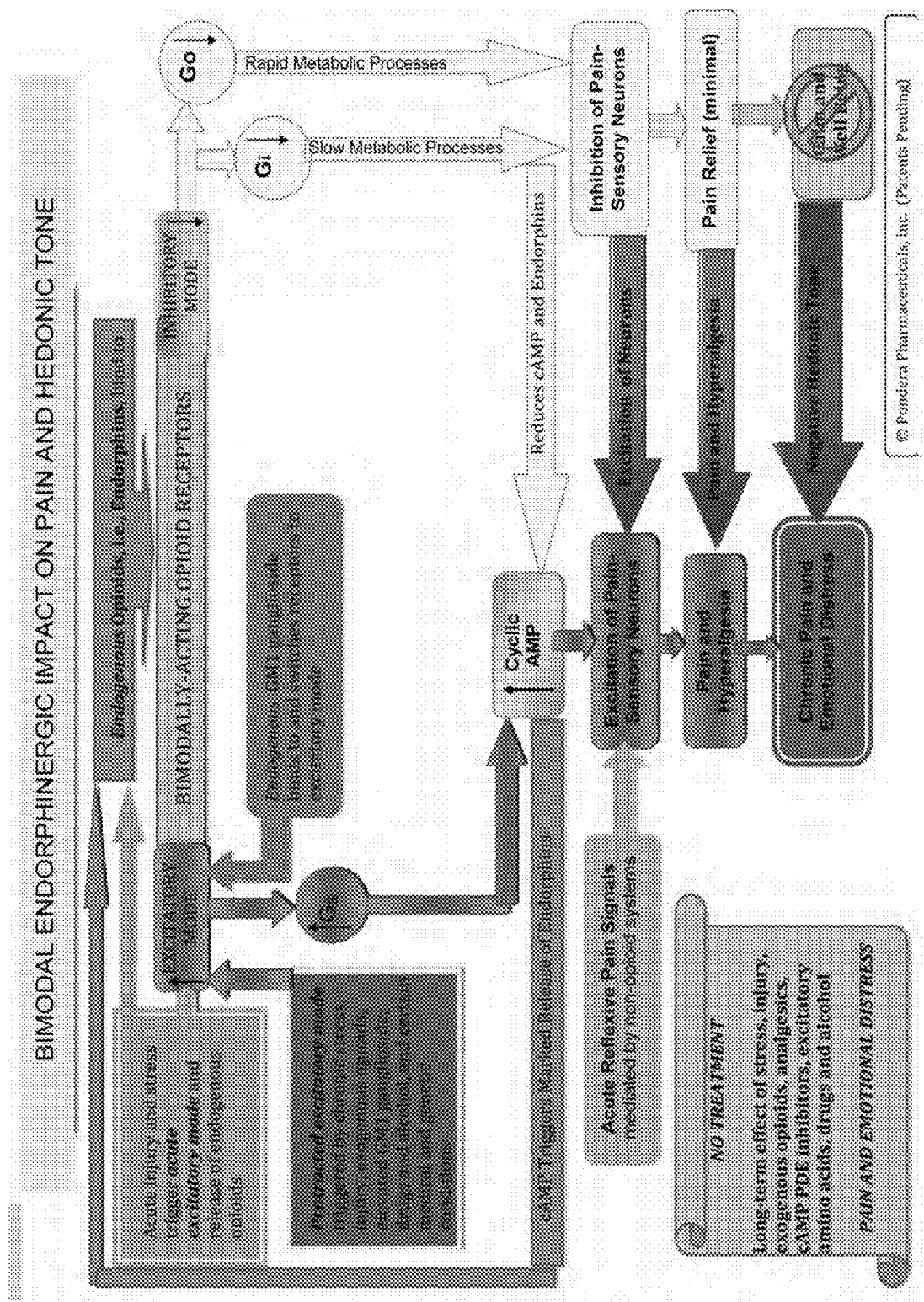
FIG. 2: Shows the transmission of normal pain and distress signals defined as Bimodal Endorphinergic Impact on Pain and Hedonic Tone (transmission of normal pain and distress signals)
Figure 3:
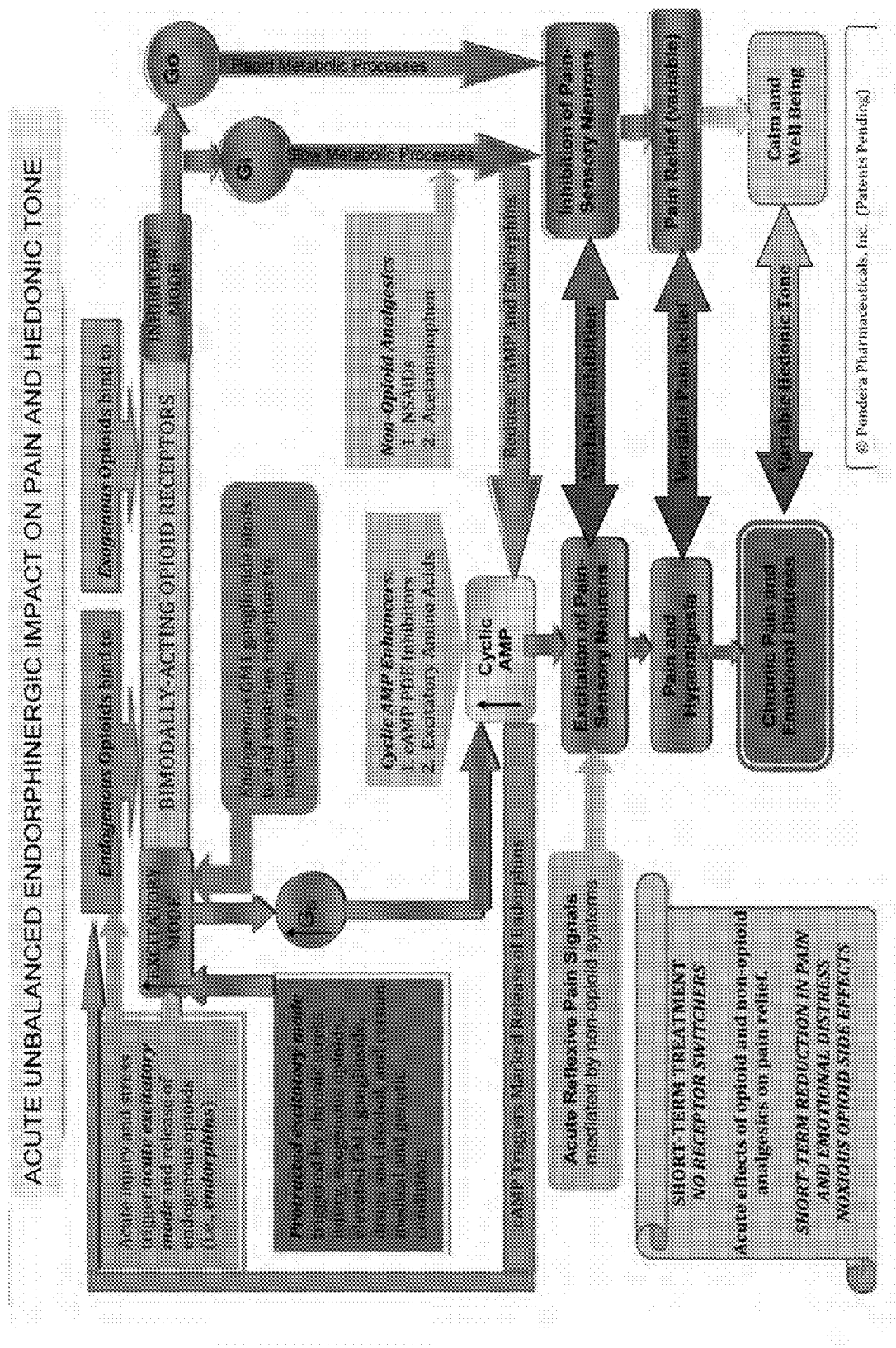
FIG. 3: Shows the acute impact of conventional drugs defined as Acute Unbalanced Endorphinergic Impact on Pain and Hedonic Tone.
Figure 4:
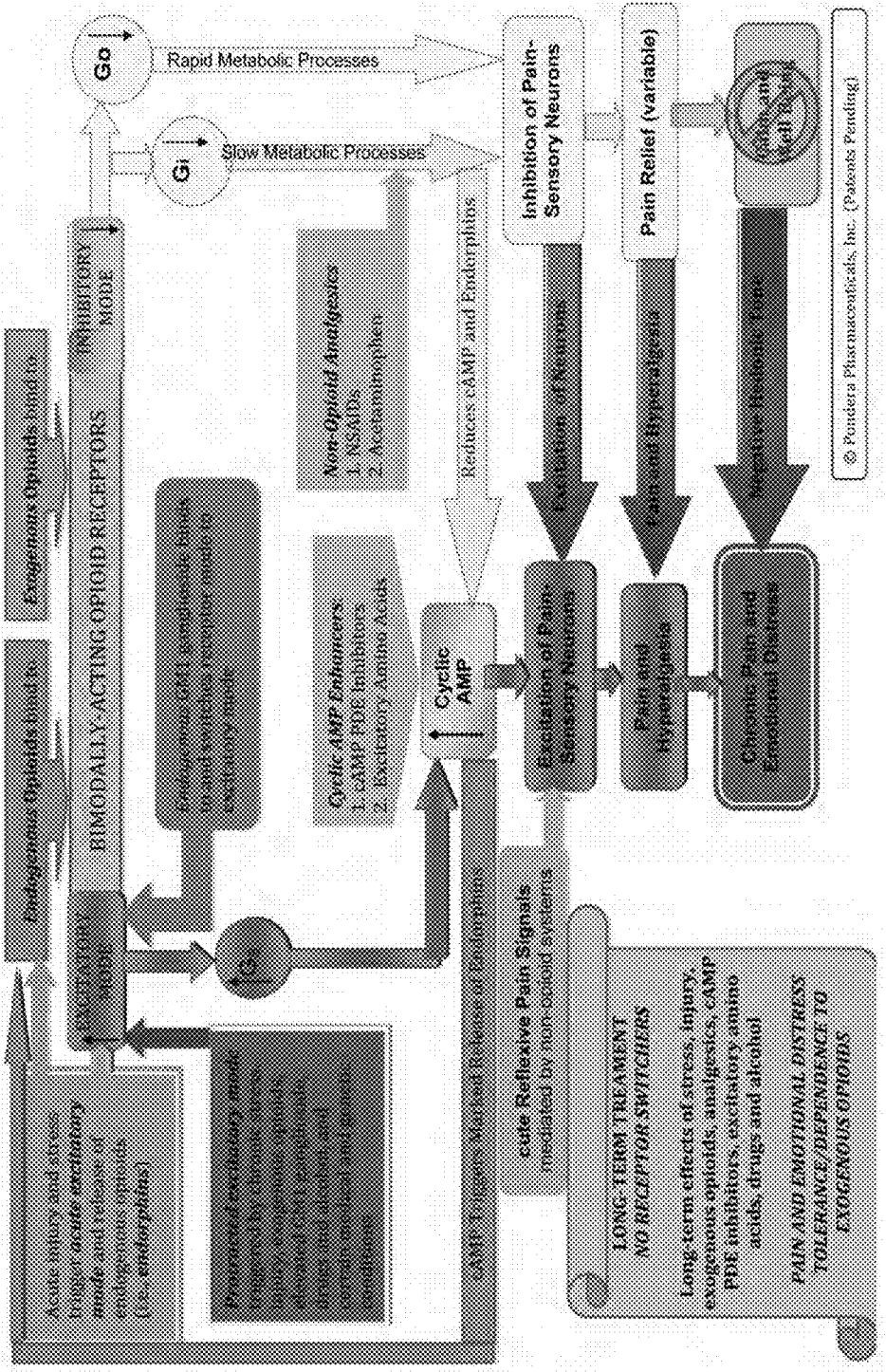
FIG. 4: Shows the long-term impact of conventional drugs defined as Chronic Unbalanced Endorphinergic Impact on Pain and Hedonic Tone.
Figure 5:
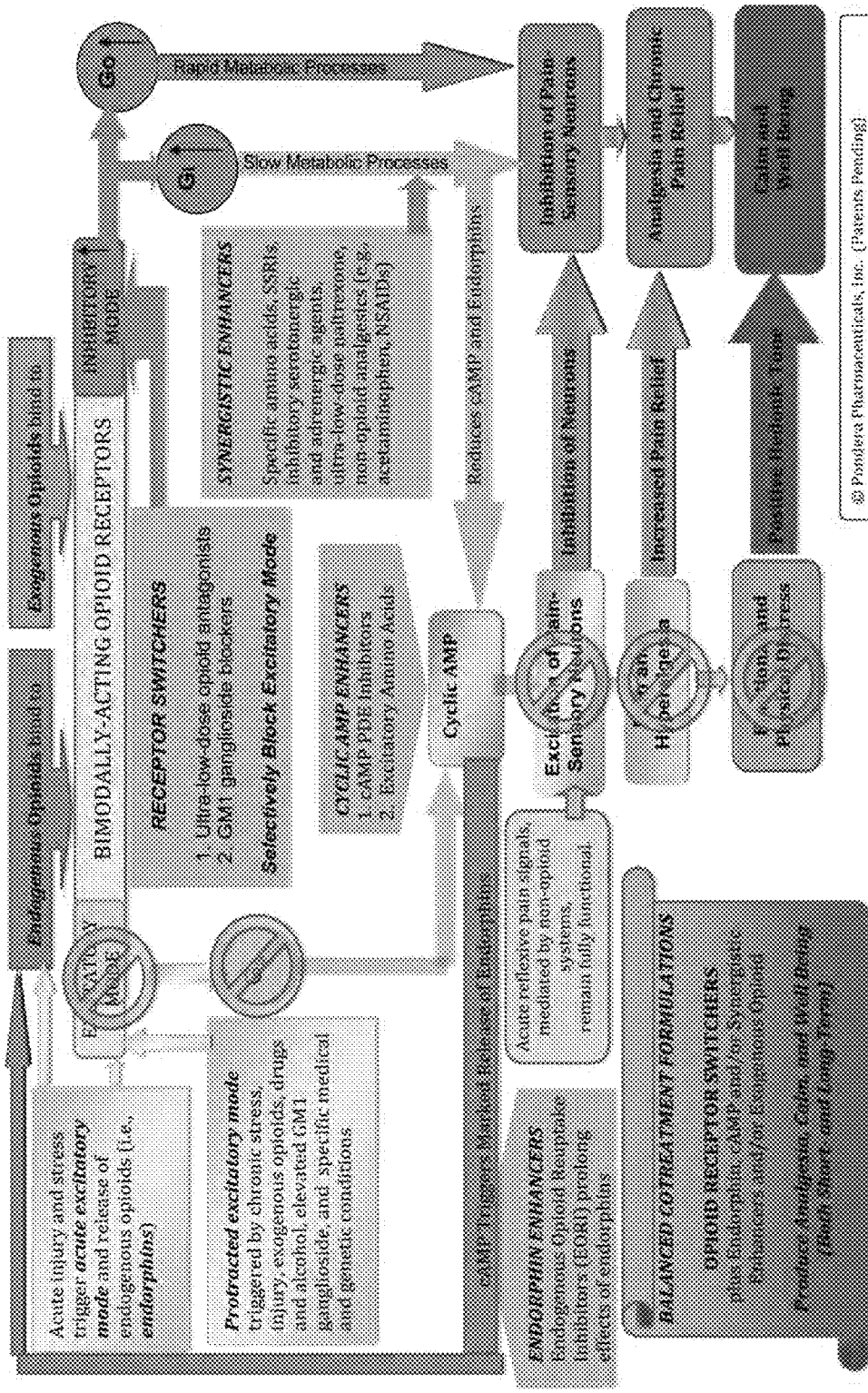
FIG. 5: Shows acute and long-term impact of novel balanced cotreatment formulations defined as Balanced Endorphinergic Impact on Pain and Hedonic Tone.

This invention provides innovative methods that have a profound impact on reducing a wide variety of emotional and physical distress dysfunction syndromes. By using principles that combine agents in a novel way that restore homeostatic balance to the underlying stress-related neurotransmitter systems, for the first time, this paradigm teaches a method of developing formulations that simultaneously reduce and resolve a wide variety of emotional and physical distress dysfunction syndromes. In contrast, the prior art teaches symptom-based medical treatments that often iatrogenically exacerbate dysfunctional distress symptoms (side effects).

This invention describes the discovery of methods and compositions that reduce protracted emotional and physical distress by restoring and maintaining homeostatic balance in the endogenous opioid system as well as homeostatically related neurotransmitter systems. The fundamental key to this invention is the surprising and remarkably effective synergistic effect that has been discovered when one or more agents that switch opioid receptors from a protracted excitatory mode to a basal inhibitory mode (Receptor Switchers), are combined with one or more agents from three other classes that impact on opioidergic, serotoninergic, dopaminergic, glutamergic, epinephrinergic, and norepinephrinergic neurotransmitter systems: (1) Endorphin Enhancers; (2) Exogenous Opioids; and (3) Synergistic Enhancers.

Receptor Switchers, including ultra-low-dose, very-low-dose, and low-dose opioid antagonists, such as ultra-low-dose naltrexone (ULDN), very-low-dose naltrexone (VLDN), or low-dose naltrexone (LDN), and ultra-low-dose, very-low-dose, or low-dose naloxone, GM1 ganglioside attenuators, such as neuraminidase inhibitors (e.g., magnesium sulfate, sodium sulfate, and n-acetyl-cysteine (NAC)), and agents that increase sulfates in the body (e.g., methylsulfonylmethane (MSM)) selectively block the opioid receptor excitatory mode. Therefore, protracted excitatory signaling is eliminated, and inhibitory receptor signaling is enhanced. As a result, when endogenous opioids (i.e., endorphins) bind with the opioid receptor, the result is increased inhibitory signaling, producing analgesia and a sense of calm and well being. These agents have the potential to reverse both acute and protracted excitatory mode imbalances, helping to restore normal homeostatic functioning. However, since protracted excitatory conditions lead to chronically diminished endogenous opioids, Receptor Switchers alone are typically insufficient to reduce Distress Dysfunction symptoms and to produce analgesia or to restore a sense of well being. Therefore, this invention describes the critical importance of combining Receptor Switchers (e.g., NAC, MSM, ULDN) with Endorphin Enhancers (e.g., guarana, ginkgo biloba, caffeine) and/or Synergistic Enhancers (e.g., white willow bark, SAMe, 5HTP) and/or Exogenous Opioids (e.g., morphine, oxycodone, tramadol), for the treatment of Distress Dysfunction, nociceptive pain, HIV-induced and diabetic neuropathy, and certain respiratory and gastrointestinal disorders.

I. BACKGROUND REGARDING DISTRESS DYSFUNCTION

A. Description of Distress Dysfunction

This invention details the discovery of a discrete condition that had previously been diagnosed and treated as a wide variety of unrelated disorders and syndromes. Distress Dysfunction underlies many of the symptoms and functional impairments that are now identified as components of emotional and physical distress. Not only does this invention provide an explanation of the neurophysiological imbalances that underlie many symptoms of emotional and physical distress, but it offers a clear set of principles that identify specific classes of agents that, when combined together in formulations guided by these principles, provide a remarkably safe and effective treatment for individuals suffering from Distress Dysfunction as well as a method for maintaining healthy neurotransmitter functioning to prevent the development of dysfunctional distress.

Distress Dysfunction can be identified by the experience of one or more of a wide variety of forms of emotional and physical distress, including, but not limited to hyperalgesia, distressing pain, anxiety and panic, exaggerated worries and fears, hypervigilance, physical and emotional hypersensitivity, impulsivity, irritability and anger, obsessions and compulsions, agitation, distractibility, concentration and attention impairments, despair and depression, anhedonia, sleeping difficulties, sexual problems, interpersonal conflicts, a sense of danger and that "something is wrong", as well as desperate cravings for anything that can reduce this protracted distress. These cravings are often for substances, such as drugs, alcohol, and food, as well as stress-reducing behaviors and situations, such as sexual activity, gambling, and other compulsions. In contrast to nociceptive pain, which is a direct adaptive reaction to real injury, distressing pain is an exaggerated dysfunctional reaction to perceived and anticipated danger, which typically includes hyperalgesia and hypersensitivity to perceived or real injury as well as neuropathic and psychogenic pain.

This invention teaches that these symptoms of emotional and physical distress, at least in part, are signs of an underlying dysfunctional imbalance in stress-related neurotransmitter systems that reflect a protracted state of alert and diminished capacity to respond effectively. Traditional medical, psychiatric, and psychological diagnoses are often made based on symptoms that reflect this underlying neurophysiological imbalance. For the first time, this invention teaches methods that can be used to restore healthy balances in the underlying neurotransmitter systems that are responsible for the symptoms of emotional and physical distress. Therefore, these novel formulations and methods can be used to safely and effectively treat symptoms and conditions presented by individuals diagnosed with a variety of disorders that, we postulate, are, in fact, manifestations of Distress Dysfunction.

To functionally assess Distress Dysfunction, the inventors suggest that the following constellation of conditions, symptoms, and disorders be considered, whether (a) the result of an endogenous condition or (b) the result or side effect of an exogenous medication, drug, or other agent, wherein a component thereof is the presence of one or more of the following: (i) signs or symptoms of emotional and/or physical distress (and/or a diminution of happiness, pleasure, contentment and a positive sense of well being), which interferes with an individual's quality of life and functioning, or (ii) unpleasant or deleterious side effects of a medication, drug, or other agent, which may, or may not, interfere with its potential therapeutic benefits.

Distress Dysfunction includes, but is not limited to, the following conditions, symptoms and/or disorders: (1) Anxiety Disorders, including, but not limited to, Panic Disorders, Agoraphobia, Specific Phobias, Social Phobias, Obsessive-Compulsive Disorder, Post-Traumatic Stress Disorder, Acute Stress Disorder, Generalized Anxiety Disorder, Substance-Induced Anxiety, Anxiety Related to Medical Disorders, Anxiety Disorder Not Otherwise Specified (NOS), as well as signs and symptoms of anxiety, stress, agitation, and worry that are not classified as an Anxiety Disorder; (2) Mood Disorders, including, but not limited to, Depressive Disorders, Dysthymic Disorder, Bipolar I Disorder, Bipolar II Disorder, Bipolar Disorder NOS, Cyclothymic Disorder, Mood Disorders Related to Medical Conditions, Seasonal Affective Disorder, Mood Disorders NOS, as well as signs and symptoms of depressed mood, anhedonia, despair, anhedonia, hypomania, mania, and negative hedonic tone that are not classified as a Mood Disorder; (3) Somatoform Disorders, including, but not limited to, Somatization Disorder, Somatoform Disorder, Conversion Disorder, Pain Disorder Associated with Psychological Factors, Pain Disorder Associated with Medical Conditions, Hypochondriasis, Body Dysmorphic Disorder, and Somatoform Disorder NOS; (4) Factitious Disorders, including but not limited to, Factitious Disorders with Psychological Signs and Symptoms, Factitious Disorders with Physical Signs and Symptoms Factitious Disorders with Combined Psychological and Physical Signs and Symptoms, and Factitious Disorder NOS; (5) Dissociative Disorders; (6) Sexual Dysfunction, including, but not limited to, Sexual Desire Disorders, Sexual Arousal Disorders, Orgasmic Disorders, Premature Ejaculation, Erectile Dysfunction, Sexual Pain Disorder, Sexual Dysfunction to a General Medical Condition, Substance-Induced Sexual Dysfunction, Sexual Dysfunction NOS, as well as signs and symptoms of sexual dissatisfaction and dysfunction that are not classified as a Sexual Dysfunction disorder; (7) Eating Disorders, including, but not limited to, Bulimia Nervosa, Anorexia Nervosa, Binge Eating, Eating Disorder NOS, as well as signs and symptoms of eating and appetite problems that are not classified as an Eating Disorder; (8) Gastrointestinal Disorders, including, but not limited to, Irritable Bowel Syndrome (IBS) with Predominately Diarrhea, IBS with Predominately Constipation, and IBS Mixed Type, Crohn's Disease, as well as GI distress including, but not limited to, nausea, vomiting, diarrhea, constipation, and bloating; (9) Pre-Menstrual Syndrome (PMS) and other hormonally-related distress signs and symptoms; (9) Movement Disorders, including, but not limited to, Restless Leg Syndrome; (10) Fibromyalgia; (11) Sleep Disorders, including, but not limited to, Insomnia, Dyssomnias Parasomnias as well as signs and symptoms of sleep problems that are not classified as a Sleep Disorder; (12) Impulse-Control Disorders, including, but not limited to, Intermittent Explosive Disorder, Kleptomania, Pyromania, Pathological Gambling, Trichotillomania, Impulse Control Disorder NOS as well as signs and symptoms of impulsivity that are not classified as an Impulse-Control Disorder; (13) Psychological Factors Affecting Medical Conditions; (14) Medication-Induced Movement Disorders; (15) Alcohol-Related Disorders, including, but not limited to, Alcohol Dependence, Alcohol Abuse, Alcohol Addiction, Alcohol-Induced Disorders, Alcohol-Related Disorder NOS as well as alcohol-related problems that are not classified as an Alcohol-Related Disorder; (16) Opioid-Related Disorders, including, but not limited to, Opioid Dependence, Opioid Addiction, Opioid Abuse, Opioid-Induced Disorders, Opioid-Related Disorder NOS, as well as opioid-related problems that are not classified as an Opioid-Related Disorder; (17) Caffeine-Related Disorders, including, but not limited to, Caffeine Dependence, Caffeine Addiction, Caffeine Abuse, Caffeine-Induced Disorders, Caffeine-Related Disorders NOS as well as caffeine-related problems that are not classified as a Caffeine-Related Disorder; (18) Cannabis-Related Disorders, including, but not limited to, Cannabis Dependence, Cannabis Addiction, Cannabis Abuse, Cannabis-Induced Disorders, and Cannabis-Related Disorder NOS; (19) Amphetamine (or Amphetamine-Like)-Related Disorders, including but not limited to, Amphetamine Dependence, Amphetamine Addiction, Amphetamine Abuse, Amphetamine-Induced Disorders, and Amphetamine-Related Disorder NOS; (20) Cocaine-Related Disorders, including, but not limited to, Cocaine Dependence, Cocaine Addiction, Cocaine Abuse, Cocaine-Induced Disorders, and Cocaine-Related Disorder NOS; (21) Nicotine-Related Disorders, including, but not limited to, Nicotine Dependence, Nicotine Addiction, Nicotine Abuse, Nicotine-Induced Disorders, and Nicotine-Related Disorder NOS; (22) Inhalant-Related Disorders, including, but not limited to, Inhalant Dependence, Inhalant Addiction, Inhalant Abuse, Inhalant-Induced Disorders, and Inhalant-Related Disorder NOS; (23) Phencyclidine-Related Disorders, including, but not limited to, Phencyclidine Dependence, Phencyclidine Addiction, Phencyclidine Abuse, Phencyclidine-Induced Disorders, and Phencyclidine-Related Disorder NOS; (24) Sedative-, Hypnotic-, or Anxiolytic-Related Disorders, including, but not limited to, Sedative-, Hypnotic-, or Anxiolytic Dependence, Addiction, and/or Abuse, Sedative-, Hypnotic-, or Anxiolytic-Induced Disorders, and Sedative-, Hypnotic-, or Anxiolytic-Related Disorder NOS; (25) Polysubstance-Related Disorders; (26) Pervasive Developmental Disorders, including, but not limited to, Autism Disorder, Rhett's Disorder, Asperger's Disorder, or Pervasive Developmental Disorder NOS; (27) Attention-Deficit and Disruptive Behavior Disorders, including, but not limited to Attention-Deficit/Hyperactivity Disorder, Conduct Disorder, Oppositional Disorder, Disruptive Behavior Disorder NOS as well as attentional and concentration problems that are not classified as an Attention-Deficit Disorder; (28) Chronic Fatigue Disorder, (29) Psychotic Disorders, (30) Behavioral addictions, compulsions, and dysfunctions, including, but not limited to, sex, pornography, gambling, shopping, eating, drinking, smoking, computer use, and cleaning, (31) Pain disorders, including, but not limited to, distressing, neuropathic, migraine psychogenic, and nociceptive pain, (32) Psychotic disorders, including, but not limited to, schizophrenia; (33) Unpleasant or deleterious side effects of CLASS II, III, or IV agents when such agents are administered alone (i.e., without co-administration with an CLASS I agent) which may, or may not, interfere with the potential therapeutic benefits of CLASS II, III, or IV agents, including, but not limited to PDE inhibitors, cAMP enhancers, opioid and non-opioid analgesics, stimulants, SSRIs, SNRIs, amino acids, and nerve growth factor; (34) Respiratory disorders including, but not limited to asthma, COPD, and neonatal apnea; (35) Nerve damage and neuropathy, including, but not limited to, HIV-induced and diabetic neuropathy; (36) Inflammatory disorders; (37) Allergic and non-allergic glutamate and mono-sodium glutamate related disorders, including "Chinese Food Syndrome", and (38) Emotional and physical malaise, distress, discomfort, pain, restlessness, irritability, worries, cravings, compulsions, obsessions, agitation, addictions, and other related complaints and signs of protracted negative hedonic tone that may, or may not, be part of a traditional medical or psychiatric disorder. Distress Dysfunction is not limited to these conditions and diagnoses and is best defined by a variety of symptoms, conditions, syndromes, and disorders, characterized by dysfunctional emotional and physical distress and pain.

This invention teaches that a fundamental neurophysiological impairment underlies the development of many of the signs and symptoms of Distress Dysfunction. There is evidence that imbalances in the endogenous opioid system as well in serotonin, dopamine, norepinephrine, epinephrine, and glutamate neurotransmitter systems play a significant role in producing a wide variety of symptoms of emotional and physical distress. Specifically, it is hypothesized that various conditions, including chronic stress, injury, drugs and alcohol, congenital factors, and maladaptive life styles, can lead to a chronic state of alert in these stress-related neurotransmitter systems, manifested by protracted opioid receptor excitatory signaling and diminished availability and functioning of endogenous opioids. Given the homeostatic processes throughout the stress-related neurotransmitter systems, including serotonin, dopamine, norepinephrine, epinephrine, and glutamate neurotransmitter systems, the result is a negative hedonic tone characterized by signs and symptoms of emotional and physical distress, described as Distress Dysfunction.

Therefore, until the teachings of this invention, all prior art and practice have resulted in limited treatment for protracted distress and many strategies that clearly exacerbate imbalances in the stress response system, resulting in even more serious protracted distress. No prior teaching or art has developed an approach that is specifically focused on simultaneously resolving both receptor and neurotransmitter imbalances in the stress-related systems that underlie protracted distress syndromes, thereby restoring healthy homeostatic functioning of the body's stress response system.

B. Bimodal Opioid Modulation of Pain and Hedonic Tone

The figures of the invention describe what is believed to be the highly complex, subtle and interrelated biochemical, biological and physiological mechanisms underlying the surprising, remarkable, novel and synergistic benefits of the co-treatment formulations set forth in this patent application. While further research may either clarify or modify these diagrams and explanations, the surprising, remarkable, novel and synergistic methods and combinations set forth in the patent application accurately describe the efficacy and utility of these methods and combinations to restore healthy functioning in humans and treat the conditions and disorders in humans as identified and described in this patent application.

Healthy Homeostatic Balance:

Normal homeostasis maintains an adaptive balance between the Excitatory and Inhibitory Modes in the Bimodally-Acting Opioid Receptors. In the absence of injury or stress, Opioid Receptors are generally in the Inhibitory Mode. Normal levels of Endogenous Opioids, (i.e., endorphins), are homeostatically maintained, producing a generally positive Hedonic Tone, including a sense of calm and well being.

Normal Acute Pain:

Acute injury or stress triggers Acute Reflexive Pain and Distress Signals mediated by non-opioid systems, leading to the adaptive reflexive experience of immediate pain and distress. Simultaneously, acute injury or stress set Opioid Receptors in the Excitatory Mode and Endogenous Opioids (i.e., endorphins) are released. The Endogenous Opioids bind with the Opioid Receptors, triggering excitatory signaling. Through $G_s$, excitatory signals enhance the release of cAMP, which by increasing Protein Kinase A (which increases $Ca^2$ conductance and decreases $K^+$ conductance), excites Pain-Sensory Neurons, which trigger the sensation of pain, increased sensitivity toward pain (hyperalgesia) as well as the experience of distress. The increased cAMP also enhances the release of Endogenous Opioids, maintaining the pain and distress cycle, leading to an extended adaptive response to the noxious stimuli. However, as soon as the acute danger is reduced, in part as a result of an adaptive response to pain and distress, the Opioid Receptors are switched to Inhibitory Mode. The Endogenous Opioids then trigger inhibitory signaling and, through $G_o$, (which decreases $Ca^{2+}$ conductance and increases $K^+$ conductance), inhibit Pain-Sensory Neurons, which triggers reduced sensation of pain and produces analgesia. At the same time, the Opioid Receptor inhibitory signaling, through $G_i$, inhibits cAMP, which in turn reduces Endogenous Opioids, which tunes down the entire endogenous opioid pain response system, restoring normal homeostatic balance and positive Hedonic Tone.

Protracted Excitatory Mode:

Chronic stress, injury, exogenous opioids, drugs, alcohol, and various medical and genetic factors can set Opioid Receptors in a protracted excitatory mode. In this condition, Endogenous Opioids trigger mostly excitatory signaling, which results in chronic pain and hyperalgesia. Any factor that triggers the release of Endogenous Opioids, including injury or stress and even reward states and various drugs, can potentiate pain. This protracted condition triggers homeostatic processes in related serotonin, dopamine, and other neurotransmitter systems, which produces a variety of signs and symptoms of emotional and physical distress. This negative Hedonic Tone state may be reflected by the experience of anxiety, irritability, depression, cravings, addictive tendencies and physical distress, including pain and gastrointestinal symptoms. Protracted opioid (and other stress-related) receptor excitatory mode conditions as well as depleted neurotransmitter levels are a major component of a wide variety of Distress Dysfunction disorders, syndromes, and symptoms. Unfortunately, typical coping patterns, including the use of drugs and alcohol, perpetuate and exacerbate protracted excitatory signaling and its negative impact on Hedonic Tone, resulting in various symptoms of Distress Dysfunction.

C. Proposed Mechanism/Rational

A basic understanding of the bimodal nature of endogenous opioid modulation of pain, distress, and hedonic tone can elucidate the potential neurophysiological mechanisms underlying the surprising and synergistic methods and compositions taught by this invention. The following description, along with the accompanying figures, depict the complex, subtle, and interrelated biochemical and physiological mechanisms underlying the novel pharmaceutical formulations of the invention. While further research may either clarify or modify these explanations and diagrams, the remarkable efficacy and safety of the novel methods and composition taught by this invention to restore healthy functioning and treat the conditions and disorders, as described in this application, are the essential teaching of this invention, regardless of the precise mechanisms underlying their therapeutic benefits.

Living organisms have a fundamental survival-based coping response to stressors. There is evidence to suggest that receptors in the stress response neurotransmitter systems, especially the endogenous opioid system, are generally maintained in a basal inhibitory mode. As a result, as long as there is no perceived danger or threat, the release of neurotransmitters, such as endogenous opioids, i.e., endorphins, triggers inhibitory signaling, minimizing pain and distress signaling. Through synergistic processes, complex endorphinergic, serotonergic, dopaminergic, epinephrinergic, glutaminergic, and norepinephringeric interactions produce a positive hedonic tone, including a sense of calm and well being.

Acute injury or stress triggers acute reflexive pain signals mediated by non-opioid systems, leading to the adaptive reflexive experience of immediate pain and distress. Simultaneously, acute injury or stress set opioid receptors in the excitatory mode and endogenous opioids (i.e., endorphins) are released. The endogenous opioids bind with the opioid receptors, triggering excitatory signaling. Through $G_s$, excitatory signals enhance the release of cAMP, which by increasing Protein Kinase A (which increases $Ca^2$ conductance and decreases $K^+$ conductance), excites pain-sensory neurons that trigger the sensation of pain as well as increased sensitivity toward pain (hyperalgesia). The increased cAMP also enhances the release of endogenous opioids, maintaining the pain and distress cycle. Through complex endorphinergic, serotonergic, dopaminergic, epinephrinergic, glutaminergic, and norepinephringeric interactions, a negative hedonic tone, characterized by a systemic state of alert, including physical and emotional distress, leads the organism to an extended adaptive response to the noxious stimuli. However, as soon as the acute danger is reduced, in part as a result of an adaptive response to pain and distress, the opioid receptors are switched to inhibitory mode. The endogenous opioids then trigger inhibitory signaling and, through $G_o$, (which decreases $Ca^{2+}$ conductance and increases $K^+$ conductance), inhibits pain-sensory neurons, which triggers reduced sensation of pain and produces analgesia. At the same time, the opioid receptor inhibitory signaling, through $G_i$, inhibits cAMP, which, in turn, reduces endogenous opioids, which tunes down the entire endogenous opioid pain response system. Again, through complex endorphinergic, serotonergic, dopaminergic, epinephrinergic, and norepinephrinergic interactions, positive hedonic tone is restored, leading to a sense of calm and well being. In this way, normal healthy homeostatic balance is maintained within the bimodal opioid receptors and neurotransmitters as well as among the endorphinergic, serotonergic, dopaminergic, epinephrinergic, and norepinephrinergic systems.

For a variety of reasons, this homeostatic stress response system can become imbalanced and dysfunctional. Chronic or particularly intense physical and emotional stress and injury, drug and alcohol use, a variety of medications and chemicals, particularly exogenous opioids and cAMP enhancers, such as PDE inhibitors and excitatory amino acids, GM1 ganglioside, congenital vulnerabilities, and certain medical conditions can impair healthy homeostatic functioning of this system. These factors can overwhelm the stress response system, leading neurotransmitter receptors to remain in a protracted excitatory mode, and neurotransmitter levels, such as endorphins, to be chronically diminished. In this condition, endogenous opioids trigger mostly excitatory signaling, which results in chronic pain and hyperalgesia. Any factor that triggers the release of endogenous opioids, including injury or stress and even reward states and various drugs, can potentiate pain.

Under some conditions, this constant state of alert and distress may be adaptive such as when physical and/or emotional survival is chronically at risk. However, in most situations this protracted excitatory signaling of distress is maladaptive. This protracted condition effectively "resets" the organism's homeostatic basal condition from positive hedonic tone to varying degrees of negative hedonic tone by triggering homeostatic processes in related serotonin, dopamine, and other neurotransmitter systems, which produce a variety of signs and symptoms of emotional and physical distress. This negative hedonic tone state may be reflected by the experience of anxiety, irritability, depression, cravings, addictive tendencies, and physical distress, including pain, hyperalgesia, and gastrointestinal symptoms. Protracted opioid (and other stress-related) receptor excitatory mode conditions, together with depleted neurotransmitter levels, are a major component of a wide variety of Distress Dysfunction disorders, syndromes, and symptoms. Unfortunately, typical coping patterns, including the use of drugs and alcohol, including exogenous opioids, perpetuate and exacerbate protracted excitatory signaling and its negative impact on negative hedonic tone.

This protracted state of alert is reflected in the experience of protracted distress manifested by hypervigilance, physical and emotional hypersensitivity, exaggerated perception and feeling of threat, hyperalgesia, distressing pain, impulsivity, irritability and anger, unwarranted fears, anxiety and panic, obsessions and compulsions, agitation, distractibility, concentration and attention impairments, despair and depression, anhedonia, sleeping difficulties, sexual problems, interpersonal conflicts, a sense of danger and that "something is wrong", as well as desperate cravings for anything that can reduce this protracted distress. These cravings are often for substances, such as drugs, alcohol, and food, as well as stress-reducing behaviors and situations, such as sexual activity, gambling, and other compulsions, even if inappropriate or ultimately maladaptive, leading to a vicious cycle. In effect, these cravings, stemming from protracted receptor excitatory signaling, together with depleted neurotransmitter levels, compel the individual toward substances and situations in an attempt to trigger receptor inhibitory signaling as well as raise neurotransmitter levels. Unfortunately, increasing release of endorphins, when the receptors are fixed in the excitatory mode, triggers distress signals. This increase in distress may occur paradoxically in any emotional situation, even when the context is positive, or when drugs and alcohol are consumed to increase neurotransmitter levels.

In contrast to nociceptive pain, which is a direct adaptive reaction to real injury, distressing pain is an exaggerated emotional and physical reaction to perceived and anticipated danger, which typically includes hyperalgesia and dysfunctional hypersensitivity to perceived or real injury. The key is that all of these symptoms are signs of an underlying protracted state of dysfunctional distress, produced by protracted receptor excitatory signaling combined with diminished neurotransmitter levels. When dysfunctional emotional and physical distress is alleviated, a basal positive hedonic tone and a general sense of emotional and physical well being is restored and the individual is able to realistically experience and respond adaptively to actual stress, injury, and nociceptive pain, through normal reflexive pain transmission processes.

This protracted state of distress underlies the symptoms suffered by individuals diagnosed with a wide variety of medical, psychiatric and psychological disorders. Therefore, rather than treat each of these difficulties as different disorders, this invention's novel approach is the discovery of a method that naturally restores homeostatic balance in the stress response, resolving the common neurophysiological condition that causes the dysfunctional distress. By switching receptors from a protracted excitatory mode to a basal state of inhibitory signaling, and enhancing sufficient release of neurotransmitters to normal levels, healthy homeostatic balance can be restored. In this state, a basal sense of calm and well-being is experienced, adaptively reflecting the relatively safe and benign state of the environment. When stressors occur during healthy homeostasis, an immediate distress signal is triggered, but quickly inhibited as the individual adaptively responds to the situation. By focusing upon and treating the underlying protracted distress condition, this invention provides a treatment that safely and effectively reduces and/or eliminates a wide variety of dysfunctional symptoms, conditions, and disorders.

D. Discovery of Invention

The discovery of this invention came from the sudden and unexpected convergence of two independent lines of research, one from the world of the psychotherapy consultation room and the other from the nervous tissue culture laboratory.

In his clinical psychotherapy practice over thirty years, Dr. Steven Crain, present co-inventor, identified the existence of a clearly definable syndrome, which appeared to emerge in patients suffering from a wide variety of disorders and conditions. Despite major progress in psychotherapy in which cognitive and psychodynamic dysfunctional patterns, family issues, irrational and maladaptive beliefs and values were resolved, many patients clearly continued to suffer from a syndrome characterized by chronic or recurrent emotional and physical distress—unwarranted fears and worries, ruminations and obsessions that they could not stop, a sense of catastrophic dread, hypervigilance, emotional hypersensitivity, irritability and anger, impulsive reactions, compulsive behaviors, as well as cravings and addictions for food, alcohol, drugs, opioids, and stimulants. Many of these patients complained of chronic aches and pains, hyperalgesia, and distressing pain. All of these symptoms seemed highly related—a sense of emotional and physical distress, a sense of alert producing a basal state of negative hedonic tone, despite the fact that their personal life circumstances would normally be expected to produce a positive hedonic tone and a sense of calm and well being. Although conventional SSRIs, SNRIs, and tranquillizers could sometimes help, they were often were insufficient and their benefits frequently deteriorated over time.

Dr. Crain continued to search for biochemical answers. He began to identify what seemed like an imbalance in the stress-related neurotransmitter systems, which were locked into an alert distress mode. While many patients had had trauma in their life, stressful situations, and conflicted family history, as well as alcohol and drug abuse, many individuals simply seemed to be "wired" with these dysfunctional patterns. Dr. Crain also observed that many people who never sought treatment seemed to be suffering from various forms of the same problem. Dr. Crain further observed that long term drug and alcohol use, and even treatment with SSRIs, SNRIs, tranquilizers, analgesics, and stimulants often made their symptoms worse over time. Over the years, Dr. Crain systematically explored the importance of nutrition and exercise, and discovered the clinical utility of certain supplements and vitamins. However, a critical part of the puzzle was missing, until the set of discoveries that led to this invention.

A completely independent line of research, Dr. Stanley Crain's basic neurophysiological preclinical tissue culture and animal studies, over the same 30-year period, eventually focused on the mechanisms underlying the impact of exogenous opioids on the nervous system. This line of research led to a series of discoveries in Dr. Crain's search for a safe and non-addictive medication for nociceptive pain.

The present invention arose from a series of clinical studies initially conducted to test Dr. Crain's formulations in preliminary human trials. A series of unexpected and serendipitous discoveries revealed an entirely novel understanding of the neurophysiological mechanisms underlying the emotional and physical distress syndrome that Dr. Steven Crain had been observing in his patients over the years. Dr. Stanley Crain's basic opioid studies provided the stimulus for the discovery of the remarkably safe and effective novel methods to reduce and eliminate the protracted emotional and physical distress symptoms and restore healthy functioning to the body's emotional and physical stress response system.

From this serendipitous convergence between the psychotherapy office and the nervous tissue culture laboratory emerged the discovery of Distress Dysfunction as a discrete and identifiable syndrome that is amenable to a safe and effective treatment. Moreover, these converging lines of research have led to an hypothesized understanding of the neurophysiological mechanisms that may explain the dramatic success of this novel treatment.

The moment of discovery arose when, in providing certain agents, which were suggested from Dr. Crain's preclinical nociceptive pain studies, to subjects in a simple induced pain paradigm, these initial formulations resulted in dramatic and completely unexpected transformations in emotional and physical symptoms that were not predicted from any prior research or clinical practice. Subjects surprisingly and unexpectedly reported a dramatic reduction in unrealistic fears, initially focused on the pain paradigm itself. However, these emotional changes clearly reflected a much more profound sense of calm and well being, and a reduction in the individual's protracted emotional and physical distress. They reported a dramatic reduction in worries and anxieties as well as irritability and anger. They felt much more "right with their lives". Aches and pains were reduced, and when nociceptive pain did occur, there was a greater sense of acceptance and adaptive coping response, without their typical maladaptive reactions. Subjects who had craving issues in their lives found that these cravings were significantly ameliorated, including food, alcohol, and opioid and non-opioid drugs. Instead of their normal emotional and physical distress, they felt a greater sense of peace and comfort. There were no reports of "highs", euphoria, or any "drug effects" at all. Moreover, no side effects were reported. The discovery of a treatment for protracted dysfunctional distress suddenly emerged, launching over a year of informal trials and clinical case studies.

For example, Example 1 below describes a study in which one of the following Endorphin Enhancers was used in relatively low dose—caffeine (about 50-about 200 mg), theophylline (100-300 mg), rolipram (about 1-about 50 µg), and forskolin (200 mg)—in combination with a Receptor Switcher, either an ultra-low-dose of naltrexone (1-100 µg) (ULDN) or a moderately low-dose of magnesium sulfate (0.7-5 g). In addition, each of these agents was administered alone, to determine the potential synergistic effects of co-treatment. Spontaneous, unsolicited reports from the majority of subjects in these trials revealed an unexpected set of therapeutic benefits from these co-treatment formulations, separate and distinct from the issue of nociceptive pain relief which was, at the outset, the sole purpose of the study. Completely unplanned and unexpected was the entirely new discovery that these agents, in all co-treatment formulations, dramatically reduced a surprising variety of symptoms in the subjects separate and distinct from nociceptive pain, including anxiety and depressed mood, gastrointestinal disturbances, emotional and physical agitation, impulsive anger, premature ejaculation, drug cravings, and PMS symptoms. In further studying this phenomenon, another surprising pattern emerged. The formulations were most effective in reducing these non-pain-related symptoms in subjects who initially had relatively low pain thresholds and tolerance prior to taking the drugs, suggesting underlying hyperalgesia.

The surprising set of findings in these preliminary trials led to a search for an explanation. In reviewing the scientific and clinical literature, an interesting pattern emerged. Patients with certain clinical disorders, such as IBS, PMS, acting out anger, psychogenic pain, alcohol and drug abuse, premature ejaculation, restless leg syndrome, substance abuse, and many children with autism have been found to have unusually low pain thresholds in standard pain tolerance studies. Inference from these patterns suggested that these disorders could be linked to a disturbance in the endogenous opioid system. In reflecting on the importance of hyperalgesia and the concept of distressing pain, a sudden connection was made as to the critical role of emotional and physical distress as a common characteristic throughout many of these disorders. These findings and observations strongly suggested that a common condition, Distress Dysfunction, underlies these diverse clinical patterns that have heretofore been considered to be separate and diverse as to both etiology and treatment. Furthermore, given the dramatic effectiveness of these formulations, which were known to impact the endogenous opioid system, it suddenly and unexpectedly became clear that the neuropsychological mechanism underlying Distress Dysfunction involved imbalances in the endogenous opioid system as well as with related neurotransmitter systems that mediate hedonic tone.

Moreover, in addition to validating the existence of Distress Dysfunction, the elusive treatment for emotional and physical distress that Dr. Steven Crain had been searching for had suddenly been discovered. This pivotal study, as well as subsequent research and clinical case studies, suggested that a safe and effective treatment for a wide variety of clinical disorders and symptoms had unexpectedly been discovered. [See Examples 1-12.] This treatment could consist of surprisingly low doses of specific agents that, when combined using principles that are based on this novel understanding of the stress response neurotransmitter systems, have a dramatic and synergistic effect on reducing hyperalgesia as well as a variety of other noxious symptoms of Distress Dysfunction. Specifically, the combination of a Receptor Switcher, such as ULDN, VLDN, MSM, NAC, or magnesium sulfate, with an Endorphin Enhancer, such as ginkgo biloba, guarana, roflumilast, caffeine or theophylline, simultaneously blocked protracted excitatory opioid signaling and increased endorphin levels, thereby reducing emotional and physical distress and enhancing a sense of well-being.

Another embodiment of the invention is directed to the combination of a composition of a Receptor Switcher and an Endorphin Enhancer, together with a Synergistic Enhancer, such as an analgesic agent. Example 2 describes the discovery that the addition of one or more low-dose non-opioid analgesics can produce synergistic results. Since there is evidence that the analgesic effect of acetaminophen and acetylsalicylic acid may be the result of increased opioid receptor inhibitory signaling (Example 2), it is reasonable to conclude that acetaminophen, and other non-opioid analgesics, act synergistically to achieve balance in the endogenous opioid system.

Therefore, in another embodiment, the Distress Dysfunction treatment formulation includes one or more Receptor Switchers, such as ULDN, VLND, NAC, MSM, or magnesium sulfate, together with one or more Endorphin Enhancers, such as guarana, ginkgo biloba, caffeine, theophylline, or roflumilast, co-administered with one or more Synergistic Enhancers, including low-dose non-opioid analgesics, such as celecoxib, acetylsalicylic acid, acetaminophen, or white willow bark. The case studies and trials described in Example 9 clearly suggest that this enhanced formulation can resolve a wide variety of Distress Dysfunction symptoms, including chronic emotional distress and agitation, drug and alcohol cravings and abuse, addictions, psychogenic and neuropathic pain, gastrointestinal distress, anxiety and depression, irritability and angry outbursts, hypersensitivity, anhedonia, leading to emotional stability and a sense of well-being. There appears to be a dramatic and unexpected synergistic effect wherein the addition of a modest dose of a non-opioid analgesic (Synergistic Enhancer) can potentiate the therapeutic efficacy of cotreatment formulations in order to relieve more serious symptoms of Distress Dysfunction. Evidence has rapidly accrued during these validation studies to support the remarkable analgesic potency of combining a Receptor Switcher, such as NAC, MSM, VLDN, and ULDN, with Synergistic Enhancers, such as NSAIDs. Case 12 describes the surprising analgesic benefits of adding a Receptor Switcher, such as ULDN or MSM, to long-term celecoxib treatment. Similarly, relatively low doses of Exogenous Opioid analgesics, such as oxycodone and tramadol, have been shown to have remarkable synergistic analgesic effects when combined with a Receptor Switcher, such as VLDN or ULDN, and an Endorphin Enhancer, such as gluatmic acid, as seen in Example 9.

Yet another embodiment of the invention is directed to combining Receptor Switchers with other Synergistic Enhancers such as SSRI and SNRI medications. As reflected in Examples 5 and 9, remarkable synergistic therapeutic benefits have been unexpectedly discovered when combining a Receptor Switcher with Synergistic Enhancers, such as an SSRI. Treatment for various Distress Dysfunction symptoms, including depression and anxiety has been enhanced further by the addition of an Endorphin Enhancer, such as ginkgo biloba, caffeine or guarana. While it is well-known that SSRI agents have therapeutic serotonergic effects, a growing body of research has revealed opioidergic effects as well. These opioidergic mechanisms appear to be responsible for certain analgesic effects of SSRI agents. In fact, high dose naltrexone has been shown to block these analgesic effects, suggesting the involvement of the endogenous opioid system as well as the endogenous serotonin system. (Duman et al., *J. Pharmacol Sci.*, 94(2):161-5 (2004)). Therefore, an explanation for the unexpected findings emerged, suggesting that SSRI and SNRI activity synergistically interacts with the endogenous opioid, serotonin, norepinephrine and related neurotransmitter systems. Together, Receptor Switchers and Synergistic Enhancers, such as SSRI/SNRI agents appear to attenuate an underlying dysfunction in the endogenous opioid system and perhaps the serotonin and dopamine systems as well. The case studies described in Example 9 show dramatic clinical support for these novel formulations. Thus the present invention describes, for the first time, the dramatic synergistic therapeutic impact of combining Receptor Switchers with an SSRI and other serotonin-related agents, together with Endorphin Enhancers, such as guarana and ginkgo biloba. Combined, these agents provide a new generation of pharmaceutical formulations for the safe and effective treatment of a wide variety of Distress Dysfunction conditions, including chronic anxiety, depression, drug and food cravings, pain, addictions, agitation, emotional and physical hypersensitivity, anger and irritability, agitation and distress, and other neuropsychological symptoms and disorders.

Yet another embodiment of this invention is directed toward combining a Receptor Switcher with another group of Synergistic Enhancers, amino acids, such as 5HTP and GABA. SAMe, Myhhr, and Boswellia have also been found to be potent Synergistic Enhancers for Distress Dysfunction. The case studies and trials summarized in Example 9 demonstrate the remarkable, and unexpected, synergistic therapeutic benefits discovered when adding certain amino acids, and other supplements, to Receptor Switchers, as well as when combining these agents with an Endorphin Enhancer.

Serious emotional disorders, such as depression, anxiety, and addiction were successfully treated, simply by combining Receptor Switchers, such as NAC and/or MSM, with Endorphin Enhancers, such as gingko biloba and/or guarana, together with Synergistic Enhancers, such as 5HTP, GABA, and/or SAMe as well as myhhr and/or boswellia.

Yet another embodiment of this invention is directed toward the discovery that conventional stimulant treatment for ADHD can be remarkably potentiated with the addition of a Receptor Switcher, such as ULDN or NAC. Case 10 describes case studies that demonstrate the unexpected synergistic effects of combining a Receptor Switcher, such as VLDN or NAC, with a Synergistic Enhancer, such as methylphenidate. Moreover, novel "nutraceutical" formulations, such as the combination of NAC and/or magnesium sulfate with a safe and innocuous amino acid, acetyl-L-carinitine (ALC), have been shown to rapidly reduce ADHD symptoms.

E. Novel Treatment for Distress Dysfunction

A fundamental principle of this novel invention teaches that an appropriate method for reducing dysfunctional emotional and physical distress involves restoring and maintaining a healthy stress response system. To restore balance in the stress-related neurotransmitter systems, treatment needs to simultaneously restore balance in the stress-related receptors and neurotransmitters. Specifically, protracted excitatory signaling in opioid receptors needs to be switched to basal homeostatic inhibitory signaling, and healthy levels of endogenous opioids needs to be restored. If endogenous opioids remain insufficient, exogenous opioids may be used to supplement this insufficiency. This invention also teaches that, in addition to rebalancing opioid receptors and endogenous/exogenous opioids, agents can be added to the formulation to treat certain symptoms of Distress Dysfunction (e.g., pain, depression) that have synergistic impact on the endogenous opioid system as well as on the homeostatically related serotonin, dopamine, norepinephrine, epinephrine, and glutamate neurotransmitter systems.

Effective endorphinergic treatment of Distress Dysfunction includes both: (1) at least one Class I agent that restores and maintains stress-related neurotransmitter receptors in a basal inhibitory mode (Receptor Switcher), and (2) at least one of the following (a) one or more Class II agents that restore, maintain, and release sufficient levels of endogenous opioids (i.e., endorphins) for healthy functioning (Endorphin Enhancers), and/or (b) one or more Class III agents that bind with opioid receptors (i.e., exogenous opioid agonists) (Exogenous Opioids), and/or (c) one or more Class IV agents that have a synergistic effect with the endogenous opioid system as well as related neurotransmitter systems (Synergistic Enhancers). Treatment methods that do not restore and maintain balance in both receptor mode and neurotransmitter levels are not only insufficient, but can actually exacerbate imbalances and, therefore, distress symptoms in many individuals. A visual comparison of the dramatically different effects of the balanced cotreatment formulations taught by this invention and conventional unbalanced formulations is shown in the figures.

The classes of agents used in this invention are all known to have an impact on one or more of the stress-related neurotransmitter systems, including the endogenous opioid, serotonin, dopamine, glutamate, epinephrine, norepinephrine and other related systems. Since there is growing evidence that all of these neurotransmitter systems function in homeostatic balance as the organism responds to stress, modifying important functions of one system has powerful effects across the stress response system. Therefore, while the agents used in these novel formulations may be thought to have impact on one particular neurotransmitter system, it is clear that therapeutically impacting one system has important effects throughout the entire stress response system. There is also growing evidence to suggest that the agents used in this method have an impact on more than one neurotransmitter system.

F. Balanced Pharmaceutical Formulations

An entirely new generation of pharmaceutical formulations for the treatment of a wide variety of Distress Dysfunction has been discovered by the combination of at least one Receptor Switcher together with at least one Endorphin Enhancer, Synergistic Enhancer and/or Exogenous Opioid. These novel formulations restore homoeostatic balance in the endogenous opioid and related neurotransmitter systems, thereby producing a completely unexpected and dramatic reduction in a wide range of distress-related symptoms including hypervigilance, physical and emotional hypersensitivity, exaggerated perception and fears of threat, distressing pain, impulsivity, irritability and anger, unwarranted fears, anxiety and panic, obsessions and compulsions, agitation, distractibility, concentration and attention impairments, despair and depression, anhedonia, sleeping difficulties, attention deficits, sexual problems, interpersonal conflicts, a sense of danger and that "something is wrong", as well as desperate cravings for anything that can reduce this protracted distress, including substances, such as drugs, alcohol, and food, and stress-reducing behaviors and situations, such as addictions and compulsions. By reducing protracted emotional and physical distress, these cotreatment formulations produce a positive basal hedonic tone, providing a general sense of well-being and satisfaction, thereby reducing and/or eliminating dysfunctional compulsive and addictive behaviors as well. An adaptive response to stressors, including painful stimuli, is maintained, but the maladaptive distress reactions are reduced and/or eliminated.

This invention also teaches that formulations that contain Receptor Switchers (e.g., very-low-dose opioid antagonists or neuraminidase inhibitors) alone, or in combination with Endorphin Enhancers (e.g., PDE inhibitors or excitatory amino acids) and/or Synergistic Enhancers (e.g., amino acids or NSAIDs) can be administered therapeutically when an individual is already taking certain Synergistic Enhancers (e.g, SSRI/SNRI, stimulants, or NGF) or Exogenous Opioids (e.g., tramadol, oxycodone or morphine) for the treatment of Distress Dysfunction in order to enhance their therapeutic benefit, reduce side effects, and minimize the dose of the medications.

With regard to nociceptive pain, this invention teaches a novel set of agents that can be used in formulations that represent a dramatic improvement from prior art in safety and effectiveness for clinical treatment. Specifically, Receptor Switcher agents, such n-acetyl-cysteine (NAC) and methylsulfonylmethane (MSM), have additional therapeutic characteristics as compared to ULDN; and Endorphin Enhancer agents, such as guarana, ginkgo biloba and roflumilast, have fewer noxious side effects and greater therapeutic benefits as compared to caffeine, rolipram and theophylline. In addition, this invention teaches that Exogenous Opioids should only be used in formulations that contain not only a Receptor Switcher, but also an Endorphin Enhancer, in order to maximize endorphinergic effects and minimize exogenous opioid doses. Finally, this invention teaches the therapeutic benefits of adding Synergistic Enhancers, such as SSRI/SNRIs, NSAIDs, and specific amino acids, to Receptor Switchers and Endorphin Enhancers, for their remarkable synergistic enhancement of analgesia.

This invention also teaches the development of a new generation of pharmaceutical formulations for the treatment of certain medical conditions that are traditionally treated by medications that are known to impair the healthy functioning of the endogenous opioid or related neurotransmitter systems when administered alone (e.g., PDE inhibitors, analgesics, stimulants). These medications appear to trigger protracted excitatory opioid signaling as well as inhibit the release of endorphins. In particular, the treatment of respiratory conditions, such as COPD and asthma, often includes cAMP PDE inhibitors, such as theophylline and roflumilast. Unfortunately, these cAMP PDE inhibitors are known to produce Distress Dysfunction by triggering protracted excitatory opioid signaling which produces side effects, such as hyperalgesia, anxiety, and gastrointestinal symptoms, which are counter-productive in their treatment of these medical conditions. Therefore, a new generation of pharmaceutical formulations for the treatment of respiratory disorders is taught by this invention, as seen in Example 7. These novel enhanced formulations contain one or more Receptor Switchers (e.g., ULDN, VLDN, MSM, or NAC) and a cAMP PDE inhibitor (e.g., roflumilast or theophylline). Given NAC's anti-inflammatory, anti-oxidant, and anti-viral effects, which are known to improve respiratory conditions, and roflumilast's specific PDE-4 inhibitory effects which are particularly potent with regard to respiratory conditions, the combination of NAC and roflumilast is a preferred embodiment of a novel formulation for respiratory conditions, such as COPD and asthma, simultaneously improving respiration and pain relief while reducing noxious side effects.

An important application of this invention is in the treatment of neonatal apnea. More than half of premature infants suffer from apnea of prematurity, which is most often treated by methylxanthines, such as caffeine citrate, theophylline, or aminophylline. However, these PDE inhibitors produce side effects, characteristic of Distress Dysfunction, including CNS and GI irritability, agitation, jitteriness, tachycardia, and vomiting. Our invention teaches that cotreatment with a Receptor Switcher, such as ULDN, VLDN, MSM, NAC, or magnesium sulfate, is expected to significantly reduce these side effects, thereby preventing the development of iatrogenic Distress Dysfunction in these premature infants.

This invention also teaches the development of a new generation of pharmaceutical formulations for the treatment of HIV-induced and diabetic neuropathy. Nerve growth factor (NGF) is an effective treatment for HIV-induced and diabetic neuropathy as well as other medical conditions, but is known to produce serious side effects, such as pain and hyperalgesia, due to the development of protracted excitatory opioid signaling and diminished endorphin levels. For the first time, safe and effective cotreatment formulations have been discovered, by combining one or more Receptor Switchers, as defined in this patent, with NGF, for the treatment of HIV-induced and diabetic neuropathy and other medical conditions. These formulations include NGF combined with Receptor Switchers, such as ULDN, VLSN, NAC, or MSM. Synergistic Enhancers, such as amino acids or SSRI/SNRIs, could be added to potentiate these formulations.

This invention also teaches the development of a new generation of pharmaceutical formulations for the treatment of ADD and ADHD. The combination of conventional stimulant medication, such as methylphenidate, with Receptor Switchers, such as ULDN, VLDN, NAC, and/or magnesium sulfate, provides a dramatic improvement in the treatment of these serious disorders. Moreover, the combination of safe and innocuous amino acids, such as ALC, and Endorphin Enhancers, such as ginkgo biloba, together with Receptor Switchers, such as NAC and magnesium sulfate, provides a new generation of "nutraceutical" formulations that can be safely and effectively be used with even young children.

A detailed description of the bimodal opioid modulation of pain and hedonic tone is included in the Appendix. In addition, diagrams are included that detail: (1) Bimodal Endorphinergic Modulation of Pain and Hedonic Tone (basic biochemical processes); (2) Bimodal Endorphinergic Impact on Pain and Hedonic Tone (transmission of normal pain and distress signals); (3) Acute Unbalanced Endorphinergic Impact on Pain and Hedonic Tone (acute impact of conventional drugs); (4) Chronic Unbalanced Endorphinergic Impact on Pain and Hedonic Tone (long-term impact of conventional drugs); and (5) Balanced Endorphinergic Impact on Pain Hedonic Tone (acute and long-term impact of novel balanced cotreatment formulations).

Validation studies, based on this invention, using a variety of the agents used in these balanced cotreatment formulations for Distress Dysfunction, indicate that, while certain agents are thought to impact a particular neurotransmitter systems, they appear to have more general effects on a variety of symptoms of emotional and physical distress, confirming the homeostatic interconnections among these stress-related neurotransmitter systems. These studies have determined that a wide variety of Endorphin Enhancers, when combined with one or more Receptor Switchers, have surprising and remarkable therapeutic effects on the reduction and/or elimination of a wide variety of emotional and physical symptoms of distress, including unwarranted and/or exaggerated fears and worries, irritability and anger, anxiety, depression, distressing pain, cravings, obsessions and compulsions, sexual problems, and addictions. Further studies will help determine, together with the skills of a person skilled in the art, the particular combination of Receptor Switchers, Endorphin Enhancers, Exogenous Opioids, and Synergistic Enhancers that have the most therapeutic impact on reducing Distress Dysfunction symptoms.

The principles taught by this invention result in a large number of formulations that can be effectively used to reduce and/or eliminate a wide variety of symptoms of emotional and physical dysfunctional distress. Given the synergistic homeostatic balancing processes within the Stress Response system, evidence accumulated during the development of these principles suggest that, as long as the principles are appropriately applied, and therapeutic doses of appropriate agents are chosen by those skilled in the art, a variety of formulas can be therapeutically used to restore balance in the stress response system. Therefore, while certain agents may be more effective than others for certain indications and individual cases, as long as these principles are used, any one of a number of formulations can be used to reduce a wide variety of symptoms of emotional and physical distress, reflecting an effective restoration of homeostatic balance in the stress response system.

In general, this invention teaches that an initial assessment should indicate that the individual is experiencing any one or more symptoms of emotional and/or physical distress, as described by this patent. One or more Receptor Switchers should be selected, by a person skilled in the art, and combined with one or more Endorphin Enhancers. This combination can be used both for the acute and long-term reduction and/or elimination of these emotional and physical distress-related symptoms. For most individuals, this formula will be sufficient to reduce and/or eliminate most symptoms of dysfunctional distress.

When the combination of Receptor Switchers and Endorphin Enhancers and/or Synergistic Enhancers is insufficient to reduce symptoms of emotional and/or physical distress, an Exogenous Opioid can be added to the formula, acutely or chronically. This strategy is most likely encountered in reducing distressing pain, in which case a low-dose analgesic agent can be added to the basic formula. Evidence accumulated in the development of this invention suggests that low-dose analgesics are dramatically potentiated when combined with Receptor Switchers and Endorphin Enhancers. In fact, non-opioid analgesics, such as white willow bark and celecoxib, have been shown to have powerful synergistic pain-relieving effects in these formulations. While opioid analgesics are generally not required, and to be avoided given their noxious side effects, relatively lower opioid doses have been found to have equipotent synergistic therapeutic effects in these formulations, with reduced side effects.

This invention also teaches that these novel formulations can be used to restore and maintain healthy homeostatic balance in the stress response system and, in this way, help to prevent the development of Distress Dysfunction. As a formula to maintain healthy functioning, no presenting symptoms of distress dysfunction need to be present. The stress and toxic elements of modern civilization can often cause dysfunctional distress. The use of these formulations can support and strengthen an individual's basal homeostatic state of positive hedonic tone. In particular, these formulations are strongly encouraged for anyone predisposed to, experiencing, or with a history of Distress Dysfunction, as well as those who use drugs or other agents that impact on the stress response system.

The clinical studies that led to the development of this invention have demonstrated the remarkable therapeutic effects of these safe and healthy formulations for a wide variety of emotional and physical dysfunctional distress syndromes. What is particularly striking about these findings is that the formulas use agents that on their own provide little or no relief for distress dysfunction, yet have healthy benefits for other concerns, such as the anti-oxidant and anti-viral benefits of NAC or the circulation benefits and potential reduction of memory impairments of ginkgo biloba. Therefore, rather than using drugs that often have noxious impact, such as high dose narcotic opioid drugs, stimulants, NSAIDs, and tranquillizers, these novel formulations combine agents that enhance healthy functioning of the neurotransmitter systems, and minimize the iatrogenic effects when using relatively low levels of these conventional drugs.

While these formulations have been shown to reduce a variety of symptoms of dysfunctional emotional and physical distress, further studies will be needed to clarify relative efficacy for specific indications and populations. Future studies will also provide individualized assessments that include neurotransmitter levels and receptor mode analysis in addition to symptom evaluation in order to further refine the selection of specific agents, doses, and formulations. Furthermore, those trained in the art are expected to use the novel principles taught by this invention to select appropriate agents, doses, formulations, and methods of administration that would be most appropriate for the individual application.

II. DEFINITIONS

The present invention is described herein using several definitions, as set forth below and throughout the application. The terms defined herein are used in the singular and plural as context indicates.

As used herein, the term ABOUT, will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

The term ACTIVE AGENT is used herein to refer to a chemical material or compound that induces a desired effect when administered topically or subcutaneously, and includes agents that are therapeutically and/or prophylactically effective as pharmaceuticals ("pharmacologically active agents"), as well as agents that are cosmeceutically effective ("cosmeceutically active agents"). Also included are derivatives and analogs of those compounds or classes of compounds specifically mentioned that also induce the desired effect. An "effective" amount of an active agent is a nontoxic but sufficient amount of an active agent to provide the desired beneficial effect. More specifically, a "therapeutically effective," "prophylactically effective," or "cosmeceutically effective" amount is a nontoxic but sufficient amount of a beneficial agent to provide the desired therapeutic, prophylactic, or cosmeceutical effect.

DISTRESS means emotional and/or physical pain or suffering affecting the body, behavior, and/or the mind.

DISTRESS DYSFUNCTION means a constellation of conditions, symptoms, and disorders, whether (a) the result of an endogenous condition or (b) the result or side effect of an exogenous medication, drug, or other agent, wherein a component thereof is the presence of one or more of the following: (a) signs or symptoms of distress (and/or a diminution of happiness, pleasure, contentment and a positive sense of well being), which interferes with an individual's quality of life and functioning, or (b) unpleasant or deleterious side effects of a medication, drug, or other agent, which may, or may not, interfere with its potential therapeutic benefits. Distress Dysfunction includes, but is not limited to, the following conditions, symptoms and/or disorders: (1) Anxiety Disorders, including, but not limited to, Panic Disorders, Agoraphobia, Specific Phobias, Social Phobias, Obsessive-Compulsive Disorder, Post-Traumatic Stress Disorder, Acute Stress Disorder, Generalized Anxiety Disorder, Substance-Induced Anxiety, Anxiety Related to Medical Disorders, Anxiety Disorder Not Otherwise Specified (NOS), as well as signs and symptoms of anxiety, stress, agitation, and worry that are not classified as an Anxiety Disorder; (2) Mood Disorders, including, but not limited to, Depressive Disorders, Dysthymic Disorder, Bipolar I Disorder, Bipolar II Disorder, Bipolar Disorder NOS, Cyclothymic Disorder, Mood Disorders Related to Medical Conditions, Seasonal Affective Disorder, Mood Disorders NOS, as well as signs and symptoms of depressed mood, anhedonia, despair, anhedonia, hypomania, mania, and negative hedonic tone that are not classified as a Mood Disorder; (3) Somatoform Disorders, including, but not limited to, Somatization Disorder, Somatoform Disorder, Conversion Disorder, Pain Disorder Associated with Psychological Factors, Pain Disorder Associated with Medical Conditions, Hypochondriasis, Body Dysmorphic Disorder, and Somatoform Disorder NOS; (4) Factitious Disorders, including but not limited to, Factitious Disorders with Psychological Signs and Symptoms, Factitious Disorders with Physical Signs and Symptoms Factitious Disorders with Combined Psychological and Physical Signs and Symptoms, and Factitious Disorder NOS; (5) Dissociative Disorders; (6) Sexual Dysfunction, including, but not limited to, Sexual Desire Disorders, Sexual Arousal Disorders, Orgasmic Disorders, Premature Ejaculation, Erectile Dysfunction, Sexual Pain Disorder, Sexual Dysfunction to a General Medical Condition, Substance-Induced Sexual Dysfunction, Sexual Dysfunction NOS, as well as signs and symptoms of sexual dissatisfaction and dysfunction that are not classified as a Sexual Dysfunction disorder; (7) Eating Disorders, including, but not limited to, Bulimia Nervosa, Anorexia Nervosa, Binge Eating, Eating Disorder NOS, as well as signs and symptoms of eating and appetite problems that are not classified as an Eating Disorder; (8) Gastrointestinal Disorders, including, but not limited to, Irritable Bowel Syndrome (IBS) with Predominately Diarrhea, IBS with Predominately Constipation, and IBS Mixed Type, Crohn's Disease, as well as GI distress including, but not limited to, nausea, vomiting, diarrhea, constipation, and bloating; (9) Pre-Menstrual Syndrome (PMS) and other hormonally-related distress signs and symptoms; (9) Movement Disorders, including, but not limited to, Restless Leg Syndrome; (10) Fibromyalgia; (11) Sleep Disorders, including, but not limited to, Insomnia, Dyssomnias Parasomnias as well as signs and symptoms of sleep problems that are not classified as a Sleep Disorder; (12) Impulse-Control Disorders, including, but not limited to, Intermittent Explosive Disorder, Kleptomania, Pyromania, Pathological Gambling, Trichotillomania, Impulse Control Disorder NOS as well as signs and symptoms of impulsivity that are not classified as an Impulse-Control Disorder; (13) Psychological Factors Affecting Medical Conditions; (14) Medication-Induced Movement Disorders; (15) Alcohol-Related Disorders, including, but not limited to, Alcohol Dependence, Alcohol Abuse, Alcohol Addiction, Alcohol-Induced Disorders, Alcohol-Related Disorder NOS as well as alcohol-related problems that are not classified as an Alcohol-Related Disorder; (16) Opioid-Related Disorders, including, but not limited to, Opioid Dependence, Opioid Addiction, Opioid Abuse, Opioid-Induced Disorders, Opioid-Related Disorder NOS, as well as opioid-related problems that are not classified as an Opioid-Related Disorder; (17) Caffeine-Related Disorders, including, but not limited to, Caffeine Dependence, Caffeine Addiction, Caffeine Abuse, Caffeine-Induced Disorders, Caffeine-Related Disorders NOS as well as caffeine-related problems that are not classified as a Caffeine-Related Disorder; (18) Cannabis-Related Disorders, including, but not limited to, Cannabis Dependence, Cannabis Addiction, Cannabis Abuse, Cannabis-Induced Disorders, and Cannabis-Related Disorder NOS; (19) Amphetamine (or Amphetamine-Like)-Related Disorders, including but not limited to, Amphetamine Dependence, Amphetamine Addiction, Amphetamine Abuse, Amphetamine-Induced Disorders, and Amphetamine-Related Disorder NOS; (20) Cocaine-Related Disorders, including, but not limited to, Cocaine Dependence, Cocaine Addiction, Cocaine Abuse, Cocaine-Induced Disorders, and Cocaine-Related Disorder NOS; (21) Nicotine-Related Disorders, including, but not limited to, Nicotine Dependence, Nicotine Addiction, Nicotine Abuse, Nicotine-Induced Disorders, and Nicotine-Related Disorder NOS; (22) Inhalant-Related Disorders, including, but not limited to, Inhalant Dependence, Inhalant Addiction, Inhalant Abuse, Inhalant-Induced Disorders, and Inhalant-Related Disorder NOS; (23) Phencyclidine-Related Disorders, including, but not limited to, Phencyclidine Dependence, Phencyclidine Addiction, Phencyclidine Abuse, Phencyclidine-Induced Disorders, and Phencyclidine-Related Disorder NOS; (24) Sedative-, Hypnotic-, or Anxiolytic-Related Disorders, including, but not limited to, Sedative-, Hypnotic-, or Anxiolytic Dependence, Addiction, and/or Abuse, Sedative-, Hypnotic-, or Anxiolytic-Induced Disorders, and Sedative-, Hypnotic-, or Anxiolytic-Related Disorder NOS; (25) Polysubstance-Related Disorders; (26) Pervasive Developmental Disorders, including, but not limited to, Autism Disorder, Rhett's Disorder, Asperger's Disorder, or Pervasive Developmental Disorder NOS; (27) Attention-Deficit and Disruptive Behavior Disorders, including, but not limited to Attention-Deficit/Hyperactivity Disorder, Conduct Disorder, Oppositional Disorder, Disruptive Behavior Disorder NOS as well as attentional and concentration problems that are not classified as an Attention-Deficit Disorder; (28) Chronic Fatigue Disorder; (29) Behavioral addictions, compulsions, and dysfunctions, including, but not limited to, sex, pornography, gambling, shopping, eating, drinking, smoking, computer use, and cleaning; (30) Pain disorders, including, but not limited to, distressing, neuropathic, nociceptive, migraine and psychogenic pain; (31) Psychotic disorders, including, but not limited to, schizophrenia; (32) Unpleasant or deleterious side effects of CLASS II, III, or IV agents when such agents are administered alone (i.e., without co-administration with an CLASS I agent) which may, or may not, interfere with the potential therapeutic benefits of CLASS II, III, or IV agents, including, but not limited to PDE inhibitors, opioid and non-opioid analgesics, stimulants, SSRIs, SNRIs, NGF, and amino acids; (33) Respiratory disorders including, but not limited to, asthma, COPD, neonatal apnea; (34) Nerve damage and neuropathy including, but not limited to, HIV-induced and diabetic neuropathy; (35) Inflammatory disorders; (36) Allergic and non-allergic glutamate and mono-sodium glutamate related disorders, including "Chinese Food Syndrome"; and (37) Emotional and physical malaise, distress, discomfort, pain, restlessness, irritability, worries, cravings, compulsions, obsessions, agitation, addictions, and other related complaints and signs of protracted negative hedonic tone that may, or may not, be part of a traditional medical or psychiatric disorder. Distress Dysfunction is not limited to these conditions and diagnoses and is best defined by a variety of symptoms, conditions, syndromes, and disorders, characterized by dysfunctional emotional and physical distress and pain.

DISTRESSING PAIN means an exaggerated emotional and/or physical reaction to perceived, anticipated and/or real danger or harm, which typically includes hyperalgesia and hypersensitivity to perceived or real injury.

ENDORPHIN ENHANCERS (CLASS II AGENTS) means an exogenous agent that directly or indirectly enhances the production, release and/or functioning of endogenous opioids, i.e., endorphins, and/or inhibits their reuptake. CLASS II agents are functionally defined such that, when co-administered with CLASS I agents, they reduce and/or resolve Distress Dysfunction symptoms. CLASS I agents include, but are not limited to, cyclic adenosine monophosphate (cAMP) phosphodiesterase (PDE) inhibitors or agents that directly enhance cAMP, a cAMP phosphodiesterase (PDE) inhibitor, an agent that directly enhances cAMP, a specific or non-specific cAMP PDE inhibitor, a specific cAMP PDE-4 inhibitor, ginkgo biloba, theophylline, roflumilast, ibudilast, cilomilast, ardenafil, tadalafil, sildenafil, zaprinast, rolipram, methylxanthine, milrinone, inaminone, cilostazol, caffeine, guarana, ginkgo biloba, forskolin, celecoxib, excitatory amino acids, a salt of an excitatory amino acid, all forms of excitatory amino acids, glutamic acid, aspartic acid, glutamine, mono-sodium glutamate (MSG), N-methyl-D-asparate (NMDA), phenylalanine, dl-phenylalanine (DLPA), and nerve growth factor (NGF).

EXOGENOUS OPIOIDS (CLASS III AGENTS) means exogenous agents that activate and/or bind with opioid receptors, triggering inhibitory and/or excitatory signaling. CLASS III agents include, but are not limited to, exogenous opioid agonists (full, partial, mixed), tramadol, morphine, oxycodone, hydrocodone, papaverine, codeine, dihydrocodeine, fentanyl, hydromorphone, buprenorphine, butorphanol, methadone, loperamide, alfentanil, levorphanol, menthol, meperidine, nalbuphine, oxymorphone, pentazocine, pentazocine, propoxyphene, remifentanil, and sufenta.

HEDONIC TONE HOMEOSTASIS means the tendency of the opioidergic, serotonergic, dopaminergic and related neurotransmitter systems to maintain positive hedonic tone, when adaptive, and to restore positive hedonic tone following stressful conditions and stimuli, which may acutely produce negative hedonic tone.

HOMEOSTASIS means the tendency of an organism to actively regulate its internal conditions, usually by a system of feedback controls, so as to stabilize health and functioning, regardless of the changing conditions, as well as the ability of the body to actively seek and maintain a condition of equilibrium or stability within its internal environment when dealing with external changes.

LOW-DOSE-NALTREXONE means a dose of about 500 μg to about 1000 μg.

NEGATIVE HEDONIC TONE means the diminution of happiness, pleasure, and contentment, and is typically associated with the experience of emotional and/or physical distress and alert.

POSITIVE HEDONIC TONE means a positive sense of well-being, happiness, pleasure and contentment.

RECEPTOR SWITCHERS (CLASS I AGENTS) means an exogenous agent that blocks opioid excitatory receptor signaling, thereby switching protracted excitatory mode to homeostatic basal inhibitory mode. CLASS I agents are functionally defined such that, when co-administered with CLASS II, III, and/or IV agents, reduce and/or resolve Distress Dysfunction symptoms. CLASS I agents include, but are not limited to: ultra-low-dose, very-low-dose and low-dose opioid antagonists, ultra-low-dose, very-low-dose, and low-dose naltrexone, naloxone, diprenorphine, nalmefene, and norbinaltorphimine, agents that inhibit synthesis or activity of GM1 ganglioside, neuraminidase inhibitors, agents that increase sulfates in the body, methylsulfonylmethane (MSM), magnesium sulfate, chondroitin sulfate, n-acetyl-cysteine (NAC), oseltamivir, zanamivir, laninamivir, peramivir, scutellaria, and 5,7,4'-trihydroxy-8-methoxyflavone.

SYNERGISTIC ENHANCERS (CLASS IV AGENTS) means exogenous agents that have a synergistic effect with the endogenous opioid system. CLASS IV agents are functionally defined such that, when co-administered with CLASS I agents, they reduce and/or resolve Distress Dysfunction symptoms. The addition of CLASS II and/or III agents may further enhance the therapeutic effects of a combination of CLASS I and IV agents. CLASS IV agents include, but are not limited to, agents that support the functioning, production and release of endogenous opioid, serotonin, dopamine, epinephrine, norepinephrine, and glutamate neurotransmitters, non-opioid analgesics, non-steroidal anti-inflammatory drugs (NSAIDs), acetaminophen, celecoxib, white willow bark, acetylsalicylic acid, salicin, ibuprofen, naproxen, ketoprofen, indomethacin, fenoprofen, tolmetin, sulindac, meclofenamate, piroxicam, flurbiprofen, diclofenac, stimulants, selective serotonin reuptake inhibitors (SSRI), serotonin agonists, antagonists and modulators, selective norepinephrine reuptake inhibitors (SNRIs), citalopram, dapoxetine, escitalopram, fluoxetine fluvoxamine, paroxetine, sertraline, fluvoxamine, zimelidine, dapoxetine, alosetron, ondansetron, granisetron, bemesetron, eplivanserine, deramciclane, agomelatine, elazasonan, pruvanserin, asenapine, zomari, valazodone, bifeprunox, buspirone, ritanseron, geperone, paliperidone, clomipram, doxepin, haloperidol, risperidone, methylphenidate, amino acids, a salt of an inhibitory amino acid, all forms of amino acids, gamma-aminobutrynic acid (GABA), PharmaGABA, glycine, taurine, tryptophan, 5HTP, phenylalanine, dl-phenylalanine (DLPA), acetyl-L-carinitine (ALC), valine, threonine, methionine, lysine, leucine, isoleucine, tyrosine, alanine, arginine, histidine, serine, selenocfystiene, proline, glycine, cysteine, aspargine, alanine, S-adenosylmethionine (SAMe), cannabis, all forms and derivatives of cannabis, L-DOPA, vitamins and minerals, luteolin, quercetin, qercetin-3-O-methylether (3-MQ, 2), quercetin-3,7,4'-O-trimethylether, ayanin, quercetin-3,7,3',4'-O-tetramethylether, quercetin-3,5,7,3',4'-O-petamethylether, quercetin-3,5,7,3',4'-O-pentaacetate, quercetin-3-O-methyl-5,7,3', 4'-O-tetraacetate, methylcobalamin, vitamin C, vitamin D, vitamin D-3, vitamins B1, B2, B3, B6, and B12 folic acid, niacin, or niacinamide, folinic acid, calcium folinate, methylcobalamin, pyridoxal-5'-phosphate (P5P), alkaloids, flavonoids, and saponins, hesperetin, hesperidin, naringin, naringenin, epigallocatechin-3-gallate (EGCG), dioclein, genistein, daidzein, eriodictyol, prunetin, biochanin A, apigenin, myricetin, liquiritigenin, liquiritin, kaempferol, isoliquiritigenin, chrysin, rutin, cyanidin, delphinidin, pelargonidin, isorhamnetin, vitamin C, St. John's Wort, passion flower, hyperforin, hypericin, biotin, vitamin B5 (pantothenic acid), magnesium, alpha-ketoglutarate, copper, zinc, L-theanine, iron, california poppy, ginseng (*Panax* spp.), licorice, night-blooming cereus (Selenicereus grandiflorus; Cactus grandiflorus), hordenine, nutmeg, myristicin, tyramine, scotch broom, green tea, ephedra, yohimbe, myrrh, boswellia, frankincense, peppermint oil, and menthol.

VERY-LOW-DOSE NALTREXONE means a dose of about 125 μg to about 500 μg.

ULTRA-LOW-DOSE NALTREXONE means a dose of about 1 μg to about 125 μg.

III. COMPONENTS OF THE COMPOSITIONS OF THE INVENTION

The compositions of the invention comprise components which act synergistically to treat, prevent, mitigate, and/or reduce the symptoms of Distress Dysfunction, as defined herein. Specifically, the compositions of the invention, as defined herein, comprise at least one Receptor Switcher in combination with one or more (1) Endorphin Enhancers; (2) Exogenous Opioids; and/or (3) Synergistic Enhancers.

An entirely new generation of pharmaceutical formulations for the treatment of a wide variety of Distress Dysfunctions has been discovered by the combination of at least one Receptor Balancer together with at least one Endorphin Enhancer, Synergistic Enhancer and/or Exogenous Opioid. These novel formulations restore homoeostatic balance in the endogenous opioid and related neurotransmitter systems, thereby producing a completely unexpected and dramatic reduction in a wide range of distress-related symptoms, including hypervigilance, physical and emotional hypersensitivity, exaggerated perception and fears of threat, distressing pain, impulsivity, irritability and anger, unwarranted fears, anxiety and panic, obsessions and compulsions, agitation, distractibility, concentration and attention impairments, despair and depression, anhedonia, sleeping difficulties, attention-deficits, sexual problems, interpersonal conflicts, a sense of danger and that "something is wrong", as well as desperate cravings for anything that can reduce this protracted distress, including substances, such as drugs, alcohol, and food, and stress-reducing behaviors and situations, such as addictions and compulsions.

By reducing protracted emotional and physical distress, these cotreatment formulations produce a positive basal hedonic tone, providing a general sense of well-being and satisfaction, thereby reducing and/or eliminating dysfunctional compulsive and addictive behaviors as well. An adaptive response to stressors, including painful stimuli, is maintained, but the maladaptive distress reactions are reduced and/or eliminated.

While the comprehensive principles and formulations taught by this invention are directed toward Distress Dysfunction, as defined herein, novel discoveries have been made regarding nociceptive pain as well. The evidence indicates that the same principles and formulations described in this patent application are safe and effective analgesics for nociceptive pain. The discoveries leading to this invention have revealed a novel set of specific agents that can be used in nociceptive pain formulations that represent a dramatic improvement from prior art in safety and effectiveness for clinical treatment. Evidence presented in this patent suggest that these novel formulations are safer and at least as effective as conventional and widely used pain medications, including acetaminophen, aspirin, ibuprofen, and even certain opioid products, such as hyrdrocodone/acetaminophen. Furthermore, these novel formulations provide critical advancements over all prior teachings including those that are referenced in the Prior Arts section of this patent. Specifically, Receptor Switcher agents, such n-acetyl-cysteine (NAC) and methylsulfonylmethane (MSM), have additional therapeutic characteristics as compared to ULDN; and Endorphin Enhancer agents, such as ginkgo biloba, guarana, DLPA, and roflumilast, have reduced side effects as compared to rolipram, MSG, caffeine, and theophylline, as well as additional therapeutic benefits of their own. In addition, this invention teaches that Exogenous Opioids should only be used in formulations that contain not only a Receptor Switcher, but also an Endorphin Enhancer, to maximize endorphinergic effects and minimize exogenous opioid doses. Finally, this invention teaches the therapeutic benefits of adding Synergistic Enhancers, such as SSRI/SNRIs, NSAIDs, specific amino acids, and SAMe, to Receptor Switchers and Endorphin Enhancers, for their remarkable synergistic enhancement of analgesia.

This invention also teaches that formulations that contain Receptor Balancers (e.g., ultra-low-dose and very-low-dose opioid antagonists and/or neuraminidase inhibitors) alone, or in combination with Endorphin Enhancers (e.g., PDE inhibitors or excitatory amino acids) and/or Synergistic Enhancers (e.g., amino acids), can be administered therapeutically when an individual is already taking certain Synergistic Enhancers (e.g., stimulants, SSRI or SNRI) or Exogenous Opioids (e.g., tramadol, oxycodone or morphine) to enhance their therapeutic benefit, reduce side effects, and minimize the dose of the medications.

Finally, this invention teaches the development of a new generation of pharmaceutical formulations for the treatment of certain medical conditions that are traditionally treated by any drugs or medications that impair the healthy functioning of the endogenous opioid or related neurotransmitter systems when administered alone (e.g., methylxantines, PDE inhibitors, analgesics, stimulants, nerve growth factor). In particular, the treatment of respiratory conditions, such as COPD and asthma, often includes cAMP PDE inhibitors, such as theophylline and roflumilast. Unfortunately, these cAMP PDE inhibitors are known to produce Distress Dysfunction, triggering side effects such as hyperalgesia, anxiety, and gastrointestinal symptoms, which are counter-productive in their treatment of these medical conditions. Similar side effects are commonly observed when caffeine and other methyxathines are used to treat neonatal apnea. Therefore, a new generation of pharmaceutical formulations for the treatment of respiratory disorders is taught by this invention. These novel enhanced formulations contain one or more Receptor Balancers (e.g., ULDN, VLDN, MSM, magnesium sulfate, or NAC) and a cAMP PDE inhibitor (e.g., roflumilast, caffeine, or theophylline). Given NAC's anti-inflammatory and anti-viral effects, which are known to improve respiratory conditions, and roflumilast's potent specific PDE-4 inhibitory effects, which are particularly potent with regard to respiratory conditions, the combination NAC and roflumilast is a preferred embodiment of a novel formulation for respiratory conditions, such as COPD and asthma, simultaneously improving respiration and pain relief, with minimal side effects. Given the effectiveness of IV caffeine for neonatal apnea, a preferred embodiment of this novel treatment includes the addition of ultra-low-dose naloxone, magnesium sulfate, or NAC. Similarly, an effective treatment for HIV-induced and diabetic neuropathy is nerve growth factor (NGF). Unfortunately, NGF characteristically produces pain, a symptom of Distress Dysfunction due to its triggering of protracted opioid receptor excitatory signaling. Cotreatment of NGF with a Receptor Switcher, such as ULDN, VLDN, MSM, or NAC, as taught by this invention, provides the first safe and effective therapy for HIV-induced and diabetic neuropathy that eliminates painful side effects.

No prior art reference teaches a method to reduce and/or resolve the fundamental experience of emotional and physical distress, restoring a sense of basal positive hedonic tone and well-being. And no prior art reference teaches the therapeutic benefits for Distress Dysfunction of combining agents such as NAC, an amino acid compound known for boosting the immune system, with agents such as ginkgo biloba, an herb known for enhancing memory functions, or roflumilast, a drug for treating COPD, or MSG, a flavor enhancer. Moreover, while certain agents have been used for treating certain forms of Distress Dysfunctions, such as SSRIs, SNRIs, DLPA, 5HTP, GABA, SAMe, DLPA, and L-Tryptophan, there is no prior art teaching suggesting that adding ULDN, VLDN, MSM, magnesium sulfate, or NAC could dramatically potentiate the therapeutic benefit of these agents. Furthermore, no prior art teaches that adding innocuous agents such as a small amount of Epsom salts or an amino acid, such as NAC, could reduce the distressing side effects, and may also improve the efficacy, of many commonly used drugs, such as medications for asthma, COPD, neonatal apnea, pain, neuropathy, and ADHD.

Class I agents, including ultra-low-dose, very-low-dose, and low-dose opioid antagonists and GM1 ganglioside blockers, such as neuramindase inhibitors, switch and rebalance the mode of endogenous opioid receptors, and potentially other stress-related neurotransmitter receptors, from protracted excitatory signaling to homeostatic basal inhibitory signaling (Receptor Switchers). Class II agents, such as cyclic AMP phosphodiesterase (PDE) inhibitors, particularly specific cAMP PDE-4 inhibitors, methylxanthines, excitatory amino acids, nerve growth factor (NGF), and endogenous opioid reuptake inhibitors (EORI), enhance and prolong the release of endogenous opioids, i.e., endorphins (Endorphin Enhancers). Class III agents are exogenous opioid agonists (full, partial, mixed), such as tramadol, morphine and oxycodone, which function like endogenous opioids and bind to opioid receptors, triggering inhibitory and excitatory signaling (Exogenous Opioids). Class IV agents, including non-opioid analgesics, such as non-steroidal anti-inflammatory drugs (NSAID) and acetaminophen, selective serotonin reuptake inhibitors (SSRI), inhibitory serotonergic and adrenergic agents, selective norepineprhine reuptake inhibitors (SNRI), amphetamines, specific amino acids, vitamins and minerals, herbs and other supplements, enhance the production, release, and functioning of neurotransmitters in the opioid, serotonin, dopamine, glutamate, norepinephrine, and epinephrine systems and have synergistic interactions with the endogenous opioid system (Synergistic Enhancers). Certain agents, such as ultra-low-dose, very-low-dose, and low-dose naltrexone (Class I and IV), celecoxib (CLASS II and IV), and tramadol (Class III and IV), have multiple class functions, making them particularly effective in these cotreatment formulations.

This invention teaches that dysfunctional emotional and physical distress and pain is more effectively reduced, calm and well being is enhanced, and healthy homeostatic neurotransmitter balance is better maintained when at least one agent from Class I agents is combined with at least one agent from Classes II and/or III and/or IV, as compared to the administration of the agents from each class alone. Furthermore, this invention teaches that the tendency of Class II and III agents to produce Distress Dysfunction symptoms, such as hyperalgesia, tolerance and dependence, are reversed when combined with one or more Class I agents. Therefore, this invention teaches the surprising discovery of an entire new set of pharmaceutical formulations for the remarkably safe and effective treatment of a wide variety of Distress Dysfunctions, including anxiety, depression, anger, pain, addiction, eating disorders, gastrointestinal disorders, and sexual disorders. In addition, this invention teaches the surprising discovery that the administration of one of these novel formulations can be used to synergistically potentiate the therapeutic benefit and reduce the dysfunctional distress ("side effects") caused by a variety of drugs and medications, such as analgesics, anti-anxiety, anti-depressants, stimulants, methylxanthines, and nerve growth factor. Finally, this invention teaches the surprising discovery of a new set of pharmaceutical formulations for the treatment of respiratory disorders that combine certain Class I agents, such as ultra-low-dose naltrexone (ULDN), very-low-dose naltrexone (VLDN), and low-dose naltrexone (LDN), MSM, magnesium sulfate, and n-acetyl-cysteine (NAC), with certain Class II agents, such as roflumilast, caffeine, and theophylline, such that the therapeutic benefits and/or side effect profile of the cotreatment formulation are improved as compared to the use of these drugs alone. Similarly, this invention teaches that a remarkably safe and effective treatment for HIV-induced and diabetic neuropathy is formulated by combining certain Class I agents, such as ULDN, VLDN, LDN, MSM, magnesium sulfate, and NAC, with certain Class II agents, such as NGF.

A. Class 1 Agents: Receptor Switchers

Regarding agents that switch stress-related neurotransmitter receptors from a protracted excitatory mode to a basal inhibitory mode, two categories of agents have been discovered that function for this purpose: (1) ultra-low doses, very-low doses, and low-doses of opioid antagonists; and (2) agents that inhibit synthesis or activity of GM1-ganglioside. Opioid antagonists include, but are not limited to, naltrexone, naloxone, norbinaltorphimine, diprenorphine, and similarly acting opioid peptides and alkaloids. Agents that inhibit synthesis or activity of GM-1 ganglioside include, but are not limited to, neuraminidase inhibitors, agents that increase sulfates in the body, magnesium sulfate, sodium sulfate, chondroitin sulfate, n-acetyl cysteine (NAC), methylsulfonylmethane (MSM), oseltamivir, zanamivir, laninamivir, peramivir, *scutellaria*, 5,7,4'-trihydroxy-8-methoxyflavone, and similarly acting neuraminidase inhibitors.

While prior teachings suggest that these classes of agents block or inhibit excitatory signaling in the endogenous opioid system, the discoveries underlying this invention suggest that these agents have synergistic serotoninergic, dopaminergic, epinephrinergic, norepinephrinergic, and glutamatergic effects, given the homeostatic interconnectedness of the stress-related neurotransmitter systems. In addition, while not characterized in prior arts as a neuraminidase inhibitor, the anti-viral qualities of n-acetyl-cysteine (NAC), in addition to the case studies leading to this invention, suggest that NAC functions remarkably well as a Receptor Switcher. In addition, agents that increase the levels of sulfates in the body have been determined by our trials and case studies to function well as Receptor Switchers, including, but not limited to, methylsulfonylmethane (MSM). Magnesium sulfate can be very useful as a Receptor Switcher. While the sulfate is the critical component that switches receptor mode, magnesium sulfate provides the additional benefits of magnesium, which can further reduce distress as well as certain GI problems, such as constipation.

Therefore, these two categories of agents, ultra-low-dose, very-low-dose, and low-dose opioid antagonists and GM1 ganglioside inhibitors, are used in this invention for the functional Class I agents that selectively switch stress-related neurotransmitter receptors from a protracted excitatory mode to a basal inhibitory mode. This invention includes these and any other agents that inhibit or block excitatory receptor signaling and/or enhance inhibitory receptor signaling in the opioid, serotonin, dopamine, glutamate, epinephrine, and/or norepinephrine neurotransmitter systems. Alone, these Class I agents have less impact on reducing dysfunctional distress and nocieptive pain compared to the synergistic benefits that result from combining Class I agents with Class II and/or III and/or IV agents. In fact, in many cases, Receptor Switchers, when administered alone, have minimal or no therapeutic impact on reducing symptoms of Distress Dysfunction.

Preferred Receptor Switchers are ultra-low-dose and very-low-dose naltrexone and naloxone as well as n-acetyl-cysteine (NAC), magnesium sulfate, and methylsulfonylmethane (MSM). All of these agents have been shown to have very surprising and dramatic synergistic effects in the cotreatment formulations studied using the principles taught by this invention. They also are all known for being remarkably safe and provide additional therapeutic benefits. Since they all appear to be effective in combination with a variety of agents, which are known to enhance different neurotransmitter systems, and these combination have been shown to reduce a variety of symptoms, including both physical and emotional dysfunctional distress, these Receptor Switchers appear to function in a similar way. This set of findings also suggests that they restore basal opioid receptor inhibitory signaling in such a way that the Receptor Switcher impacts a variety of stress-related neurotransmitter systems. The choice of Receptor Switcher can be made dependent on a variety of factors including further studies to determine maximum benefit for different indications NAC, MSM, and magnesium are preferred agents for non-prescription and nutraceutical formulations for the treatment and prevention of Distress Dysfunction.

For certain embodiments of this invention, the preferred Receptor Switchers are naltrexone and naloxone.

For certain embodiments of this invention, the preferred Receptor Switcher is ultra-low-dose naltrexone (about 125 micrograms or less daily). Our trials and case studies have demonstrated remarkable effectiveness using about 1-about 125 micrograms of ULDN. Evidence suggests that while doses of about 5 micrograms can be remarkably effective for certain indications and populations, the higher end of this dosing range (about 100-about 125 micrograms) appears to be more reliable with more consistent therapeutic benefits over time for more people. In other embodiments of the invention, the daily dosage of naltrexone can be selected from the group consisting of about 0.001, about 0.01, or about 0.1 micrograms. In other embodiments of the invention, the daily dosage of naltrexone can be selected from the group consisting of about 1, about 2, about 3, about 4, about 5, about 10, about 15, about 20, about 25, about 65, about 70, about 75, about 80, about 85, about 90, about 95, about 100, about 105, about 110, about 115, about 120, or about 125 micrograms.

For certain embodiments of this invention, the preferred Receptor Switcher is very-low-dose naltrexone (about 125-about 500 micrograms daily). Validation studies for this invention suggest that the low end of VLDN dosing (about 125-about 150 micrograms) results in maximal and consistent therapeutic benefits for certain conditions. In other embodiments of the invention, the daily dosage of naltrexone can be selected from the group consisting of about 125 about 130, about 135, about 140, about 145, about 150, about 155, about 160, about 165, about 170, about 175, about 180, about 185, about 190, about 195, about 200, about 205, about 210, about 215, about 220, about 225, about 250, about 275, about 300, about 350, about 400, about 450, or about 500 micrograms.

For certain embodiments of this invention, the preferred Receptor Switcher is low-dose naltrexone (about 500-about 1000 micrograms daily). In other embodiments of the invention, the daily dosage of naltrexone can be selected from the group consisting, about 550, about 600, about 650, about 700, about 750, about 800, about 850, about 900, about 950, or about 1000 micrograms.

For certain embodiments of this invention, the preferred Receptor Switcher is n-acetyl-cysteine (NAC). Successful preliminary trials and case studies have been done using about 300-about 1200 mg daily, but lower doses are likely to be effective for certain formulations and conditions. In other embodiments of the invention, the daily dosage of NAC is selected from the group consisting of about 100, about 150, about 200, about 250, about 300, about 350, about 400, about 450, about 500, about 550, about 600, about 650, about 700, about 750, about 800, about 850, about 900, about 950, about 1000, about 1050, about 1100, about 1150, about 1200, about 1250, about 1300, about 1350, about 1400, about 1450, or above 1500 mg.

For certain embodiments of this invention, the preferred Receptor Switcher is magnesium sulfate. Successful preliminary trials and case studies have been done using about 25-about 1000 mg daily, but lower and higher doses are likely to be effective for certain formulations and conditions. In other embodiments of the invention, the daily dosage of magnesium sulfate is selected from the group consisting of about 5, about 10, about 15, about 20, about 25, about 50, about 100, about 150, about 200, about 250, about 300, about 350, about 400, about 450, about 500, about 550, about 600, about 650, about 700, about 750, about 800, about 850, about 900, about 950, or above 1000 mg.

For certain embodiments of this invention, the preferred Receptor Switcher is methylsulfonylmethane (MSM). Successful preliminary trials and case studies have been done using about 100-about 1000 mg daily, but lower and higher doses are likely to be effective for certain formulations and conditions. In other embodiments of the invention, the daily dosage of MSM is selected from the group consisting of about 25, about 50, about 75, about 100, about 150, about 200, about 250, about 300, about 350, about 400, about 450, about 500, about 550, about 600, about 650, about 700, about 750, about 800, about 850, about 900, about 950, about 1000, about 1050, about 1100, about 1150, about 1200, about 1250, about 1300, about 1350, about 1400, about 1450, or above 1500 mg.

Validation studies of this invention have suggested that ultra-low-dose and very-low-dose naltrexone is particularly effective in most oral cotreatment formulations for a wide variety of Distress Dysfunction symptoms. Given oral bioavailabiity of naltrexone, evidence suggests that while remarkably low doses of naltrexone, of 5 micrograms or less can be effective, relatively higher doses of ULDN and VLDN, in the range of 100-150 micrograms appear to be more consistently and reliably therapeutic for more people and conditions over time. Ultra-low-dose, very-low-dose, and low-dose naloxone is the preferred Receptor Balancer for intravenous and sublingual administrations. Lower doses of naloxone are particularly effective given the relative bioavailability of intravenous and sublingual administration. Since the formulations used in this invention involve naltrexone doses that are about 500-1,000 times lower than those used for other indications, ULDN and VLDN is a remarkably innocuous and safe agent for this application. At the same time, since opioid antagonists are effective as Receptor Switchers only at very low doses, and can create Distress Dysfunction at higher doses, it has been difficult to determine the most effective dose ranges. This concern may become particularly problematic in long-term administration since there is evidence to suggest that these agents may accumulate in the body. Therefore, other Receptor Switchers may be preferred for certain applications. Other agents, such as NAC, MSM, and magnesium sulfate, have the advantage of being less dose-dependent. Moreover, since they were in general use in the United States prior to Oct. 15, 1994, they not considered to be "grandfathered dietary supplements" and are not classified as either "drugs" or "new dietary supplements". ((21 CFR §312.2; 21 USC §350b; 21 USC §355.) Accordingly, they may be offered for sale to the public without the time and expense that would be required to do so with regard to drugs or new dietary supplements. However, NAC is an excellent Receptor Switcher since it has the added benefit of anti-inflammatory, anti-oxidant, and anti-viral effects, which may be important in many applications, as in the treatment of respiratory conditions. MSM is also a preferred Receptor Switcher since is known to have pain-relieving effects as well as an ability to increase concentration and attention. Magnesium sulfate, or Epsom salts, can be useful in certain indications to prevent constipation, such as in the treatment of certain forms of IBS, as well as additional benefits as a calming agent. However, its use should be carefully evaluated since it does have laxative effect.

B. Class II Agents: Endorphin Enhancers

One class of agents that have remarkable synergy with Receptor Switchers are those that enhance the production, release, or functioning of endogenous opioids (Endorphin Enhancers). Cyclic AMP enhancers, particularly specific cAMP PDE-4 inhibitors, such as roflumilast and ginkgo biloba, as well as non-specific cAMP PDE inhibitors, such as theophylline, caffeine, guarana, and ibudilast, enhance the release of cAMP, which, in turn, enhances the release of endogenous opioids (i.e., endorphins). In addition to cAMP PDE inhibitors, less potent cAMP enhancers include excitatory amino acids, such as glutamic acid, as well as forskolin and nerve growth factor (NGF). In addition, endogenous opioid reuptake inhibitors, such as DLPA, which both enhance the release of endogenous opioids as well as block the enzymes that reuptake them, provide an enhanced level of endorphins for longer periods of time. There is also evidence to suggest that celecoxib functions, in part, by enhancing the release of endorphins, making it an important Endorphin Enhancer for certain indications, such as arthritic pain.

When administered alone, Endorphin Enhancers have the potential to produce increased inhibitory signaling. However, since they would typically be administered when injuries or stress are present, or when the receptors are set in an excitatory mode, they are more likely to produce excitatory signaling, thereby iatrogenically triggering symptoms of Distress Dysfunction, such as pain, hyperalgesia, anxiety, and gastrointestinal symptoms, rather than reducing them. Unfortunately, most clinical use of these agents is conducted in the treatment of conditions and diagnoses that are, in fact, forms of Distress Dysfunction but heretofore have not been so identified. This mechanism explains many of the typical side effects seen with these agents. However, when co-administered with Receptor Switchers, Endorphin Enhancers trigger inhibitory signaling, leading to enhanced and prolonged analgesia and well being. Therefore, combining one or more Receptor Switchers, such as ULDN, MSM, NAC, or magnesium sulfate, with one or more Endorphin Enhancers, such as roflumilast, ginkgo biloba, guarana, celecoxib, glutamic acid, caffeine, theophylline, ibudilast, forskolin or NGF, creates a remarkable new generation of non-opioid pharmaceutical and nutraceutical formulations for the treatment of a wide variety of Distress Dysfunctions, by rebalancing the endogenous opioid system, restoring a basal homeostatic inhibitory mode together with normal levels of endorphins.

Regarding agents that enhance the production, release and/or functioning of endogenous opioids (i.e., endorphins), several categories of agents have been discovered that function for this purpose. All of these agents have variable impact on Distress Dysfunction when taken without co-administration with an agent that reduces excitatory opioid receptor signaling (Receptor Switchers). In fact, Endorphin Enhancers can have a negative impact if taken alone when the opioid receptors are in a protracted excitatory mode, which is typical when treating Distress Dysfunction. In this condition, the increased release of endorphins triggered by these agents can result in excitatory signaling, producing increased pain and negative hedonic tone, creating and exacerbating Distress Dysfunction. Without the understanding that is taught by this invention, there was no clear explanation for the highly variable findings of studies and treatments using Endorphin Enhancers alone.

However, when combined with an agent that reduces protracted excitatory signaling (Receptor Switcher), these Endorphin Enhancers have a surprising and dramatic effect on reducing acute and chronic emotional and physical distress. These agents, by enhancing the release of endorphins, facilitate endogenous opioid receptor inhibitory signaling, as long as a Receptor Switcher is present to maintain opioid receptors in the inhibitory mode. This cotreatment formulation is remarkably effective in reducing and/or resolving a wide variety of Distress Dysfunction symptoms, providing positive hedonic tone, including calm, well being, and relief from pain.

Endorphin Enhancers include agents that enhance the release of endogenous opioids (i.e., endorphins) directly, such as forskolin. Preferred Endorphin Enhancers also include agents that enhance endorphins indirectly. Many of these agents trigger the release of cyclic-AMP (cAMP), which in turn enhances the release of endorphins. Endorphin Enhancers that can be effective for this purpose include excitatory amino acids, such as glutamic acid and aspartic acid as well as salts of excitatory amino acids, such as monosodium glutamate (MSG). Glutamic acid and MSG have been shown to be remarkably effective for a wide variety of Distress Dysfunction symptoms when combined with Receptor Switchers in all validation studies for this invention. Certain amino acids, such as phenylalanine and dl-phenylalanine (DLPA), not only trigger the release of endorphins, but also block the enzymes that remove endorphins from the system. DLPA is a particularly effective selective endorphin reuptake inhibitor (SERI) and has been shown to enhance and prolong the therapeutic benefits of a variety of balanced cotreatment formulations in the validation studies for this invention. These amino acids have been widely used for other applications and have an excellent safety profile.

A particularly effective group of agents that trigger the release of cAMP, and therefore endorphins, are cAMP phosphodiesterase (PDE) inhibitors. The most potent of this group are specific cAMP PDE-4 inhibitors, known for their impact on the release of cAMP and, therefore, can be used at remarkably low doses. Therefore, preferred Endorphin Enhancers include specific cAMP PDE-4 inhibitors, such as roflumilast and ginkgo biloba. Roflumilast is a particularly compelling choice since it has been recommended for approval as safe and effective in Europe for the treatment of COPD, and is currently being reviewed in the U.S. for this purpose. Remarkably low doses of roflumilast have been shown to be extremely effective for a wide variety of Distress Dysfunction symptoms, when combined with a Receptor Switcher, in validation studies for this invention. Gingko biloba also functions as a cAMP PDE-4 inhibitor, and has certain benefits as a natural non-prescription agent and is known to improve circulation, memory, and concentration. Gingko biloba has also been shown in our preliminary trials to be quite effective, when combined with Receptor Balancers, such as NAC, for a variety of Distress Dysfunction symptoms, particularly emotional distress, which makes this a preferred non-prescription formulation. Non-specific cAMP PDE inhibitors, such as theophylline, ibudilast, methyxanthines, guarana, caffeine, and isobutylmethylxanthine (IBMX), also function as Endorphin Enhancers, though require higher doses than specific PDE-4 inhibitors. Theophylline and caffeine have been shown to be effective for a variety of Distress Dysfunction symptoms, when combined with Receptor Switchers, in validation studies for this invention. Theophylline has the advantage of decades of clinical use as a prescription medication for asthma. However, guarana is a preferred non-prescription Endorphin Enhancer since it has a more gradual release and longer-acting effects than other agents, such as caffeine, and has other known benefits regarding concentration, attention, and energy. Therefore, for OTC and nutraceutical formulations, preferred Endoprhin Enhancers include guarana, gingko biloba, and DLPA.

Another important Endorphin Enhancer is nerve growth factor (NGF). NGF produces hyperalgesia, which we have discovered is reversed by ULDN and other Receptor Switchers. Since NGF has been shown to reduce a variety of stress conditions, including depression and anxiety, but has a characteristic side effect of pain and hyperalgesia, the combination of NGF with a Receptor Switcher, such as ULDN or NAC, is a preferred formulation for the treatment of Distress Dysfunction. Since this formulation reverses the hyperalgesia produced by NGF administered alone, resulting in analgesia, it can be particularly effective for the treatment of distressing pain.

Celecoxib is also a particularly effective Endorphin Enhancer for certain applications, including chronic inflammation, as seen in conditions such as arthritis. While celecoxib is known to have anti-inflammatory effects, its analgesic effects can be dramatically potentiated with the addition of a Receptor Switcher, such as ULDN, NAC, or MSM. Side effects are also likely to be reduced in this novel formulation.

For certain embodiments of this invention, the preferred Endorphin Enhancer is roflumilast. Successful preliminary trials and case studies have used dosing of about 1-about 500 micrograms daily, depending on the formulations and indications. In other embodiments of the invention, the daily dosage of roflumilast is selected from the group consisting of about 0.01, about 0.1, about 0.5, about 1, about 5, about 10, about 15, about 20, about 25, about 50, about 75, about 100, about 125, about 150, about 175, about 200, about 225, about 250, about 275, about 300, about 350, about 400, about 450, about 500, or about 600 micrograms.

For certain embodiments of this invention, the preferred Endorphin Enhancer is theophylline. Successful preliminary trials and case studies have been doing using about 25-about 600 mg daily, though higher or lower doses are likely to be effective for certain formulations and indications. In other embodiments of the invention, the daily dosage of theophylline is selected from the group consisting of about 5, about 10, about 15, about 20, about 25, about 50, about 75, about 100, about 125, about 150, about 175, about 200, about 225, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, or about 900 mg.

For certain embodiments of this invention, the preferred Endorphin Enhancer is ginkgo biloba. Successful preliminary trials and case studies have done using about 60-about 240 mg daily, though higher or lower doses are likely to be effective for certain formulations and indications. In other embodiments of the invention, the daily dosage of ginkgo biloba is selected from the group consisting of about 10, about 20, about 30, about 40, about 50, about 60, about 70, about 80, about 90, about 100, about 110, about 120, about 130, about 140, about 150, about 160, about 170, about 180, about 190, about 200, about 210, about 220, about 230, about 240, about 250, about 260, about 270, about 280, about 290, or about 300 mg.

For certain embodiments of this invention, the preferred Endorphin Enhancer is guarana. Successful case studies have been done using about 100-about 400 mg daily, though higher or lower doses are likely to be effective for certain formulations and indications. In other embodiments of the invention, the daily dosage of caffeine is selected from the group consisting of about 10, about 20, about 30, about 40, about 50, about 60, about 70, about 80, about 90, about 100, about 110, about 120, about 130, about 140, about 150, about 160, about 170, about 180, about 190, about 200, about 210, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 420 mg, about 440 mg, about 460 mg, about 480 mg, or about 500 mg.

For certain embodiments of this invention, the preferred Endorphin Enhancer is caffeine. Successful preliminary trials and case studies have been done using about 25-about 100 mg daily, though higher or lower doses are likely to be effective for certain formulations and indications. In other embodiments of the invention, the daily dosage of caffeine is selected from the group consisting of about 1, about 5, about 10, about 20, about 30, about 40, about 50, about 60, about 70, about 80, about 90, about 100, about 110, about 120, about 130, about 140, about 150, about 160, about 170, about 180, about 190, or about 200 mg.

For certain embodiments of this invention, the preferred Endorphin Enhancer is glutamic acid or MSG. Successful preliminary trials and case studies have been done using about 25-about 100 mg daily, though higher or lower doses are likely to be effective for certain formulations and indications. In other embodiments of the invention, the daily dosage of glutamic acid or MSG is selected from the group consisting of about 0.1, about 1, about 5, about 10, about 20, about 30, about 40, about 50, about 60, about 70, about 80, about 90, about 100, about 110, about 120, about 130, about 140, about 150, about 160, about 170, about 180, about 190, about 200, or about 225 mg.

For certain embodiments of this invention, the preferred Endorphin Enhancer is DLPA. Successful preliminary trials and case studies have been done using about 50-about 500 mg daily, though higher or lower doses are likely to be effective for certain formulations and indications. In other embodiments of the invention, the daily dosage of DLPA is selected from the group consisting of about 10, about 20, about 30, about 40, about 50, about 60, about 70, about 80, about 90, about 100, about 110, about 120, about 130, about 140, about 150, about 160, about 170, about 180, about 190, about 200, about 210, about 220, about 230, about 240, about 250, about 260, about 270, about 280, about 290, about 300, about 325, about 350, about 375, about 400, about 425, about 450, about 475, about 500, about 525, about 550, about 575, about 600, about 625, about 650, about 675, about 700, about 725, about 750, about 775, about 800 mg, about 850, about 900, or about 1000 mg.

For certain embodiments of this invention, the preferred Endorphin Enhancer is ibudilast. Preferred dosing for ibudilast in these formulations will depend on the particular indication and will depend on the outcome of clinical trials. Conventional doses or lower will be sufficient to safely and effectively treat Distress Dysfunction.

For certain embodiments of this invention, the preferred Endorphin Enhancer is forskolin. Successful preliminary trials and case studies have been done using about 50-about 125 mg daily, though higher or lower doses are likely to be effective for certain formulations and indications. In other embodiments of the invention, the daily dosage of forskolin is selected from the group consisting of about 1, about 10, about 20, about 30, about 40, about 50, about 60, about 70, about 80, about 90, about 100, about 110, about 120, about 130, about 140, about 150, about 160, about 170, about 180, about 190, about 200 or about 250 mg.

For certain embodiments of this invention, the preferred Endorphin Enhancer is nerve growth factor. Preferred dosing for nerve growth factor in these formulations will depend on the particular form of administration and indication as well as the outcome of clinical trials. Conventional doses (about 0.1 µg/kg rhNGF-about 0.3 µg/kg rhNGF) should be effective when combined with a Receptor Switcher; lower doses should be also be effective when combined with a Receptor Switcher and will have an equal or better safely profile; and higher doses may be appropriate for specific conditions and circumstances.

For certain embodiments of this invention, the preferred Endorphin Enhancer is celecoxib. Preferred dosing for celecoxib is about 50-about 500 mg, though in our novel formulations, lower doses may be effective. Further testing will be necessary to maximize therapeutic dosage. In other embodiments of the invention, the daily dosage of celecoxib is selected from the group consisting of about 10, about 20, about 30, about 40, about 50, about 60, about 70, about 100, about 125, about 150, about 175, about 200, about 225, about 250, about 275, about 300, about 350, about 375, about 400, about 425, about 450, about 275, or about 500 mg.

In certain circumstances, this invention teaches the method that at least one Receptor Switcher can be administered to a subject who is already taking an Endorphin Enhancer. For instance, when cAMP PDE inhibitors, such as theophylline, caffeine, or roflumilast, are administered in the treatment of respiratory conditions, such as COPD, asthma, or neonatal apnea, they can cause various side effects, including emotional and physical distress, hyperalgesia, agitation, anxiety, and GI symptoms, essentially producing Distress Dysfunction. Similar side effects are produced by other Endorphin Enhancers, such as nerve growth factor, celecoxib, caffeine, guarana, ginkgo biloba, MSG, and glutamic acid. The administration of at least one Receptor Switcher, such as ULDN (naltrexone or naloxone), MSM, magnesium sulfate or NAC, can not only reduce and/or eliminate these side effects, but can also reverse these effects, producing greater pain relief and calm.

This invention also teaches a novel treatment for respiratory conditions, such as COPD, asthma, or neonatal apnea. By combining an appropriate cAMP PDE inhibitor, such as roflumilast, theophylline, caffeine, methylxanthines, forskolin or ginkgo biloba, with a Receptor Switcher, such as ULDN (naltrexone or naloxone), MSM, magnesium sulfate or NAC, an enhanced formulation for the treatment of respiratory conditions is created, which reduces and/or eliminates side effects and produces greater relief and calm. A preferred Receptor Switcher for these formulations is NAC, since it provides potent anti-inflammatory, anti-oxidant, and anti-viral effects, which can enhance the relief of respiratory symptoms in addition to reducing side effects and increasing pain relief and calm. Given its potency in respiratory therapy, a preferred prescription formulation is roflumilast or theophylline with NAC, MSM, magnesium sulfate, or ULDN. While less potent, a potential non-prescription formulation for the treatment of respiratory conditions is NAC, MSM and/or magnesium sulfate with ginkgo biloba, caffeine, and/or forskolin. For neonatal apnea, a preferred formulation is IV caffeine, or another methylxathine, combined with ULDN, magnesium sulfate, NAC, and/or MSM.

This invention also teaches a novel treatment for HIV-induced and diabetic neuropathy. Nerve growth factor (NGF) has been shown to be effective for the treatment of these serious conditions. However, a characteristic side effect of NGF is pain and hyperalgesia. Since cotreatment with a Receptor Switcher, as defined in this patent, reduces and, at times, reverses these side effects, this discovery describes a novel formulation for the treatment of HIV-induced and diabetic neuropathy. Preferred formulations for the treatment of HIV-induced and diabetic neuropathy include NGF combined with ULDN, NAC, MSM or magnesium sulfate.

C. Class III Agents: Exogenous Opioids

A second class of agents that has remarkable synergy with Receptor Switchers is exogenous opioid agonists (Exogenous Opioids). Exogenous Opioid agonist drugs (full, partial, mixed), such as tramadol, oxycodone, and morphine, clearly have a dramatic impact on the endogenous opioid system. Exogenous Opioids act like endogenous opioids, binding with opioid receptors, and their impact depends on the mode of the bimodally-acting opioid receptors. In a balanced system, their impact initially leads to inhibitory signaling, resulting in analgesia and even a sense of well being. However, fairly quickly, this increased inhibitory signaling results in a homeostatic balancing response that includes, through cAMP, a reduction in endogenous opioid levels as well as a receptor shift to the excitatory mode. Over time, this leads to a protracted excitatory receptor mode and diminished endogenous opioid levels, producing chronic pain, hyperalgesia, tolerance, dependence, and addiction as well as emotional and physical distress. These iatrogenic problems are greatly exacerbated when the endogenous opioid system is already in a protracted excitatory mode, resulting more immediately in excitatory signaling, leading to an exacerbation of pain and hyperalgesia, tolerance, as well as negative hedonic mode. Thus, while often initially therapeutic, Exogenous Opioids can rapidly lead to the development of serious and significant Distress Dysfunction, even long after the Exogenous Opioids are discontinued.

However, by administering one or more Receptor Switchers with one or more Exogenous Opioids, excitatory signaling is minimized, resulting in enhanced analgesia as well as a dramatic reduction in protracted excitatory mode conditions, reducing and/or eliminating many of the noxious effects of Exogenous Opioids, including hyperalgesia, tolerance, dependence, addiction, and other side effects. Therefore, if a particular patient is determined to require administration of an Exogenous Opioids, these should only be co-administered with Receptor Switchers in the treatment of Distress Dysfunction conditions, including distressing pain, addiction, anxiety, and depression. Given the inherent problems with Exogenous Opioids, however, formulations that primarily include Receptor Switchers with Endorphin Enhancers are preferable, thereby utilizing endogenous opioids rather than exogenous opioids that can both interfere with the body's natural opioid system and, as a result, cause significant, undesirable side effects. However, low-dose Exogenous Opioids can be added to these formulations, with remarkable synergistic effects, for particularly severe and resistant symptoms. Therefore, this discovery leads to the development of a new generation of remarkably safe and effective pharmaceutical formulations for the treatment of Distress Dysfunctions, including severe chronic distressing pain and addiction, that include the combination of Receptor Switchers, such as ULDN, VLDN, NAC, MSM and/or magnesium sulfate, Endorphin Enhancers, such as roflumilast, ginkgo biloba, guarana, DLAP, and/or caffeine, and low-dose Exogenous Opioids, such as tramadol, morphine, hydrocodone, codeine, and/or oxycodone. Compared to Exogenous Opioids administered alone, these formulations are also equally or more potent analgesics for the treatment of nociceptive pain while, at the same time, they reduce noxious opioid side effects Exogenous opioid agonists bind with opioid receptors in ways similar to endogenous opioids, thereby triggering excitatory or inhibitory signaling, depending on the mode of the receptor. However, the use of these Exogenous Opioids can create serious problems since they tend to inhibit the release of endogenous opioids and lock the opioid receptors in an excitatory mode over time. Given the well-known side effects of exogenous opioid agonists such as oxycodone and morphine, preferred formulations for the treatment of Distress Dysfunction consist of at least one Receptor Switcher with at least one Endorphin Enhancer. This method uses the natural healing power of balancing opioid receptors and neurotransmitters, maximizing use of endorphins in resolving Distress Dysfunction. This endorphinergic treatment has been shown to be remarkably effective in reducing and/or resolving a wide variety of Distress Dysfunction symptoms, including moderate-to-severe distressing pain.

However, there may be circumstances in which the endogenous opioids may be insufficient to effectively resolve symptoms. In this case, low-dose exogenous opioid agonists (Exogenous Opioids) can be added to the combination of Receptor Switcher and Endorphin Enhancer, to supplement the endogenous opioids (i.e., endorphins). The evidence strongly suggests that, as long as at least one Receptor Switcher is included in the formulation, most noxious side effects of the Exogenous Opioid are reduced and/or eliminated including tolerance, dependence, hyperalgesia, and GI symptoms. However, the preferred treatment includes at least one Receptor Switcher and Endorphin Enhancer with an Exogenous Opioid. There is also evidence to suggest that this formulation enhances the analgesic potency of the Exogenous Opioid for nociceptive pain.

Exogenous Opioids include tramadol, morphine, oxycodone, hydrocodone, papaverine, codeine, dihydrocodeine, fentanyl, hydromorphone, buprenorphine, butorphanol, methadone, alfentanil, loperamide, levorphanol, meperidine, nalbuphine, oxymorphone, pentazocine, pentazocine, propoxyphene, remifentanil, and sufenta. While a much weaker opioid, tramadol is a preferred Exogenous Opioid since it has therapeutic benefits through both the endogenous opioid and serontergic neurotransmitter systems, through the $G_i$ coupling. Evidence suggests that, in addition to mild analgesia, tramadol has anti-depressant characteristics. Therefore, tramadol, has great potential in formulations for the treatment of Distress Dysfunction, since both the analgesic and mood enhancing effects are likely to be potentiated by cotreatment with Receptor Switchers through $G_1$. These synergistic therapeutic benefits of cotreatment with tramadol have consistently been demonstrated in our validation studies. Tramadol has the additional benefit have having a much better side effect profile than most opioids and, as result, does not have the regulatory restrictions of most other opioids, such as oxycodone and morphine. At the same time, low-dose oxycodone is still a preferred Exogenous Opioid since the balanced cotreatment formulation has been shown to enhance its pain relieving effects, while dramatically reducing its side effects. Low-dose morphine is also preferred in balanced cotreatment formulations, using ultra-low-dose naloxone, for intravenous and sublingual administration.

For certain embodiments of this invention, the preferred Exogenous Opioid is tramadol. Successful preliminary trials and case studies have been done with about 5-about 50 mg daily, though higher or lower doses may be effective for certain formulations or indications. In other embodiments of the invention, the daily dosage of tramadol is selected from the group consisting of about 0.1, about 1, about 5, about 10, about 15, about 20, about 25, about 30, about 35, about 40, about 45, about 50, about 55, about 60, about 65, about 70, about 75, about 80, about 85, about 90, about 95, about 100, about 110, about 120, about 130, about 140, about 150, about 160, about 170, about 180, about 190, or about 200 mg.

For certain embodiments of this invention, the preferred Exogenous Opioid is oxycodone. Successful preliminary trials and case studies have been done with about 2.5-about 25 mg daily, though higher or lower doses may be effective for certain formulations or indications. In other embodiments of the invention, the daily dosage of oxycodone is selected from the group consisting of about 0.01, about 0.1, about 1, about 2, about 3, about 4, about 5, about 6, about 7, about 8, about 9, about 10, about 11, about 12, about 13, about 14, about 15, about 20, about 25, about 30, about 35, about 40, about 45, about 50, about 60, about 70, about 80, about 90, about 100, about 110, about 120, or above 125 mg.

For certain embodiments of this invention, the preferred Exogenous Opioid is morphine. Preferred dosing for morphine in these formulations will depend on the particular form of administration and indication. Conventional IV doses (0.25 µgNTX/kg-1 µgNTX/kg) should be sufficient to safely and effectively treat Distress Dysfunction, although higher or lower doses may be appropriate in particular circumstances.

For certain embodiments of this invention, the preferred Exogenous Opioid is hydrocodone. Successful preliminary trials and case studies have been done with about 2.5-about 25 mg daily, though higher or lower doses may be effective for certain formulations or indications. In other embodiments of the invention, the daily dosage of hydrocodone is selected from the group consisting of about 0.1, about 1, about 2, about 3, about 4, about 5, about 6, about 7, about 8, about 9, about 10, about 11, about 12, about 13, about 14, about 15, about 20, about 25, about 30, about 35, about 40, about 45, or about 50 mg.

For certain embodiments of this invention, the preferred Exogenous Opioid is buprenorphine. Preferred dosing for buprenorphren in these formulations will depend on the particular form of administration and indication. Conventional doses or lower will be sufficient to safely and effectively treat Distress Dysfunction.

For certain embodiments of this invention, the preferred Exogenous Opioid is methadone. Preferred dosing for methadone in these formulations will depend on the particular form of administration and indication. Conventional doses or lower will be sufficient to safely and effectively treat Distress Dysfunction.

A preferred non-prescription formulation for localized pain utilizes a topical application, such as gel, cream or lotion, which administers loperamide in combination with a Receptor Switcher, such as MSM, magnesium sulfate, or NAC. Loperamide is an Exogenous Opioid that has the advantage of local absorption without penetration into the CNS, and is also available as an over-the-counter medication. Preferred dosing for loperamide in these formulations will depend on the particular form of administration and indication. Conventional doses or lower will be sufficient to safely and effectively treat Distress Dysfunction. The addition of menthol appears to be an effective Synergistic Enhancer for this topical formulation. DMSO may be added to enhance transdermal penetration.

This invention also teaches the method in which at least one Receptor Switcher alone, or in combination with an Endorphin Enhancer and/or Synergistic Enhancer, can be administered to a subject already taking an Exogenous Opioid. This strategy can be useful to reduce the potentially serious side effects produced by the exogenous opioid agonist as well as enhance its therapeutic benefits.

D. Class IV Agents: Synergistic Enhancers

A third agent class that has remarkable synergy with Receptor Switchers includes a variety of agents having a synergistic effect with the endogenous opioid system through the $G_i$-mediated metabolic processes that trigger the inhibition of pain-sensory neurons (Synergistic Enhancers). There is evidence to suggest that higher levels of Gi, which are produced by enhanced inhibitory signaling potentiate the pain-relieving effects of non-opioid analgesics, such as NSAIDs and acetaminophen. Therefore, there is a synergistic potentiation produced by the combination of non-opioid analgesics, such as acetaminophen, celecoxib, ibuprofen, aspirin, or white willow bark, with Receptor Switchers, such as ULDN, VLDN, MSM, NAC, or magnesium sulfate, creating a new generation of enhanced non-opioid analgesics.

These novel formulations can be further potentiated by combining one or more Receptor Switchers, such as ULDN, VLDN, LDN, MSM, magnesium sulfate or NAC, together with an Endorphin Enhancer, such as roflumilast, caffeine, guarana, DLPA, glutamic acid or ginkgo biloba, and a Synergistic Enhancer, such as acetaminophen, ibuprofen, aspirin, celecoxib or white willow bark.

Similarly, synergistic potentiation occurs with selective serotonin reuptake inhibitors (SSRIs) and selective norepinephrine reuptake inhibitors (SNRIs), such that increased relief from depression, anxiety, distressing pain, addiction, and other Distress Dysfunctions is produced by the combination of SSRIs and SNRIs, such as escitalopram oxalate and venlafaxine, with Receptor Switchers, such as ULDN, MSM, magnesium sulfate, or NAC. Therefore, a new generation of enhanced SSRI/SNRI formulations for depression, anxiety, pain, and addiction are created by this invention. In addition to SSRIs and SNRIs, inhibitory serontonergic and adrenergic agents can function as Synergistic Enhancers.

Specific amino acids that enhance release of stress-related neurotransmitters, including serotonin and dopamine, such as tryptophan, taurine, tyrosine, GABA, ALC, and 5HTP, can also act as Synergistic Enhancers in these novel cotreatment formulations. For certain conditions, one or more Endorphin Enhancers, such as ginkgo biloba, guarana, DLPA, glutamic acid, caffeine or roflumilast, could be added to the combination of Receptor Switcher, such as NAC, MSM, magnesium sulfate or ULDN, and Synergistic Enhancer, such as 5HTP, GABA, ALC, and/or an SSRI/SNRI.

Another preferred Synergistic Enhancer is cannabis since it has been found to have a variety of therapeutic benefits for Distress Dysfunction including reduction of pain, depression, anxiety, and gastrointestinal symptoms. Given the interaction between cannabinoid and opioid receptors, there is evidence to suggest that the addition of Receptor Switchers to cannabis will potentiate these beneficial effects. As in all these cotreatment formulations, the combination of cannabis together with a Receptor Switcher, such as ULDN or NAC, and an Endorphin Enhancer, such as caffeine or glutamic acid, creates a potent treatment for anxiety, depression, pain, and other Distress Dysfunction conditions.

Another preferred Synergistic Enhancer is myhhr. While known as a ancient herb with "healing powers," there has been little evidence of its therapeutic benefits until this set of discoveries. Preliminary case studies have shown that the calming and analgesic benefits of myhhr are synergized in combination with Receptor Switchers, such as NAC, MSM, or magnesium sulfate. Similarly, we have found synergistic effects of combining boswellia with Receptor Switchers, producing calming and analgesic effects. Therefore, a novel formulation for the treatment of Distress Dysfunction as well as nociceptive pain is one or more Receptor Switchers combined with myhhr and/or boswellia. Endoprhin Enhancers, such as ginkgo biloba, guarana, and/or DLPA, can be added for additional benefits.

Another preferred Synergistic Enhancer is S-adenosyl methionine (SAMe). Preliminary case studies have shown a remarkable synergistic benefit from combining SAMe (50-400 mg daily) with Receptor Switchers, such as NAC, MSM, and magnesium sulfate, in reducing emotional and physical distress, including pain, anxiety, depression, and addiction.

Another preferred Synergistic Enhancer is methylphenidate since it is so widely used for ADD and ADHD. Case studies have shown that the therapeutic benefits of methylphenidate can be potentiated by the addition of a Receptor Switcher, such as ULDN, NAC, MSM or magnesium sulfate. Alternatively, ALC can be combined with these Receptor Switchers to create a relatively safe and effective treatment for ADD and ADHD, even for children.

Finally, there is evidence to suggest that ULDN has a synergistic effect through this $G_i$ metabolic process in addition to its function as a Receptor Switcher, making ULDN a particularly powerful agent in all cotreatment formulations. Similarly, certain multi-function agents, such as tramadol, have particularly potent therapeutic effects in these novel pharmaceutical formulations since they function as both Exogenous Opioids and Synergistic Enhancers. Therefore, given their relative potency in cotreatment formulations, ULDN, tramadol, and roflumilast are preferred agents in formulations for certain indications. At the same time, over-the-counter agents, such as NAC, gingko biloba, and white willow bark, would be useful as non-prescription formulations.

For certain embodiments of this invention, the preferred Synergistic Enhancer is a selective serotonin reuptake inhibitor (SSRI) or a selective norepinephrine reuptake inhibitor (SNRI). While dose ranges of SSRI and SNRI agents vary, cases studies demonstrate an SSRI and SNRI sparing effect when using cotreatment formulations, which, in turn, concomitantly reduces SSRI/SNRI negative side effects.

For certain embodiments of this invention, the preferred Synergistic Enhancer is escitalopram oxalate. Preferred dosing for specific for escitalopram oxalate in these formulations will depend on the particular indication and the outcome of further clinical trials. In general, dosing is expected to be in the conventional clinical range or lower, and will be sufficient to safely and effectively treat Distress Dysfunction. While dose ranges of escitalopram oxalate will vary, related cases studies have demonstrated an analogous active agent sparing effect when using cotreatment formulations, which, in turn, concomitantly reduces negative side effects often associated with this agent.

For certain embodiments of this invention, the preferred Synergistic Enhancer is venlafaxine. Preferred dosing for specific for venlafaxine in these formulations will depend on the particular indication and the outcome of further clinical trials. In general, dosing is expected to be in the conventional clinical range or lower, and will be sufficient to safely and effectively treat Distress Dysfunction. While dose ranges of venlafaxine will vary, related cases studies have demonstrated an analogous active agent sparing effect when using cotreatment formulations, which, in turn, concomitantly reduces negative side effects often associated with this agent.

For certain embodiments of this invention, the preferred Synergistic Enhancer is fluoxetine. Preferred dosing for specific for fluoxetine in these formulations will depend on the particular indication and the outcome of further clinical trials. In general, dosing is expected to be in the conventional clinical range or lower, and will be sufficient to safely and effectively treat Distress Dysfunction. While dose ranges of fluoxetine will vary, related cases studies have demonstrated an analogous active agent sparing effect when using cotreatment formulations, which, in turn, concomitantly reduces negative side effects often associated with this agent.

For certain embodiments of this invention, the preferred Synergistic Enhancer is citalopram. Preferred dosing for specific for citalopram in these formulations will depend on the particular indication and the outcome of further clinical trials. In general, dosing is expected to be in the conventional clinical range or lower, and will be sufficient to safely and effectively treat Distress Dysfunction. While dose ranges of citalopram will vary, related cases studies have demonstrated an analogous active agent sparing effect when using cotreatment formulations, which, in turn, concomitantly reduces negative side effects often associated with this agent.

For certain embodiments of this invention, the preferred Synergistic Enhancer is paroxetine. Preferred dosing for specific for paroxetine in these formulations will depend on the particular indication and the outcome of further clinical trials. In general, dosing is expected to be in the conventional clinical range or lower, and will be sufficient to safely and effectively treat Distress Dysfunction. While dose ranges of paroxetine will vary, related cases studies have demonstrated an analogous active agent sparing effect when using cotreatment formulations, which, in turn, concomitantly reduces negative side effects often associated with this agent.

For certain embodiments of this invention, the preferred Synergistic Enhancer is a non-steroidal anti-inflammatory drug (NSAID).

For certain embodiments of this invention, the preferred Synergistic Enhancer is acetaminophen. Successful preliminary trials and case studies have been done with about 100-about 500 mg daily, though higher or lower doses may be effective for certain formulations or indications. In other embodiments of the invention, the daily dosage of acetaminophen is selected from the group consisting of about 1, about 10, about 20, about 30, about 40, about 50, about 60, about 70, about 80, about 90, about 100, about 110, about 120, about 130, about 140, about 150, about 160, about 170, about 180, about 190, about 200, about 210, about 220, about 230, about 240, about 250, about 260, about 270, about 280, about 290, about 300, about 325, about 350, about 375, about 400, about 425, about 450, about 475, about 500, about 525, about 550, about 575, about 600, about 625, about 650, about 675, about 700, about 725, about 750, about 775, about 800, about 850, about 900, about 100, or about 1000 mg.

For certain embodiments of this invention, the preferred Synergistic Enhancer is white willow bark. Successful preliminary trials and case studies have been done with about 50-about 500 mg daily, though higher or lower doses may be effective for certain formulations or indications. In other embodiments of the invention, the daily dosage of white willow bark is selected from the group consisting of about 1, 10, about 20, about 30, about 40, about 50, about 60, about 70, about 80, about 90, about 100, about 110, about 120, about 130, about 140, about 150, about 160, about 170, about 180, about 190, about 200, about 210, about 220, about 230, about 240, about 250, about 260, about 270, about 280, about 290, about 300, about 325, about 350, about 375, about 400, about 425, about 450, about 475, about 500, about 525, about 550, about 575, about 600, about 625, about 650, about 675, about 700, about 725, about 750, about 775, or about 800 mg.

For certain embodiments of this invention, the preferred Synergistic Enhancer is aspirin. Successful preliminary trials and case studies have been done with about 50-about 250 mg daily, though higher or lower doses may be effective for certain formulations or indications. In other embodiments of the invention, the daily dosage of aspirin is selected from the group consisting of about 1, about 10, about 20, about 30, about 40, about 50, about 60, about 70, about 80, about 90, about 100, about 110, about 120, about 130, about 140, about 150, about 160, about 170, about 180, about 190, about 200, about 210, about 220, about 230, about 240, about 250, about 260, about 270, about 280, about 290, about 300, about 325, about 350, about 375, about 400, about 425, about 450, about 475, or about 500 mg.

For certain embodiments of this invention, the preferred Synergistic Enhancer is ibuprofen. Successful preliminary trials and case studies have been done with about 100-about 800 mg daily, though higher or lower doses may be effective for certain formulations or indications. In other embodiments of the invention, the daily dosage of ibuprofen is selected from the group consisting of about 1, about 10, about 20, about 30, about 40, about 50, about 60, about 70, about 80, about 90, about 100, about 110, about 120, about 130, about 140, about 150, about 160, about 170, about 180, about 190, about 200, about 210, about 220, about 230, about 240, about 250, about 260, about 270, about 280, about 290, about 300, about 325, about 350, about 375, about 400, about 425, about 450, about 475, about 500, about 525, about 550, about 575, about 600, about 625, about 650, about 675, about 700, about 725, about 750, about 775, about 800 mg, about 825, about 850, about 875, about 900, about 925, about 950, about 975, or about 1000 mg.

For certain embodiments of this invention, the preferred Synergistic Enhancer is celecoxib. Preferred dosing for celecoxib is about 50-about 500 mg, though in our novel formulations, lower doses may be effective. Further testing will be necessary to maximize therapeutic dosage. In other embodiments of the invention, the daily dosage of celecoxib is selected from the group consisting of about 1, about 10, about 20, about 30, about 40, about 50, about 60, about 70, about 80, about 90, about 100, about 110, about 120, about 130, about 140, about 150, about 160, about 170, about 180, about 190, about 200, about 210, about 220, about 230, about 240, about 250, about 260, about 270, about 280, about 290, about 300, about 325, about 350, about 375, about 400, about 425, about 450, about 475, about 500, about 525, about 550, about 575, about 600, about 625, about 650, about 675, about 700, about 725, about 750, about 775, about 800 mg, about 825, about 850, about 875, about 900, about 925, about 950, about 975, or about 1000 mg.

For certain embodiments of this invention, the preferred Synergistic Enhancer is tramadol. Successful preliminary trials and case studies have been done with about 10-about 50 mg daily, though higher or lower doses may be effective for certain formulations or indications. In other embodiments of the invention, the daily dosage of tramadol is selected from the group consisting of about 0.1, about 1, about 2, about 3, about 4, about 5, about 6, about 7, about 8, about 9, about 10, about 15, about 20, about 25, about 30, about 35, about 40, about 45, about 50, about 55, about 60, about 65, about 70, about 75, about 80, about 85, about 90, about 95, or about 100 mg.

For certain embodiments of this invention, the preferred Synergistic Enhancer is an amino acid.

For certain embodiments of this invention, the preferred Synergistic Enhancer is tryptophan. Successful preliminary case studies have been done with about 100-about 500 mg daily, though higher or lower doses may be effective for certain formulations or indications. In other embodiments of the invention, the daily dosage of tryptophan is selected from the group consisting of about 10, about 20, about 30, about 40, about 50, about 60, about 70, about 80, about 90, about 100, about 110, about 120, about 130, about 140, about 150, about 160, about 170, about 180, about 190, about 200, about 210, about 220, about 230, about 240, about 250, about 260, about 270, about 280, about 290, about 300, about 325, about 350, about 375, about 400, about 425, about 450, about 475, about 500, about 525, about 550, about 575, about 600, about 625, about 650, about 675, about 700, about 725, about 750, about 775, about 800 mg, about 825, about 850, about 875, about 900, about 925, about 950, about 975, or about 1000 mg.

For certain embodiments of this invention, the preferred Synergistic Enhancer is 5HTP. Successful preliminary case studies have been done with about 50-about 150 mg daily, though higher or lower doses may be effective for certain formulations or indications. In other embodiments of the invention, the daily dosage of 5HTP is selected from the group consisting of about 1, about 10, about 20, about 30, about 40, about 50, about 60, about 70, about 80, about 90, about 100, about 110, about 120, about 130, about 140, about 150, about 160, about 170, about 180, about 190, about 200, about 210, about 220, about 230, about 240, about 250, about 260, about 270, about 280, about 290, about 300, or about 400 mg.

For certain embodiments of this invention, the preferred Synergistic Enhancer is L-tyrosine. Successful preliminary case studies have been done with about 100-about 800 mg daily, though higher or lower doses may be effective for certain formulations or indications. In other embodiments of the invention, the daily dosage of L-tyrosine is selected from the group consisting of about 10, about 20, about 30, about 40, about 50, about 60, about 70, about 80, about 90, about 100, about 110, about 120, about 130, about 140, about 150, about 160, about 170, about 180, about 190, about 200, about 210, about 220, about 230, about 240, about 250, about 260, about 270, about 280, about 290, about 300, about 325, about 350, about 375, about 400, about 425, about 450, about 475, about 500, about 525, about 550, about 575, about 600, about 625, about 650, about 675, about 700, about 725, about 750, about 775, about 800 mg, about 825, about 850, about 875, about 900, about 925, about 950, about 975, about 1000, or about 1250 mg.

For certain embodiments of this invention, the preferred Synergistic Enhancer is taurine. Successful case studies have been done with about 100-about 800 mg daily, though higher or lower doses may be effective for certain formulations or indications. In other embodiments of the invention, the daily dosage of taurine is selected from the group consisting of about 10, about 20, about 30, about 40, about 50, about 60, about 70, about 80, about 90, about 100, about 110, about 120, about 130, about 140, about 150, about 160, about 170, about 180, about 190, about 200, about 210, about 220, about 230, about 240, about 250, about 260, about 270, about 280, about 290, about 300, about 325, about 350, about 375, about 400, about 425, about 450, about 475, about 500, about 525, about 550, about 575, about 600, about 625, about 650, about 675, about 700, about 725, about 750, about 775, about 800 mg, about 825, about 850, about 875, about 900, about 925, about 950, about 975, about 1000, about 1250, or about 1500 mg.

For certain embodiments of this invention, the preferred Synergistic Enhancer is s-adenosyl-methionine (SAMe). Successful case studies have been done with about 200-about 400 mg daily, though higher or lower doses may be effective for certain formulations or indications. In other embodiments of the invention, the daily dosage of SAM-e is selected from the group consisting of about 10, about 20, about 30, about 40, about 50, about 60, about 70, about 80, about 90, about 100, about 110, about 120, about 130, about 140, about 150, about 160, about 170, about 180, about 190, about 200, about 210, about 220, about 230, about 240, about 250, about 260, about 270, about 280, about 290, about 300, about 325, about 350, about 375, about 400, about 425, about 450, about 475, about 500, about 525, about 550, about 575, about 600, about 625, about 650, about 675, about 700, about 800, about 900, or about 1000 mg.

For certain embodiments of this invention, the preferred Synergistic Enhancer is GABA, particularly PharmaGABA. Successful case studies have been done with about 200-about 400 mg daily, though higher or lower doses may be effective for certain formulations or indications. In other embodiments of the invention, the daily dosage of GABA or PharmaGABA is selected from the group consisting of about 10, about 20, about 30, about 40, about 50, about 60, about 70, about 80, about 90, about 100, about 110, about 120, about 130, about 140, about 150, about 160, about 170, about 180, about 190, about 200, about 210, about 220, about 230, about 240, about 250, about 260, about 270, about 280, about 290, about 300, about 325, about 350, about 375, about 400, about 425, about 450, about 475, about 500, about 525, about 550, about 575, about 600, about 625, about 650, about 675, about 700, about 800, about 900, or about 1000 mg For certain embodiments of this invention, the preferred Synergistic Enhancer is acetyl-L-carintine (ALC). Successful case studies have been done with about 100-about 1000 mg. Further studies will be needed to specify the most effective dosage for particular conditions and age groups. In other embodiments of the invention, the daily dosage of ALC is selected from the group consisting of about 10, about 20, about 30, about 40, about 50, about 60, about 70, about 80, about 90, about 100, about 110, about 120, about 130, about 140, about 150, about 160, about 170, about 180, about 190, about 200, about 210, about 220, about 230, about 240, about 250, about 260, about 270, about 280, about 290, about 300, about 325, about 350, about 375, about 400, about 425, about 450, about 475, about 500, about 525, about 550, about 575, about 600, about 625, about 650, about 675, about 700, about 800, about 900, or about 1000 mg For certain embodiments of this invention, the preferred Synergistic Enhancer is methylphenidate. Successful case studies have been done with about 10-30 mg. Further studies will be needed to specify the most effective dosage for particular conditions and age groups. In other embodiments of the invention, the daily dosage of methylphenidate is selected from the group consisting of about 0.1, about 1, about 2, about 3, about 4, about 5, about 6, about 7, about 8, about 9, about 10, about 15, about 20, about 25, about 30, about 35, about 40, about 45, about 50, about 55, about 60, about 65, about 70, about 75, about 80, about 85, about 90, about 95, or about 100 mg.

For certain embodiments of this invention, the preferred Synergistic Enhancer is cannabis, and all forms and derivatives of cannabis. Preferred dosing for cannabis in these formulations will depend on the particular form and derivative, and will be sufficient to safely and effectively treat Distress Dysfunction.

For certain embodiments of this invention, the preferred Synergistic Enhancer is menthol. Preferred dosing for menthol in these formulations will depend on the particular form and derivative, and will be sufficient to safely and effectively treat Distress Dysfunction.

For certain embodiments of this invention, the preferred Synergistic Enhancer is myhhr. Successful treatment of Distress Dysfunction has used formulations that have included about 200-about 1000 mg. Preferred dosing for myhhr in these formulations will depend on the particular form and derivative, and will be sufficient to safely and effectively treat Distress Dysfunction. In other embodiments of the invention, the daily dosage of myhhr is selected from the group consisting of about 10, about 20, about 30, about 40, about 50, about 60, about 70, about 80, about 90, about 100, about 110, about 120, about 130, about 140, about 150, about 160, about 170, about 180, about 190, about 200, about 210, about 220, about 230, about 240, about 250, about 260, about 270, about 280, about 290, about 300, about 325, about 350, about 375, about 400, about 425, about 450, about 475, about 500, about 525, about 550, about 575, about 600, about 625, about 650, about 675, about 700, about 725, about 750, about 775, about 800 mg, about 825, about 850, about 875, about 900, about 925, about 950, about 975, about 1000, or about 1250 mg.

For certain embodiments of this invention, the preferred Synergistic Enhancer is boswellia. Successful treatment of Distress Dysfunction has used formulations that have included about 100-about 800 mg. Preferred dosing for boswellia in these formulations will depend on the particular form and derivative, and will be sufficient to safely and effectively treat Distress Dysfunction. derivative, and will be sufficient to safely and effectively treat Distress Dysfunction. In other embodiments of the invention, the daily dosage of boswellia is selected from the group consisting of about 10, about 20, about 30, about 40, about 50, about 60, about 70, about 80, about 90, about 100, about 110, about 120, about 130, about 140, about 150, about 160, about 170, about 180, about 190, about 200, about 210, about 220, about 230, about 240, about 250, about 260, about 270, about 280, about 290, about 300, about 325, about 350, about 375, about 400, about 425, about 450, about 475, about 500, about 525, about 550, about 575, about 600, about 625, about 650, about 675, about 700, about 725, about 750, about 775, about 800 mg, about 825, about 850, about 875, about 900, about 925, about 950, about 975, or about 1000 mg.

For certain embodiments of this invention, the preferred Synergistic Enhancer is a vitamin or mineral. Successful treatment of Distress Dysfunction has used formulations that have included conventional daily doses of folic acid (about 5-about 40 mg), Vitamin B-12 (about 0.25-about 1 mg), and pyridoxical 5 phosphate (about 0.25-about 1 mg). Preferred dosing for vitamins and minerals in these formulations will depend on the particular agents, and will be sufficient to safely and effectively treat Distress Dysfunction.

E. Exemplary Commercial Formulations and Application

There is evidence to suggest that ULDN and VLDN have a synergistic effect through the $G_i$ metabolic process in addition to its function as a Receptor Switcher, making ULDN and VLDN particularly powerful agents in all cotreatment formulations. Similarly, certain multi-function agents, such as tramadol, have particularly potent therapeutic effects in these novel pharmaceutical formulations since they function as both Exogenous Opioids and Synergistic Enhancers. Tramadol has the added advantage of not being listed by the FDA as a controlled substance. Therefore, given their relative potency in cotreatment formulations, ULDN, VLDN, tramadol, and rofiumilast, are preferred agents in formulations for certain indications. Celecoxib has the added advantage of being both an Endorpin and a Synergistic Enhancer. At the same time, over-the-counter agents, such as NAC, MSM, magnesium sulfate, guarana, gingko biloba, caffeine, white willow bark, ibuprofen, acetaminophen, SAMe, and specific amino acids, such as glutamic acid, GABA, and 5HTP, are useful in non-prescription formulations.

This invention teaches a wide variety of exemplary cotreatment formulations for a comprehensive set of symptoms, conditions, and disorders, defined as Distress Dysfunction within this patent, all of which are based on the novel principles and specific combinations of agents discovered by the process depicted in this patent. Specific agents, combinations of agents, and dose ranges for many of these discoveries are described in within the Detailed Description of the Invention and Examples sections. Given the underlying common neurophysiological imbalances for Distress Dysfunction, many of the formulations discovered by this invention have clinical efficacy for a wide variety of symptoms, conditions, and disorders. However, we have found that certain formulations may have particular effectiveness for specific conditions. Therefore, the following is a list of exemplary indications and dosing with regard to potential commercial applications of this invention. While certain daily dosage examples are suggested below for purposes of illustration (oral administration, unless otherwise noted), potential dose ranges as well as modes of administration are described in more detail elsewhere in this patent.

1. Emotional Distress (e.g., Excessive Worries, Fears, Irritability, Anger, Agitation)

ULDN (about 1-about 125 μg)+Roflumilast (about 1-about 50 μg);

VLDN (about 125-about 500 μg)+Roflumilast (about 1-about 50 μg);

ULDN (about 1-about 125 μg)+Ginkgo Biloba (about 40-about 240 mg);

VLDN (about 125-about 500 μg)+Ginkgo Biloba (about 40-about 240 mg);

ULDN (about 1-about 125 μg)+Glutamic Acid (about 25-about 100 mg);

VLDN (about 125-about 500 μg)+Glutamic Acid (about 25-about 100 mg);

ULDN (about 1-about 125 μg)+Guarana (about 50-about 500 mg);

VLND (about 125-about 500 μg)+Guarana (about 50-about 500 mg);

ULDN (about 1-about 125 μg)+Caffeine (about 25-about 200 mg);

VLDN (about 125-about 500 μg)+Caffeine (about 25-about 200 mg);

ULDN (about 1-about 125 μg)+PharmaGABA (about 100-about 1000 mg);

VLDN (about 125-about 500 μg)+PharmaGABA (about 100-about 1000 mg);

ULDN (about 1-about 125 μg)+5HTP (about 50-about 300 mg);

VLDN (about 125-about 500 μg)+5HTP (about 50-about 300 mg);

ULDN (about 1-about 125 μg)+Tyrosone (about 250-about 1000 mg);

VLDN (about 125-about 500 μg)+Tyrosone (about 250-about 1000 mg);

ULDN (about 1-about 125 μg)+SAMe (about 200-about 1000 mg);

VLDN (about 125-about 500 μg)+SAMe (about 200-about 1000 mg);

ULDN (about 1-about 125 μg)+DLPA (about 200-about 1200 mg);

VLDN (about 125-about 500 μg)+DLPA (about 200-about 1200 mg);

NAC (about 400-about 1200 mg)+Ginkgo Biloba (40-about 240 mg);

NAC (about 400-about 1200 mg)+Glutamic Acid (about 25-about 100 mg);

NAC (about 400-about 100 mg)+Guarana (about 50-about 500 mg);

NAC (about 400-about 1200 mg)+Caffeine (about 25-about 200 mg);

NAC (about 400-about 1200 mg)+Roflumilast (about 1-about 50 μg);

NAC (about 400-about 1200 mg)+PharmaGABA (about 100-about 1000 mg);

NAC (about 400-about 1200 mg)+5HTP (about 50-about 300 mg);

NAC (about 400-about 1200 mg)+Tyrosone (about 250-about 1000 mg);

NAC (about 400-about 1200 mg)+SAMe (about 200-about 1000 mg);

NAC (about 400-about 1200 mg)+DLPA (about 200-about 1200 mg);

MSM (about 100-about 800 mg)+Ginkgo Biloba (about 40-about 240 mg);

MSM (about 100-about 800 mg)+Glutamic Acid (about 25-about 100 mg);

MSM (about 100-about 800 mg)+Guarana (about 50-about 500 mg);

MSM (about 100-about 800 mg)+Caffeine (about 25-about 100 mg);

MSM (about 100-about 800 mg)+Roflumilast (about 1-about 50 µg);
MSM (about 100-about 800 mg)+PharmaGABA (about 100-about 1000 mg);
MSM (about 100-about 800 mg)+5HTP (about 50-about 300 mg);
MSM (about 100-about 800 mg)+Tyrosone (about 250-about 1000 mg);
MSM (about 100-about 800 mg)+SAMe (about 200-about 1000 mg);
MSM (about 100-about 800 mg)+DLPA (about 200-about 1200 mg);
Magnesium Sulfate (about 100-about 800 mg)+Ginkgo Biloba (about 40-about 240 mg);
Magnesium Sulfate (about 100-about 800 mg)+Glutamic Acid (about 25-about 100 mg);
Magnesium Sulfate (about 100-about 800 mg)+Guarana (about 50-about 500 mg);
Magnesium Sulfate (about 100-about 800 mg)+Caffeine (about 25-about 100 mg);
Magnesium Sulfate (about 100-about 800 mg)+Roflumilast (about 1-about 50 µg);
Magnesium Sulfate (about 100-about 800 mg)+PharmaGABA (about 100-about 1000 mg);
Magnesium Sulfate (about 100-about 800 mg)+5HTP (about 50-about 300 mg);
Magnesium Sulfate (about 100-about 800 mg)+Tyrosone (about 250-about 1000 mg);
Magnesium Sulfate (about 100-about 800 mg)+SAMe (about 200-about 1000 mg);
Magnesium Sulfate (about 100-about 800 mg)+DLPA (about 200-about 1200 mg);
NAC (about 400-about 1200 mg)+Ginkgo Biloba (about 40-about 240 mg)+PharmaGABA (about 100-about 1000 mg);
NAC (about 400-about 1200 mg)+Ginkgo Biloba (about 40-about 240 mg)+Glutamic Acid (about 25-about 100 mg);
NAC (about 400-about 1200 mg)+Gingko Biloba (about 40-about 240 mg)+Taurine (about 250-about 1000 mg);
NAC (about 400-about 1200 mg)+Ginkgo Biloba (about 40-about 240 mg)+Tyrosone (about 250-about 1000 mg);
NAC (about 400-about 1200 mg)+Ginkgo Biloba (about 40-about 240 mg)+Glycine (about 200-about 800 mg);
NAC (about 400-about 1200 mg)+Ginkgo Biloba (about 40-about 240 mg)+5HTP (about 50-about 300 mg);
NAC (about 400-about 1200 mg)+Ginkgo Biloba (about 40-about 240 mg)+SAMe (about 200-about 1000 mg);
NAC (about 400-about 1200 mg)+Ginkgo Biloba (about 40-about 240 mg)+DLPA (about 200-about 1200 mg);
NAC (about 400-about 1200 mg)+Ginkgo Biloba (about 40-about 240 mg)+PharmaGABA (50-800 mg)+5HTP (about 50-about 200 mg);
NAC (about 400-about 1200 mg)+Ginkgo Biloba (about 40-about 240 mg)+SAMe (about 200-about 1000 mg)+5HTP (about 50-about 300 mg);
NAC (about 400-about 1200 mg)+Guarana (about 50-about 500 mg)+PharmaGABA (about 100-about 1000 mg);
NAC (about 400-about 1200 mg)+Guarana (about 50-about 500 mg)+Taurine (about 250-about 1000 mg);
NAC (about 400-about 1200 mg)+Guarana (about 50-about 500 mg)+Tyrosone (about 250-about 1000 mg);
NAC (about 400-about 1200 mg)+Guarana (about 50-about 500 mg)+Glycine (about 200-about 800 mg);
NAC (about 400-about 1200 mg)+Guarana (about 50-about 500 mg)+5HTP (about 50-about 300 mg);
NAC (about 400-about 1200 mg)+Guarana (about 50-about 500 mg)+SAMe (about 200-about 1000 mg);
NAC (about 400-about 1200 mg)+Guarana (about 50-about 500 mg)+DLPA (about 200-about 1200 mg);
NAC (about 400-about 1200 mg)+Guarana (about 50-about 500 mg)+PharmaGABA (about 50-about 800 mg)+5HTP (about 50-about 200 mg);
NAC (about 400-about 1200 mg)+Glutamic Acid (about 25-about 100 mg)+PharmaGABA (about 100-about 1000 mg);
NAC (about 400-about 1200 mg)+Glutamic Acid (about 25-about 100 mg)+Taurine (about 250-about 1000 mg);
NAC (about 400-about 1200 mg)+Glutamic Acid (about 25-about 100 mg)+Tyrosone (about 250-about 1000 mg);
NAC (about 400-about 1200 mg)+Glutamic Acid (about 25-about 100 mg)+Glycine (about 200-about 800 mg);
NAC (about 400-about 1200 mg)+Glutamic Acid (about 25-about 100 mg)+5HTP (about 50-about 300 mg);
NAC (about 400-about 1200 mg)+Glutamic Acid (about 25-about 100 mg)+SAMe (about 200-about 1000 mg);
NAC (about 400-about 1200 mg)+Glutamic Acid (about 25-about 100 mg)+DLPA (about 200-about 1200 mg);
NAC (about 400-about 1200 mg)+Glutamic Acid (about 25-about 100 mg)+PharmaGABA (about 50-about 800 mg)+5HTP (about 50-about 200 mg);
Magnesium Sulfate (about 100-about 800 mg)+Ginkgo Biloba (about 40-about 240 mg)+PharmaGABA (about 100-about 1000 mg);
Magnesium Sulfate (about 100-about 800 mg)+Ginkgo Biloba (about 40-about 240 mg)+Guarana (about 50-about 500 mg);
Magnesium Sulfate (about 100-about 800 mg)+Ginkgo Biloba (about 40-about 240 mg)+Glutamic Acid (about 25-about 100 mg);
Magnesium Sulfate (about 100-about 800 mg)+Gingko Biloba (about 40-about 240 mg)+Taurine (about 250-about 1000 mg);
Magnesium Sulfate (about 100-about 800 mg)+Gingko Biloba (about 40-about 240 mg)+Tyrosone (about 250-about 1000 mg);
Magnesium Sulfate (about 100-about 800 mg)+Gingko Biloba (about 40-about 240 mg)+Glycine (about 200-about 800 mg);
Magnesium Sulfate (about 100-about 800 mg)+Ginkgo Biloba (about 40-about 240 mg)+5HTP (about 50-about 300 mg);
Magnesium Sulfate (about 100-about 800 mg)+Ginkgo Biloba (about 40-about 240 mg)+SAMe (about 200-about 1000 mg);
Magnesium Sulfate (about 100-about 800 mg)+Ginkgo Biloba (about 40-about 240 mg)+DLPA (about 200-about 1200 mg);
Magnesium Sulfate (about 100-about 800 mg)+Ginkgo Biloba (about 40-about 240 mg)+PharmaGABA (about 50-about 800 mg)+5HTP (about 50-about 200 mg);
Magnesium Sulfate (about 100-about 800 mg)+Guarana (about 50-about 500 mg)+SAMe (about 200-about 1000 mg)+5HTP (about 50-about 300 mg);
Magnesium Sulfate (about 100-about 800 mg)+Guarana (about 50-about 500 mg)+PharmaGABA (about 100-about 1000 mg);
Magnesium Sulfate (about 100-about 800 mg)+Guarana (about 50-about 500 mg)+Taurine (about 250-about 1000 mg);
Magnesium Sulfate (about 100-about 800 mg)+Guarana (about 50-about 500 mg)+Tyrosone (about 250-about 1000 mg);
Magnesium Sulfate (about 100-about 800 mg)+Guarana (about 50-about 500 mg)+Glycine (about 200-about 800 mg);

Magnesium Sulfate (about 100-about 800 mg)+Guarana (about 50-about 500 mg)+5HTP (about 50-about 300 mg);
Magnesium Sulfate (about 100-about 800 mg)+Guarana (about 50-about 500 mg)+SAMe (about 200-about 1000 mg);
Magnesium Sulfate (about 100-about 800 mg)+Guarana (about 50-about 500 mg)+DLPA (about 200-about 1200 mg);
Magnesium Sulfate (about 100-about 800 mg)+Guarana (about 50-about 500 mg)+PharmaGABA (about 50-about 800 mg)+5HTP (about 50-about 200 mg);
Magnesium Sulfate (about 100-about 800 mg)+Ginkgo Biloba (about 40-about 240 mg)+SAMe (about 200-about 1000 mg)+5HTP (about 50-about 300 mg);
Magnesium Sulfate (about 100-about 800 mg)+Glutamic Acid (about 25-about 100 mg)+PharmaGABA (about 100-about 1000 mg);
Magnesium Sulfate (about 100-about 800 mg)+Glutamic Acid (about 25-about 100 mg)+Taurine (about 250-about 1000 mg);
Magnesium Sulfate (about 100-about 800 mg)+Glutamic Acid (about 25-about 100 mg)+Tyrosone (about 250-about 1000 mg);
Magnesium Sulfate (about 100-about 800 mg)+Glutamic Acid (about 25-about 100 mg)+Glycine (about 200-about 800 mg);
Magnesium Sulfate (about 100-about 800 mg)+Glutamic Acid (about 25-about 100 mg)+5HTP (about 50-about 300 mg);
Magnesium Sulfate (about 100-about 800 mg)+Glutamic Acid (about 25-about 100 mg)+SAMe (about 200-about 1000 mg);
Magnesium Sulfate (about 100-about 800 mg)+Glutamic Acid (about 25-about 100 mg)+DLPA (about 200-about 1200 mg);
Magnesium Sulfate (about 100-about 800 mg)+Glutamic Acid (about 25-about 100 mg)+PharmaGABA (about 50-about 800 mg)+5HTP (about 50-about 200 mg);
MSM (about 100-about 800 mg)+Ginkgo Biloba (about 40-about 240 mg)+PharmaGABA (about 100-about 1000 mg);
MSM (about 100-about 800 mg)+Ginkgo Biloba (about 40-about 240 mg)+Glutamic Acid (about 25-about 100 mg);
MSM (about 100-about 800 mg)+Gingko Biloba (about 40-about 240 mg)+Taurine (about 250-about 1000 mg);
MSM (about 100-about 800 mg)+Gingko Biloba (about 40-about 240 mg)+Tyrosone (about 250-about 1000 mg);
MSM (about 100-about 800 mg)+Gingko Biloba (about 40-about 240 mg)+Glycine (about 200-about 800 mg);
MSM (about 100-about 800 mg)+Ginkgo Biloba (about 40-about 240 mg)+5HTP (about 50-about 300 mg);
MSM (about 100-about 800 mg)+Ginkgo Biloba (about 40-about 240 mg)+SAMe (about 200-about 1000 mg);
MSM (about 100-about 800 mg)+Ginkgo Biloba (about 40-about 240 mg)+DLPA (about 200-about 1200 mg);
MSM (about 100-about 800 mg)+Ginkgo Biloba (about 40-about 240 mg)+PharmaGABA (about 50-about 800 mg)+5HTP (about 50-about 200 mg);
MSM (about 100-about 800 mg)+Ginkgo Biloba (about 40-about 240 mg)+SAMe (about 200-about 1000 mg)+5HTP (about 50-about 300 mg);
MSM (about 100-about 800 mg)+Guarana (about 50-about 500 mg)+PharmaGABA (about 100-about 1000 mg);
MSM (about 100-about 800 mg)+Guarana (about 50-about 500 mg)+Taurine (about 250-about 1000 mg);
MSM (about 100-about 800 mg)+Guarana (about 50-about 500 mg)+Tyrosone (about 250-about 1000 mg);
MSM (about 100-about 800 mg)+Guarana (about 50-about 500 mg)+Glycine (about 200-about 800 mg);
MSM (about 100-about 800 mg)+Guarana (about 50-about 500 mg)+5HTP (about 50-about 300 mg);
MSM (about 100-about 800 mg)+Guarana (about 50-about 500 mg)+SAMe (about 200-about 1000 mg);
MSM (about 100-about 800 mg)+Guarana (about 50-about 500 mg)+DLPA (about 200-about 1200 mg);
MSM (about 100-about 800 mg)+Guarana (about 50-about 500 mg)+PharmaGABA (about 50-about 800 mg)+5HTP (about 50-about 200 mg);
MSM (about 100-about 800 mg)+Glutamic Acid (about 25-about 100 mg)+PharmaGABA (about 100-about 1000 mg);
MSM (about 100-about 800 mg)+Glutamic Acid (about 25-about 100 mg)+Taurine (about 250-about 1000 mg);
MSM (about 100-about 800 mg)+Glutamic Acid (about 25-about 100 mg)+Tyrosone (about 250-about 1000 mg);
MSM (about 100-about 800 mg)+Glutamic Acid (about 25-about 100 mg)+Glycine (about 200-about 800 mg);
MSM (about 100-about 800 mg)+Glutamic Acid (about 25-about 100 mg)+5HTP (about 50-about 300 mg);
MSM (about 100-about 800 mg)+Glutamic Acid (about 25-about 100 mg)+SAMe (about 200-about 1000 mg);
MSM (about 100-about 800 mg)+Glutamic Acid (about 25-about 100 mg)+DLPA (about 200-about 1200 mg);
MSM (about 100-about 800 mg)+Glutamic Acid (about 25-about 100 mg)+PharmaGABA (about 50-about 800 mg)+5HTP (about 50-about 200 mg);
ULDN (about 1-about 125 µg)+Ginkgo Biloba (about 40-about 240 mg)+PharmaGABA (about 100-about 1000 mg);
VLDN (about 125-about 500 µg)+Ginkgo Biloba (about 40-about 240 mg)+PharmaGABA (about 100-about 1000 mg);
ULDN (about 1-about 125 µg)+Ginkgo Biloba (about 40-about 240 mg)+Glutamic Acid (about 25-about 100 mg);
VLDN (about 125-about 500 µg)+Ginkgo Biloba (about 40-about 240 mg)+Glutamic Acid (about 25-about 100 mg);
ULDN (about 1-about 125 µg)+Gingko Biloba (about 40-about 240 mg)+Taurine (about 250-about 1000 mg);
VLDN (about 125-about 500 µg)+Gingko Biloba (about 40-about 240 mg)+Taurine (about 250-about 1000 mg);
ULDN (about 1-about 125 µg)+Ginkgo Biloba (about 40-about 240 mg)+Tyrosone (about 250-about 1000 mg);
VLDN (about 125-about 500 µg)+Ginkgo Biloba (about 40-about 240 mg)+Tyrosone (about 250-about 1000 mg);
ULDN (about 1-about 125 µg)+Gingko Biloba (about 40-about 240 mg)+Glycine (about 200-about 800 mg);
VLDN (about 125-about 500 µg)+Gingko Biloba (about 40-about 240 mg)+Glycine (about 200-about 800 mg);
ULDN (about 1-about 125 µg)+Ginkgo Biloba (about 40-about 240 mg)+5HTP (about 50-about 300 mg);
VLDN (about 125-about 500 µg)+Ginkgo Biloba (about 40-about 240 mg)+5HTP (about 50-about 300 mg);
ULDN (about 1-about 125 µg)+Ginkgo Biloba (about 40-about 240 mg)+SAMe (about 200-about 1000 mg);
VLDN (about 125-about 500 µg)+Ginkgo Biloba (about 40-about 240 mg)+SAMe (about 200-about 1000 mg);
ULDN (about 1-about 125 µg)+Ginkgo Biloba (about 40-about 240 mg)+DLPA (about 200-about 1200 mg);
VLDN (about 125-about 500 µg)+Ginkgo Biloba (about 40-about 240 mg)+DLPA (about 200-about 1200 mg);
ULDN (about 1-about 125 µg)+Ginkgo Biloba (about 40-about 240 mg)+PharmaGABA (about 50-about 800 mg)+5HTP (about 50-about 200 mg);
VLDN (about 125-about 500 µg)+Ginkgo Biloba (about 40-about 240 mg)+PharmaGABA (about 50-about 800 mg)+5HTP (about 50-about 200 mg);

ULDN (about 1-about 125 µg)+Ginkgo Biloba (about 40-about 240 mg)+SAMe (about 200-about 1000 mg)+5HTP (about 50-about 300 mg);

VLDN (about 125-about 500 µg)+Ginkgo Biloba (about 40-about 240 mg)+SAMe (about 200-about 1000 mg)+5HTP (about 50-about 300 mg);

ULDN (about 1-about 125 µg)+Guarana (about 50-about 500 mg)+PharmaGABA (about 100-about 1000 mg);

VLDN (about 125-about 500 µg)+Guarana (about 50-about 500 mg)+PharmaGABA (about 100-about 1000 mg);

ULDN (about 1-about 125 µg)+Guarana (about 50-about 500 mg)+Taurine (about 250-about 1000 mg);

VLDN (about 125-about 500 µg)+Guarana (about 50-about 500 mg)+Taurine (about 250-about 1000 mg);

ULDN (about 1-about 125 µg)+Guarana (about 50-about 500 mg)+Tyrosone (about 250-about 1000 mg);

VLDN (about 125-about 500 µg)+Guarana (about 50-about 500 mg)+Tyrosone (about 250-about 1000 mg);

ULDN (about 1-about 125 µg)+Guarana (about 50-about 500 mg)+Glycine (about 200-about 800 mg);

VLDN (about 125-about 500 µg) Guarana (about 50-about 500 mg)+Glycine (about 200-about 800 mg);

ULDN (about 1-about 125 µg)+Guarana (about 50-about 500 mg)+5HTP (about 50-about 300 mg);

VLDN (about 125-about 500 µg)+Guarana (about 50-about 500 mg)+5HTP (about 50-about 300 mg);

ULDN (about 1-about 125 µg)+Guarana (about 50-about 500 mg)+SAMe (about 200-about 1000 mg);

VLDN (about 125-about 500 µg)+Guarana (about 50-about 500 mg)+SAMe (about 200-about 1000 mg);

ULDN (about 1-about 125 µg)+Guarana (about 50-about 500 mg)+DLPA (about 200-about 1200 mg);

VLDN (about 125-about 500 µg)+Guarana (about 50-about 500 mg)+DLPA (about 200-about 1200 mg);

ULDN (about 1-about 125 µg)+Guarana (about 50-about 500 mg)+PharmaGABA (about 50-about 800 mg)+5HTP (about 50-about 200 mg);

VLDN (about 125-about 500 µg)+Guarana (about 50-about 500 mg)+PharmaGABA (about 50-about 800 mg)+5HTP (about 50-about 200 mg);

ULDN (about 1-about 125 µg)+Glutamic Acid (about 25-about 100 mg)+PharmaGABA (about 100-about 1000 mg);

VLDN (about 125-about 500 µg)+Glutamic Acid (about 25-about 100 mg)+PharmaGABA (about 100-about 1000 mg);

ULDN (about 1-about 125 µg)+Glutamic Acid (about 25-about 100 mg)+Taurine (about 250-about 1000 mg);

VLDN (about 125-about 500 µg)+Glutamic Acid (about 25-about 100 mg)+Taurine (about 250-about 1000 mg);

ULDN (about 1-about 125 µg)+Glutamic Acid (about 25-about 100 mg)+Tyrosone (about 250-about 1000 mg);

VLDN (about 125-about 500 µg)+Glutamic Acid (about 25-about 100 mg)+Tyrosone (about 250-about 1000 mg);

ULDN (about 1-about 125 µg)+Glutamic Acid (about 25-about 100 mg)+Glycine (about 200-about 800 mg);

VLDN (about 125-about 500 µg)+Glutamic Acid (about 25-about 100 mg)+Glycine (about 200-about 800 mg);

ULDN (about 1-about 125 µg)+Glutamic Acid (about 25-about 100 mg)+5HTP (about 50-about 300 mg);

VLDN (about 125-about 500 µg)+Glutamic Acid (about 25-about 100 mg)+5HTP (about 50-about 300 mg);

ULDN (about 1-about 125 µg)+Glutamic Acid (about 25-about 100 mg)+SAMe (about 200-about 1000 mg);

VLDN (about 125-about 500 µg)+Glutamic Acid (about 25-about 100 mg)+SAMe (about 200-about 1000 mg);

ULDN (about 1-about 125 µg)+Glutamic Acid (about 25-about 100 mg)+DLPA (about 200-about 1200 mg);

VLDN (about 125-about 500 µg)+Glutamic Acid (about 25-about 100 mg)+DLPA (about 200-about 1200 mg);

ULDN (about 1-about 125 µg)+Glutamic Acid (about 25-about 100 mg)+PharmaGABA (about 50-about 800 mg)+5HTP (about 50-about 200 mg);

VLDN (about 125-about 500 µg)+Glutamic Acid (about 25-about 100 mg)+PharmaGABA (about 50-about 800 mg)+5HTP (about 50-about 200 mg);

MSM (about 300-about 1500 mg)+NAC (about 300-about 1200 mg)+Guarana (about 50-about 500 mg)+Ginkgo Biloba (about 300-about 1200 mg)+P5P (about 5-about 50 mg)+B-12 (about 0.1-about 1 mg)+Folic Acid (about 0.1-about 1 mg); or MSM (about 300-about 1500 mg)+NAC (about 300-about 1200 mg)+Guarana (about 50-about 500 mg)+Ginkgo Biloba (about 300-about 1200 mg)+5HTP (about 25-about 200 mg)+PharmaGABA (about 50-about 500 mg)+SAMe (about 50-about 500 mg)+P5P (about 5-about 50 mg)+B-12 (about 0.1-about 1 mg)+Folic Acid (about 0.1-about 1 mg).

2. Mood and Anxiety Disorders (e.g. Depression, Dysthymia, Low Energy, Insomnia, Anxiety, Panic, Phobias, OCD)

[Formulations for Emotional Distress in Addition to:]

NAC (about 400-about 1200 mg)+Escitalopram (about 10-about 60 mg);

ULDN (about 1-about 125 µg)+Escitalopram (about 10-about 60 mg);

NAC (about 400-about 1200 mg)+Fluoxetine (about 20-about 80 mg);

ULDN (about 1-about 125 µg)+Fluoxetine (about 20-about 80 mg);

NAC (about 400-about 1200 mg)+Citalopram (about 20-about 80 mg);

ULDN (about 1-about 125 µg)+Citalopram (about 20-about 80 mg);

NAC (about 400-about 1200 mg)+Venlafaxine (about 50-about 250 mg);

ULDN (about 1-about 125 µg)+Venlafaxine (about 50-about 250 mg);

VLDN (about 125-about 500 µg)+Escitalopram (about 10-about 60 mg);

VLDN (about 125-about 500 µg)+Fluoxetine (about 20-about 80 mg);

VLDN (about 125-about 500 µg)+Citalopram (about 20-about 80 mg);

VLDN (about 125-about 500 µg)+Venlafaxine (about 50-about 250 mg);

MSM (about 100-about 800 mg)+Escitalopram (about 10-about 60 mg);

MSM (about 100-about 800 mg)+Fluoxetine (about 20-about 80 mg);

MSM (100-800 mg)+Citalopram (about 20-about 80 mg);

MSM (about 100-about 800 mg)+Venlafaxine (about 50-about 250 mg);

NAC (about 400-about 1200 mg)+Ginkgo Biloba (about 40-about 240 mg)+Escitalopram (about 10-about 60 mg);

ULDN (about 1-about 125 µg)+Roflumilast (about 1-about 50 µg)+Escitalopram (about 10-about 60 mg);

NAC (about 400-about 1200 mg)+Ginkgo Biloba (about 40-about 240 mg)+Fluoxetine (about 20-about 80 mg);

ULDN (about 1-about 125 µg)+oflumilast (about 1-about 50 µg)+Fluoxetine (about 20-about 80 mg);

NAC (about 400-about 1200 mg)+Ginkgo Biloba (about 40-about 240 mg)+Citalopram (about 20-about 80 mg);

ULDN (about 1-about 125 μg)+Roflumilast (about 1-about 50 μg)+Citalopram (about 20-about 80 mg);
NAC (about 400-about 1200 mg)+Ginkgo Biloba (about 40-about 240 mg)+Venlafaxine (about 50-about 250 mg);
ULDN (about 1-about 125 μg)+Roflumilast (about 1-about 50 μg)+Venlafaxine (about 50-about 250 mg);
VLDN (about 125-about 500 μg)+Roflumilast (about 1-about 50 μg)+Escitalopram (about 10-about 60 mg);
VLDN (about 125-about 500 μg)+Roflumilast (about 1-about 50 μg)+Fluoxetine (about 20-about 80 mg);
VLDN (about 125-about 500 μg)+Roflumilast (about 1-about 50 μg)+Citalopram (about 20-about 80 mg);
VLDN (about 125-about 500 μg)+Roflumilast (about 1-about 50 μg)+Venlafaxine (about 50-about 250 mg);
MSM (about 100-about 800 mg)+Ginkgo Biloba (about 40-about 240 mg)+Escitalopram (about 10-about 60 mg);
MSM (about 100-about 800 mg)+Ginkgo Biloba (about 40-about 240 mg)+Fluoxetine (about 20-about 80 mg);
MSM (100-800 mg)+Ginkgo Biloba (about 40-about 240 mg)+Citalopram (about 20-about 80 mg);
MSM (about 100-about 800 mg)+Ginkgo Biloba (about 40-about 240 mg)+Venlafaxine (about 50-about 250 mg);
NAC (about 400-about 1200 mg)+Glutamic Acid (about 50-about 250 mg)+Escitalopram (about 10-about 60 mg);
ULDN (about 1-about 125 μg)+Guarana (about 50-about 500 mg)+Escitalopram (about 10-about 60 mg);
NAC (about 400-about 1200 mg)+Guarana (about 50-about 500 mg)+Fluoxetine (about 20-about 80 mg);
ULDN (about 1-about 125 μg)+Guarana (about 50-about 500 mg)+Fluoxetine (about 20-about 80 mg);
NAC (about 400-about 1200 mg)+Guarana (about 50-about 500 mg)+Citalopram (about 20-about 80 mg);
ULDN (about 1-about 125 μg)+Guarana (about 50-about 500 mg)+Citalopram (about 20-about 80 mg);
NAC (about 400-about 1200 mg)+Guarana (about 50-about 500 mg)+Venlafaxine (about 50-about 250 mg);
ULDN (about 1-about 125 μg)+Guarana (about 50-about 500 mg)+Venlafaxine (about 50-about 250 mg);
VLDN (about 125-about 500 μg)+Guarana (about 50-about 500 mg)+Escitalopram (about 10-about 60 mg);
VLDN (about 125-about 500 μg)+Guarana (about 50-about 500 mg)+Fluoxetine (about 20-about 80 mg);
VLDN (about 125-about 500 μg)+Guarana (about 50-about 500 mg)+Citalopram (about 20-about 80 mg);
VLDN (about 125-about 500 μg)+Guarana (about 50-about 500 mg)+Venlafaxine (about 50-about 250 mg);
MSM (about 100-about 800 mg)+Guarana (about 50-about 500 mg)+Escitalopram (about 10-about 60 mg);
MSM (about 100-about 800 mg)+Guarana (about 50-about 500 mg)+Fluoxetine (about 20-about 80 mg);
MSM (about 100-about 800 mg)+Guarana (about 50-about 500 mg)+Citalopram (about 20-about 80 mg);
MSM (about 100-about 800 mg)+Guarana (about 50-about 500 mg)+Venlafaxine (about 50-about 250 mg) ULDN (about 1-about 125 μg)+Glutamic Acid (about 50-about 250 mg)+Escitalopram (about 10-about 60 mg);
NAC (about 400-about 1200 mg)+Glutamic Acid (about 50-about 250 mg)+Fluoxetine (about 20-about 80 mg);
ULDN (about 1-about 125 μg)+Glutamic Acid (about 50-about 250 mg)+Fluoxetine (about 20-about 80 mg);
NAC (about 400-about 1200 mg)+Glutamic Acid (about 50-about 250 mg)+Citalopram (about 20-about 80 mg);
ULDN (about 1-about 125 μg)+Glutamic Acid (about 50-about 250 mg)+Citalopram (about 20-about 80 mg);
NAC (about 400-about 1200 mg)+Glutamic Acid (about 50-about 250 mg)+Venlafaxine (about 50-about 250 mg);
ULDN (about 1-about 125 μg)+Glutamic Acid (about 50-about 250 mg)+Venlafaxine (about 50-about 250 mg);
VLDN (about 125-about 500 μg)+Glutamic Acid (about 50-about 250 mg)+Escitalopram (about 10-about 60 mg);
VLDN (about 125-about 500 μg)+Glutamic Acid (about 50-about 250 mg)+Fluoxetine (about 20-about 80 mg);
VLDN (about 125-about 500 μg)+Glutamic Acid (about 50-about 250 mg)+Citalopram (about 20-about 80 mg);
VLDN (about 125-about 500 μg)+Glutamic Acid (about 50-about 250 mg)+Venlafaxine (about 50-about 250 mg);
MSM (about 100-about 800 mg)+Glutamic Acid (about 50-about 250 mg)+Escitalopram (about 10-about 60 mg);
MSM (about 100-about 800 mg)+Glutamic Acid (about 50-about 250 mg)+Fluoxetine (about 20-about 80 mg);
MSM (about 100-about 800 mg)+Glutamic Acid (about 50-about 250 mg)+Citalopram (about 20-about 80 mg);
MSM (about 100-about 800 mg)+Glutamic Acid (about 50-about 250 mg)+Venlafaxine (about 50-about 250 mg);
NAC (about 400-about 1200 mg)+Escitalopram (about 10-about 60 mg)+PharmaGABA (about 100-about 1000 mg);
ULDN (about 1-about 125 μg)+Escitalopram (about 10-about 60 mg)+PharmaGABA (about 100-about 1000 mg);
NAC (about 400-about 1200 mg)+Fluoxetine (about 20-about 80 mg)+PharmaGABA (about 100-about 1000 mg);
ULDN (about 1-about 125 μg)+Fluoxetine (about 20-about 80 mg)+PharmaGABA (about 100-about 1000 mg);
NAC (about 400-about 1200 mg)+Citalopram (about 20-about 80 mg)+PharmaGABA (about 100-about 1000 mg);
ULDN (about 1-about 125 μg)+Citalopram (about 20-about 80 mg)+PharmaGABA (about 100-about 1000 mg);
NAC (about 400-about 1200 mg)+Venlafaxine (about 50-about 250 mg)+PharmaGABA (about 100-about 1000 mg);
ULDN (about 1-about 125 μg)+Venlafaxine (about 50-about 250 mg)+PharmaGABA (about 100-about 1000 mg);
VLDN (about 125-about 500 μg)+Escitalopram (about 10-about 60 mg)+PharmaGABA (about 100-about 1000 mg);
VLDN (about 125-about 500 μg)+Fluoxetine (about 20-about 80 mg)+PharmaGABA (about 100-about 1000 mg);
VLDN (about 125-about 500 μg)+Citalopram (about 20-about 80 mg)+PharmaGABA (about 100-about 1000 mg);
VLDN (about 125-about 500 μg)+Venlafaxine (about 50-about 250 mg)+PharmaGABA (about 100-about 1000 mg);
MSM (about 100-about 800 mg)+Escitalopram (about 10-about 60 mg)+PharmaGABA (about 100-about 1000 mg);
MSM (about 100-about 800 mg)+Fluoxetine (about 20-about 80 mg)+PharmaGABA (about 100-about 1000 mg);
MSM (about 100-about 800 mg)+Citalopram (about 20-about 80 mg)+PharmaGABA (about 100-about 1000 mg);
MSM (about 100-about 800 mg)+Venlafaxine (about 50-about 250 mg)+PharmaGABA (about 100-about 1000 mg);
NAC (about 400-about 1200 mg)+Escitalopram (about 10-about 60 mg)+SAMe (about 200-about 1000 mg);
ULDN (about 1-about 125 μg)+Escitalopram (about 10-about 60 mg)+SAMe (about 200-about 1000 mg);
NAC (about 400-about 1200 mg)+Fluoxetine (about 20-about 80 mg)+SAMe (about 200-about 1000 mg);
ULDN (about 1-about 125 μg)+Fluoxetine (about 20-about 80 mg)+SAMe (about 200-about 1000 mg);
NAC (about 400-about 1200 mg)+Citalopram (about 20-about 80 mg)+SAMe (about 200-about 1000 mg);
ULDN (about 1-about 125 μg)+Citalopram (about 20-about 80 mg)+SAMe (about 200-about 1000 mg);
NAC (about 400-about 1200 mg)+Venlafaxine (about 50-about 250 mg)+SAMe (about 200-about 1000 mg);

ULDN (about 1-about 125 µg)+Venlafaxine (about 50-about 250 mg)+SAMe (about 200-about 1000 mg);
VLDN (about 125-about 500 µg)+Escitalopram (about 10-about 60 mg)+SAMe (about 200-about 1000 mg);
VLDN (about 125-about 500 µg)+Fluoxetine (about 20-about 80 mg)+SAMe (about 200-about 1000 mg);
VLDN (about 125-about 500 µg)+Citalopram (about 20-about 80 mg)+SAMe (about 200-about 1000 mg);
VLDN (about 125-about 500 µg)+Venlafaxine (about 50-about 250 mg)+SAMe (about 200-about 1000 mg);
MSM (about 100-about 800 mg)+Escitalopram (about 10-about 60 mg)+SAMe (about 200-about 1000 mg);
MSM (about 100-about 800 mg)+Fluoxetine (about 20-about 80 mg)+SAMe (about 200-about 1000 mg);
MSM (about 100-about 800 mg)+Citalopram (about 20-about 80 mg)+SAMe (about 200-about 1000 mg); or
MSM (about 100-about 800 mg)+Venlafaxine (about 50-about 250 mg+SAMe (about 200-about 1000 mg).

3. Attention and Concentration
(e.g., ADD, ADHD, Distractibility)
[Formulations for Emotional Distress and Mood and Anxiety Disorders in Addition to:]

ULDN (about 1-about 125 µg)+Actyl-L-Carnitine (about 250-about 1000 mg);
ULDN (about 1-about 125 µg)+Ginkgo Biloba (about 80-about 360 mg)+Actyl-L-Carnitine (about 250-about 1000 mg);
ULDN (about 1-about 125 µg)+Guarana (about 50-about 500 mg)+Actyl-L-Carnitine (about 250-about 1000 mg);
ULDN (about 1-about 125 µg)+Glutamic Acid (about 50-about 500 mg)+Actyl-L-Carnitine (about 250-about 1000 mg);
VLDN (about 125-about 500 µg)+Actyl-L-Carnitine (about 250-about 1000 mg);
VLDN (about 125-about 500 µg)+Ginkgo Biloba (about 80-about 360 mg)+Actyl-L-Carnitine (about 250-about 1000 mg);
VLDN (about 125-about 500 µg)+Guarana (about 50-about 500 mg)+Actyl-L-Carnitine (about 250-about 1000 mg);
VLDN (about 125-about 500 µg)+Glutamic Acid (about 50-about 500 mg)+Actyl-L-Carnitine (about 250-about 1000 mg);
NAC (about 400-about 1200 mg)+Actyl-L-Carnitine (about 250-about 1000 mg);
NAC (about 400-about 1200 mg)+Ginkgo Biloba (about 80-about 360 mg)+Actyl-L-Carnitine (about 250-about 1000 mg);
NAC (about 400-about 1200 mg)+Guarana (about 50-about 500 mg)+Actyl-L-Carnitine (about 250-about 1000 mg);
NAC (about 400-about 1200 mg)+Glutamic Acid (about 50-about 500 mg)+Actyl-L-Carnitine (about 250-about 1000 mg);
Magnesium Sulfate (about 100-about 1000 mg)+Actyl-L-Carnitine (about 250-about 1000 mg);
Magnesium Sulfate (about 100-about 1000 mg)+Ginkgo Biloba (about 80-about 360 mg)+Actyl-L-Carnitine (about 250-about 1000 mg);
Magnesium Sulfate (about 100-about 1000 mg)+Guarana (about 50-about 500 mg)+Actyl-L-Carnitine (about 250-about 1000 mg);
Magnesium Sulfate (about 100-about 1000 mg)+Glutamic Acid (about 50-about 500 mg)+Actyl-L-Carnitine (about 250-about 1000 mg);
ULDN (about 1-about 125 µg)+Actyl-L-Carnitine (about 250-about 1000 mg)+SAMe (about 200-about 1000 mg);
ULDN (about 1-about 125 µg)+Ginkgo Biloba (about 80-about 360 mg)+Actyl-L-Carnitine (about 250-about 1000 mg)+SAMe (about 200-about 1000 mg);
ULDN (about 1-about 125 µg)+Guarana (about 50-about 500 mg)+Actyl-L-Carnitine (about 250-about 1000 mg))+SAMe (about 200-about 1000 mg);
ULDN (about 1-about 125 µg)+Glutamic Acid (about 50-about 500 mg)+Actyl-L-Carnitine (about 250-about 1000 mg)+SAMe (about 200-about 1000 mg);
VLDN (about 125-about 500 µg)+Actyl-L-Carnitine (about 250-about 1000 mg)+SAMe (about 200-about 1000 mg);
VLDN (about 125-about 500 µg)+Guarana (about 50-about 500 mg)+Actyl-L-Carnitine (about 250-about 1000 mg)+SAMe (about 200-about 1000 mg);
VLDN (about 125-about 500 µg)+Ginkgo Biloba (about 80-about 360 mg)+Actyl-L-Carnitine (about 250-about 1000 mg)+SAMe (about 200-about 1000 mg);
VLDN (about 125-about 500 µg)+Glutamic Acid (about 50-about 500 mg)+Actyl-L-Carnitine (about 250-about 1000 mg)+SAMe (about 200-about 1000 mg);
NAC (about 400-about 1200 mg)+Actyl-L-Carnitine (about 250-about 1000 mg)+SAMe (about 200-about 1000 mg);
NAC (about 400-about 1200 mg)+Ginkgo Biloba (about 80-about 360 mg)+Actyl-L-Carnitine (about 250-about 1000 mg)+SAMe (about 200-about 1000 mg);
NAC (about 400-about 1200 mg)+Guarana (about 50-about 500 mg)+Actyl-L-Carnitine (about 250-about 1000 mg)+SAMe (about 200-about 1000 mg);
NAC (about 400-about 1200 mg)+Glutamic Acid (about 50-about 500 mg)+Actyl-L-Carnitine (about 250-about 1000 mg)+SAMe (about 200-about 1000 mg);
Magnesium Sulfate (about 100-about 1000 mg)+Actyl-L-Carnitine (about 250-about 1000 mg)+SAMe (about 200-about 1000 mg);
Magnesium Sulfate (about 100-about 1000 mg)+Ginkgo Biloba (about 80-about 360 mg)+Actyl-L-Carnitine (about 250-about 1000 mg)+SAMe (about 200-about 1000 mg);
Magnesium Sulfate (about 100-about 1000 mg)+Guarana (about 50-about 500 mg)+Actyl-L-Carnitine (about 250-about 1000 mg)+SAMe (about 200-about 1000 mg);
Magnesium Sulfate (about 100-about 1000 mg)+Glutamic Acid (about 50-about 500 mg)+Actyl-L-Carnitine (about 250-about 1000 mg)+SAMe (about 200-about 1000 mg);
MSM (about 100-about 1000 mg)+Actyl-L-Carnitine (about 250-about 1000 mg);
MSM (about 100-about 1000 mg)+Ginkgo Biloba (about 80-about 360 mg)+Actyl-L-Carnitine (about 250-about 1000 mg);
MSM (about 100-about 1000 mg)+Guarana (about 50-about 500 mg)+Actyl-L-Carnitine (about 250-about 1000 mg);
MSM (about 100-about 1000 mg)+Glutamic Acid (about 50-about 500 mg)+Actyl-L-Carnitine (about 250-about 1000 mg);
MSM (about 100-about 1000 mg)+Actyl-L-Carnitine (about 250-about 1000 mg)+SAMe (about 200-about 1000 mg);
MSM (about 100-about 1000 mg)+Ginkgo Biloba (about 80-about 360 mg)+Actyl-L-Carnitine (about 250-about 1000 mg)+SAMe (about 200-about 1000 mg);
MSM (about 100-about 1000 mg)+Guarana (about 50-about 500 mg)+Actyl-L-Carnitine (about 250-about 1000 mg)+SAMe (about 200-about 1000 mg);
MSM (about 100-about 1000 mg)+NAC (400-1600 mg)+Guarana (about 50-about 500 mg)+Ginkgo Biloba (about 80-about 360 mg)+Actyl-L-Carnitine (about 250-about 1000 mg);
MSM (about 100-about 1000 mg)+NAC (400-1600 mg)+Magnesium Sulfate (about 100-about 1000 mg)+Guarana (about 50-about 500 mg)+Ginkgo Biloba (about 80-about 360 mg)+Actyl-L-Carnitine (about 250-about 1000 mg);
MSM (about 100-about 1000 mg)+NAC (about 400-about 1600 mg)+Guarana (about 50-about 500 mg)+Ginkgo Biloba (about 80-about 360 mg)+Actyl-L-Carnitine (about 250-about 1000 mg)+SAMe (about 200-about 1000 mg);
MSM (about 100-about 1000 mg)+Glutamic Acid (about 50-about 500 mg)+Actyl-L-Carnitine (about 250-about 1000 mg)+SAMe (about 200-about 1000 mg);
ULDN (about 1-about 125 μg)+Methylphenidate (about 10-about 60 mg);
ULDN (about 1-about 125 μg)+Ginkgo Biloba (about 80-about 360 mg)+Methylphenidate (about 10-about 60 mg);
ULDN (about 1-about 124 μg)+Glutamic Acid (about 50-about 500 mg)+Methylphenidate (about 10-about 60 mg);
VLDN (about 125-about 500 μg)+Methylphenidate (about 10-about 60 mg);
VLDN (about 125-about 500 μg)+Ginkgo Biloba (about 80-about 360 mg)+Methylphenidate (about 10-about 60 mg);
VLDN (about 125-about 500 μg)+Guarana (about 50-about 500 mg)+Methylphenidate (about 10-about 60 mg);
VLDN (about 125-about 500 μg)+Glutamic Acid (about 50-about 500 mg)+Methylphenidate (about 10-about 60 mg);
NAC (about 400-about 1200 mg)+Methylphenidate (about 10-about 60 mg);
NAC (about 400-about 1200 mg)+Ginkgo Biloba (about 80-about 360 mg)+Methylphenidate (about 10-about 60 mg);
NAC (about 400-about 1200 mg)+Guarana (about 50-about 500 mg)+Methylphenidate (about 10-about 60 mg);
NAC (about 400-about 1200 mg)+Glutamic Acid (about 50-about 500 mg)+Methylphenidate (about 10-about 60 mg);
Magnesium Sulfate (about 100-about 1000 mg)+Methylphenidate (about 10-about 60 mg);
Magnesium Sulfate (about 100-about 1000 mg)+Ginkgo Biloba (about 80-about 360 mg)+Methylphenidate (about 10-about 60 mg);
Magnesium Sulfate (about 100-about 1000 mg)+Guarana (about 50-about 500 mg)+Methylphenidate (about 10-about 60 mg);
Magnesium Sulfate (about 100-about 1000 mg)+Glutamic Acid (about 50-about 500 mg)+Methylphenidate (about 10-about 60 mg);
ULDN (about 1-about 125 μg)+Methylphenidate (about 10-about 60 mg)+SAMe (about 200-about 1000 mg);
ULDN (about 1-about 125 μg)+Ginkgo Biloba (about 80-about 360 mg)+Methylphenidate (about 10-about 60 mg)+SAMe (about 200-about 1000 mg);
ULDN (about 1-about 125 μg)+Guarana (about 50-about 500 mg)+Methylphenidate (about 10-about 60 mg)+SAMe (about 200-about 1000 mg);
ULDN (about 1-about 125 μg)+Glutamic Acid (about 50-about 500 mg)+Methylphenidate (about 10-about 60 mg)+SAMe (about 200-about 1000 mg);
VLDN (about 125-about 500 μg)+Methylphenidate (about 10-about 60 mg)+SAMe (about 200-about 1000 mg);
VLDN (about 125-about 500 μg)+Ginkgo Biloba (about 80-about 360 mg)+Methylphenidate (about 10-about 60 mg)+SAMe (about 200-about 1000 mg);
VLDN (about 125-about 500 μg)+Guarana (about 50-about 500 mg)+Methylphenidate (about 10-about 60 mg)+SAMe (about 200-about 1000 mg);
VLDN (about 125-about 500 μg)+Glutamic Acid (about 50-about 500 mg)+Methylphenidate (about 10-about 60 mg)+SAMe (about 200-about 1000 mg);
NAC (about 400-about 1200 mg)+Methylphenidate (about 10-about 60 mg)+SAMe (about 200-about 1000 mg);
NAC (about 400-about 1200 mg)+Ginkgo Biloba (about 80-about 360 mg)+Methylphenidate (about 10-about 60 mg)+SAMe (about 200-about 1000 mg);
NAC (about 400-about 1200 mg)+Guarana (about 50-about 500 mg)+Methylphenidate (about 10-about 60 mg)+SAMe (about 200-about 1000 mg);
NAC (about 400-about 1200 mg)+Glutamic Acid (about 50-about 500 mg)+Methylphenidate (about 10-about 60 mg)+SAMe (about 200-about 1000 mg);
Magnesium Sulfate (about 100-about 1000 mg)+Methylphenidate (about 10-about 60 mg)+SAMe (about 200-about 1000 mg);
Magnesium Sulfate (about 100-about 1000 mg)+Ginkgo Biloba (about 80-about 360 mg)+Methylphenidate (about 10-about 60 mg)+SAMe (about 200-about 1000 mg);
Magnesium Sulfate (about 100-about 1000 mg)+Guarana (about 50-about 500 mg)+Methylphenidate (about 10-about 60 mg)+SAMe (about 200-about 1000 mg);
Magnesium Sulfate (about 100-about 1000 mg)+Glutamic Acid (about 50-about 500 mg)+Methylphenidate (about 10-about 60 mg)+SAMe (about 200-about 1000 mg);
MSM (about 100-about 1000 mg)+Methylphenidate (about 10-about 60 mg);
MSM (about 100-about 1000 mg)+Ginkgo Biloba (about 80-about 360 mg)+Methylphenidate (about 10-about 60 mg);
MSM (about 100-about 1000 mg)+Guarana (about 50-about 500 mg)+Methylphenidate (about 10-about 60 mg);
MSM (about 100-about 1000 mg)+Glutamic Acid (about 50-about 500 mg)+Methylphenidate (about 10-about 60 mg);
MSM (about 100-about 1000 mg)+Actyl-L-Carnitine (about 250-about 1000 mg)+SAMe (about 200-about 1000 mg);
MSM (about 100-about 1000 mg)+Ginkgo Biloba (about 80-about 360 mg)+Actyl-L-Carnitine (about 250-about 1000 mg)+SAMe (about 200-about 1000 mg);
MSM (about 100-about 1000 mg)+Guarana (about 50-about 500 mg)+Methylphenidate (about 10-about 60 mg)+SAMe (about 200-about 1000 mg); or
MSM (about 100-about 1000 mg)+Glutamic Acid (about 50-about 500 mg)+Methylphenidate (about 10-about 60 mg)+SAMe (about 200-about 1000 mg).

4. Sexual Problems (e.g., PE, ED, Low Arousal)

[Formulations for Emotional Distress in Addition to:]

NAC (about 400-about 1200 mg)+Tadalafil (about 2.5-about 25 mg);
ULDN (about 1-about 125 μg)+Tadalafil (about 2.5-about 25 mg);
NAC (about 400-about 1200 mg)+Sildenafil Citrate (about 25-about 100 mg);
ULDN (about 1-about 125 μg)+Sildenafil Citrate (about 25-about 100 mg);
NAC (about 400-about 1200 mg)+Vardenafil (about 2.5-about 25 mg);
ULDN (about 1-about 125 μg)+Vardenafil (about 2.5-about 25 mg);
NAC (about 400-about 1200 mg)+DHEA (about 10-about 75 mg);
ULDN (about 1-about 125 μg)+DHEA (about 10-about 75 mg);
VLDN (about 125-about 500 μg)+Tadalafil (about 2.5-about 25 mg);
VLDN (about 125-about 500 μg)+Sildenafil Citrate (about 25-about 100 mg);
VLDN (about 125-about 500 μg)+Vardenafil (about 2.5-about 25 mg);
VLDN (about 125-about 500 μg)+DHEA (about 10-about 75 mg);

MSM (about 100-about 800 mg)+Tadalafil (about 2.5-about 25 mg);
MSM (about 100-about 800 mg)+Sildenafil Citrate (about 25-about 100 mg);
MSM (100-800 mg)+Vardenafil (about 2.5-about 25 mg);
MSM (about 100-about 800 mg)+DHEA (about 10-about 75 mg);
NAC (about 400-about 1200 mg)+Ginkgo Biloba (about 40-about 240 mg)+Tadalafil (about 2.5-about 25 mg);
ULDN (about 1-about 125 µg)+Roflumilast (about 1-about 50 µg)+Tadalafil (about 2.5-about 25 mg);
NAC (about 400-about 1200 mg)+Ginkgo Biloba (about 40-about 240 mg)+Sildenafil Citrate (about 25-about 100 mg);
ULDN (about 1-about 125 µg)+Roflumilast (about 1-about 50+Sildenafil Citrate (about 25-about 100 mg);
NAC (about 400-about 1200 mg)+Ginkgo Biloba (about 40-about 240 mg)+Vardenafil (about 2.5-about 25 mg);
ULDN (about 1-about 125 µg)+Roflumilast (about 1-about 50+Vardenafil (about 2.5-about 25 mg);
NAC (about 400-about 1200 mg)+Ginkgo Biloba (about 40-about 240 mg)+DHEA (about 10-about 75 mg);
ULDN (about 1-about 125 µg)+Roflumilast (about 1-about 50+DHEA (about 10-about 75 mg);
VLDN (about 125-about 500 µg)+Roflumilast (about 1-about 50+Tadalafil (about 2.5-about 25 mg);
VLDN (about 125-about 500 µg)+Roflumilast (about 1-about 50+Sildenafil Citrate (about 25-about 100 mg);
VLDN (about 125-about 500 µg)+Roflumilast (about 1-about 50+Vardenafil (about 2.5-about 25 mg);
VLDN (about 125-about 500 µg)+Roflumilast (about 1-about 50+DHEA (about 10-about 75 mg);
MSM (about 100-about 800 mg)+Ginkgo Biloba (about 40-about 240 mg)+Tadalafil (about 2.5-about 25 mg);
MSM (about 100-about 800 mg)+Ginkgo Biloba (about 40-about 240 mg)+Sildenafil Citrate (about 25-about 100 mg);
MSM (about 100-about 800 mg)+Ginkgo Biloba (about 40-about 240 mg)+Vardenafil (about 2.5-about 25 mg);
MSM (about 100-about 800 mg)+Ginkgo Biloba (about 40-about 240 mg)+DHEA (about 10-about 75 mg);
NAC (about 400-about 1200 mg)+Glutamic Acid (about 50-about 250 mg)+Tadalafil (about 2.5-about 25 mg);
ULDN (about 1-about 125 µg)+Guarana (about 50-about 500 mg)+Tadalafil (about 2.5-about 25 mg);
NAC (about 400-about 1200 mg)+Guarana (about 50-about 500 mg)+Sildenafil Citrate (about 25-about 100 mg);
ULDN (about 1-about 125 µg)+Guarana (about 50-about 500 mg)+Sildenafil Citrate (about 25-about 100 mg);
NAC (about 400-about 1200 mg)+Guarana (about 50-about 500 mg)+Vardenafil (about 2.5-about 25 mg)
ULDN (about 1-about 125 µg)+Guarana (about 50-about 500 mg)+Vardenafil (about 2.5-about 25 mg);
NAC (about 400-about 1200 mg)+Guarana (about 50-about 500 mg)+DHEA (about 10-about 75 mg);
ULDN (about 1-about 125 µg)+Guarana (about 50-about 500 mg)+Venlafaxine (about 50-about 250 mg);
VLDN (about 125-about 500 µg)+Guarana (about 50-about 500 mg)+Tadalafil (about 2.5-about 25 mg);
VLDN (about 125-about 500 µg)+Guarana (about 50-about 500 mg)+Sildenafil Citrate (about 25-about 100 mg);
VLDN (about 125-about 500 µg)+Guarana (about 50-about 500 mg)+Vardenafil (about 2.5-about 25 mg);
VLDN (about 125-about 500 µg)+Guarana (about 50-about 500 mg)+Venlafaxine (about 50-about 250 mg);
MSM (about 100-about 800 mg)+Guarana (about 50-about 500 mg)+Tadalafil (about 2.5-about 25 mg);
MSM (about 100-about 800 mg)+Guarana (about 50-about 500 mg)+Sildenafil Citrate (about 25-about 100 mg);
MSM (100-800 mg)+Guarana (about 50-about 500 mg)+Vardenafil (about 2.5-about 25 mg);
MSM (about 100-about 800 mg)+Guarana (about 50-about 500 mg)+DHEA (about 10-about 75 mg);
ULDN (about 1-about 125 µg)+Glutamic Acid (about 50-about 250 mg)+Tadalafil (about 2.5-about 25 mg);
NAC (about 400-about 1200 mg)+Glutamic Acid (about 50-about 250 mg)+Sildenafil Citrate (about 25-about 100 mg);
ULDN (about 1-about 125 µg)+Glutamic Acid (about 50-about 250 mg)+Sildenafil Citrate (about 25-about 100 mg);
NAC (about 400-about 1200 mg)+Glutamic Acid (about 50-about 250 mg)+Vardenafil (about 2.5-about 25 mg);
ULDN (about 1-about 125 µg)+Glutamic Acid (about 50-about 250 mg)+Vardenafil (about 2.5-about 25 mg);
NAC (about 400-about 1200 mg)+Glutamic Acid (about 50-about 250 mg)+DHEA (about 10-about 75 mg);
ULDN (about 1-about 125 µg)+Glutamic Acid (about 50-about 250 mg)+Venlafaxine (about 50-about 250 mg);
VLDN (about 125-about 500 µg)+Glutamic Acid (about 50-about 250 mg)+Tadalafil (about 2.5-about 25 mg);
VLDN (about 125-about 500 µg)+Glutamic Acid (about 50-about 250 mg)+Sildenafil Citrate (about 25-about 100 mg);
VLDN (about 125-about 500 µg)+Glutamic Acid (about 50-about 250 mg)+Vardenafil (about 2.5-about 25 mg);
VLDN (about 125-about 500 µg)+Glutamic Acid (about 50-about 250 mg)+Venlafaxine (about 50-about 250 mg);
MSM (about 100-about 800 mg)+Glutamic Acid (about 50-about 250 mg)+Tadalafil (about 2.5-about 25 mg);
MSM (about 100-about 800 mg)+Glutamic Acid (about 50-about 250 mg)+Sildenafil Citrate (about 25-about 100 mg);
MSM (100-800 mg)+Glutamic Acid (about 50-about 250 mg)+Vardenafil (about 2.5-about 25 mg);
MSM (about 100-about 800 mg)+Glutamic Acid (about 50-about 250 mg)+DHEA (about 10-about 75 mg);
NAC (about 400-about 1200 mg)+Tadalafil (about 2.5-about 25 mg)+PharmaGABA (about 100-about 1000 mg);
ULDN (about 1-about 125 µg)+Tadalafil (about 2.5-about 25 mg)+PharmaGABA (about 100-about 1000 mg);
NAC (about 400-about 1200 mg)+Sildenafil Citrate (about 25-about 100 mg)+PharmaGABA (about 100-about 1000 mg);
ULDN (about 1-about 125 µg)+Sildenafil Citrate (about 25-about 100 mg)+PharmaGABA (about 100-about 1000 mg);
NAC (about 400-about 1200 mg)+Vardenafil (about 2.5-about 25 mg)+PharmaGABA (about 100-about 1000 mg);
ULDN (about 1-about 125 µg)+Vardenafil (about 2.5-about 25 mg)+PharmaGABA (about 100-about 1000 mg);
NAC (about 400-about 1200 mg)+DHEA (about 10-about 75 mg)+PharmaGABA (about 100-about 1000 mg);
ULDN (about 1-about 125 µg)+DHEA (about 10-about 75 mg)+PharmaGABA (about 100-about 1000 mg);
VLDN (about 125-about 500 µg)+Tadalafil (about 2.5-about 25 mg)+PharmaGABA (about 100-about 1000 mg);
VLDN (about 125-about 500 µg)+Sildenafil Citrate (about 25-about 100 mg)+PharmaGABA (about 100-about 1000 mg);
VLDN (about 125-about 500 µg)+PharmaGABA (about 100-about 1000 mg);
VLDN (about 125-about 500 µg)+DHEA (about 10-about 75 mg)+PharmaGABA (about 100-about 1000 mg);

MSM (about 100-about 800 mg)+Tadalafil (about 2.5-about 25 mg)+PharmaGABA (about 100-about 1000 mg);
MSM (about 100-about 800 mg)+Sildenafil Citrate (about 25-about 100 mg)+PharmaGABA (about 100-about 1000 mg);
MSM (100-800 mg)+Vardenafil (about 2.5-about 25 mg)+PharmaGABA (about 100-about 1000 mg);
MSM (about 100-about 800 mg)+DHEA (about 10-about 75 mg)+PharmaGABA (about 100-about 1000 mg);
NAC (about 400-about 1200 mg)+Tadalafil (about 2.5-about 25 mg)+SAMe (about 200-about 1000 mg);
ULDN (about 1-about 125 µg)+Tadalafil (about 2.5-about 25 mg)+SAMe (about 200-about 1000 mg);
NAC (about 400-about 1200 mg)+Sildenafil Citrate (about 25-about 100 mg)+SAMe (about 200-about 1000 mg);
ULDN (about 1-about 125 µg)+Sildenafil Citrate (about 25-about 100 mg)+SAMe (about 200-about 1000 mg);
NAC (about 400-about 1200 mg)+Vardenafil (about 2.5-about 25 mg)+SAMe (about 200-about 1000 mg);
ULDN (about 1-about 125 µg)+Vardenafil (about 2.5-about 25 mg)+SAMe (about 200-about 1000 mg);
NAC (about 400-about 1200 mg)+DHEA (about 10-about 75 mg)+SAMe (about 200-about 1000 mg);
ULDN (about 1-about 125 µg)+DHEA (about 10-about 75 mg)+SAMe (about 200-about 1000 mg);
VLDN (about 125-about 500 µg)+Tadalafil (about 2.5-about 25 mg)+SAMe (about 200-about 1000 mg);
VLDN (about 125-about 500 µg)+Sildenafil Citrate (about 25-about 100 mg)+SAMe (about 200-about 1000 mg);
VLDN (about 125-about 500 µg)+Vardenafil (about 2.5-about 25 mg)+SAMe (about 200-about 1000 mg);
VLDN (about 125-about 500 µg)+DHEA (about 10-about 75 mg)+SAMe (about 200-about 1000 mg);
MSM (about 100-about 800 mg)+Tadalafil (about 2.5-about 25 mg)+SAMe (about 200-about 1000 mg);
MSM (about 100-about 800 mg)+Sildenafil Citrate (about 25-about 100 mg)+SAMe (about 200-about 1000 mg);
MSM (100-800 mg)+Vardenafil (about 2.5-about 25 mg)+SAMe (about 200-about 1000 mg); or
MSM (about 100-about 800 mg)+DHEA (about 10-about 75 mg)+SAMe (about 200-about 1000 mg).

5. Autistic Spectrum Disorders
  (e.g, Asberger's and Autism)
[Formulations for Emotional Distress, Anxiety and Mood Disorders, and Attention]

6. Addiction, Dependence, and Cravings
  (e.g., Drugs. Alcohol, Food, Behavior)
[Formulations for Emotional Distress and Mood and Anxiety Disorders in Addition to:]
ULDN (about 1-about 125 µg)+Roflumilast (about 1-about 50 µg);
ULDN (about 1-about 125 µg)+Ginkgo Biloba (about 40-about 240 mg)
ULDN (about 1-about 125 µg)+Guarana (about 50-about 500 mg);
ULDN (about 1-about 125 µg)+Glutamic Acid (about 25-about 100 mg);
ULDN (about 1-about 125 µg)+Caffeine (about 25-about 200 mg);
ULDN (about 1-about 125 µg)+PharmaGABA (about 100-about 1000 mg);
ULDN (about 1-about 125 µg)+5HTP (about 50-about 300 mg);
ULDN (about 1-about 125 µg)+Tyrosone (about 250-about 1000 mg);
ULDN (about 1-about 125 µg)+SAMe (about 200-about 1000 mg);
ULDN (about 1-about 125 µg)+DLPA (about 200-about 1200 mg);
ULDN (about 1-about 125 µg)+Ginkgo Biloba (about 40-about 240 mg)+PharmaGABA (about 100-about 1000 mg);
ULDN (about 1-about 124 µg)+Ginkgo Biloba (about 40-about 240 mg)+Glutamic Acid (about 25-about 100 mg);
ULDN (about 1-about 125 µg)+Gingko Biloba (about 40-about 240 mg)+Tyrosone (about 250-about 1000 mg);
ULDN (about 1-about 125 µg)+Gingko Biloba (about 40-about 240 mg)+Glycine (about 200-about 800 mg);
ULDN (about 1-about 124 µg)+Ginkgo Biloba (about 40-about 240 mg)+5HTP (about 50-about 300 mg);
ULDN (about 1-about 125 µg)+Gingko Biloba (about 40-about 240 mg)+SAMe (about 200-about 1000 mg);
ULDN (about 1-about 124 µg)+Ginkgo Biloba (about 40-about 240 mg)+DLPA (about 200-about 1200 mg);
ULDN (about 1-about 124 µg)+Ginkgo Biloba (about 40-about 240 mg)+PharmaGABA (about 50-about 800 mg)+5HTP (about 50-about 200 mg);
ULDN (about 1-about 125 µg)+Ginkgo Biloba (about 40-about 240 mg)+SAMe (about 200-about 1000 mg)+5HTP (about 50-about 300 mg);
ULDN (about 1-about 125 µg)+Guarana (about 50-about 500 mg)+PharmaGABA (about 100-about 1000 mg);
ULDN (about 1-about 125 µg)+Guarana (about 50-about 500 mg)+Taurine (about 250-about 1000 mg);
ULDN (about 1-about 125 µg)+Guarana (about 50-about 500 mg)+Tyrosone (about 250-about 1000 mg);
ULDN (about 1-about 125 µg)+Guarana (about 50-about 500 mg)+Glycine (about 200-about 800 mg);
ULDN (about 1-about 125 µg)+Guarana (about 50-about 500 mg)+5HTP (about 50-about 300 mg)
ULDN (about 1-about 125 µg)+Guarana (about 50-about 500 mg)+SAMe (about 200-about 1000 mg);
ULDN (about 1-about 125 µg)+Guarana (about 50-about 500 mg)+DLPA (about 200-about 1200 mg);
ULDN (about 1-about 125 µg)+Guarana (about 50-about 500 mg)+PharmaGABA (about 50-about 800 mg)+5HTP (about 50-about 200 mg);
ULDN (about 1-about 125 µg)+Glutamic Acid (about 25-about 100 mg)+PharmaGABA (about 100-about 1000 mg);
ULDN (about 1-about 125 µg) Glutamic Acid (about 25-about 100 mg)+Taurine (about 250-about 1000 mg);
ULDN (about 1-about 125 µg)+Glutamic Acid (about 25-about 100 mg)+Tyrosone (about 250-about 1000 mg);
ULDN (about 1-about 125 µg)+Glutamic Acid (about 25-about 100 mg)+Glycine (about 200-about 800 mg);
ULDN (about 1-about 125 µg)+Glutamic Acid (about 25-about 100 mg)+5HTP (about 50-about 300 mg);
ULDN (about 1-about 125 µg)+Glutamic Acid (about 25-about 100 mg)+SAMe (about 200-about 1000 mg);
ULDN (about 1-about 125 µg) Glutamic Acid (about 25-about 100 mg)+DLPA (about 200-about 1200 mg);
ULDN (about 1-about 125 µg)+Glutamic Acid (about 25-about 100 mg)+PharmaGABA (about 50-about 800 mg)+5HTP (about 50-about 200 mg);
VLDN (about 125-about 500 µg)+Roflumilast (about 1-about 50 µg); VLDN (about 125-about 500 µg)+Ginkgo Biloba (about 40-about 240 mg);
VLDN (about 125-about 500 µg)+Guarana (about 50-about 500 mg);
VLDN (about 125-about 500 µg)+Glutamic Acid (about 25-about 100 mg);
VLDN (about 125-about 500 µg)+Caffeine (about 25-about 200 mg);

VLDN (about 125-about 500 μg)+PharmaGABA (about 100-about 1000 mg);
VLDN (about 125-about 500 μg)+5HTP (about 50-about 300 mg);
VLDN (about 125-about 500 μg)+Tyrosone (about 250-about 1000 mg);
VLDN (about 125-about 250 μg)+sAMe (about 200-about 1000 mg);
VLDN (about 125-about 500 μg)+DLPA (about 200-about 1200 mg);
VLDN (about 125-about 500 μg)+Ginkgo Biloba (about 40-about 240 mg)+PharmaGABA (about 100-about 1000 mg);
VLDN (about 125-about 500 μg)+Ginkgo Biloba (about 40-about 240 mg)+Glutamic Acid (about 25-about 100 mg);
VLDN (about 125-about 500 μg)+Gingko Biloba (about 40-about 240 mg)+Tyrosone (about 250-about 1000 mg);
VLDN (about 125-about 500 μg)+Gingko Biloba (about 40-about 240 mg)+Glycine (about 200-about 800 mg);
VLDN (about 125-about 500 μg)+Ginkgo Biloba (about 40-about 240 mg)+5HTP (about 50-about 300 mg);
VLDN (about 125-about 500 μg)+Ginkgo Biloba (about 40-about 240 mg)+SAMe (about 200-about 1000 mg);
VLDN (about 125-about 500 μg)+Ginkgo Biloba (about 40-about 240 mg)+DLPA (about 200-about 1200 mg);
VLDN (about 125-about 500 μg)+Ginkgo Biloba (about 40-about 240 mg)+PharmaGABA (about 50-about 800 mg)+5HTP (about 50-about 200 mg);
VLDN (about 125-about 500 μg)+Ginkgo Biloba (about 40-about 240 mg)+SAMe (about 200-about 1000 mg)+5HTP (about 50-about 300 mg);
VLDN (about 125-about 500 μg)+Guarana (about 50-about 500 mg)+PharmaGABA (about 100-about 1000 mg);
VLDN (about 125-about 500 μg)+Guarana (about 50-about 500 mg)+Taurine (about 250-about 1000 mg);
VLDN (about 125-about 500 μg)+Guarana (about 50-about 500 mg)+Tyrosone (about 250-about 1000 mg);
VLDN (about 125-about 500 μg)+Guarana (about 50-about 500 mg)+Glycine (about 200-about 800 mg);
VLDN (about 125-about 500 μg)+Guarana (about 50-about 500 mg)+5HTP (about 50-about 300 mg);
VLDN (about 125-about 500 μg)+Guarana (about 50-about 500 mg)+SAMe (about 200-about 1000 mg);
VLDN (about 125-about 500 μg)+Guarana (about 50-about 500 mg)+DLPA (about 200-about 1200 mg);
VLDN (about 125-about 500 μg)+Guarana (about 50-about 500 mg)+PharmaGABA (about 50-about 800 mg)+5HTP (about 50-about 200 mg);
VLDN (about 125-about 500 μg)+Glutamic Acid (about 25-about 100 mg)+PharmaGABA (about 100-about 1000 mg);
VLDN (about 125-about 500 μg)+Glutamic Acid (about 25-about 100 mg)+Taurine (about 250-about 1000 mg);
VLDN (about 125-about 500 μg)+Glutamic Acid (about 25-about 100 mg)+Tyrosone (about 250-about 1000 mg);
VLDN (about 125-about 500 μg)+Glutamic Acid (about 25-about 100 mg)+Glycine (about 200-about 800 mg);
VLDN (about 125-about 500 μg)+Glutamic Acid (about 25-about 100 mg)+5HTP (about 50-about 300 mg);
VLDN (about 125-about 500 μg)+Glutamic Acid (about 25-about 100 mg)+SAMe (about 200-about 1000 mg);
VLDN (about 125-about 500 μg)+Glutamic Acid (about 25-about 100 mg)+DLPA (about 200-about 1200 mg);
VLDN (about 125-about 500 μg)+Glutamic Acid (about 25-about 100 mg)+PharmaGABA (50-800 mg)+5HTP (about 50-about 200 mg);
MSM (about 300-about 1500 mg)+NAC (about 300-about 1200 mg)+Guarana (about 50-about 500 mg)+Ginkgo Biloba (about 300-about 1200 mg)+Tryosine (about 250-about 1000 mg)+P5P (about 5-about 50 mg)+B-12 (about 0.1-about 1 mg)+Folic Acid (about 0.1-about 1 mg); or
MSM (about 300-about 1500 mg)+NAC (about 300-about 1200 mg)+Guarana (about 50-about 500 mg)+Ginkgo Biloba (about 300-about 1200 mg)+Tryosine (about 250-about 1000 mg)+5HTP (about 25-about 200 mg)+PharmaGABA (about 50-about 500 mg)+SAMe (about 50-about 500 mg)+P5P (about 5-about 50 mg)+B-12 (about 0.1-about 1 mg)+Folic Acid (about 0.1-about 1 mg).

6. Physical Distress (e.g., Distressing Pain, Hypersensitivity, and Hyperalgesia)

[Formulations for Emotional Distress and Mood and Anxiety Disorders in Addition to:]

ULDN (about 1-about 125 μg)+Roflumilast (about 10-about 200 μg);
ULDN (about 1-about 125 μg)+Tramadol (about 5-about 80 mg);
ULDN (about 1-about 125 μg)+Oxycodone (about 2-about 80 mg);
ULDN (about 1-about 125 μg)+Hydrocodone (about 5-about 80 mg);
ULDN (about 1-about 125 μg)+Roflumilast (about 10-about 200 μg)+Tramadol (about 5-about 80 mg);
ULDN (about 1-about 125 μg)+Roflumilast (about 10-about 200 μg)+Oxycodone (about 2-about 80 mg);
ULDN (about 1-about 125 μg)+Roflumilast (about 10-about 200 μg)+Hydrocodone (about 5-about 80 mg);
ULDN (about 1-about 125 μg)+Guarana (about 50-about 500 mg);
ULDN (about 1-about 125 μg)+Glutamic Acid (about 25-about 250 mg);
ULDN (about 1-about 125+Caffeine (about 25-about 200 mg);
ULDN (about 1-about 125 μg)+Ginkgo Biloba (about 40-about 240 mg);
ULDN (about 1-about 125 μg)+Ginkgo Biloba (about 40-about 240 mg)+Tramadol (about 5-about 80 mg);
ULDN (about 1-about 125 μg)+Ginkgo Biloba (about 40-about 240 mg)+Oxycodone (about 2-about 80 mg);
ULDN (about 1-about 125 μg)+Ginkgo Biloba (about 40-about 240 mg)+Hydrocodone (about 5-about 80 mg);
ULDN (about 1-about 125+Guarana (about 50-about 500 mg)+Tramadol (about 5-about 80 mg);
ULDN (about 1-about 125 μg)+Guarana (about 50-about 500 mg)+Oxycodone (about 2-about 80 mg);
ULDN (about 1-about 125 μg)+Guarana (about 50-about 500 mg)+Hydrocodone (about 5-about 80 mg);
ULDN (about 1-about 125+Glutamic Acid (about 25-about 250 mg)+Tramadol (about 5-about 80 mg);
ULDN (about 1-about 125 μg)+Glutamic Acid (about 25-about 250 mg)+Oxycodone (about 2-about 80 mg);
ULDN (about 1-about 125 μg)+Glutamic Acid (about 25-about 250 mg)+Hydrocodone (about 5-about 80 mg);
VLDN (about 125-about 500 μg)+Roflumilast (about 10-about 200 μg);
VLDN (about 125-about 500 μg)+Tramadol (about 5-about 80 mg);
VLDN (about 125-about 500 μg)+Oxycodone (about 2-about 80 mg);
VLDN (about 125-about 500 μg)+Hydrocodone (about 5-about 80 mg);
VLDN (about 125-about 500 μg)+Roflumilast (about 10-about 200 μg)+Tramadol (about 5-about 80 mg);

VLDN (about 125-about 500 μg)+Roflumilast (about 10-about 200 μg)+Oxycodone (about 2-about 80 mg);
VLDN (about 125-about 500 μg)+Roflumilast (about 10-about 200 μg)+Hydrocodone (about 5-about 80 mg);
VLDN (about 125-about 500 μg)+Guarana (about 50-about 500 mg);
VLDN (about 125-about 500 μg)+Glutamic Acid (about 25-about 250 mg);
VLDN (about 125-about 500 μg)+Caffeine (about 25-about 200 mg);
VLDN (about 125-about 500 μg)+Ginkgo Biloba (about 40-about 240 mg);
VLDN (about 125-about 500 μg)+Ginkgo Biloba (about 40-about 240 mg)+Tramadol (about 5-about 80 mg);
VLDN (about 125-about 500 μg)+Ginkgo Biloba (about 40-about 240 mg)+Oxycodone (about 2-about 80 mg);
VLDN (about 125-about 500 μg)+Ginkgo Biloba (about 40-about 240 mg)+Hydrocodone (about 5-about 80 mg);
VLDN (about 125-about 500 μg)+Guarana (about 50-about 500 mg)+Tramadol (about 5-about 80 mg);
VLDN (about 125-about 500 μg)+Guarana (about 50-about 500 mg)+Oxycodone (about 2-about 80 mg);
VLDN (about 125-about 500 μg)+Guarana (about 50-about 500 mg)+Hydrocodone (about 5-about 80 mg);
VLDN (about 125-about 500 μg)+Glutamic Acid (about 25-about 250 mg)+Tramadol (about 5-about 80 mg);
VLDN (about 125-about 500 μg)+Glutamic Acid (about 25-about 250 mg)+Oxycodone (about 2-about 80 mg);
VLDN (about 125-about 500 μg)+Glutamic Acid (about 25-about 250 mg)+Hydrocodone (about 5-about 80 mg);
MSM (about 100-about 1000 mg)+Roflumilast (about 10-about 200 μg);
MSM (about 100-about 1000 mg)+Guarana (about 50-about 500 mg);
NAC (about 200-about 1200 mg)+Guarana (about 50-about 500 mg);
MSM (about 100-about 1000 mg)+Glutamic Acid (about 25-about 250 mg) NAC (about 200-about 1200 mg)+Glutamic Acid (about 25-about 250 mg)
MSM (about 100-about 1000 mg)+Roflumilast (about 10-about 200 μg)+DLPA (about 100-about 1000 mg);
MSM (about 100-about 1000 mg)+Guarana (about 50-about 500 mg)+DLPA (about 100-about 1000 mg);
NAC (about 200-about 1200 mg)+Guarana (about 50-about 500 mg)+DLPA (about 100-about 1000 mg);
ULDN (about 1-about 125 μg)+Guarana (about 50-about 500 mg)+DLPA (about 100-about 1000 mg);
VLDN (about 125-about 500 μg)+Guarana (about 50-about 500 mg)+DLPA (about 100-about 1000 mg);
MSM (about 100-about 1000 mg)+Glutamic Acid (about 25-about 250 mg)+DLPA (about 100-about 1000 mg);
NAC (about 200-about 1200 mg)+Glutamic Acid (about 25-about 250 mg)+DLPA (about 100-about 1000 mg);
ULDN (about 1-about 125 μg)+Glutamic Acid (about 25-about 250 mg)+DLPA (about 100-about 1000 mg);
VLDN (about 125-about 500 μg)+Glutamic Acid (about 25-about 250 mg)+DLPA (about 100-about 1000 mg);
MSM (about 100-about 1000 mg)+Ginkgo Biloba (about 40-about 240 mg);
MSM (about 100-about 1000 mg)+Roflumilast (about 20-about 200 μg)+Tramadol (about 5-about 80 mg);
MSM (about 100-about 1000 mg)+Roflumilast (about 20-about 200 μg)+Oxycodone (about 2-about 80 mg);
MSM (about 100-about 1000 mg)+Roflumilast (about 20-about 200 μg)+Hydrocodone (about 5-about 80 mg);
MSM (about 100-about 1000 mg)+Ginkgo Biloba (about 40-about 240 mg)+Tramadol (about 5-about 80 mg);
MSM (about 100-about 1000 mg)+Ginkgo Biloba (about 40-about 240 mg)+Oxycodone (about 2-about 80 mg);
MSM (about 100-about 1000 mg)+Ginkgo Biloba (about 40-about 240 mg)+Hydrocodone (about 5-about 80 mg);
MSM (about 100-about 1000 mg)+White Willow Bark (about 200-about 800 mg);
NAC (about 200-about 1200 mg)+White Willow Bark (about 200-about 800 mg);
MSM (about 100-about 1000 mg)+Tramadol (about 5-about 80 mg);
MSM (about 100-about 1000 mg)+Oxycodone (about 2-about 80 mg);
MSM (about 100-about 1000 mg)+Hydrocodone (about 5-about 80 mg);
MSM (about 100-about 1000 mg)+Acetaminophen (about 200-about 800 mg);
NAC (about 200-about 1200 mg)+Hydrocodone (about 5-about 80 mg);
NAC (about 200-about 1200 mg)+Tramadol (about 5-about 80 mg);
NAC (about 200-about 1200 mg)+Oxycodone (about 2-about 80 mg);
NAC (about 200-about 1200 mg)+Acetaminophen (about 200-about 800 mg);
ULDN (about 1-about 125 μg)+Celecoxib (about 50-about 500 mg);
VLDN (about 125-about 500 μg)+Celecoxib (about 50-about 500 mg);
ULDN (about 1-about 125 μg)+White Willow Bark (about 200-about 800 mg);
VLDN (about 125-about 500 μg)+White Willow Bark (about 200-about 800 mg);
ULDN (about 1-about 125 μg)+Acetaminophen (about 200-about 1000 mg);
VLDN (about 125-about 500 μg)+Acetaminophen (about 200-about 1000 mg);
NAC (about 400-about 1200 mg)+Celecoxib (about 50-about 500 mg);
MSM (about 100-about 1000 mg)+Celecoxib (about 50-about 500 mg);
NAC (about 400-about 1200 mg)+Acetaminophen (about 200-about 800 mg)+Caffeine (about 25-about 75 mg);
MSM (about 100-about 1000 mg)+Acetaminophen (about 200-about 1000 mg)+Caffeine (about 25-about 200 mg);
ULDN (about 1-about 125 μg)+Acetaminophen (about 200-about 1000 mg)+Caffeine (about 25-about 200 mg);
VLDN (about 125-about 500 μg)+Acetaminophen (about 200-about 1000 mg)+Caffeine (about 25-about 200 mg);
MSM (about 100-about 1000 mg)+White Willow Bark (about 200-about 800 mg)+Glutamic Acid (about 25-about 200 mg);
NAC (about 400-about 1200 mg)+White Willow Bark (about 200-about 800 mg)+Glutamic Acid (about 25-about 200 mg);
MSM (about 100-about 1000 mg)+White Willow Bark (about 200-about 800 mg)+DLPA (about 100-about 1000 mg);
NAC (about 400-about 1200 mg)+White Willow Bark (about 200-about 800 mg)+DLPA (about 100-about 1000 mg);
MSM (about 100-about 1000 mg)+White Willow Bark (about 200-about 800 mg)+SAMe (about 50-about 500 mg);
NAC (about 400-about 1200 mg)+White Willow Bark (about 200-about 800 mg)+SAMe (about 50-about 500 mg);
ULDN (about 1-about 125 μg)+White Willow Bark (about 200-about 800 mg)+SAMe (about 50-about 500 mg);
ULDN (about 1-about 125 μg)+Acetaminophen (about 200-about 1000 mg)+DLPA (about 100-about 1000 mg);
ULDN (about 1-about 125 μg)+Acetaminophen (about 200-about 1000 mg)+Glutamic Acid (about 25-about 100 mg);

ULDN (about 1-about 125 μg)+Acetylsalicylic acid (about 75-about 750 mg)
VLDN (about 125-about 500 μg)+White Willow Bark (about 200-about 800 mg)+SAMe (about 50-about 500 mg);
VLDN (about 125-about 500 μg)+Acetaminophen (about 200-about 1000 mg)+DLPA (about 100-about 1000 mg);
VLDN (about 125-about 500 μg)+Acetaminophen (about 200-about 1000 mg)+Glutamic Acid (about 25-about 100 mg);
VLDN (about 125-about 500 μg)+Acetylsalicylic acid (about 75-about 750 mg);
MSM (about 100-about 1000 mg)+Acetylsalicylic acid (about 75-about 750 mg);
NAC (about 400-about 1200 mg)+Acetylsalicylic acid (about 75-about 750 mg);
ULDN (about 1-about 125 μg)+Acetylsalicylic acid (about 75-about 750 mg)+Caffeine (about 25-about 200 mg);
VLDN (about 125-about 500 μg)+Acetylsalicylic acid (about 75-about 750 mg)+Caffeine (about 25-about 200 mg);
MSM (about 100-about 1000 mg)+Acetylsalicylic acid (about 75-about 750 mg)+Caffeine (about 25-about 200 mg);
NAC (about 400-about 1200 mg)+Acetylsalicylic acid (about 75-about 750 mg)+Caffeine (about 25-about 200 mg);
Magnesium Sulfate (about 75-about 1000 mg)+Guarana (about 50-about 500 mg);
Magnesium Sulfate (about 75-about 1000 mg)+Glutamic Acid (about 25-about 200 mg);
Magnesium Sulfate (about 75-about 1000 mg)+Caffeine (about 25-about 120 mg);
Magnesium Sulfate (about 75-about 1000 mg)+Gingko Biloba (about 40-about 240 mg);
Magnesium Sulfate (about 75-about 1000 mg)+Guarana (about 50-about 500 mg)+DLPA (about 100-about 1000 mg);
Magnesium Sulfate (about 75-about 1000 mg)+Glutamic Acid (about 25-about 200 mg)+DLPA (about 100-about 1000 mg);
Magnesium Sulfate (about 75-about 1000 mg)+Caffeine (about 25-about 200 mg)+DLPA (about 100-about 1000 mg);
Magnesium Sulfate (about 75-about 1000 mg)+Gingko Biloba (about 40-about 240 mg)+DLPA (about 100-about 1000 mg);
NAC (about 400-about 1200 mg)+Myrrh Gum (about 50-about 200 mg);
MSM (about 100-about 1000 mg)+Myrrh Gum (about 50-about 200 mg);
Magnesium Sulfate (about 75-about 1000 mg)+Myrrh Gum (about 50-about 200 mg);
NAC (about 400-about 1200 mg)+Menthol;
MSM (about 100-about 1000 mg)+Menthol;
Magnesium Sulfate (about 75-about 1000 mg)+Menthol;
NAC (about 400-about 1200 mg)+Guarana (about 50-about 500 mg)+Myrrh Gum (about 50-about 200 mg);
MSM (about 100-about 1000 mg)+Guarana (about 50-about 500 mg)+Myrrh Gum (about 50-about 200 mg);
Magnesium Sulfate (about 75-about 1000 mg)+Guarana (about 50-about 500 mg)+Myrrh Gum (about 50-about 200 mg);
NAC (about 400-about 1200 mg)+Guarana (about 50-about 500 mg)+Ginkgo Biloba (about 40-about 240 mg)+Myrrh Gum (about 50-about 200 mg);
MSM (about 100-about 1000 mg)+Guarana (about 50-about 500 mg)+Ginkgo Biloba (about 40-about 240 mg)+Myrrh Gum (about 50-about 200 mg);
Magnesium Sulfate (about 75-about 1000 mg)+Guarana (about 50-about 500 mg)+Ginkgo Biloba (about 40-about 240 mg)+Myrrh Gum (about 50-about 200 mg);
MSM (about 300-about 1500 mg)+NAC (about 300-about 1200 mg)+Guarana (about 50-about 500 mg)+Ginkgo Biloba (about 300-about 1200 mg)+White Willow Bark (about 100-about 800 mg)+DLPA (about 100-about 1000 mg)+P5P (about 5-about 50 mg)+B-12 (about 0.1-about 1 mg)+Folic Acid (about 0.1-about 1 mg); or
MSM (about 300-about 1500 mg)+NAC (about 300-about 1200 mg)+Magnesium Sulfate (about 100-about 800 mg)+Guarana (about 50-about 500 mg)+Ginkgo Biloba (about 300-about 1200 mg)+Myhhr Gum (about 100-about 1000 mg)+Boswellia (about 100-about 800 mg)+P5P (about 5-about 50 mg)+B-12 (about 0.1-about 1 mg)+Folic Acid (about 0.1-about 1 mg).

7. Nociceptive Pain

Oral

ULDN (about 1-about 125 μg)+Roflumilast (about 1-about 200 μg); ULDN (about 1-about 125 μg)+Roflumilast (about 1-about 200 μg)+Tramadol (about 5-about 80 mg);
ULDN (about 1-about 125 μg)+Roflumilast (about 1-about 200 μg)+Oxycodone (about 2-about 80 mg);
ULDN (about 1-about 125 μg)+Roflumilast (about 1-about 200 μg)+Hydrocodone (about 5-about 80 mg);
ULDN (about 1-about 125 μg)+Ginkgo Biloba (about 40-about 240 mg);
ULDN (about 1-about 125 μg)+Ginkgo Biloba (about 40-about 240 mg)+Tramadol (about 5-about 80 mg);
ULDN (about 1-about 125 μg)+Ginkgo Biloba (about 40-about 240 mg)+Oxycodone (about 2-about 80 mg);
ULDN (about 1-about 125 μg)+Ginkgo Biloba (about 40-about 240 mg)+Hydrocodone (about 5-about 80 mg);
ULDN (about 1-about 125 μg)+Guarana (about 50-about 500 mg)+Tramadol (about 5-about 80 mg);
ULDN (about 1-about 125 μg)+Guarana (about 50-about 500 mg)+Oxycodone (about 2-about 80 mg);
ULDN (about 1-about 125 μg)+Guarana (about 50-about 500 mg)+Hydrocodone (about 5-about 80 mg);
ULDN (about 1-about 125 μg)+Glutamic Acid (about 50-about 300 mg)+Tramadol (about 5-about 80 mg);
ULDN (about 1-about 125 μg)+Glutamic Acid (about 50-about 300 mg)+Oxycodone (about 2-about 80 mg);
ULDN (about 1-about 125 μg)+Glutamic Acid (about 50-about 300 mg)+Hydrocodone (about 5-about 80 mg);
VLDN (about 125-about 500 μg)+Roflumilast (about 1-about 200 μg); VLDN (about 125-about 500 μg)+Roflumilast (about 1-about 200 μg)+Tramadol (about 5-about 80 mg);
VLDN (about 125-about 500 μg)+Roflumilast (about 1-about 200 g)+Oxycodone (about 2-about 80 mg);
VLDN (about 125-about 500 μg)+Roflumilast (about 1-about 200 μg)+Hydrocodone (about 5-about 80 mg)
VLDN (about 125-about 500 μg)+Ginkgo Biloba (about 40-about 240 mg);
VLDN (about 125-about 500 μg)+Ginkgo Biloba (about 40-about 240 mg)+Tramadol (about 5-about 80 mg);
VLDN (about 125-about 500 μg)+Ginkgo Biloba (about 40-about 240 mg)+Oxycodone (about 2-about 80 mg);
VLDN (about 125-about 500 μg)+Ginkgo Biloba (about 40-about 240 mg)+Hydrocodone (about 5-about 80 mg);
VLDN (about 125-about 500 μg)+Guarana (about 50-about 500 mg)+Tramadol (about 5-about 80 mg);
VLDN (about 125-about 500 μg)+Guarana (about 50-about 500 mg)+Oxycodone (about 2-about 80 mg);
VLDN (about 125-about 500 μg)+Guarana (about 50-about 500 mg)+Hydrocodone (about 5-about 80 mg);
VLDN (about 125-about 500 μg)+Glutamic Acid (about 50-about 300 mg)+Tramadol (about 5-about 80 mg);
VLDN (about 125-about 500 μg)+Glutamic Acid (about 50-about 300 mg)+Oxycodone (about 2-about 80 mg);

VLDN (about 125-about 500 µg)+Glutamic Acid (about 50-about 300 mg)+Hydrocodone (about 5-about 80 mg);
MSM (about 100-about 1200 mg)+Roflumilast (2-100 µg);
MSM (about 100-about 1200 mg)+Guarana (about 50-about 500 mg);
NAC (about 200-about 1200 mg)+Guarana (about 50-about 500 mg);
MSM (about 100-about 1200 mg)+Glutamic Acid (about 50-about 300 mg);
NAC (about 200-about 1200 mg)+Glutamic Acid (about 50-about 300 mg);
MSM (about 100-about 1200 mg)+Roflumilast (about 1-about 200 µg)+DLPA (about 100-about 1000 mg);
MSM (about 100-about 1200 mg)+Guarana (about 50-about 500 mg)+DLPA (about 100-about 1000 mg);
NAC (about 200-about 1200 mg)+Guarana (about 50-about 500 mg)+DLPA (about 100-about 1000 mg);
ULDN (about 1-about 125 µg)+Guarana (about 50-about 500 mg)+DLPA (about 100-about 1000 mg);
VLDN (about 125-about 500 µg)+Guarana (about 50-about 500 mg)+DLPA (about 100-about 1000 mg);
MSM (about 100-about 1200 mg)+Glutamic Acid (about 50-about 300 mg)+DLPA (about 100-about 1000 mg);
NAC (about 200-about 1200 mg)+Glutamic Acid (about 50-about 300 mg)+DLPA (about 100-about 1000 mg);
ULDN (about 1-about 125 µg)+Glutamic Acid (about 50-about 300 mg)+DLPA (about 100-about 1000 mg);
VLDN (about 125-about 500 µg)+Glutamic Acid (about 50-about 300 mg)+DLPA (about 100-about 1000 mg);
MSM (about 100-about 1200 mg)+Ginkgo Biloba (about 40-about 240 mg);
MSM (about 100-about 1200 mg)+Roflumilast (about 1-about 200 µg)+Tramadol (about 5-about 80 mg);
MSM (about 100-about 1200 mg)+Roflumilast (about 1-about 200 µg)+Oxycodone (about 2-about 80 mg);
MSM (about 100-about 1200 mg)+Roflumilast (about 1-about 200 µg)+Hydrocodone (about 5-about 80 mg);
MSM (about 100-about 1200 mg)+Ginkgo Biloba (about 40-about 240 mg)+Tramadol (about 5-about 80 mg);
MSM (about 100-about 1200 mg)+Ginkgo Biloba (about 40-about 240 mg)+Oxycodone (about 2-about 80 mg);
MSM (about 100-about 1200 mg)+Ginkgo Biloba (about 40-about 240 mg)+Hydrocodone (about 5-about 80 mg);
MSM (about 100-about 1200 mg)+White Willow Bark (about 200-about 800 mg);
NAC (about 200-about 1200 mg)+White Willow Bark (about 200-about 800 mg);
MSM (about 100-about 1200 mg)+Tramadol (about 5-about 80 mg);
MSM (about 100-about 1200 mg)+Oxycodone (about 2-about 80 mg);
MSM (about 100-about 1200 mg)+Hydrocodone (about 5-about 80 mg);
MSM (about 100-about 1200 mg)+Acetaminophen (about 200-about 800 mg);
NAC (about 200-about 1200 mg)+Hydrocodone (about 5-about 80 mg);
NAC (about 200-about 1200 mg)+Tramadol (about 5-about 80 mg);
NAC (about 200-about 1200 mg)+Oxycodone (about 2-about 80 mg);
NAC (about 200-about 1200 mg)+Acetaminophen (about 200-about 800 mg);
ULDN (about 1-about 125 µg)+Celecoxib (about 50-about 500 mg);
ULDN (about 1-about 125 µg)+White Willow Bark (about 200-about 800 mg);
ULDN (about 1-about 125 µg)+Acetaminophen (about 200-about 1000 mg);
VLDN (about 125-about 500 µg)+Celecoxib (about 50-about 500 mg);
VLDN (about 125-about 500 µg)+White Willow Bark (about 200-about 800 mg);
VLDN (about 125-about 500 µg)+Acetaminophen (about 200-about 1000 mg);
NAC (about 400-about 1200 mg)+Celecoxib (about 50-about 500 mg);
MSM (about 100-about 1200 mg)+Celecoxib (about 50-about 500 mg);
NAC (about 400-about 1200 mg)+Acetaminophen (about 200-about 1000 mg)+Caffeine (about 25-about 200 mg);
MSM (about 100-about 800 mg)+Acetaminophen (about 200-about 800 mg)+Caffeine (about 25-about 200 mg);
ULDN (about 1-about 125 µg)+Acetaminophen (about 200-about 1000 mg)+Caffeine (about 25-about 200 mg);
VLDN (about 125-about 500 µg)+Acetaminophen (about 200-about 1000 mg)+Caffeine (about 25-about 200 mg);
MSM (about 100-about 1200 mg)+White Willow Bark (about 200-about 800 mg)+Guarana (about 50-about 500 mg);
NAC (about 400-about 1200 mg)+White Willow Bark (about 200-about 800 mg)+Guarana (about 50-about 500 mg);
MSM (about 100-about 1200 mg)+White Willow Bark (about 200-about 800 mg)+Glutamic Acid (about 50-about 200 mg);
NAC (about 400-about 1200 mg)+White Willow Bark (about 200-about 800 mg)+Glutamic Acid (about 50-about 200 mg);
MSM (about 100-about 1200 mg)+White Willow Bark (about 200-about 800 mg)+DLPA (about 100-about 1000 mg);
NAC (about 400-about 1200 mg)+White Willow Bark (about 200-about 800 mg)+DLPA (about 100-about 1000 mg);
MSM (about 100-about 1200 mg)+White Willow Bark (about 200-about 800 mg)+SAMe (about 50-about 500 mg);
NAC (about 400-about 1200 mg)+White Willow Bark (about 200-about 800 mg)+SAMe (about 50-about 1000 mg);
ULDN (about 1-about 125 µg)+White Willow Bark (about 200-about 800 mg)+SAMe (about 50-about 1000 mg);
ULDN (about 1-about 125 µg)+Acetaminophen (about 200-about 1000 mg)+DLPA (about 100-about 1200 mg);
ULDN (about 1-about 125 µg)+Acetaminophen (about 200-about 1000 mg)+Guarana (about 50-about 500 mg);
ULDN (about 1-about 125 µg)+Acetaminophen (about 200-about 1000 mg)+Glutamic Acid (about 50-about 200 mg);
ULDN (about 1-about 125 µg)+Acetylsalicylic acid (about 75-about 750 mg);
MSM (about 100-about 1200 mg)+Acetylsalicylic acid (about 75-about 750 mg);
NAC (about 400-about 1200 mg)+Acetylsalicylic acid (about 75-about 750 mg);
ULDN (about 1-about 125 µg)+Acetylsalicylic acid (about 75-about 750 mg)+Caffeine (about 25-about 200 mg);
VLDN (about 125-about 500 µg)+White Willow Bark (about 200-about 800 mg)+SAMe (50-1000 mg);
VLDN (about 125-about 500 µg)+Acetaminophen (about 200-about 1000 mg)+DLPA (about 100-about 1200 mg);
VLDN (about 125-about 500 µg)+Acetaminophen (about 200-about 1000 mg)+Guarana (about 50-about 500 mg);
VLDN (about 125-about 500 µg)+Acetaminophen (about 200-about 1000 mg)+Glutamic Acid (about 50-about 200 mg);
VLDN (about 125-about 500 µg)+Acetylsalicylic acid (about 7'5-about 750 mg);
VLDN (about 125-about 500 µg)+Acetylsalicylic acid (about 75-about 750 mg)+Guarana (about 25-about 500 mg);
MSM (about 100-about 1200 mg)+Acetylsalicylic acid (about 75-about 750 mg)+Guarana (about 25-about 500 mg);

NAC (about 400-about 1200 mg)+Acetylsalicylic acid (about 75-about 750 mg)+Guarana (about 25-about 500 mg);
VLDN (about 125-about 500 μg)+Acetylsalicylic acid (about 75-about 750 mg)+Caffeine (about 25-about 200 mg);
MSM (about 100-about 1200 mg)+Acetylsalicylic acid (about 75-about 750 mg)+Caffeine (about 25-about 200 mg);
NAC (about 400-about 1200 mg)+Acetylsalicylic acid (about 75-about 750 mg)+Caffeine (about 25-about 200 mg);
NAC (about 400-about 1200 mg)+Myrrh Gum (about 50-about 200 mg);
MSM (about 100-about 1200 mg)+Myrrh Gum (about 50-about 200 mg);
Magnesium Sulfate (about 75-about 1000 mg)+Myrrh Gum (about 50-about 200 mg);
NAC (about 400-about 1200 mg)+Guarana (about 50-about 500 mg)+Myrrh Gum (about 50-about 200 mg);
MSM (about 100-about 1000 mg)+Guarana (about 50-about 500 mg)+Myrrh Gum (about 50-about 200 mg);
Magnesium Sulfate (about 75-about 1000 mg)+Guarana (about 50-about 500 mg)+Myrrh Gum (about 50-about 200 mg);
NAC (about 400-about 1200 mg)+Guarana (about 50-about 500 mg)+Ginkgo Biloba (about 40-about 240 mg)+Myrrh Gum (about 50-about 200 mg);
MSM (about 100-about 1000 mg)+Guarana (about 50-about 500 mg)+Ginkgo Biloba (about 40-about 240 mg)+Myrrh Gum (about 50-about 200 mg);
Magnesium Sulfate (about 75-about 1000 mg)+Guarana (about 50-about 500 mg)+Ginkgo Biloba (about 40-about 240 mg)+Myrrh Gum (about 50-about 200 mg);
MSM (about 300-about 1500 mg)+NAC (about 300-about 1200 mg)+Guarana (about 50-about 500 mg)+Ginkgo Biloba (about 300-about 1200 mg)+White Willow Bark (about 100-about 800 mg)+DLPA (about 100-about 1000 mg)+P5P (about 5-about 50 mg)+B-12 (about 0.1-about 1 mg)+Folic Acid (about 0.1-about 1 mg); or
MSM (about 300-about 1500 mg)+NAC (about 300-about 1200 mg)+Magnesium Sulfate (about 100-about 800 mg)+Guarana (about 50-about 500 mg)+Ginkgo Biloba (about 300-about 1200 mg)+Myhhr Gum (about 100-about 1000 mg)+Boswellia (about 100-about 800 mg)+P5P (5-50 mg)+B-12 (0.1-1 mg)+Folic Acid (about 0.1-about 1 mg).

IV/Sublingual (Dosage Varies by Indication and Time)
Naloxone+Morphine+Acetaminophen;
Naloxone+Morphine+Acetaminophen+Arginine;
Naloxone+Morphine+Ibuprofen;
Naloxone+Morphine+Ibuprofen+Arginine;
Naloxone+Tramadol+Ibuprofen;
Naloxone+Tramadol+Ibuprofen+Arginine;
Magnesium Sulfate+Morphine+Acetaminophen;
Magnesium Sulfate+Morphine+Acetaminophen+Arginine;
Magnesium Sulfate+Morphine+Ibuprofen;
Magnesium Sulfate+Morphine+Ibuprofen+Arginine;
MSM+Morphine;
MSM+Morphine+Acetaminophen;
MSM+Morphine+Acetaminophen+Arginine;
MSM+Morphine+Ibuprofen;
MSM+Morphine+Ibuprofen+Arginin;
MSM+Tramadol;
MSM+Tramadol+Acetaminophen;
MSM+Tramadol+Acetaminophen+Arginine;
MSM+Tramadol+Ibuprofen; or
MSM+Tramadol+Ibuprofen+Arginine.

Topical (e.g., Gel, Lotion, Patch)
ULDN (about 1-about 125 μg)+Loperamide (about 50-about 500 mg);
VLDN (about 125-about 500 μg)+Loperamide (about 50-about 500 mg);
LDN (500-1000 μg)+Loperamide (about 50-about 500 mg);
Naloxone (1-25 μg)+Loperamide (about 50-about 500 mg);
MSM (about 100-about 1200 mg)+Loperamide (about 50-about 500 mg);
NAC (about 100-about 1200 mg)+Loperamide (about 50-about 500 mg);
Magnesium Sulfate (about 100-about 1000 mg)+Loperamide (about 50-about 500 mg);
ULDN (about 1-about 125 μg)+Fentyanyl (about 25-about 100 μg/hr);
Naloxone (1-25 μg)+Fentyanyl (about 25-about 100 μg/hr);
VLDN (about 125-about 500 μg)+Fentyanyl (about 25-about 100 μg/hr);
LDN (500-1000 μg)+Fentyanyl (about 25-about 100 μg/hr);
MSM (about 100-about 1200 mg)+Fentyanyl (about 25-about 100 μg/hr);
NAC (100-1200 mg)+Fentyanyl (about 25-about 100 μg/hr);
Magnesium Sulfate (about 100-about 1000 mg)+Fentyanyl (about 25-about 100 μg/hr);
ULDN (about 1-about 125 μg)+Oxycodone (about 10-about 100 mg);
VLDN (about 125-about 500 μg)+Oxycodone (about 10-about 100 mg);
LDN (about 500-about 1000 μg)+Oxycodone (about 10-about 100 mg);
Naloxone (about 1-about 25 μg)+Oxycodone (about 10-about 100 mg);
MSM (about 100-about 1200 mg)+Oxycodone (about 10-about 100 mg);
NAC (about 100-about 1200 mg)+Oxycodone (about 10-about 100 mg);
Magnesium Sulfate (about 100-about 1000 mg)+Oxycodone (about 10-about 100 mg);
ULDN (about 1-about 125 μg)+Loperamide (about 50-about 500 mg)+DMSO;
VLDN (about 125-about 500 μg)+Loperamide (about 50-about 500 mg)+DMSO;
LDN (about 500-about 1000 μg)+Loperamide (about 50-about 500 mg)+DMSO;
Naloxone (1-25 μg)+Loperamide (about 50-about 500 mg)+DMSO;
MSM (about 100-about 1200 mg)+Loperamide (about 50-about 500 mg)+DMSO;
NAC (about 100-about 1200 mg)+Loperamide (about 50-about 500 mg)+DMSO;
Magnesium Sulfate (about 100-about 1000 mg)+Loperamide (about 50-about 500 mg)+DMSO;
Naloxone (about 1-about 25 μg)+Fentanyl (about 25-about 100 μg/hr)+DMSO;
ULDN (about 1-about 125 μg)+Fentanyl (about 25-about 100 μg/hr)+DMSO;
VLDN (about 125-about 500 μg)+Fentanyl (about 25-about 100 μg/hr)+DMSO;
LDN (about 500-about 1000 μg)+Fentanyl (about 25-about 100 μg/hr)+DMSO;
MSM (about 100-about 1200 mg)+Fentanyl (about 25-about 100 μg/hr)+DMSO;
NAC (about 100-about 1200 mg)+Fentanyl (about 25-about 100 μg/hr)+DMSO
Magnesium Sulfate (about 100-about 1000 mg)+Fentanyl (about 25-about 100 μg/hr)+DMSO;
Naloxone (about 1-about 25 μg)+Naloxone (about 1-about 25 μg)+DMSO;
ULDN (about 1-about 125 μg)+Oxycodone (about 10-about 100 mg)+DMSO;

VLDN (about 125-about 500 µg)+Oxycodone (about 10-about 100 mg)+DMSO;
LDN (500-1000 µg)+Oxycodone (about 10-about 100 mg)+DMSO;
MSM (about 100-about 1200 mg)+Oxycodone (about 10-about 100 mg)+DMSO;
NAC (about 100-about 1200 mg)+Oxycodone (about 10-about 100 mg)+DMSO;
Magnesium Sulfate (about 100-about 1000 mg)+Oxycodone (about 10-about 100 mg)+DMSO;
ULDN (about 1-about 125 µg)+Loperamide (about 50-about 500 mg)+Menthol;
VLDN (about 125-about 500 µg)+Loperamide (about 50-about 500 mg)+Menthol;
LDN (about 500-about 1000 µg)+Loperamide (about 50-about 500 mg)+Menthol;
Naloxone (about 1-about 25 µg)+Loperamide (about 50-about 500 mg)+Menthol;
MSM (about 100-about 1200 mg)+Loperamide (about 50-about 500 mg)+Menthol;
NAC (about 100-about 1200 mg)+Loperamide (about 50-about 500 mg)+Menthol;
Magnesium Sulfate (about 100-about 1000 mg)+Loperamide (about 50-about 500 mg)+Menthol;
ULDN (about 1-about 125 µg)+Fentyanyl (about 25-about 100 µg/hr)+Menthol;
VLDN (about 125-about 500 µg)+Fentyanyl (about 25-about 100 µg/hr)+Menthol;
LDN (about 500-about 1000 µg)+Fentyanyl (about 25-about 100 µg/hr)+Menthol;
Naloxone (about 1-about 25 µg)+Fentanyl (about 25-about 100 µg/hr)+Menthol;
MSM (about 100-about 1200 mg)+Fentanyl (about 25-about 100 µg/hr)+Menthol;
NAC (about 100-about 1200 mg)+Fentanyl (about 25-about 100 µg/hr)+Menthol;
Magnesium Sulfate (about 100-about 1000 mg)+Fentanyl (about 25-about 100 µg/hr)+Menthol;
ULDN (about 1-about 125 µg)+Oxycodone (about 10-about 100 mg)+Menthol;
VLDN (about 125-about 500 µg)+Oxycodone (about 10-about 100 mg)+Menthol;
LDN (about 500-about 1000 µg)+Oxycodone (about 10-about 100 mg)+Menthol;
Naloxone (about 1-about 25 µg)+Oxycodone (about 10-about 100 mg)+Menthol;
MSM (about 100-about 1200 mg)+Oxycodone (about 10-about 100 mg)+Menthol;
NAC (about 100-about 1200 mg)+Oxycodone (about 10-about 100 mg)+Menthol; or
Magnesium Sulfate (about 100-about 1000 mg)+Oxycodone (about 10-about 100 mg)+Menthol.

8. Neuropathy
  (e.g, HIV-Induced and Diabetic)
[Formulations for Nociceptive Pain in Addition to:]
  IV/Subcutaneous Injection (Dosage Varies by Indication, Time, and Form of Administration)
Naloxone+rhNGF (about 0.1-about 0.5 µg/kg) (Nerve Growth Factor);
ULDN (about 1-about 125 µg)+rhNGF (about 0.1-about 0.5 µg/kg) (Nerve Growth Factor);
VLDN (about 125-about 500 µg)+rhNGF (about 0.1-about 0.5 µg/kg) (Nerve Growth Factor);
NAC (about 400-about 1200 mg)+rhNGF (about 0.1-about 0.5 µg/kg) (Nerve Growth Factor);
MSM (about 100-about 600 mg)+rhNGF (about 0.1-about 0.5 µg/kg (Nerve Growth Factor);
Magnesium Sulfate (about 100-about 1000 mg)+rhNGF (about 0.1-about 0.5 µg/kg (Nerve Growth Factor);
Naloxone+Roflumilast (about 1-about 250+rhNGF (about 0.1-about 0.5 µg/kg (Nerve Growth Factor);
ULDN (about 1-about 125 µg)+Roflumilast (about 1-about 250+rhNGF (about 0.1-about 0.5 µg/kg (Nerve Growth Factor);
VLDN (about 125-about 500 µg)+Roflumilast (about 1-about 250+rhNGF (about 0.1-about 0.5 µg/kg (Nerve Growth Factor);
ULDN (about 1-about 125 µg)+Glutamic Acid (about 50-about 1000 µg)+rhNGF (about 0.1-about 0.5 µg/kg (Nerve Growth Factor); or
VLDN (about 125-about 500 µg)+Glutamic Acid (50-1000+rhNGF (about 0.1-about 0.5 µg/kg (Nerve Growth Factor).

9. Respiratory Conditions
  (e.g., Asthma, COPD, and Neonatal Apnea)
[Formulations for Emotional and Physical Distress in Addition to:]
  Oral
ULDN (about 1-about 125 µg)+Roflumilast (about 100-about 600 µg);
ULDN (about 1-about 125 µg)+Theophylline (about 200-about 800 mg);
ULDN (about 1-about 125 µg)+Caffeine (about 50-about 250 mg);
VLDN (about 125-about 500 µg)+Roflumilast (about 100-about 600 µg);
VLDN (about 125-about 500 µg)+Caffeine (about 50-about 250 mg);
VLDN (about 125-about 500 µg)+Theophylline (about 200-about 800 mg);
NAC (about 600-about 1800 mg)+Roflumilast (about 100-about 600 µg);
NAC (about 600-about 1800 mg)+Theophylline (about 200-about 800 mg);
NAC (about 600-about 1800 mg)+Caffeine (about 50-about 250 mg);
MSM (about 200-about 1200 mg)+Roflumilast (about 100-about 600 µg);
MSM (about 200-about 1200 mg)+Theophylline (about 200-about 800 mg);
MSM (about 200-about 1200 mg)+Caffeine (about 50-about 250 mg);
NAC (about 600-about 1800 mg)+Ginkgo Biloba (about 120-about 360 mg);
NAC (about 600-about 1800 mg)+Ginkgo Biloba (about 120-about 360 mg)+Roflumilast (about 100-about 600 µg);
NAC (about 600-about 1800 mg)+Ginkgo Biloba (about 120-about 360 mg)+Theophylline (100-500 µg);
ULDN (about 1-about 125 µg)+Ginkgo Biloba (about 120-about 360 mg)+Theophylline (100-500 µg);
ULDN (about 1-about 125 µg)+Ginkgo Biloba (about 120-about 360 mg)+Roflumilast (about 100-about 600 µg);
VLDN (about 125-about 500 µg)+Ginkgo Biloba (about 120-about 360 mg)+Theophylline (100-500 µg); or
VLDN (about 125-about 500 µg)+Ginkgo Biloba (about 120-about 360 mg)+Roflumilast (about 100-about 600 µg).

IV. SUBCUTANEOUS INJECTION (DOSAGE VARIES BY INDICATION, TIME, AND FORM OF ADMINISTRATION)

Naloxone+Caffeine Citrate;
Naloxone+Theophylline;
Magnesium Sulfate+Caffeine Citrate;
Magnesium Sulfate+Theophylline;

MSM+Caffeine Citrate;
MSM+Theophylline;
NAC+Caffeine Citrate; or
NAC+Theophylline.

10. Gastrointestinal Conditions
    (e.g., IBS, PMS, Crohn's, GI Distress)
[Formulations for Emotional and Physical Distress in Addition to:]
ULDN (about 1-about 125 μg)+Ginkgo Biloba (about 40-about 240 mg);
ULDN (about 1-about 125 μg)+Ginkgo Biloba (about 40-about 240 mg);
ULDN (about 1-about 125 μg)+Ginkgo Biloba (about 40-about 240 mg)+Glutamine (about 200-about 800 mg);
VLDN (about 125-about 500 μg)+Ginkgo Biloba (about 40-about 240 mg);
VLDN (about 125-about 500 μg)+Ginkgo Biloba (about 40-about 240 mg);
VLDN (about 125-about 500 μg)+Ginkgo Biloba (about 40-about 240 mg)+Glutamine (about 200-about 800 mg);
LDN (500-1000 μg)+Ginkgo Biloba (about 40-about 240 mg);
LDN (500-1000 μg)+Ginkgo Biloba (about 40-about 240 mg);
LDN (500-1000 μg)+Ginkgo Biloba (about 40-about 240 mg)+Glutamine (about 200-about 800 mg);
NAC (about 400-about 1200 mg)+Ginkgo Biloba (about 40-about 240 mg);
NAC (about 400-about 1200 mg)+Glutamine (about 200-about 800 mg);
NAC (about 400-about 1200 mg)+Ginkgo Biloba (about 40-about 240 mg)+Glutamine (about 200-about 800 mg);
MSM (about 200-about 800 mg)+Ginkgo Biloba (about 40-about 240 mg);
MSM (about 200-about 800 mg)+Glutamine (about 200-about 800 mg);
MSM (about 200-about 800 mg)+Ginkgo Biloba (about 40-about 240 mg)+Glutamine (about 200-about 800 mg);
Magnesium Sulfate (about 100-about 1000 mg)+Gingko Biloba (about 40-about 240 mg);
Magnesium Sulfate (about 100-about 1000 mg)+Glutamine (about 200-about 800 mg);
Magnesium Sulfate (about 100-about 1000 mg)+Gingko Biloba (about 40-about 240 mg)+Glutamine (about 200-about 800 mg);
ULDN (about 1-about 125 μg)+Ginkgo Biloba (about 40-about 240 mg)+Peppermint Oil;
ULDN (about 1-about 125 μg)+Ginkgo Biloba (about 40-about 240 mg)+Glutamine (about 200-about 800 mg)+Peppermint Oil;
VLDN (about 125-about 500 μg)+Ginkgo Biloba (about 40-about 240 mg)+Peppermint Oil;
VLDN (about 125-about 500 μg)+Ginkgo Biloba (about 40-about 240 mg)+Glutamine (about 200-about 800 mg)+Peppermint Oil;
LDN (about 500-about 1000 μg)+Ginkgo Biloba (about 40-about 240 mg)+Peppermint Oil;
LDN (about 500-about 1000 μg)+Ginkgo Biloba (about 40-about 240 mg)+Glutamine (about 200-about 800 mg)+Peppermint Oil;
NAC (about 400-about 1200 mg)+Ginkgo Biloba (about 40-about 240 mg)+Peppermint Oil;
NAC (about 400-about 1200 mg)+Glutamine (about 200-about 800 mg)+Peppermint Oil;
NAC (about 400-about 1200 mg)+Ginkgo Biloba (about 40-about 240 mg)+Glutamine (about 200-about 800 mg)+Peppermint Oil;
MSM (about 200-about 800 mg)+Ginkgo Biloba (about 40-about 240 mg)+Peppermint Oil;
MSM (about 200-about 800 mg)+Glutamine (about 200-about 800 mg)+Peppermint Oil;
MSM (about 200-about 800 mg)+Ginkgo Biloba (about 40-about 240 mg)+Glutamine (about 200-about 800 mg)+Peppermint Oil;
Magnesium Sulfate (about 100-about 1000 mg)+Gingko Biloba (about 40-about 240 mg)+Peppermint Oil;
Magnesium Sulfate (about 100-about 1000 mg)+Glutamine (about 200-about 800 mg)+Peppermint Oil;
Magnesium Sulfate (about 100-about 1000 mg)+Gingko Biloba (about 40-about 240 mg)+Glutamine (about 200-about 800 mg)+Peppermint Oil;
Magnesium Sulfate (about 100-about 1000 mg)+Peppermint Oil;
MSM (about 200-about 800 mg)+Peppermint Oil; or
NAC (about 200-about 1200 mg)+Peppermint Oil.

11. Food Additive
    (e.g., Flavoring, Condiment)
MSG+ULDN (about 1-about 125 μg/50 mg MSG);
MSG+VLDN (about 125-about 500 μg/50 mg MSG);
MSG+LDN (about 500-about 1000 μg/50 mg MSG);
MSG+MSM (about 50-about 400 mg/50 mg MSG); or
MSG+NAC (about 100-about 500 mg/50 mg MSG).

There has been no prior teaching that has developed a comprehensive understanding of Distress Dysfunction, as defined in this invention, nor of the neurophysiological process that underlie the wide variety of disorders, conditions, and symptoms that are manifested by Distress Dysfunction, as defined in this invention. Therefore, there has been no prior teaching or art regarding the improved safety, side effect profile, or therapeutic efficacy of combining Receptor Switchers, as defined in this patent, with Endorphin Enhancers, as defined in this patent, for the purpose of reducing emotional and physical distress, as defined in this patent, such as dysfunctional fears and anxieties, anger and irritability, despair and depression, gastrointestinal disorders, sexual disorders, eating disorders, distressing pain, as well as alcohol, drug, and behavioral addictions. Furthermore, there has been no prior teaching regarding the increased safety, side effect profile, or therapeutic efficacy of combining Receptor Switchers and Endorphin Enhancers, with low-dose Exogenous Opioids, as defined in this patent, for the purpose of reducing emotional and physical distress, as defined in this patent. Furthermore, there has been no prior teaching or art regarding the increased safety, side effect profile, or therapeutic efficacy of combining Receptor Switchers, as defined by this patent, with Synergistic Enhancers, as defined in this patent, for the purpose of reducing emotional and physical distress, as defined in this patent.

V. EXAMPLES

The invention is further described by reference to the following clinical examples, which are provided for illustration only. The invention is not limited to the examples, but rather includes all variations that are evident from the teachings provided herein. Particular materials, dosages, and conditions employed are merely illustrative and not intended to limit the scope of the invention in any way.

All publicly available documents referenced herein, including but not limited to U.S. patents, are specifically incorporated by reference.

Example 1

The surprising discovery that led to the novel method and composition of the present invention came from a series of clinical trials using drug formulations that were developed by present co-inventor Dr. Stanley M. Crain. Dr. Crain demonstrated that a combination of certain agents, such as rolipram, caffeine, and isobutylmethylxanthine (IBMX), combined with other agents, such as naltrexone and naloxone, resulted in a formulation that could increase mouse tail-flick latencies in a hot-water immersion analgesia study.

The study of Example 1 was designed and intended to ascertain whether the analgesia (pain relief) demonstrated in the preclinical tail-flick studies could be duplicated in humans. The co-treatment formulations for these studies included combinations of two agents.

Study Design:

For these trials, a hot-water finger-immersion pain paradigm was used, measuring both pain threshold and tolerance. The index finger of the non-dominant hand was submerged in 130° F. water, and the time to the experience of pain (threshold) and the need to withdraw (tolerance) were measured. Baseline scores were compared to those obtained under experimental conditions. Experimental conditions were not blinded for this study.

For the preliminary part of this study, 18 subjects (10 males, 8 females; ages 27-86) were given each of the following single-dose formulations on separate days, to determine the best doses for pain reduction and side-effect profiles:

(1) Caffeine (50 mg)+Magnesium Sulfate (750 mg)
(2) Caffeine (50 mg)+Magnesium Sulfate (5 g)
(3) Caffeine (200 mg)+Magnesium Sulfate (2 g)
(4) Theophylline (100 mg)+ULDN (1 µg)
(5) Theophylline (300 mg)+ULDN (10 µg)
(6) Theophylline (300 mg)+ULDN (100 µg)
(7) Rolipram (1 µg)+ULDN (1 µg)
(8) Rolipram (1 µg)+ULDN (10 µg)
(9) Rolipram (50 µg)+ULDN (100 µg)
(10) Forskolin (200 mg)+Magnesium Sulfate (750 mg)
(11) Forskolin (200 mg)+Magnesium Sulfate (2 g)

These co-treatment formulations generally increased pain thresholds and tolerance as compared to baseline latencies. However, rolipram and forskolin produced undesirable side effects, which led to their elimination in the second phase of the trial. Rolipram, especially at the higher dose (50 µg), produced a queasy sensation for several of the subjects. [One subject took 250 µg of rolipram and experienced nausea, vomiting, and diarrhea. This side-effect profile has been seen in the literature, and has led to rolipram being excluded from clinical development, despite its therapeutic potential.] Forskolin produced mild agitation for several subjects. In addition, the higher doses of magnesium sulfate (2 g, 5 g) produced mild queasy feelings for several subjects, suggesting that the lower dose would be more tolerable for the second phase of the study. Finally, the highest dose of caffeine (200 mg) produced mild agitation for several subjects, and was eliminated from the second phase of the study.

For the remaining conditions, not only was analgesia observed, but also many of the subjects noted a variety of unexpected positive experiences, including a sense of well being and calm, when taking the formulations. However, it was not until the second phase of the study did the clinical importance of these incidental reports become clear.

The same induced pain paradigm was used for the second phase of this study. 60 subjects (38 males, 22 females, ages 18-86), including all of the subjects in the first phase of the study, participated in the study. All subjects were administered each of the following formulations in a single dose, on separate days; while 18 of these subjects (10 males, 8 females) were given these formulations using a twice daily administration over the course of 3 consecutive days. The following formulations were administered to each subject to assess the effect of each agent, as compared to baseline, as well as the synergistic impact of co-treatment:

(1) Caffeine (50 mg)+ULDN (5 µg)
(2) Caffeine (50 mg)+Magnesium Sulfate (750 mg)
(3) Theophylline (300 mg)+ULDN (5 µg)
(4) Theophylline (300 mg)+Magnesium Sulfate (750 mg)
(5) Caffeine (50 mg)
(6) Theophylline (300 mg)
(7) ULDN (5 µg)
(8) Magnesium Sulfate (750 mg)

Two subjects continued to take theophylline (300 mg)+ULDN (5 µg), twice daily, for more than 8 months; a third subject continued to take caffeine (50 mg)+ULDN (5 µg), twice daily, for six months.

As seen in the first phase of the trial, the co-treatment formulations generally increased pain thresholds and tolerance, as compared to baseline latencies. Furthermore, there was generally no analgesic effect when agents were administered alone. In fact, there was a trend toward increased pain sensitivity (hyperalgesia) when caffeine and theophylline were given alone. No side effects were reported for any of the experimental conditions. These findings clearly support Dr. Crain's theory that the combination of these specific drugs produces analgesia.

As noted in the first phase of this study, spontaneous, unsolicited reports from the majority of subjects in these trials revealed an unexpected set of therapeutic benefits from these co-treatment formulations, separate and distinct from the issue of nociceptive pain relief, which was, at the outset, the sole purpose of the study. Completely unplanned and unexpected was the entirely new discovery that these agents, in all co-treatment formulations, dramatically reduced a surprising variety of symptoms in the subjects separate and distinct from nociceptive pain, including gastrointestinal disturbances, emotional and physical agitation, impulsive anger, premature ejaculation, drug cravings, and PMS symptoms. In further studying this phenomenon, another surprising pattern emerged. The formulations were most effective in reducing symptoms (unrelated to the hot water-induced nociceptive pain) in subjects who initially had relatively low pain thresholds and tolerance prior to taking the drugs, suggesting underlying hyperalgesia.

Nearly half the subjects, after taking the co-treatment formulations, indicated that they experienced a positive sense of well-being (positive hedonic tone), in contrast to their accustomed level of stress, anxiety, and irritability. When asked, the others reported that their baseline emotional state was one of a positive feeling of well-being. Thus, in addition to changing physical pain thresholds and tolerance, these formulations demonstrated a remarkable ability to reduce long-standing emotional distress. In fact, two subjects reported an improved ability to control their tendency to respond to events with inappropriate anger and reactivity, giving them a sense of relative peace and self-control.

Another unexpected and surprising finding was seen in the reports of eight subjects who reported that they felt a calming sensation in their gut. They reported that they typically experience discomfort and bloating in their gut, as well as frequent urges to defecate, typical of IBS patients. However, during the days of the trials, they noticed that these gastrointestinal symptoms had remarkably decreased.

Yet another unexpected and surprising finding concerned a female subject who reported that she had been, as was typical for her, experiencing PMS symptoms at the start of the study. Her symptoms included malaise, irritability, and upset stomach. After taking the study formulations, she reported a rapid and dramatic reduction of her PMS symptoms.

One of the more dramatic and surprising findings of the trial was the report by one subject that her long-standing cravings for opioid drugs and alcohol had essentially disappeared, and that she was finally able to completely stop abusing these substances. Needless to say, she is being continued on a combination of theophylline (300 mg) and ultra-low-dose naltrexone (5 μg), twice daily, for maintenance, which has been successful for the past eight months.

Yet another unexpected and surprising finding concerned a male who has asthma and has taken theophylline for over 25 years. Therefore, for the purpose of the study, the only addition to his normal drugs was ultra-low-dose naltrexone (1 μg) taken with each normal dose of theophylline (300 mg SR), twice daily, other than the first day when 100 μg of naltrexone was administered. The subject felt a fairly rapid elimination of symptoms that he had experienced for years, including restlessness, muscular tension, irritability, anger, and anxiety. After a few days, the subject experienced a sense of well-being, contentment, relaxation and calm. These dramatic improvements, emotionally and physically, were sustained throughout a year-long trial, using theophylline (500 mg) with ULDN (5 μg), twice daily. The therapeutic benefits slowly lessened during periods when the naltrexone was withdrawn for a few days and the prior symptoms began to return. However, symptom relief was rapidly restored within hours of adding naltrexone back to the formulation.

Another subject clearly benefited from the combination of caffeine (50 mg) with magnesium sulfate (750 mg). Chronic aches and pains, underlying fears and anxieties, a sense of long-standing dissatisfaction and distress, all were reduced by this treatment. These benefits increased over time, so that subject chose to continue taking the formulation regularly over the following six months. When the formulation was discontinued, the benefits continued with no signs of relapse.

With a common thread of lowered pain thresholds and the benefits of these particular drug combinations, it became evident that these subjects had various forms of Distress Dysfunction, and that a safe and effective treatment for Distress Dysfunction had been discovered for the first time.

Once this discovery was made, a series of retrospective questions were posed to the subjects to assess whether any other benefits occurred. Obviously, this type of inquiry may not be as valid as the independent and spontaneous reports of the subjects during the trial. Nevertheless, this inquiry resulted in confirmation of these symptom relief patterns as well as several other unexpected findings. For instance, these inquiries revealed that two males in the study had experienced significant reduction in premature ejaculation while in the study, a satisfying effect that continued for several days. They both reported a decrease in penile hypersensitivity and increase in ejaculatory control. This finding is consistent with an understanding that premature ejaculation is a manifestation of Distress Dysfunction hypersensitivity.

A consistent pattern among these findings was that symptom reduction remained steady or increased over the course of the twice daily dosing, multi-day trials, suggesting the potential for successful long-term treatment.

One feature of these trials was that the subjects were not aware of whether they were being administered a single agent or combined agents, to determine the potential synergy of cotreatment as well as to reduce placebo effects.

Moreover, another remarkable, unexpected, surprising, synergistic and paradoxical finding concerned the substances used in the study. Theophylline and caffeine are well known for increasing anxiety, restlessness, headaches, and various gastrointestinal symptoms. A number of subjects in these trials complained of these symptoms when given these drugs alone. However, the addition of ultra-low-dose naltrexone or low-dose magnesium sulfate paradoxically reversed the ordinary and expected effect of these drugs, and resulted in a positive, unexpected, dramatic and synergistic effect, reversing patterns of negative, unpleasant effects normally associated with these drugs when administered alone. Not only were complaints of side effects and hyperalgesia eliminated in the co-treatment condition, but, as reported above, subjects experienced a dramatic improvement in positive hedonic tone, which included a significant reduction in symptoms that they had been experiencing prior to the study. At the same time the low-dose naltrexone and magnesium sulfate, alone, had neither benefit nor side effects. Not only did these findings confirm the unexpected synergistic therapeutic effects of these co-treatment formulations, but they also suggested a completely novel method for reducing the typical side effects of these medications.

Example 2

A preliminary study of Distress Dysfunction included four patients in psychotherapy, all of whom suffered from years of Distress Dysfunction, characterized by chronic emotional distress, anxiety, irritability, and anhedonia, which were not improved by traditional psychiatric medication or years of psychotherapy.

The four patients (2 males, 2 females; ages 28-56) took a twice-daily formulation of caffeine pills (50 mg) and magnesium sulfate solution (500 mg), which, within two days, produced meaningful relief from these chronic symptoms. The patients reported a significant reduction in anxiety, irritability, and depression, and an increase in satisfaction and well being. This rapid relief of chronic intractable symptoms was remarkable. However, when it became clear that one patient had dramatically greater improvement than the others, an assessment revealed that he regularly consumed acetylsalicylic acid and acetaminophen to help him sleep.

Theorizing that these agents were having a dramatic and synergistic interaction with the tested formulation, the other three patients agreed to add one of these analgesics as well. All patients continued to take the caffeine and magnesium sulfate, and added acetaminophen (500 mg, twice daily). The results showed an increased improvement in all four patients. As one of these patients described the effect of this enhanced formulation, "for the first time in my life I feel normal, like I have a thicker skin."

More recently, these patients were given a consistent twice-daily formulation of acetaminophen (500 mg), caffeine (65 mg), and naltrexone (1 μg). This formulation has produced very reliable relief of chronic emotional distress for the past twelve months with no side effects.

Given these unexpected, dramatic findings, a 42 year old female patient, suffering from Distress Dysfunction characterized by chronic alcohol and opioid cravings and abuse over many years, was given this formulation. Much to her surprise, the simple combination of acetaminophen, (500 mg), caffeine, (65 mg), and very-low-dose naltrexone (50 μg), given three times daily, completely eliminated her alcohol and drug cravings as well as any substance use. Years of psychotherapy and traditional medications had little or no impact on these serious symptoms. This treatment has been completely successful for the past ten months. To test the efficacy of the formula, without the patient's awareness, the naltrexone was replaced by a placebo for one week. Within a few days, cravings returned and the patient was tempted to relapse on several occasions. The full formula was continued after the week, and the patient's cravings were, once again, completely eliminated.

Example 3

To assess the efficacy of this innovative treatment for Distress Dysfunction with a very serious, chronic disorder that is typically considered to be "untreatable", a 28 year old female, diagnosed with Autistic Spectrum Disorder, was treated with ultra-low-dose naltrexone and caffeine.

Relevant symptoms included the following: limited eye contact, avoidance of even minor stimulation or frustration, highly reactive emotionally and physically to minor frustrations, extremely irritable and quick to anger, fearful of any arousal (both positive and negative), isolation and anhedonia. The subject historically avoided caffeine as well as physical exertion and excitement of any kind, since she felt that caffeine and these activities tended to make her intensely agitated. Despite this chronic caffeine reaction, the treatment consisted of ULDN (5 μg daily) and caffeine (150 mg daily). Therapeutic benefits were evident within the first few days of treatment, and steadily increased over the next few weeks.

Paradoxically, for the first time in the patient's life, she experienced positive hedonic tone (a positive sense of well-being, happiness, pleasure and contentment): paradoxically, she felt a calming as well as an energizing response from the caffeine with none of the agitation she had always experienced in the past. Moreover, the patient began to realize that her normal reactivity to even minor stresses disappeared. She felt "normal" for the first time in her life, able to experience some simple pleasures, including a budding enjoyment of spending time with others, and even laughing with them. As she put it, "I don't have to keep myself in an emotional straightjacket for fear of getting all worked up and losing control." Treatment has continued for the past six months, with the therapeutic benefits maintained. Recently, she has been able to enter a successful romantic relationship for the first time in her life.

This novel treatment of a patient with Autistic Spectrum Disorder is a striking example of the power of this co-treatment paradigm. The patient had been in treatment of various types, including psychiatric medications, for most of her life, with no meaningful improvement. Within a few days of taking the described formulation, her life-long chronic condition began to improve for the first time in her life. This finding supports our conclusion that this treatment can resolve chronic Distress Dysfunction symptoms and disorders with relatively innocuous agents. This case also specifically reveals the relevance of this formulation for the treatment of autism. The paradoxical caffeine reaction supports our conceptual understanding of the role of, and the ability to restore healthy functioning to the opioid and related neurotransmitter systems.

Example 4

In conducting these trials, it became clear that certain subjects had a markedly greater increase in pain thresholds and pain tolerance when given a co-treatment of a Receptor Switcher with Endorphin and Synergistic Enhancers, as compared to the more typical response of either given alone. Upon questioning the subjects, a completely unexpected discovery was made. Most of these "outliers" were, coincidentally, taking some form of exogenous non-opioid analgesic, such as acetaminophen, ibuprofen, or "baby aspirin." (The investigators had not screened for non-prescription drug usage prior to study participation.) What was particularly surprising and unexpected was that the subjects who took an exogenous non-opioid analgesic during the study, did not, on average, have higher baseline pain threshold/tolerance scores than subjects who were not. Therefore, there was clear evidence of a marked synergistic combination of the exogenous non-opioid analgesic with the Receptor Switcher, since this produced the greatest analgesic response.

To confirm this finding, the same pain threshold/tolerance hot-water finger-immersion paradigm was used with five subjects who were given, during separate testing sessions: (1) acetaminophen (500 mg) alone; (2) theophylline (300 mg) combined with ultra low dose naltrexone (1 μg); and (3) (1) and (2) combined. The increase in pain threshold/tolerance (over baseline), in order of greatest pain relief, was (3), then (2) then (1). Moreover, a dramatic synergy was uncovered since the increase in pain tolerance scores for (3) was greater than the sum of (1)+(2). In fact, the same results were found when using "baby aspirin" (81 mg) instead of acetaminophen. Although the "baby aspirin" showed no change in pain threshold when administered alone, surprisingly and unexpectedly, the combined formulation produced the most dramatic analgesia, again demonstrating the synergistic potentiation of the exogenous non-opioid analgesic using this formula.

These findings were dramatic and completely unexpected since there had been no prior teaching regarding the ability of a Receptor Switcher and an Endorphin Enhancer to potentiate analgesia produced by an exogenous non-opioid analgesic; nor had there been any teaching to suggest combining either a Receptor Switcher or an Endorphin Enhancer with an exogenous non-opioid analgesic to enhance its pain-relieving effects. The implications are significant. For the first time, there is evidence to suggest that an enhanced non-opioid formulation might be sufficiently potent for moderate-to-severe pain. Although it is generally accepted that exogenous opioid drugs create analgesia through their impact on the endogenous opioid system, there is no well-accepted understanding of how exogenous non-opioid analgesics actually work. There has been, however, some speculation that the analgesic effect of NSAIDs (Pernia-Andrade et al., *Eur. J. of Pharmacology*, 111(1):19 about 1-about 200 (2004)) and acetaminophen (Raffa & Walker, Eur. J. of Pharmacology, 503(1-2):209-210 (2004)) involve opioidergic mechanisms.

Example 5

To determine the relative benefits of administering agents alone as compared to their combined synergistic benefits, a trial was conducted over a 10 month period with 19 patients in psychotherapy suffering from various Distress Dysfunction conditions, including anxiety, obsessive-compulsive disorders, depression, drug and alcohol addictions, behavioral addictions, psychogenic and neuropathic pain, eating disorders, and sexual dysfunctions.

Without identifying the agents, each patient was given one of the following agents, once daily, for a period of two weeks: ultra-low-dose naltrexone (5 μg), very-low-dose roflumilast (5 μg), caffeine (65 mg), and acetaminophen (500 mg). Over the course of 8 weeks, each patient was administered all of the individual agents. During the next 8 weeks, each patient rotated through the following formulations, each given for a 2 week period:

(1) ULDN (5 μg)+Roflumilast (5 μg)
(2) ULDN (5 μg)+Caffeine (65 mg)
(3) ULDN (5 μg)+Acetaminophen (500 mg)

(4) ULDN (5 μg)+Caffeine (65 mg)+Acetaminophen (500 mg)

The results of this initial 4 month phase of the study were remarkably compelling and supported the critical importance of combining a Receptor Switcher (e.g., ULDN) with an Endorphin Enhancer (e.g., roflumilast or caffeine) and/or a Synergistic Enhancer (e.g., acetaminophen). When roflumilast, caffeine, or acetaminophen was administered alone, no therapeutic benefits were reported or observed, and at least half of the patients reported some degree of increased distress symptoms. When ULDN was combined with any of the other agents, a wide variety of Distress Dysfunction symptoms were reduced within the first 1-2 days, including anxiety, obsessive thoughts, compulsive behaviors, cravings, alcohol abuse, as well as aches and pains. Of these co-treatment formulations, the combination of ULDN, Caffeine, and Acetaminophen seemed to be generally the most effective. These benefits generally increased over the two week treatment period.

However, a very unexpected and surprising finding occurred when administering the ULDN alone. While nearly half of the patients experienced no effect from ULDN alone, 10 patients had dramatic improvement in their symptoms simply by the taking the naltrexone. Long-standing symptoms that were significantly reduced and/or eliminated included depression, anxiety, drug and food cravings, anger and irritability, emotional hypersensitivity and reactivity, aches and pains, as well as general malaise and agitation. Instead, for the first time in years, these patients felt a sense of normalcy and well-being, without their normal feelings of distress and unease.

Inquiry into the differences between this subset of patients and the others revealed a very clear, yet surprising pattern— therapeutic benefits occurred for patients that were on SSRI and SNRI medications, including Lexapro, Prozac, Paxil, and Effexor. Suddenly, and unexpectedly, it became clear that ULDN was able to combine in a synergistic way with an SSRI or SNRI to dramatically potentiate their therapeutic benefits in reducing chronic Distress Dysfunction symptoms, which had not significantly improved despite several years of psychotherapy and medication. Furthermore, when ULDN, a Receptor Switcher, was combined with Endorphin Enhancers (caffeine or roflumilast), and added to the patient's ongoing SSRI or SNRI, (Synergistic Enhancers), maximal therapeutic benefits were seen, especially with the most chronic and resistant symptoms of depression, anxiety, and addictions. Clearly, completely novel formulations had been discovered, which led to, and validated, the novel principles for treating Distress Dysfunction that define this invention.

Given these remarkable and unexpected findings, the focus of the remaining six months of the clinical study shifted to maintaining each patient on the formulation that worked best for their symptoms. All patients already on an SSRI or SNRI continued on this medication in combination with ULDN. Five of these patients also continued to take caffeine to maximize relief from emotional distress symptoms. Two of the patients not taking an SSRI or SNRI prior to the study were prescribed one to add to the ULDN treatment, which contributed to their clinical improvement. The remaining seven patients were maintained effectively on the combination of ULDN and caffeine. Acetaminophen was used effectively by four pain patients on an "as needed" basis for breakthrough pain during this phase of the study.

Example 6

To test the effects of an ultra-low dose of a selective cAMP PDE4 inhibitor and a Receptor Switcher on Distress Dysfunction symptoms, eight subjects were given ultra-low-dose roflumilast (1 μg) with ultra-low-dose naltrexone (1 μg), once daily, for a period of four weeks. All subjects suffered from long-standing problems with catastrophic worries, emotional and physical tension, distressing pain, and low-grade depression. Roflumilast was chosen given its potential potency and safety profile, as compared to theophylline, and reduced side effects, as compared to rolipram.

All four subjects reported similar benefits from the co-treatment formulation within the first two days of initiating the treatment. Each of them independently described that they felt an increased calm, a greater sense of general "well being" and a decrease in worries and stresses. They all indicated that they were less emotionally reactive to minor stresses, yet more able than usual to respond appropriately to situations without being distracted by their usual exaggerated "catastrophic" emotional and cognitive overreactions. They also noted that they had less of their normal aches and pains, particularly for an individual with mild arthritis who felt a much greater sense of mobility in addition to a reduction in pain. Moreover, all of them noted that they did not feel any type of "drugged state" or "high" of any kind, just a sense of normalcy. One subject noted that he had a very mild headache during the trial, but that it went away by the end of the fourth day. All therapeutic benefits consistently improved over the two-month trial.

What was remarkable about this small trial was the remarkably ultra-low-doses of both agents—one microgram of each agent, twice daily. Roflumilast is conventionally used at 500 micrograms for COPD, and naltrexone is used at 50 milligrams for addiction. Therefore, these doses are $\frac{1}{500}^{th}$ to $\frac{1}{50,000}^{th}$ of the normal doses of these agents. Yet, this novel cotreatment formulation had significant effects in reducing symptoms of Distress Dysfunction, regarding emotional and cognitive anxieties and worries as well as aches and pains of conditions and mobility problems, such as arthritis. What was also remarkable, with the exception of one mild headache that resolved within days and did not return during the 2 month trial, was that these low doses produced no side effects or signs of withdrawal or any altered cognitive or emotional states, other than a sense of normal well being. Thus, this simple formulation was able to produce positive emotional and physical hedonic homeostasis.

Example 7

Six subjects with asthma, already taking theophylline (300-600 mg daily) for many years, were given ultra-low-dose naltrexone (5 μg, once daily) over periods ranging from one month to a year.

Remarkably and unexpectedly, these subjects experienced a dramatic reduction in a variety of side effects from the medication, including hyperalgesia, agitation, anxiety, and various gastrointestinal symptoms, within the first 2-3 days of adding ULDN. Sensitivity to pain was greatly reduced, including chest pain associated with asthma.

Three subjects were switched from theophylline to roflumilast (250 mg, once daily). Roflumilast alone, like theophylline, is known to produce side effects, such as increased pain sensitivity, anxiety, and GI symptoms. However, when cotreated with ultra-low-dose naltrexone (5 μg, once daily), these side effects were eliminated. Furthermore, given the increased calming influence and pain relief from the cotreatment formula, it clearly provided a more effective treatment for asthma.

This finding with asthma sufferers suggests that this increased therapeutic efficacy and safety would also occur when using this cotreatment formula for COPD patients.

More recently, the three subjects were transitioned to roflumilast (250 mg, once daily) and n-acetyl-cysteine (600 mg, twice daily). The results have been even more compelling, especially over the three-month trial. Asthma has been consistently controlled, with an increased sense of calm and well being, and an absence of typical theophylline and roflumilast side effects. A clear synergistic effect has been discovered between these two agents, both regarding their respiratory benefits, but also their ability to resolve symptoms of Distress Dysfunction that are a function of the asthmatic condition as well as a side effect of the medications. Therefore, a novel treatment for asthma and COPD has been discovered that combines a PDE inhibitor, known for its therapeutic benefits for respiratory conditions, and a Receptor Switcher, which blocks the noxious side-effects of the PDE inhibitor and increases a sense of well being and calm.

Example 8

Summary of Validation Studies

In summary, a series of studies have been conducted to validate the science and formulations contained in this application. This research has consisted of two primary forms of investigation: induced pain and clinical case studies.

A. Induced Pain Trials

More than 100 subjects have participated in hot and cold water induced pain trials, dramatically supporting the principles and formulations discovered by this invention for the safe and effective relief of pain. In addition to the hot-water finger immersion studies described above, two Jeio Tech cold-pressor testing units were purchased since this methodology represents the state-of-the art in induced pain research. Consensus in the research literature, as well as the findings described herein, suggest that over-the-counter analgesics, such as acetaminophen, aspirin, and ibuprofen, have no greater analgesic effect than placebo in cold-pressor pain tolerance testing. Only exogenous opioid drugs, such as oxycodone, have been shown to have a significant analgesic effect, making the cold-pressor the "gold standard" for moderate-to-severe pain assessment.

Following several preliminary multi-site trials using a wide variety of agents, doses, and formulations, a cold-pressor induced pain study was conducted in order to determine the impact of specific agents on the experience of pain threshold and tolerance. Healthy volunteers were recruited who were not taking any relevant medications or supplements, resulting in a total of 12 subjects (7 men, 5 women; ages 18-86). During the initial phase of this study, the following agents and doses were administered to subjects and pain threshold and tolerance latencies were assessed. Receptor Switchers were ULDN (5 μg), NAC (600 mg), and MSM (500 mg). Endorphin Enhancers were roflumilast (50 μg), ginkgo biloba (120 mg), glutamic acid (50 mg), and DLPA (250 mg). Exogenous Opioids were tramadol (5, 10 mg), hydrocodone (5 mg)/acetaminophen (500 mg), and oxycodone (2.5, 5 mg). Synergistic Enhancers were acetaminophen (500 mg), aspirin (300 mg), and white willow bark (400 mg). Subjects were blinded as to each condition. Active agents were compared to each subject's baseline and placebo latencies, using a within-subject design.

As predicted, the only individual agents that produced a clear trend toward increased pain threshold and tolerance latencies, as compared to baseline and placebo scores, were Exogenous Opioids; moreover, only oxycodone (5 mg) consistently showed this effect. Tramadol, lower dose oxycodone, hydrocodone/acetaminophen, and the non-opioid analgesics did not generally exhibit analgesia on the cold pressor. This finding is consistent with prior studies in the literature. When administered alone, none of the experimental agents showed any trend toward pain relief; instead, roflumilast and glutamic acid showed clear hyperalgesic effects when administered alone. Therefore, if co-treatment formulations were to show analgesic effects, dramatic synergy with the Receptor Switcher would be necessary. Regarding side effects, all of the opioid drugs produced classic narcotic side effects including nausea, light-headedness, dizziness, a feeling of being "high," and a desire to obtain more of the drug. None of the other agents exhibited such effects, including the non-opioid analgesics.

For the second phase of this cold pressor induced pain study, the subjects were given a variety of co-treatment formulations as well as a placebo. Formulations were selected based upon results in previous testing, side effect and known safety profiles, and marketing potential. The subjects were blinded to the specific agents administered. For each testing session, each subject was administered one of the following formulations:

(1) ULDN (5 μg)+Roflumilast (50 μg)
(2) NAC (600 mg)+Ginkgo Biloba (120 mg)
(3) NAC (600 mg)+Glutamic Acid (50 mg)
(4) MSM (500 mg)+Ginkgo Biloba (120 mg)
(5) MSM (500 mg)+Glutamic Acid (50 mg)
(6) NAC (600 mg)+Ginkgo Biloba (120 mg)+DLPA (250 mg)
(7) NAC (600 mg)+Ginkgo Biloba (120 mg)+WWB (400 mg)
(8) NAC (600 mg)+Ginkgo Biloba (120 mg)+Tramadol (5 mg)
(9) NAC (600 mg)+Ginkgo Biloba (120 mg)+Oxycodone (2.5 mg)
(10) ULDN (5 μg)+Roflumilast (50+Tramadol (5 mg)
(11) ULDN (5 μg)+Roflumilast (50 μg)+Oxycodone (2.5 mg)

In addition to the single-dose administrations, 6 of these subjects (4 men, 2 women) participated in a twice-daily dosing study over seven consecutive days. Cold pressor testing was done during the first, third and seventh day. The following formulations were used for this multi-day trial:

(1) ULDN (5+Roflumilast (50 μg)
(2) NAC (600 mg)+Gingko Biloba (120 mg)
(3) NAC (600 mg)+Ginkgo Biloba (120 mg)+WWB (400 mg)

When administered alone, these agents were shown to be no better than placebo. In fact, many of the Endorphin Enhancers, such as roflumilast, theophylline, caffeine, and glutamic acid, when given alone, tended to result in shorter pain tolerance latencies, indicating hyperalgesic effects. In contrast, when a Receptor Switcher (ULDN, NAC, or MSM) was combined with an Endorphin Enhancer (roflumilast, ginkgo biloba, or glutamic acid), these formulations were generally more effective in producing analgesia than placebo and non-opioid analgesics (including acetaminophen, ibuprophen and aspirin, which were no more effective than placebo in the cold pressor paradigm). The combination of ULDN and roflumilast was slightly more effective in increasing pain tolerance for most subjects. Moreover, the addition of a third agent to these formulations, white willow bark or DLPA, potentiated analgesia to the level of oxycodone (5 mg). Finally the addition of a subclinical dose of tramadol (5 mg) or oxycodone (2.5 mg) in combination with a Receptor Switcher and Endorphin Enhancer produced analgesic effects that were generally more potent than 5 mg of oxycodone administered alone. This synergistic effect was particularly pronounced when the very low dose Exogenous Opioid was added to ULDN and roflumilast. All of these results have been consistent for both single dose and 7-day, twice daily dosing, with a clear tendency toward increased and more consistent pain relief with repeated dosing over the course of one week.

Therefore, these remarkably safe, novel non-opioid formulations, simply combining a Receptor Switcher, such as ULDN, NAC, or MSM, with an Endorphin Enhancer, such as roflumilast, ginkgo biloba, or glutamic acid, were able to reduce moderate-to-severe pain more effectively than conventional NSAIDs. Furthermore, the addition of a NSAID, such as white willow bark, or a second Endorphin Enhancer, such as DLPA, created a formulation that was generally as effective as an Exogenous Opioid, without the noxious side effects and safety issues, such as tolerance and dependence, of narcotic drugs. Alternatively, the addition of 5 mg of tramadol a less regulated "weak" opioid (10 mg of tramadol is equipotent to 1 mg oxycodone), created a formulation that was potentially more effective than 5 mg of oxycodone. Obviously, there are enormous clinical benefits to have discovered, for the first time in clinical trials, remarkably safe formulations that can either replace exogenous opioids or potentiate remarkably low doses of both weak (tramadol) and powerful (oxycodone) opioids for the relief of moderate-to-severe pain.

Subjects in these induced pain trials consistently reported an absence of side effects using the formulations (in contrast to the typical side effect profile reported when conventional dose exogenous opioids were administered, including constipation, itching, emotional and cognitive disorientation, and yearnings to take more of the opioid). Normal acute reflexive pain was always maintained, with no changes in cognitive abilities (again, in contrast to the "conventional dose" opioids, often characterized by blurred judgment and logic, and interference with adaptive acute reflexive pain). Moreover, subjects frequently reported many remarkable therapeutic benefits, consistent with a reduction in Distress Dysfunction, including an increased sense of calm and well being, and a significant decrease in anxiety, worries, obsessions, anger, irritability, distractibility, cravings, GI symptoms, and general aches and pains. Five subjects in this study with chronic back, shoulder, and arm pain reported remarkable relief during the study, particularly when using co-treatment formulations that included white willow bark and very low dose opioids. Many of the subjects in the study chose to continue a non-opioid, non-prescription formulation on their own, preferring them to any conventional pain and anxiety medications currently on the market. Therefore, these novel formulations were able to simultaneously reduce emotional and physical distress and pain, with no side effects. While similar in pain relief, the cognitive and emotional differences between the formulations of the invention and exogenous opioids were quite remarkable.

B. Clinical Case Studies

More than 100 outpatient psychotherapy patients with various forms of Distress Dysfunction have participated in clinical case studies using the formulations of the invention, from one month to more than one year. Patients were selected to be in included in this project who had moderate-to-severe emotional and physical distress disorders, which were not effectively being treated by conventional therapies including psychotherapy and prescription medications, such as antidepressant medication (e.g., SSRIs, SNRIs), anti-anxiety medication (e.g., benzodiazepines), and pain medication (e.g., opioids, NSAIDs). Therefore, the disorders presented by these patients were particularly challenging and resistant to conventional treatment. Many of these patients (45) suffered from emotional distress, including anxiety, obsessive-compulsive symptoms, panic, social fears, depression, dysthymia, anger, irritability, and emotional agitation and outbursts. Another group of patients (21) suffered from pain, including fibromyalgia, neuropathic pain, arthritis, headaches as well as back, shoulder, and neck pain. Many of these patients also suffered from anxiety and depression. Another group of patients suffered from alcohol (13) and opioid (4) dependence, which lasted for several years with daily abuse. Another group of patients (8) suffered from eating disorders. Another group (7) suffered from IBS, primarily diarrheal. Finally, 4 patients were diagnosed with adult Autistic Spectrum Disorder, particularly Asperger's Syndrome. A number of these patients also had co-existing problems, including sexual dysfunction, behavioral addictions, premenstrual syndrome, seasonal affective disorder, and social and relationship conflicts.

All treatment was unblinded, and explained as novel formulations for Distress Dysfunction. Patients were administered formulations that included at least one Receptor Switcher, including ULDN (5 or 125 ng, once daily), NAC (600 mg, twice daily), MSM (250 mg, twice daily), and magnesium sulfate (250 mg, twice daily). Most formulations also included at least one Endorphin Enhancer including ginkgo biloba (120 mg, twice daily), caffeine (50 mg, twice daily), glutamic acid or MSG (50 mg, twice daily), and DLPA (250 mg, twice daily). Synergistic Enhancers were often included in the formulations, particularly SSRI and SNRI medications that the patients were typically taking prior to adding the experimental formulations (about 25% of patients). For those patients already on an SSRI or SNRI, the following daily doses were used, once the patient was stabilized on the co-treatment formulation: escitalopram (10 mg, once daily), fluoxetine (20 mg, once daily), citalopram (20 mg, once daily), or venlafaxine (75 mg, once daily). For most patients, this was either the same or lower dose than previously prescribed. If the patient was not already on an SSRI or SNRI, one or more Synergistic Enhancers were added to the formulation for more serious conditions, including SHIP (50 mg, twice daily), SAMe (200 mg, once daily), PharmaGABA (200 mg, once daily), and tyrosine (500 mg, once daily) (about 18% of patients). Ten pain patients began the treatment program using a prescription narcotic pain medication. Once stabilized on the cotreatment formulation, patients either were able to completely withdraw from these drugs, or were able to maintain a relatively low dose of the opioid medication: tramadol (10 mg, twice daily) or oxycodone (5 mg, twice daily). As an alternative to narcotic pain medications, NSAIDs, especially white willow bark (250 mg, twice daily) were added to the formulation (about 10% of patients). Nearly all of the patients were given more than one formulation over time to assess the differential benefits, using intrasubject comparisons, as well as to maximize therapeutic effects.

The most recent formulations that were used for each patient, which maximized symptom reduction, are listed below. The formulations are categorized by clinical indication, with the number of patients taking the specific formulation indicated. Specific agent doses for each agent in the formulation are indicated above.

TABLE 1

Emotional Distress (Anxiety, Depression, Anger)

| # Patients | Formulation |
|---|---|
| 9 | NAC + Ginkgo Biloba |
| 9 | NAC + Ginkgo Biloba + 5-HTP |
| 7 | NAC + Ginkgo Biloba + 5-HTP + PharmaGABA |
| 3 | NAC + Ginkgo Biloba + Escitalopram |
| 3 | NAC + Ginkgo Biloba + Venlafaxine |
| 3 | ULDN + Fluoxetine |
| 3 | ULDN + Escitalopram |
| 3 | ULDN + Ginkgo Biloba + Escitalopram |
| 3 | MSM + Caffeine + Citalopram |
| 3 | NAC + Escitalopram |
| 3 | NAC + Ginkgo Biloba + PharmaGABA |

TABLE 2

Physical Distress (Pain)

| # Patients | Formulation |
|---|---|
| 4 | MSM + Ginkgo Biloba |
| 4 | MSM + Ginkgo Biloba + White Willow Bark |
| 4 | NAC + Ginkgo Biloba + White Willow Bark |
| 3 | MSM + Glutamic Acid + White Willow Bark + DLPA |
| 2 | NAC + Glutamic Acid + White Willow Bark + DLPA |
| 2 | NAC + Ginkgo Biloba + Tramadol |
| 2 | ULDN + Glutamic Acid + Oxycodone |
| 2 | ULDN + Ginkgo Biloba + Escitalopram |

TABLE 3

Addiction (Alcohol & Drug Dependence, Behavioral Addictions, Cravings)

| # Patients | Formulation |
|---|---|
| 4 | NAC + Ginkgo Biloba + Escitalopram |
| 4 | NAC + Ginkgo Biloba + GABA + Tryosine |
| 4 | NAC + Ginkgo Biloba + Glutamic Acid + 5-HTP |
| 3 | NAC + Ginkgo Biloba + GABA |
| 3 | NAC + Ginkgo Biloba + SAME-e |
| 3 | ULDN + Ginkgo Biloba + Escitalopram + Tryosine |
| 3 | NAC + Glutamic Acid + White Willow Bark |

TABLE 4

Gastrointestinal (IBS, PMS, Crohn's)

| # Patients | Formulation |
|---|---|
| 2 | NAC + Ginkgo Biloba |
| 2 | Magnesium Sulfate + Ginkgo Biloba |
| 2 | Magnesium Sulfate + Ginkgo Biloba + GABA |
| 2 | ULDN + Gingko Biloba |

TABLE 5

Autistic Spectrum

| # Patients | Formulation |
|---|---|
| 2 | NAC + Caffeine + GABA |
| 2 | NAC + Ginkgo Biloba + Magnesium |

Although placebo factors must always be considered, the results of these case studies were, nevertheless, remarkable, especially given the limited success of conventional treatments with these patients. All patients reported clear, and at times dramatic, improvements in their emotional and physical distress, including pain and GI symptoms. For many patients, the initial formulation was effective; for others, modifying the formula, including adding Synergistic Enhancers, was needed to achieve maximal benefits. Regardless of the Distress Dysfunction indication, therapeutic benefits of this novel treatment were only observed when at least one Receptor Switcher was included in the formulation. All of these patients had been suffering from significant symptoms for over a year, and many for more than a decade. For those on an SSRI or SNRI and/or in psychotherapy, prior benefits were compared to those obtained with the addition of our novel cotreatment formulations. Furthermore, many of the patients had previously taken many of the agents used in these formulations, such as ginkgo biloba, caffeine, SHIP, GABA, SSRIs, SNRIs, and NSAIDs, with either limited or no relief, and often with undesirable side effects. The key for all patients in these case studies is that most had never taken any of the Receptor Switchers, such as ULDN, NAC, MSM, or magnesium sulfate, and none had ever taken these agents in combination with the Endorphin and/or Synergistic Enhancers used in these formulations.

The most reliable therapeutic benefit these novel formulations provided for these patients was a dramatic reduction in emotional distress, particularly a remarkable decrease in anxiety, irrational fears and worries, panic, obsessions, compulsions, anger and irritability, and depression. Increased attention, concentration, productivity, and overall social and emotional functioning were consistently reported. Nearly all patients experienced a greater calm and sense of well being than they felt in years, a benefit that was maintained consistently during the entire course of treatment. One 87-year-old female, with severe arthritis, chronic worries, and depression, remarked that "I felt for the first time in years that life is worth living."

Eight patients with obsessive-compulsive symptoms that were not controlled by psychotherapy or medication, including SSRIs and SNRIs, experienced a dramatic reduction in the symptoms that had previously controlled their lives. SSRI treatment was clearly enhanced using Receptor Switchers and Endorphin Enhancers. The addition of Synergistic Enhancers, particularly GABA and SHIP, also increased therapeutic benefits. IBS symptoms were reduced for the first time in years for seven patients. Eating disorder symptoms (that had remained unchanged despite years of psychotherapy and conventional medication) were remarkably reduced, including a decrease in food cravings, binging, purging, and general sense of emptiness often experienced by many of these patients. Increased sexual functioning, including a reduction in premature ejaculation was reported by several patients. Four patients with Asperger's Syndrome were able to relax and become more social, as well as less irritable with a great reduction in emotional outbursts. All 17 patients with alcohol and opioid dependence were able to completely eliminate their substance abuse after years of unsuccessful treatment, and also experienced a greater sense of well being and reduction in cravings and anxieties.

Overall, physical distress was dramatically reduced, with benefits increasing significantly over time. Complaints about moderate-to-severe pain, regardless of the etiology, were generally reduced, without use of opioid analgesics. No tolerance was ever experienced, and the formulations maintained their effectiveness throughout all case studies. For nearly all patients, continued improvement was seen over time. No side effects were reported, with all cognitive and emotional functions improved, in contrast to the experience reported by patients when they have used conventional medications, especially exogenous opioid drugs and traditional anti-anxiety medications. Cognitive and emotional functions were significantly improved, with greater clarity, judgment, attention, mood, and motivation.

Therefore, while placebo factors and concurrent psychotherapy were potential confounding factors, these case studies offer compelling evidence of meaningful therapeutic benefits for a wide variety of Dysfunctional Distress disorders, conditions, and symptoms, using these remarkably safe pharmaceutical formulations. Specifically, these case studies, which always included a Receptor Switcher (ULDN, NAC, MSM and/or magnesium sulfate) combined with an Endorphin Enhancer (ginkgo biloba, caffeine, glutamic acid, and/or DLPA) and/or a Synergistic Enhancer (SSRI, SNRI, white willow bark, SHIP, SAMe, pharmaGABA, tryosine), provide validation for the remarkable safety and clinical effectiveness of these pharmaceutical formulations.

While both dosing levels of naltrexone were generally effective, the benefits from using the relatively higher dose (125 micrograms) were more consistent within and among patients. Therefore, these clinical case studies support the conclusion that greater efficacy and reliability is produced, over all populations and indications, when using VLDN in the 100-150 microgram range. Variable bioavailabilty of oral naltrexone among individuals probably accounts for the need for this dosing range to produce the most consistent therapeutic effects. Clearly, more trials will be needed to determine the most effective dosing of all agents in these formulations for different populations and indications.

A striking aspect of these case studies was the remarkable safety and effectiveness of "grandfathered nutraceuticals." These active agents are generally regarded as safe (GRAS) and were available for purchase in the United States prior to 1994, and, therefore, are regulated by the FTC for 'truth in marketing' claims rather than the FDA. These relatively safe agents have been shown to be effective, in the correct combination, for patients with serious emotional and physical distress disorders. No benzodiazepines were used throughout this treatment program, which is unusual given the extent of anxiety presented by these patients. At the onset of the program, 10 pain patients were taking prescribed narcotic opioid medications that were ineffective, including Vicodin and Oxycontin. Six of these patients discontinued these opioid medications altogether, once the novel formulations were begun, and the remaining 4 patients were able to lower their opioid drugs significantly as part of the overall formulation. In addition, the 4 patients who began the program addicted to, and abusing, narcotic opioid drugs (that were not taken specifically for pain), were able to discontinue these drugs altogether, once they began taking the novel formulation. Finally, while the 30 patients who began the program on anti-depressant medication generally continued on it as part of their overall formulation, they were able to maintain or lower the dose and yet experience remarkable reductions in symptoms of emotional and physical distress. Most dramatically, 72 patients participating in this program (over 70% of all cases) were able to experience remarkable reduction in chronic symptoms of emotional and physical distress, including pain and addiction, using only grandfathered nutraceutical formulations, which included NAC, MSM, ginkgo biloba, glutamic acid, caffeine, white willow bark, 5HTP, GABA, and SAMe. These agents have been used for decades, are well-known to be relatively safe for long-term use, and have very clear health benefits for the immune, circulatory, respiratory, and other systems of the body.

In sum, a series of clinical trials and case studies have been conducted which surprisingly and dramatically support the emotional and physical health restoring benefits of these novel formulations. Over 200 subjects and patients have been given one or more of these novel formulations. There have been virtually no side effects or any adverse events observed in any of these individuals. In addition, all reports indicate that these formulations do not produce any feeling of "taking a drug," in contrast to the "drugged" experience typically seen in most medications currently available for the treatment of symptoms of Distress Dysfunction, such as tranquillizers and opioid drugs. At the same time, the therapeutic benefits of these novel formulations have been extremely positive, and dramatically more effective that any of the agents when taken alone, or in combinations within each functional category of agents, thereby validating the surprising synergistic healing power of this invention's unique formulations. Therefore, evidence indicates that the addition of Reeptor Switchers creates synergistic therapeutic benefits well beyond the reduction of tolerance, since the benefits are remarkably better than the administration of the agents or drugs when taken alone, from the very start of treatment.

Using this invention's principles, new formulations, using different agents with similar functional properties, have reliably been effective, validating these principles and the entire invention. Furthermore, since these formulations clearly are safer and more effective than conventional treatment, they provide validation for both the existence of Distress Dysfunction, as defined in this patent, and for a revolutionary group of pharmaceutical formulations, which restore healthy homeostatic balance to the neurotransmitter systems within the nervous system.

Example 9

A revealing clinical example of the relative effectiveness of these novel formulations for Distress Dysfunction is reflected in a case study of a professional couple, married for over 20 years. They both suffered from chronic alcoholism and tobacco use for most of their marriage, and the husband regularly abused a variety of other drugs, including marijuana, tranquillizers, and narcotic pain medications. Despite several hospitalizations for toxic effects of chronic alcohol abuse, neither partner was able to reduce their alcohol use. Both spouses also suffered from moderate depression and anxiety; while the husband had episodic panic attacks and periods of severe depression. The husband often had angry outbursts that were considered abusive and often went on for hours and even days. Each spouse had been in individual psychotherapy for years, and the couple has been in marital therapy for the past three years. The husband has been taking a variety of SSRI medications and anti-anxiety medications for years. None of these treatment approaches were effective.

Initially, the husband was given ultra-low-dose naltrexone (5 micrograms daily) in addition to continuing escitalopram. For the first time, with the addition of ULDN, he was able to reduce his alcohol and tobacco use, and his depression, anxiety and anger lessened. However, he continued to suffer from moderate levels of all of these problems. After several months, the couple agreed to a more comprehensive treatment that included, for both of them, the following formulation, twice daily: NAC (600 mg), magnesium sulfate (75 mg), ginkgo biloba (120 mg), and glutamic acid (50 mg) as well as recommended vitamins and minerals. In addition, since the wife was not on a serotonin enhancer, she was also given 5HTP (5 mg), once daily. During this time, the husband continued to take the naltrexone, which was increased to 125 micrograms daily, and escitalopram as well as NSAIDs, as needed for break-through aches and pains. (The ULDN dose was increased based on the relative benefits of this VLDN dosing range discovered in other case studies.) In addition, they both maintain a regular intake of caffeine through daily coffee consumption.

Remarkably, within a week of the onset of this formulation, both partners were able to completely abstain from alcohol and the husband was able to stop smoking cigarettes, though he has continued to use marijuana regularly. The wife has continued to smoke cigarettes, though cut her consumption in about half. Both reported a rapid decline in symptoms of depression and anxiety. Most dramatically, the husband's anger literally disappeared, and he became calm and reasonable for the first time in years. Their moods lifted and their marital satisfaction improved significantly. A variety of fairly serious aches and pains were greatly reduced, and their sense of health and well-being improved significantly. Their sex life returned for the first time in several years, and has been very satisfying. This treatment has continued over the past six months, and these improvements have been maintained consistently throughout this time. This case study is consistent with the clear therapeutic benefits observed in all validation trials, supporting the critical importance of combining one or more Receptor Switchers with one or more Endorphin Enhancers and one or more Synergistic Enhancers, for the treatment of a wide variety of Distress Dysfunction symptoms, conditions, and disorders.

Example 10

To assess the therapeutic benefit of the novel cotreatment formulations of the invention with Attention-Deficit Disorders, three ongoing case studies are being conducted, one focused on the use of stimulants and the other based on "nutriceuticals."

A 13-year old male with severe uncontrolled ADHD has had serious problems with his inappropriate behaviors, emotions, and attitudes, both at school and at home, for more than 8 years. He has been taking methylphenidate (5 mg, twice daily) for the past 6 months, with only modest improvements. The medication also produced mild restlessness, sleep difficulties, and reduced appetite. NAC (600 mg, twice daily) was added to the ongoing medication. Within 3 days, observable differences were reported by both parents and teachers. The young man was able to sit quietly for longer periods of time and was clearly more cooperative and socially appropriate. Reduced side effects from the methylphenidate were also reported. Increased improvement has been observed over the past month, and the cotreatment formulation is being continued.

A 10-year old male with moderate ADHD has had difficulties paying attention at school and cooperating at home. He has never been given prescription medications for the problem, and behavioral interventions have not been successful. The child was initially given acetyl-L-carnitine (500 mg, twice daily) for a period of one week with no observable benefits. Then, NAC (600 mg, twice daily), magnesium sulfate (500 mg, twice daily), and ginkgo biloba (120 mg, once daily) were added to the ALC. Within 3 days, school and home reports indicated a significant improvement in attitude, behavior, and attention. No side effects have been observed, and an ongoing mild problem with constipation has been improved. Progress has been steadily improving, using this novel cotreatment formulation during this 3 week trial, which is ongoing.

A 24 year old male with severe ADHD has had problems in all aspects of his life due to this disorder. Despite above average intelligence, he was unable to complete high school. After dropping out of school, he was able to earn a GED. Over time, he was unable to hold regular employment. He has taken a variety of drugs for ADHD with almost no benefit, including methylphenidate. Recently, the man was given methylphenidate (5 mg), again with almost no benefit, and several undesirable side-effects, including insomnia, anorexia, and agitation. The addition of VLDN (125 micrograms) resulted in a remarkable improvement, within the first two days, in his ability to maintain attention and concentration as well as task motivation, with a significant reduction in side effects. He will continue this co-treatment formulation, given its obvious benefits.

These case studies demonstrate the relative safety and therapeutic benefits of our novel cotreatment formulations for attentional and behavioral problems, such as ADHD. Evidence suggests that conventional stimulant treatment can be significantly improved with the addition of a Receptor Switcher, such as VLDN and NAC. In addition, a pure "nutraceutical" approach, using a combination of Receptor Switchers, such as NAC and magnesium sulfate, with Endorphin and Synergistic Enhancers, such as ginkgo biloba and ALC, has potential, at least for moderate levels of ADHD.

Example 11

In search of a topical cotreatment formulation for localized pain, loperamide was chosen since it functions as an Exogenous Opioid, but does not enter the CNS and, therefore, has minimal side effects and is available without a prescription. The cotreatment principles were used to develop a novel formulation of loperamide with MSM. A lotion was created by combining a penetrating skin cream with powdered loperamide (10-2 mg tablets) and MSM (2 g).

Four subjects (2 men, 2 women, ages 42-72) with moderate-to-severe chronic arthritic joint pain were given a supply of the formulated lotion. They were instructed to use the lotion on the painful parts of their body, up to 4 times daily, over a period of one week. All subjects reported at least a moderate improvement in joint pain that they had only experienced using prescription oral medications, which typically produced undesirable side effects. No reports of side effects were reported by the subjects. After one week, a menthol gel was added to the lotion, and 3 of the subjects reported additional relief from pain.

This application of the novel cotreatment principles of the invention has significant commercial value since it represents a potential line of safe over-the-counter products for the treatment of localized pain, which is a critical need for millions of chronic pain sufferers.

Example 12

Given the success of the cotreatment formulations for pain that include NSAIDs, such as white willow bark, several cases studies have been initiated with pain patients who have already been using celecoxib. This prescription medication is widely used for chronic pain and inflammation, including arthritic conditions, but is not always effective and has certain undesirable side effects.

Two women (ages 56 and 72) with years of chronic arthritic pain have been taking celecoxib (200 mg daily) for over 3 years, with greatly reduced benefits over time. For one week, one woman was given ULDN (5 microgram daily), and the other was given MSM (1000 mg), in addition to ongoing celecoxib. The Receptor Switcher was reversed between the women during the second week. Both women experienced a remarkable increase in overall pain relief by the second day of this novel cotreatment, which continued during the 2 weeks.

Both women were switched to VLDN (125 microgram) and celecoxib (200 mg) daily with even greater pain relief during this ongoing trial, supporting the growing evidence for the efficacy of VLDN as a Receptor Switcher.

These case studies provide further evidence for the potency of our novel non-narcotic, non-steroidal cotreatment formulations for chronic pain. The addition of a Receptor Switcher appears to not only reverse the tolerance that develops over time with celecoxib, and other analgesics, but evidence suggests that pain relief, and other therapeutic benefits, are greater with our cotreatment formulations than were experienced using the analgesic alone.

Example 13

Based upon the discoveries of the present invention as well as previous case studies and trials, four nutraceutical formulations were developed to reduce and prevent Distress Dysfunction. These formulations are detailed below with ingredients and dose, which can be administered either once or twice daily:

A. Basic Formulation Focused on Balancing Endogenous Opioid System:

| | |
|---|---|
| MSM | 600 mg |
| NAC | 600 mg |
| Guarana | 200 mg |
| Ginkgo Biloba | 120 mg |
| P5P | 20 mg |
| Folic Acid | 0.5 mg |
| Vitamin B-12 | 0.5 mg |

B. Formulation Focused on Balancing and Enhancing Endogenous Opioid System:

| | |
|---|---|
| MSM | 600 mg |
| NAC | 600 mg |
| White Willow Bark | 400 mg |
| Guarana | 200 mg |
| Ginkgo Biloba | 120 mg |
| P5P | 20 mg |
| Folic Acid | 0.5 mg |
| Vitamin B-12 | 0.5 mg |

C. Formulation Focused on Balancing and Enhancing Endogenous Opioid and Other Stress-Related Neurotransmitter Systems:

| | |
|---|---|
| MSM | 600 mg |
| NAC | 600 mg |
| SAMe | 200 mg |
| PharmaGABA | 200 mg |
| Guarana | 200 mg |
| Ginkgo Biloba | 120 mg |
| 5HTP | 50 mg |
| P5P | 20 mg |
| Folic Acid | 0.5 mg |
| Vitamin B-12 | 0.5 mg |

D. Formulation Focused on Balancing and Enhancing Endogenous Opioid System and Reducing Inflammation:

| | |
|---|---|
| MSM | 600 mg |
| NAC | 600 mg |
| Myhhr Gum | 500 mg |
| Boswellia | 250 mg |
| Magnesium Sulfate | 250 mg |
| Guarana | 200 mg |
| Ginkgo Biloba | 120 mg |
| P5P | 20 mg |
| Folic Acid | 0.5 mg |
| Vitamin B-12 | 0.5 mg |

An extensive set of case studies is underway using these nutraceutical formulations. Formulation A is primarily being used with patients suffering from mild-to-moderate emotional and physical distress. Formulations B and D are primarily being used with patients suffering from moderate-to-severe distressing and nociceptive pain. Formulation C is primarily being used with patients suffering from moderate-to-severe anxiety, depression, addictions, eating disorders, and anger. Results from these case studies will be published at the completion of the study. Preliminary findings suggest that these nutraceutical formulations are more effective than conventional treatment as well as earlier versions of these endorphinergic formulations.

It will be apparent to those skilled in the art that various modifications and variations can be made in the methods and compositions of the present invention without departing from the scope of the invention. Thus, it is intended that the present invention cover the modifications and variations of this invention provided they come within the scope of the appended claims and their equivalents.

APPENDIX

Bimodal Opioid Modulation of Pain and Hedonic Tone[1]

[1]The attached figures (with accompanying notes) describe what is believed are the highly complex, subtle and interrelated biochemical, biological and physiological mechanisms underlying the surprising, remarkable, novel and synergistic benefits of the co-treatment formulations set forth in this patent application. The surprising, remarkable, novel and synergistic methods and combinations set forth in the patent application accurately describe the efficacy and utility of these methods and combinations to restore healthy functioning in humans and treat the conditions and disorders in humans as identified and described in this patent application.

Healthy Homeostatic Balance

Normal homeostasis maintains an adaptive balance between the Excitatory and Inhibitory Modes in the Bimodally-Acting Opioid Receptors. In the absence of injury or stress, Opioid Receptors are generally in the Inhibitory Mode. Normal levels of Endogenous Opioids, (i.e., endorphins), are homeostatically maintained, producing a generally positive Hedonic Tone, including a sense of calm and well being Normal Acute Pain Acute injury or stress triggers Acute Reflexive Pain Signals mediated by non-opioid systems, leading to the adaptive reflexive experience of immediate pain and distress. Simultaneously, acute injury or stress set Opioid Receptors in the Excitatory Mode and Endogenous Opioids (i.e., endorphins) are released. The Endogenous Opioids bind with the Opioid Receptors, triggering excitatory signaling. Through $G_s$, excitatory signals enhance the release of cAMP, which by increasing Protein Kinase A (which increases $Ca^2$ conductance and decreases $K^+$ conductance), excites Pain-Sensory Neurons, which trigger the sensation of pain as well as increased sensitivity toward pain (hyperalgesia). The increased cAMP also enhances the release of Endogenous Opioids, maintaining the pain and distress cycle, leading to an extended adaptive response to the noxious stimuli. However, as soon as the acute danger is reduced, in part as a result of an adaptive response to pain and distress, the Opioid Receptors are switched to Inhibitory Mode. The Endogenous Opioids then trigger inhibitory signaling and, through $G_o$, (which decreases $Ca^{2+}$ conductance and increases $K^+$ conductance), inhibit Pain-Sensory Neurons, which triggers reduced sensation of pain and produces analgesia. At the same time, the Opioid Receptor inhibitory signaling, through $G_i$, inhibits cAMP, which in turn reduces Endogenous Opioids, which tunes down the entire endogenous opioid pain response system, restoring normal homeostatic balance and positive Hedonic Tone.

Protracted Excitatory Mode

Chronic stress, injury, exogenous opioids, drugs, alcohol, and various medical and genetic factors can set Opioid Receptors in a protracted excitatory mode. In this condition, Endogenous Opioids trigger mostly excitatory signaling, which results in chronic pain and hyperalgesia. Any factor that triggers the release of Endogenous Opioids, including injury or stress and even reward states and various drugs, can potentiate pain. This protracted condition triggers homeostatic processes in related Serotonin, Dopamine, and other neurotransmitter systems, which produces a variety of signs and symptoms of emotional and physical distress. This negative Hedonic Tone state may be reflected by the experience of anxiety, irritability, depression, cravings, addictive tendencies and physical distress, including pain and gastrointestinal symptoms. Protracted opioid receptor excitatory mode conditions are a major component of a wide variety of Distress Dysfunction disorders, syndromes, and symptoms. Unfortunately, typical coping patterns, including the use of drugs and alcohol, perpetuate and exacerbate protracted excitatory signaling and its negative impact on Hedonic Tone.

Exogenous Opioids

Exogenous Opioid analgesic drugs, such as tramadol, oxycodone, and morphine, clearly have a dramatic impact on the endogenous opioid system. Exogenous Opioids act like Endogenous Opioids, binding with Opioid Receptors, and their impact depends on the mode of the Bimodally-Acting Opioid Receptors. In a balanced system, their impact initially leads to inhibitory signaling, resulting in analgesia and even a sense of well being. However, fairly quickly, this increased inhibitory signaling results in a homeostatic balancing response that includes, through cAMP, a reduction in Endogenous Opioid levels as well as a receptor shift to the Excitatory Mode. Over time, this leads to a protracted excitatory receptor mode and diminished Endogenous Opioid levels, producing chronic pain, hyperalgesia, tolerance, dependence, and addiction as well as emotional and physical distress. These iatrogenic problems are greatly exacerbated when the endogenous opioid system is already in a protracted excitatory mode, resulting more immediately in excitatory signaling, leading to an exacerbation of pain and hyperalgesia, tolerance, as well as negative hedonic mode. Thus, while at times initially therapeutic, Exogenous Opioids can rapidly lead to the development of serious and Distress Dysfunction, even long after the Exogenous Opioids are discontinued.

Receptor Switching Agents

Opioid Receptor Switchers, including ultra-low-dose and very-low-dose opioid antagonists, such as ultra-low-dose and very-low-dose naltrexone and naloxone, and GM1 ganglioside attenuators, such as neuraminidase inhibitors (e.g., magnesium sulfate and n-acetyl-cysteine), selectively block the Opioid Receptor Excitatory Mode. Therefore, protracted excitatory signaling is eliminated, and inhibitory receptor signaling is enhanced. As a result, when Endogenous Opioids (or Exogenous Opioids) bind with the Opioid Receptor, the result is increased inhibitory signaling, producing analgesia and a sense of well being. These agents have the potential to reverse both acute and protracted excitatory mode imbalances, helping to restore normal homeostatic functioning. However, since protracted excitatory conditions lead to diminished Endogenous Opioids, Receptor Switchers alone may be insufficient to produce analgesia and a sense of well being. Therefore, Receptor Switchers are most effective with co-adminstered with an agent that boosts the level of Endogenous Opioids. Alternatively, by administering a Receptor Switcher with an Exogenous Opioid, excitatory signaling is minimized, resulting in enhanced analgesia as well as a dramatic reduction in protracted excitatory mode conditions, reducing and/or eliminating many of the noxious effects of Exogenous Opioids, including tolerance, dependence, addiction, and other side effects.

Cyclic AMP Enhancing Agents

Cyclic AMP Enhancers, particularly specific cAMP PDE-4 inhibitors, such as roflumilast, as well as non-specific cAMP PDE Inhibitors, such as theophylline and caffeine, enhance the release of cAMP, which, in turn, enhances the release of Endogenous Opioids (i.e., endorphins). In addition to cAMP PDE inhibitors, less potent cAMP Enhancers include excitatory amino acids, such as glutamic acid. When cAMP Enhancers are administered alone, the resulting increase in cAMP can directly trigger an increase in pain and hyperalgesia. Furthermore, excitatory signaling is likely if Opioid Receptors are set in the protracted excitatory mode and/or if injury or stress is present, resulting in a further increase in pain and hyperalgesia as well as emotional and physical distress. This mechanism explains the typical side effects seen with these agents. However, when co-administered with an agent that switches opioid receptors from an excitatory state to an inhibitory state, Receptor Switchers, the increase in Endogenous Opioids produced by cAMP PDE inhibitors leads to enhanced inhibitory signaling, resulting in analgesia and positive hedonic tone. Therefore, combining a Receptor Switcher and a cAMP Enhancer creates a remarkable non-opioid pharmaceutical formulation for the treatment of a wide variety of Distress Dysfunctions. Moreover, by adding a Receptor Balancer to cAMP PDE inhibitors, such as roflumilast and theophylline, enhanced formulations for the treatment of COPD and asthma are discovered with dramatically reduced side effects and increased pain relief and positive hedonic tone.

Synergistic Enhancing Agents

A variety of agents have a synergistic effect with the endogenous opioid system through the $G_i$-mediated metabolic processes that trigger the inhibition of pain-sensory neurons. There is evidence to suggest that higher levels of Gi that are produced by enhanced inhibitory signaling potentiate the pain-relieving effects of non-opioid analgesics, such as NSAIDs and acetaminophen. Therefore, there is a synergistic potentiation produced by the combination of non-opioid analgesics plus Receptor Switchers, such as ultra-low-dose naltrexone and neuraminidase inhibitors, creating a new generation of enhanced non-opioid analgesics. Similarly, synergistic potentiation occurs with serotonin reuptake inhibitors (SSRIs), suggesting increased pain relief as well as calm and well being is produced by the combination of SSRIs and Receptor Switchers. Therefore, a new generation of enhanced SSRIs for depression and anxiety are created by this discovery. In addition to SSRIs, inhibitory serontonergic and adrenergic agents can function as Synergistic Enhancers. Specific amino acids that enhance release of serotonin and dopamine, such as tryptophan and 5HIP, can also act as Synergistic Enhancers in cotreatment formulations. Finally, there is evidence to suggest that ultra-low-dose naltrexone (ULDN) has a synergistic effect through this $G_i$ metabolic process in addition to its function as a Receptor Switcher, making ULDN a particularly powerful agent in all cotreatment formulations.

Endogenous Opioid Reuptake Inhibitors

Agents, such as DLPA, both enhance the release of Endogenous Opioids as well as block the enzymes that reuptake them, providing an enhanced level of Endogenous Opioids (i.e., endorphins) for longer periods of time. When administered alone, these agents have the potential for increased inhibitory signaling, but may also produce excitatory signaling when injuries or stress are present, as well as when the receptors are set in an excitatory mode. However, when co-administered with agents that switch the receptors from an excitatory to inhibitory mode, Receptor Switchers, these agents are more likely to trigger inhibitory signaling, leading to enhanced and prolonged analgesia and well being. Therefore, DLPA is an excellent agent to complement all cotreatment formulations.

Clinical Implications

This novel understanding of the Bimodal Opioid Modulation of Pain and Hedonic Tone leads directly to new generation pharmaceutical formulations that are remarkably safe and effective for the treatment of a wide variety of Distress Dysfunctions, including chronic pain, addiction, anxiety, depression, anger, eating disorders, IBS, and other emotional and physical distress disorders. The foundation of this discovery is the power of Receptor Switchers, especially ultra-low-dose naltrexone, in blocking acute and protracted excitatory signaling. Therefore, co-administration of Receptor Switchers with cAMP Enhancing Agents is an excellent formulation for restoring healthy homeostatic balance to the endogenous opioid system, using the body's endorphins to reduce pain as well as emotional and physical distress, restoring positive hedonic tone. In this homeostatic condition, acute reflexive pain is experienced, through non-opioid systems, in response to injury or stress, but quickly is reduced when endorphins trigger inhibitory signaling. The addition of Endorphin Enhancers, such as DLPA, can enhance and prolong these therapeutic benefits. While opioid and non-opioid analgesics can potentiate these therapeutic effects when used in co-treatment with Receptor Switchers (and cAMP and Endorphin Enhancers), the evidence suggests that they can produce serious dysfunctional imbalances in the endogenous opioid system when used alone. Therefore, it is critical to co-administer Receptor Switchers whenever using opioid and non-opioid analgesic drugs in order to maximize their analgesic potency and to reduce noxious side effects including tolerance and dependence produced by protracted excitatory signaling. Finally, a new generation of enhanced anti-depressant and anti-anxiety medications is created by these discoveries by combining Receptor Switchers with SSRIs, which are remarkably effective in creating positive hedonic tone, including calm, well being, and pain relief.

What is claimed is:

1. A method to safely and effectively treat asthma or chronic obstructive pulmonary disease in a subject in need comprising:
   (a) administering a Receptor Switcher to the subject, wherein the Receptor Switcher is naltrexone in an amount of about 1 microgram to about 500 micrograms; and
   (b) administering an Endorphin Enhancer, wherein the Endorphin Enhancer is selected from the group consisting of theophylline, roflumilast, ibudilast, cilomilast, zaprinast, rolipram, methylxanthine.

2. The method of claim 1, wherein the method results in improving respiration.

3. The method of claim 1, wherein the combination of the Receptor Switcher with the Endorphin Enhancer results in a decrease in side effects associated with administration of the compounds alone.

4. The method of claim 1, wherein the Receptor Switcher, when co-administered with the Endorphin Enhancer, reduces and/or resolves one or more symptoms of asthma or chronic obstructive pulmonary disease.

5. The method of claim 1, wherein the subject has previously taken an Endorphin Enhancer, an Exogenous Opioid, a Synergistic Enhancer, or any combination thereof.

6. The method of claim 1, wherein:
   (a) the mode of administration is oral;
   (b) the pharmaceutical formulation is delivered in a pharmaceutically-acceptable carrier that is rapid release, immediate-release, slow-release, delayed-released, controlled release, a combination of immediate release and controlled release, a nano-encapsulation formulations, and an abuse and/or tamper-resistant delivery system; or (c) any combination thereof.

* * * * *